United States Patent
Han et al.

(10) Patent No.: US 11,980,089 B2
(45) Date of Patent: May 7, 2024

(54) COMPOUND AND ORGANIC LIGHT EMITTING DEVICE COMPRISING SAME

(71) Applicant: LG CHEM, LTD., Seoul (KR)

(72) Inventors: Su Jin Han, Daejeon (KR); Dong Hoon Lee, Daejeon (KR); Boonjae Jang, Daejeon (KR); Min Woo Jung, Daejeon (KR); Jungha Lee, Daejeon (KR); Seulchan Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 708 days.

(21) Appl. No.: 17/068,605

(22) Filed: Oct. 12, 2020

(65) Prior Publication Data

US 2021/0083198 A1 Mar. 18, 2021

Related U.S. Application Data

(63) Continuation-in-part of application No. PCT/KR2019/004983, filed on Apr. 25, 2019.

(30) Foreign Application Priority Data

Apr. 25, 2018 (KR) .......................... 10-2018-0047968

(51) Int. Cl.
*H01L 51/50* (2006.01)
*C07D 405/14* (2006.01)
(Continued)

(52) U.S. Cl.
CPC ......... *H10K 85/654* (2023.02); *C07D 405/14* (2013.01); *C07D 409/14* (2013.01);
(Continued)

(58) Field of Classification Search
None
See application file for complete search history.

(56) References Cited

U.S. PATENT DOCUMENTS

2010/0117064 A1   5/2010   Lee et al.
2015/0188056 A1*  7/2015   Suda .................... H10K 85/656
                                                546/307
(Continued)

FOREIGN PATENT DOCUMENTS

CN      106946853 A    7/2017
CN      108424411 A    8/2018
(Continued)

OTHER PUBLICATIONS

Yu Jin Kang et al., "Lifetime enhancement of blue thermally activated delayed fluorescent devices by separated carrier channels using dibenzofuran-triazine type hosts", Journal of Industrial and Engineering Chemistry, 62, Jan. 10, 2018, pp. 258-264, XP085383864.
(Continued)

*Primary Examiner* — Gregory D Clark
(74) *Attorney, Agent, or Firm* — Bryan Cave Leighton Paisner LLP

(57) ABSTRACT

A compound of Chemical Formula 1, and an organic light emitting device comprising the same.

[Chemical Formula 1]

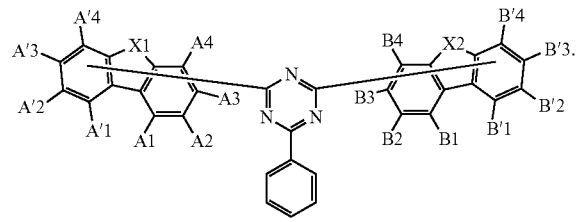

9 Claims, 1 Drawing Sheet

```
┌─────────────────────────┐
│            4            │
├─────────────────────────┴──┐
│            3               │
├────────────────────────────┴──┐
│            2                  │
├───────────────────────────────┴──┐
│            1                     │
└──────────────────────────────────┘
```

(51) Int. Cl.
  *C07D 409/14* (2006.01)
  *C07D 417/14* (2006.01)
  *C07F 7/08* (2006.01)
  *C09K 11/06* (2006.01)
  *H10K 85/40* (2023.01)
  *H10K 85/60* (2023.01)
  *H10K 50/11* (2023.01)
  *H10K 50/15* (2023.01)
  *H10K 50/16* (2023.01)
  *H10K 50/17* (2023.01)
  *H10K 50/18* (2023.01)
  *H10K 101/10* (2023.01)

(52) U.S. Cl.
  CPC .......... *C07D 417/14* (2013.01); *C07F 7/0816* (2013.01); *C09K 11/06* (2013.01); *H10K 85/40* (2023.02); *H10K 85/657* (2023.02); *H10K 85/6574* (2023.02); *H10K 85/6576* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02); *H10K 2101/10* (2023.02)

(56) References Cited

U.S. PATENT DOCUMENTS

2018/0337348 A1  11/2018  Jung et al.
2019/0198775 A1* 6/2019  Lui .................. H10K 85/6574

FOREIGN PATENT DOCUMENTS

| KR | 10-2008-0109671 A | 12/2008 |
| KR | 10-2013-0091888 A | 8/2013 |
| KR | 10-2014-0097299 A | 8/2014 |
| KR | 10-2015-0069346 A | 6/2015 |
| KR | 10-2017-0089599 A | 8/2017 |
| KR | 10-2018-0010130 A | 1/2018 |
| KR | 10-2018-0013449 A | 2/2018 |
| KR | 10-2018-0038834 A | 4/2018 |
| KR | 10-1959821 B1 | 3/2019 |

OTHER PUBLICATIONS

International Search Report from PCT/KR2019/004983, dated Aug. 2, 2019.
Written Opinion of the ISA from PCT/KR2019/004983, dated Aug. 2, 2019.

* cited by examiner

[FIG. 1]
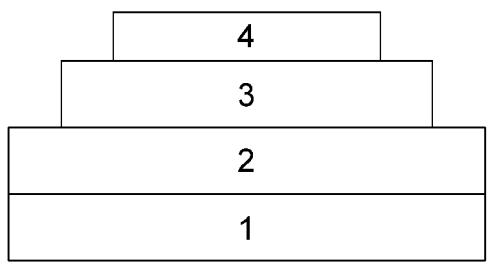
[FIG. 2]
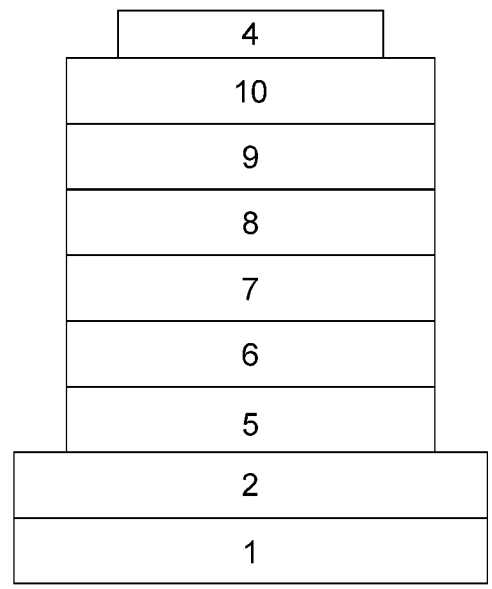

COMPOUND AND ORGANIC LIGHT EMITTING DEVICE COMPRISING SAME

This application is a Continuation-In-Part of International Application No. PCT/KR2019/004983, filed on Apr. 25, 2019, which claims priority to and the benefits of Korean Patent Application No. 10-2018-0047968, filed with the Korean Intellectual Property Office on Apr. 25, 2018, the entire contents of which are incorporated herein by reference.

TECHNICAL FIELD

The present disclosure relates to a compound of Chemical Formula 1, and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

PRIOR ART DOCUMENTS

Korean Patent Application Laid-Open Publication No. 10-2008-0109671

DISCLOSURE

Technical Problem

The present specification is directed to providing a compound of Chemical Formula 1.

The present specification is directed to providing an organic light emitting device having, by including the compound of Chemical Formula 1, a low driving voltage, high efficiency, or excellent lifetime properties.

Technical Solution

One embodiment of the present specification provides a compound of the following Chemical Formula 1.

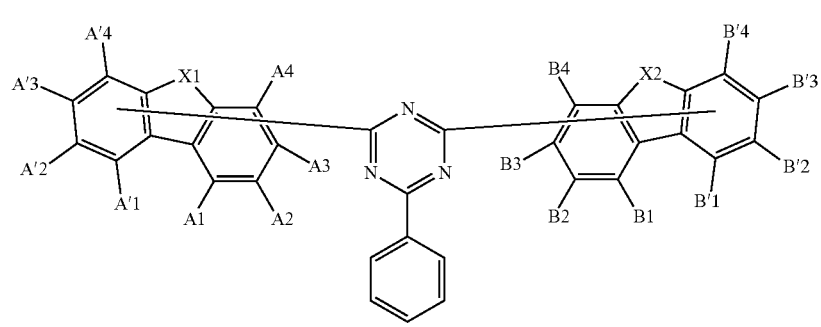

[Chemical Formula 1]

In Chemical Formula 1,
X1 is O or SiRaRb,
X2 is O or SiRcRd,
Ra to Rd are the same as or different from each other, and each independently hydrogen; deuterium; an alkyl group; or an aryl group,
any one of A1 to A4 and A'1 to A'4 is a linking group bonding to triazine, any one is Ar1, and the rest are hydrogen,
any one of B1 to B4 and B'1 to B'4 is a linking group bonding to triazine, any one is Ar2, and the rest are hydrogen,
Ar1 and Ar2 are the same as or different from each other, and each independently an aryl group; or a heteroaryl group unsubstituted or substituted with an aryl group.

Another embodiment of the present specification provides an organic light emitting device comprising a first electrode, a second electrode, and one or more organic material layers provided between the first electrode and the second electrode, wherein the organic material layer comprises the compound of Chemical Formula 1 described above.

Advantageous Effects

A compound of Chemical Formula 1 can be included in a hole injection layer; a hole transfer layer; a layer carrying out hole transfer and injection at the same time; a hole control layer; an electron control layer; an electron injection layer; an electron transfer layer and a layer carrying out electron transfer and injection at the same time; and particularly in a light emitting layer of an organic light emitting device.

In some embodiments, an organic light emitting device including the compound of Chemical Formula 1 can have enhanced efficiency, lowered driving voltage, or enhanced lifetime properties.

DESCRIPTION OF DRAWINGS

FIG. 1 illustrates an example of an organic light emitting device formed with a substrate (1), an anode (2), an organic material layer (3) and a cathode (4).

FIG. 2 illustrates an example of an organic light emitting device formed with a substrate (1), an anode (2), a hole injection layer (5), a hole transfer layer (6), a hole control layer (7), a light emitting layer (8), an electron transfer layer (9), an electron injection layer (10) and a cathode (4).

REFERENCE NUMERAL

1: Substrate
2: Anode
3: Organic Material Layer
4: Cathode
5: Hole Injection Layer
6: Hole Transfer Layer
7: Hole Control Layer
8: Light Emitting Layer
9: Electron Transfer Layer
10: Electron Injection Layer

MODE FOR DISCLOSURE

Hereinafter, the present disclosure will be described in more detail.

One embodiment of the present disclosure provides a compound of Chemical Formula 1.

In the present specification,

means a site bonding to other substituents or binding sites.

In the present specification, a term such as 'include' or 'have' means the presence of features or constituents described in the specification, and is not to exclude in advance the possibility of adding one or more other features or constituents.

In the present specification, a description of a part such as a region or a layer being provided above or on another part includes not only a case of the part being directly above the another part but a case of still another region, layer or the like being provided therebetween.

Examples of the substituents are described below, however, the substituents are not limited thereto.

In the present specification, an aryl group means a totally or partially unsaturated substituted or unsubstituted monocyclic ring or polycyclic ring. According to one embodiment, the aryl group has 6 to 25 carbon atoms. According to one embodiment, the aryl group has 6 to 20 carbon atoms. According to one embodiment, the aryl group has 6 to 18 carbon atoms. According to one embodiment, the aryl group has 6 to 13 carbon atoms. According to one embodiment, the aryl group has 6 to 12 carbon atoms. According to one embodiment, the aryl group has 6 carbon atoms.

The aryl group may be a monocyclic aryl group or a polycyclic aryl group. Examples of the monocyclic aryl group may include a phenyl group, a biphenyl group, a terphenyl group and the like, but are not limited thereto. Examples of the polycyclic aryl group may include a naphthyl group, an anthracenyl group, a phenanthrenyl group, a perylenyl group, a fluoranthenyl group, a triphenylenyl group, a pyrenyl group, a tetracenyl group, a chrysenyl group, a fluorenyl group, an indenyl group, an acenaphthyl group, a benzofluorenyl group and the like, but are not limited thereto.

In the present specification, the fluorenyl group may be substituted, and two substituents may bond to each other to form a spiro structure.

Examples of the substituted fluorenyl group may include

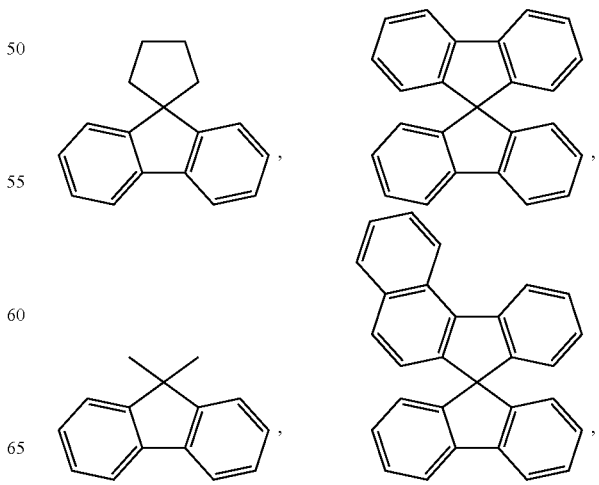

-continued

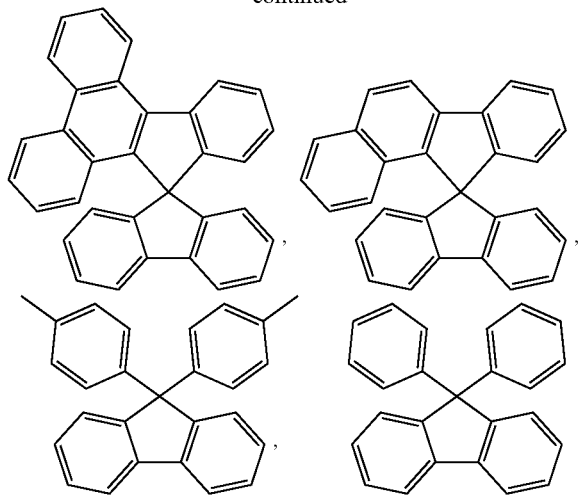

and the like, but are not limited thereto.

In the present specification, the heteroaryl group is a cyclic group including one or more of N, O and S as a heteroatom, and although not limited thereto, the number of carbon atoms is preferably from 2 to 40. According to one embodiment, the number of carbon atoms of the heteroaryl group is from 2 to 30. According to another embodiment, the number of carbon atoms of the heteroaryl group is from 2 to 20. Examples of the heteroaryl group may include a thiophenyl group, a furanyl group, a pyrrolyl group, an imidazolyl group, a triazolyl group, an oxazolyl group, an oxadiazolyl group, a triazolyl group, a pyridinyl group, a bipyridinyl group, a pyrimidinyl group, a diazinyl group, a triazinyl group, a triazolyl group, an acridinyl group, a carbolinyl group, an acenaphthoquinoxalinyl group, an indenoquinazolinyl group, an indenoisoquinolinyl group, an indenoquinolinyl group, a pyridoindolyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a dibenzofuranyl group, a phenanthrolinyl group, a triazolyl group, an isoxazolyl group, an oxadiazolyl group, a thiadiazolyl group, a phenoxazinyl group, a phenothiazinyl group and the like, but are not limited thereto.

In one embodiment of the present specification, X1 is O, and X2 is O or SiRcRd.

In one embodiment of the present specification, X1 is SiRaRb, and X2 is O or SiRcRd.

In one embodiment of the present specification, X1 is O, and X2 is O.

In one embodiment of the present specification, X1 is SiRaRb, and X2 is O.

In one embodiment of the present specification, X1 is O, and X2 is SiRcRd.

In one embodiment of the present specification, X1 is SiRaRb, and X2 is SiRcRd.

In one embodiment of the present specification, Ra to Rd are the same as or different from each other, and each independently hydrogen; deuterium; an alkyl group having 1 to 10 carbon atoms; or an aryl group having 6 to 20 carbon atoms.

In one embodiment of the present specification, Ra to Rd are the same as or different from each other, and each independently hydrogen; deuterium; an alkyl group having 1 to 6 carbon atoms; or an aryl group having 6 to 13 carbon atoms.

In one embodiment of the present specification, Ra to Rd are the same as or different from each other, and each independently hydrogen; deuterium; an alkyl group having 1 to 4 carbon atoms; or an aryl group having 6 to 10 carbon atoms.

In one embodiment of the present specification, Ra to Rd are the same as or different from each other, and each independently hydrogen; deuterium; a methyl group; or a phenyl group.

In one embodiment of the present specification, any one of A1 to A4 is a linking group bonding to triazine, any one is Ar1, the rest are hydrogen, and A'1 to A'4 are hydrogen.

In one embodiment of the present specification, any one of A1 to A4 is a linking group bonding to triazine, the rest are hydrogen, any one of A'1 to A'4 is Ar1, and the rest are hydrogen.

In one embodiment of the present specification, any one of B1 to B4 is a linking group bonding to triazine, any one is Ar2, the rest are hydrogen, and B'1 to B'4 are hydrogen.

In one embodiment of the present specification, any one of B1 to B4 is a linking group bonding to triazine, the rest are hydrogen, any one of B'1 to B'4 is Ar2, and the rest are hydrogen.

In one embodiment of the present specification, an aromatic 6-membered ring included in the compound of Chemical Formula 1 is 10 or less. When Chemical Formula 1 includes 11 or more aromatic 6-membered rings, a sublimation temperature of the compound increases due to an increase in the molecular weight, which may cause a problem in device thermal stability. In the compound of Chemical Formula 1, it may be interpreted that triazine includes one aromatic 6-membered ring, and benzofuran includes two aromatic 6-membered rings (benzene rings).

In one embodiment of the present specification, Ar1 and Ar2 are the same as or different from each other, and each independently an aryl group; or a heteroaryl group unsubstituted or substituted with an aryl group and comprising one or more of N, O and S.

In one embodiment of the present specification, Ar1 and Ar2 are the same as or different from each other, and each independently an aryl group; or a heteroaryl group unsubstituted or substituted with an aryl group and comprising a pentagonal ring.

In one embodiment of the present specification, Ar1 and Ar2 are the same as or different from each other, and each independently an aryl group having 6 to 25 carbon atoms; or a heteroaryl group having 2 to 25 carbon atoms unsubstituted or substituted with an aryl group.

In one embodiment of the present specification, Ar1 and Ar2 are the same as or different from each other, and each independently an aryl group; or a heteroaryl group unsubstituted or substituted with an aryl group having 6 to 18 carbon atoms.

In one embodiment of the present specification, Ar1 and Ar2 are the same as or different from each other, and each independently an aryl group; or a heteroaryl group unsubstituted or substituted with an aryl group having 6 to 12 carbon atoms.

In one embodiment of the present specification, Ar1 and Ar2 are the same as or different from each other, and each independently an aryl group; or a heteroaryl group unsubstituted or substituted with an aryl group and comprising pyrrole, furan, thiophene, imidazole, oxazole or thiazole.

In one embodiment of the present specification, Ar1 and Ar2 are the same as or different from each other, and each independently an aryl group having 6 to 20 carbon atoms; or a heteroaryl group having 2 to 20 carbon atoms unsubstituted or substituted with an aryl group.

In one embodiment of the present specification, Ar1 and Ar2 are the same as or different from each other, and each independently an aryl group having 6 to 20 carbon atoms; or a heteroaryl group having 7 to 20 carbon atoms unsubstituted or substituted with an aryl group.

In one embodiment of the present specification, Ar1 and Ar2 are the same as or different from each other, and each independently an aryl group having 6 to 18 carbon atoms; or a heteroaryl group having 2 to 24 carbon atoms unsubstituted or substituted with an aryl group.

In one embodiment of the present specification, Ar1 and Ar2 are the same as or different from each other, and each independently an aryl group having 6 to 18 carbon atoms; or a heteroaryl group having 2 to 20 carbon atoms unsubstituted or substituted with an aryl group.

In one embodiment of the present specification, Ar1 and Ar2 are the same as or different from each other, and each independently an aryl group having 6 to 18 carbon atoms; or a heteroaryl group having 2 to 16 carbon atoms unsubstituted or substituted with an aryl group.

In one embodiment of the present specification, Ar1 and Ar2 are the same as or different from each other, and each independently an aryl group having 6 to 18 carbon atoms; or a heteroaryl group having 2 to 20 carbon atoms unsubstituted or substituted with an aryl group.

In one embodiment of the present specification, Ar1 and Ar2 are the same as or different from each other, and each independently an aryl group having 6 to 15 carbon atoms; or a heteroaryl group having 2 to 20 carbon atoms unsubstituted or substituted with an aryl group.

In one embodiment of the present specification, Ar1 and Ar2 are the same as or different from each other, and each independently an aryl group having 6 to 13 carbon atoms; or a heteroaryl group having 2 to 16 carbon atoms unsubstituted or substituted with an aryl group.

In one embodiment of the present specification, Ar1 and Ar2 are the same as or different from each other, and each independently an aryl group having 6 to 12 carbon atoms; or a heteroaryl group having 2 to 12 carbon atoms unsubstituted or substituted with an aryl group.

In one embodiment of the present specification, Ar1 and Ar2 are the same as or different from each other, and each independently a phenyl group; a biphenyl group; a terphenyl group; a dibenzothiophenyl group; a dibenzofuranyl group; a carbazolyl group unsubstituted or substituted with a phenyl group; a benzothiazolyl group; a benzimidazolyl group unsubstituted or substituted with a phenyl group; or a benzoxazolyl group.

In one embodiment of the present specification, Chemical Formula 1 is any one of the following Chemical Formula 2 to Chemical Formula 4.

In the following Chemical Formula 2 to Chemical Formula 4, X1, X2, Ar1 and Ar2 have the same definitions as in Chemical Formula 1,

[Chemical Formula 2]

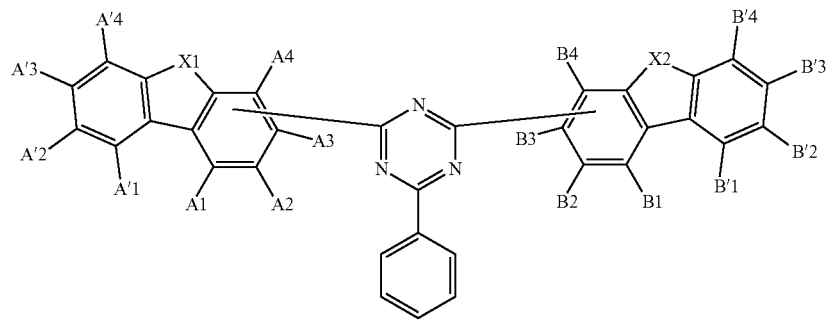

in Chemical Formula 2,
any one of A1 to A4 is a linking group bonding to triazine, and the rest are hydrogen,
any one of A'1 to A'4 is Ar1, and the rest are hydrogen,
any one of B1 to B4 is a linking group bonding to triazine, and the rest are hydrogen, and
any one of B'1 to B'4 is Ar2, and the rest are hydrogen,

[Chemical Formula 3]

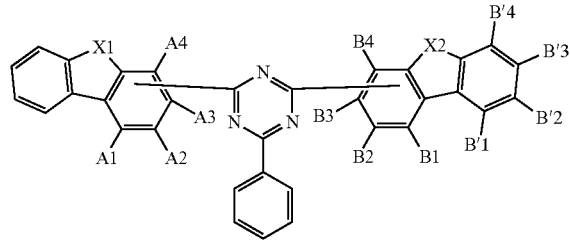

in Chemical Formula 3,
any one of A1 to A4 is a linking group bonding to triazine, any one is Ar1, and the rest are hydrogen,
any one of B1 to B4 is a linking group bonding to triazine, and the rest are hydrogen, and
any one of B'1 to B'4 is Ar2, and the rest are hydrogen,

[Chemical Formula 4]

in Chemical Formula 4,
any one of A1 to A4 is a linking group bonding to triazine, any one is Ar1, and the rest are hydrogen, and
any one of B1 to B4 is a linking group bonding to triazine, any one is Ar2, and the rest are hydrogen.

In one embodiment of Chemical Formula 2, when a linking unit bonding to triazine among A1 to A4 is Ax (x is an integer of 1 to 4), a linking unit bonding to triazine among B1 to B4 is By (y is an integer of 1 to 4), a linking unit bonding to Ar1 among A'1 to A'4 is A'x' (x' is an integer of 1 to 4), and a linking unit bonding to Ar2 among B'1 to B'4 is B'y' (y' is an integer of 1 to 4), x is the same as y, and x' is the same as y'.

In one embodiment of Chemical Formula 3, when a linking unit bonding to triazine among A1 to A4 is Am (m is an integer of 1 to 4), a linking unit bonding to triazine among B1 to B4 is Bn (n is an integer of 1 to 4), a linking unit bonding to Ar1 among A1 to A4 is Am' (m' is an integer of 1 to 4), and a linking unit bonding to Ar2 among B'1 to B'4 is B' n' (n' is an integer of 1 to 4), m is the same as n, and m' is the same as n'.

In one embodiment of Chemical Formula 4, when a linking unit bonding to triazine among A1 to A4 is Ap (p is an integer of 1 to 4), a linking unit bonding to triazine among B1 to B4 is Bq (q is an integer of 1 to 4), a linking unit bonding to Ar1 among A1 to A4 is Ap' (p' is an integer of 1 to 4), and a linking unit bonding to Ar2 among B1 to B4 is Bq' (q' is an integer of 1 to 4), p is the same as q, and p' is the same as q'.

In one embodiment of the present specification, Chemical Formula 1 is any one of the following Chemical Formula 1-A to Chemical Formula 1-C.

[Chemical Formula 1-A]

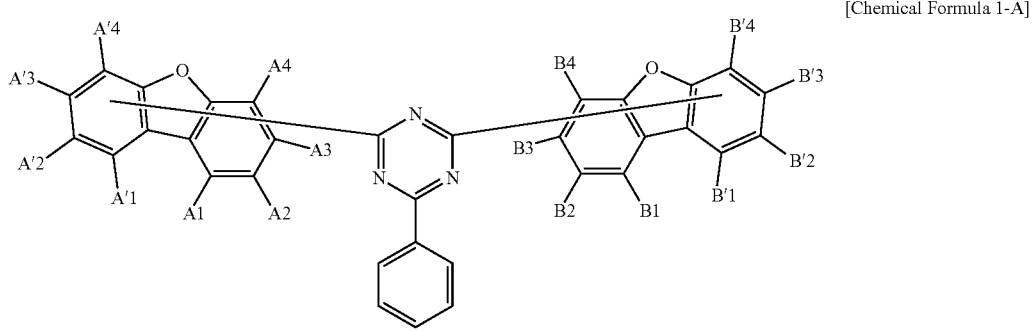

[Chemical Formula 1-B]
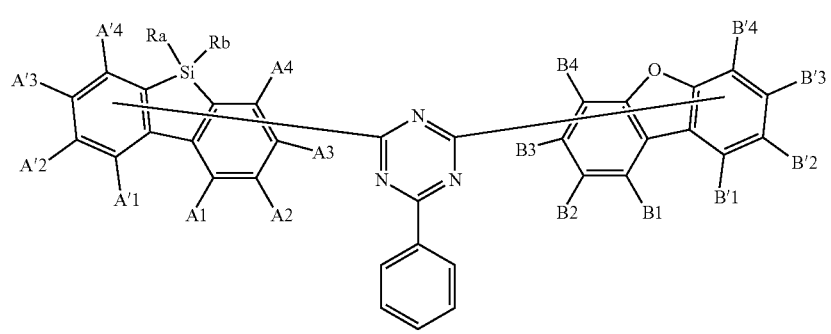
[Chemical Formula 1-C]
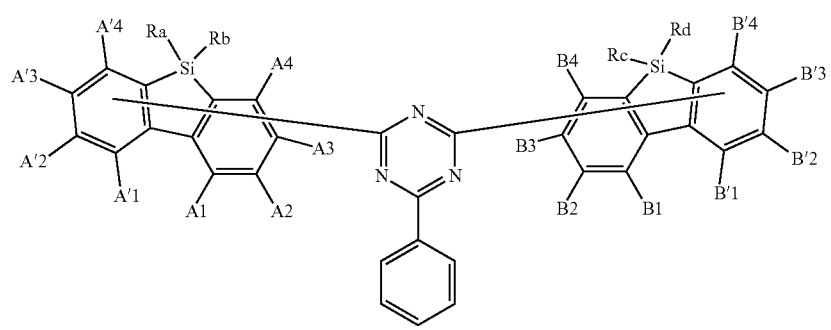
In Chemical Formula 1-A to Chemical Formula 1-C, Ra to Rd, A1 to A4, A'1 to A'4, B1 to B4 and B'1 to B'4 have the same definitions as in Chemical Formula 1.
In one embodiment of the present specification, the compound of Chemical Formula 1 is any one selected from among the following compounds.
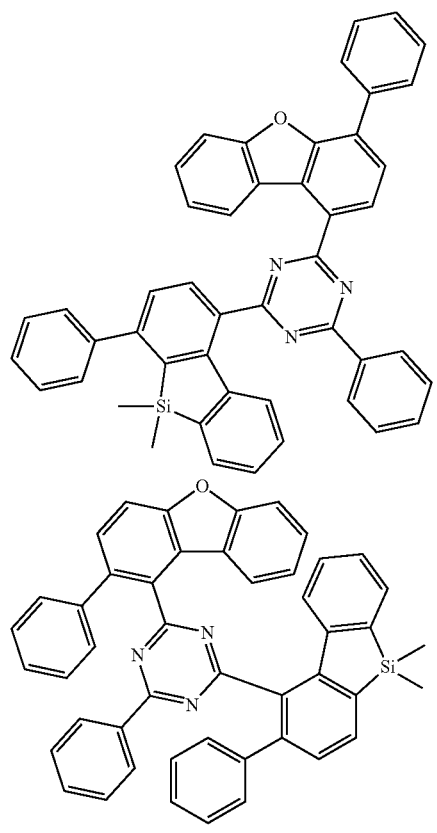
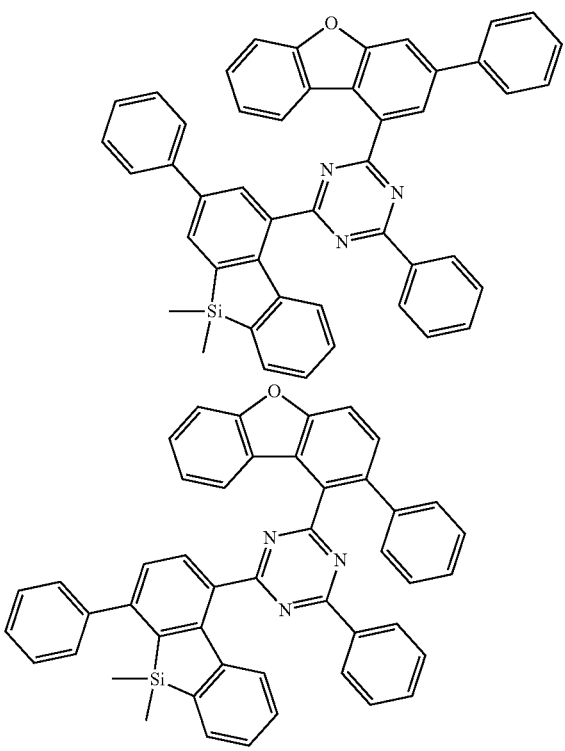

-continued
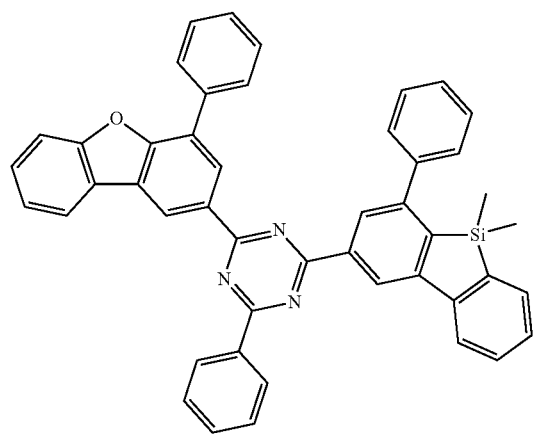
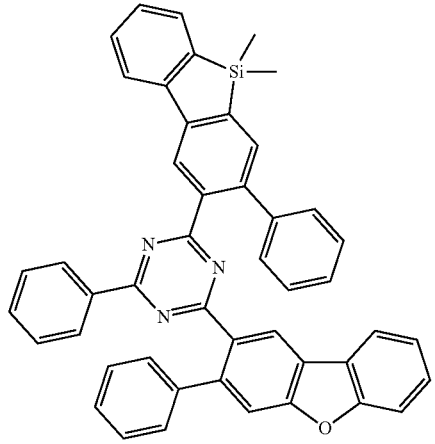
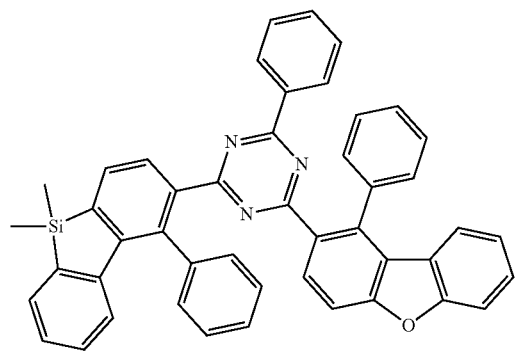
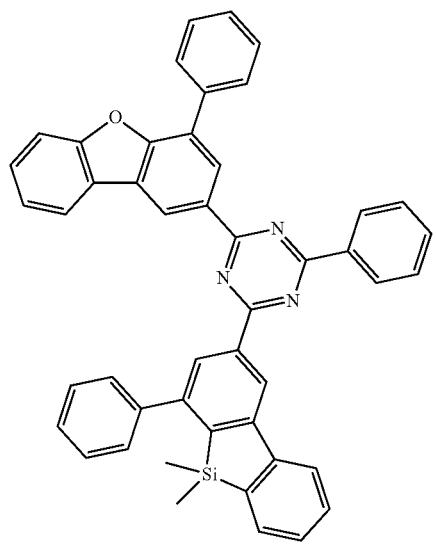
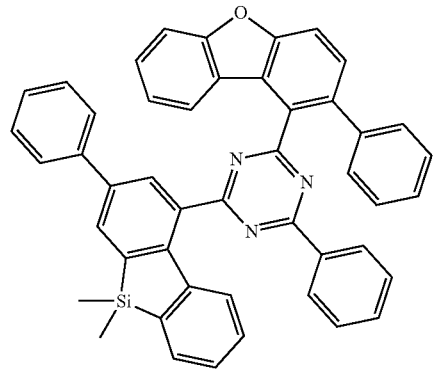
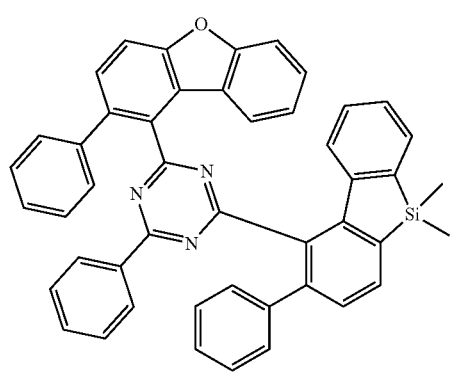

-continued
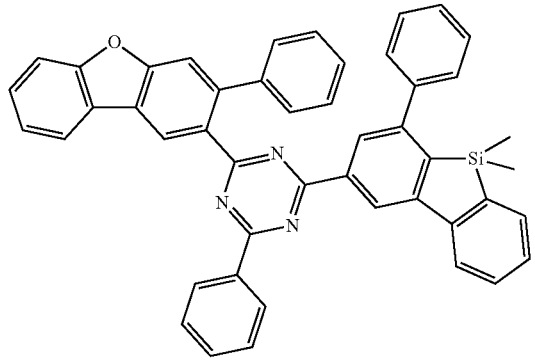
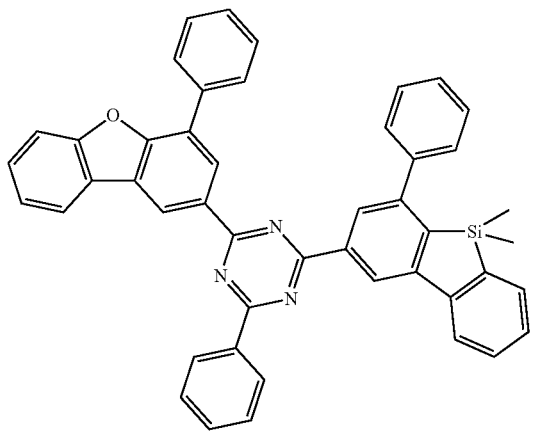
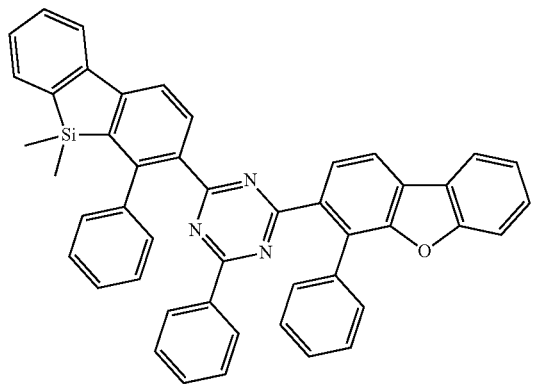
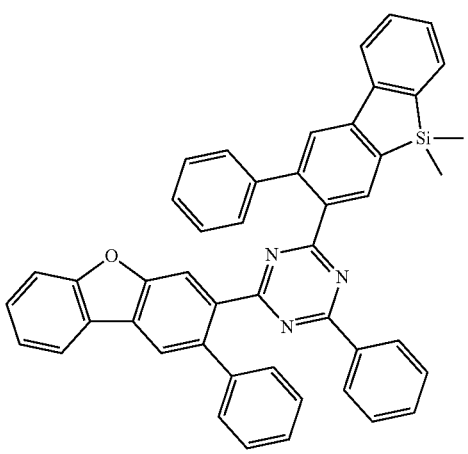
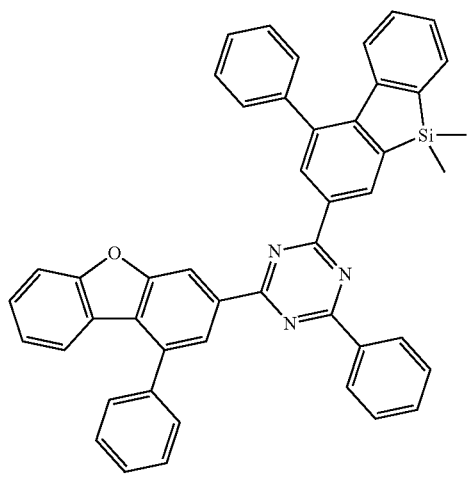
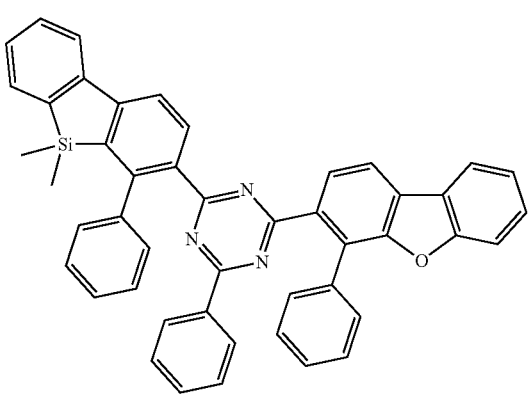

-continued
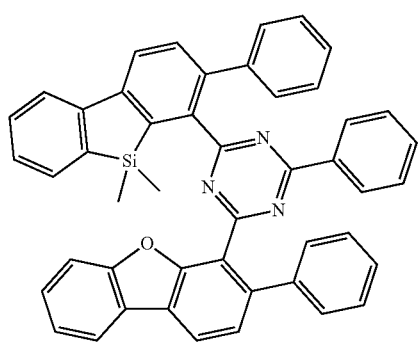
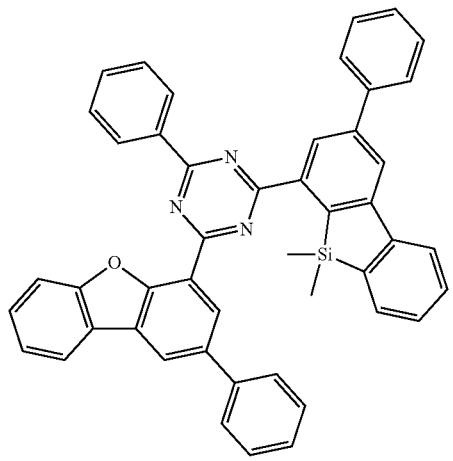
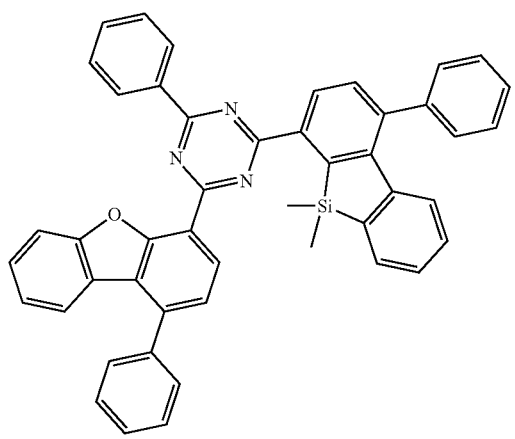
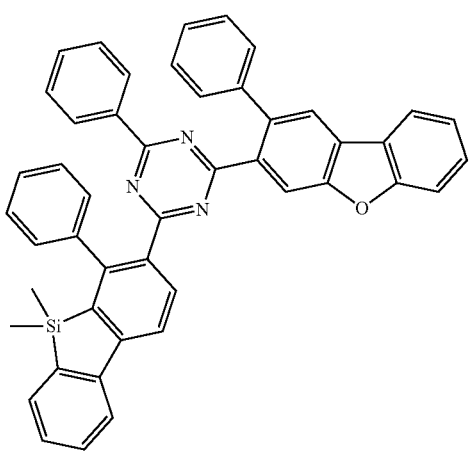
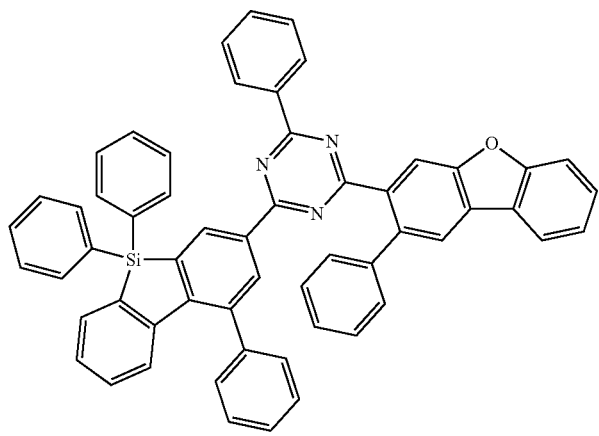
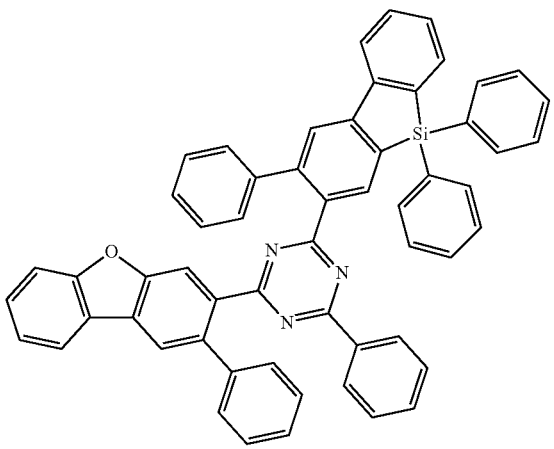

-continued
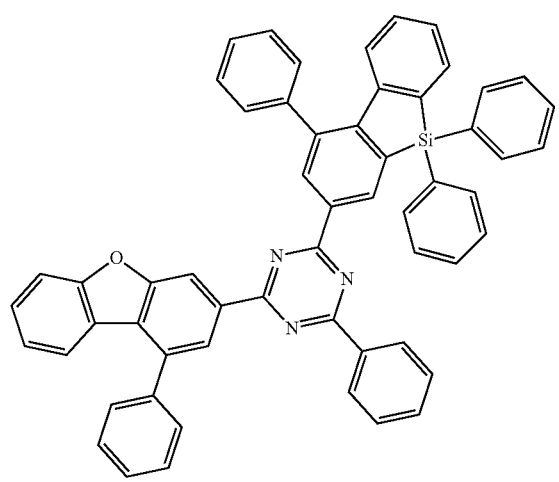
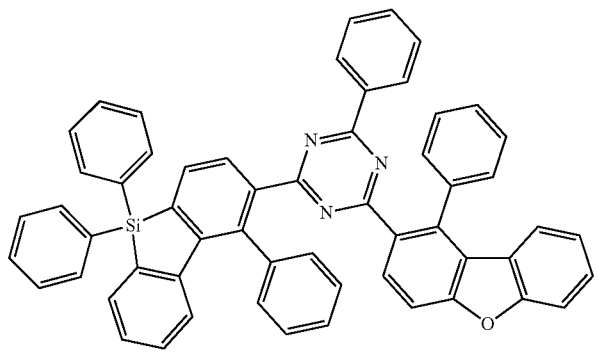
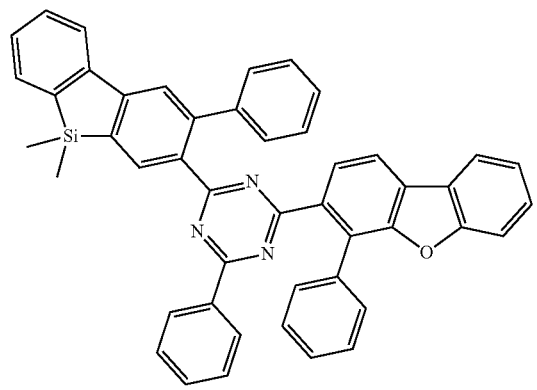
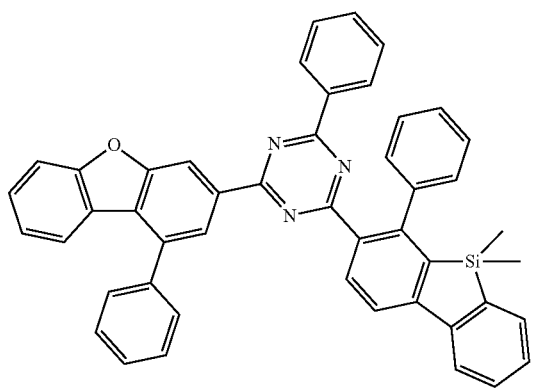
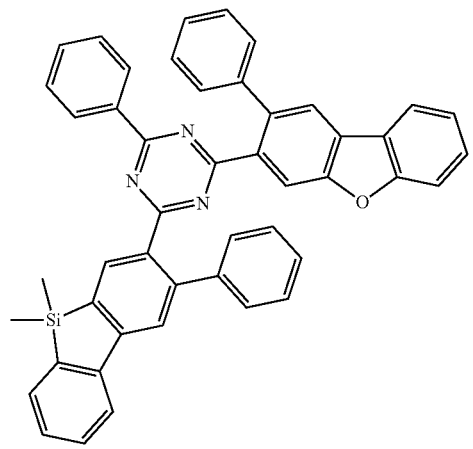
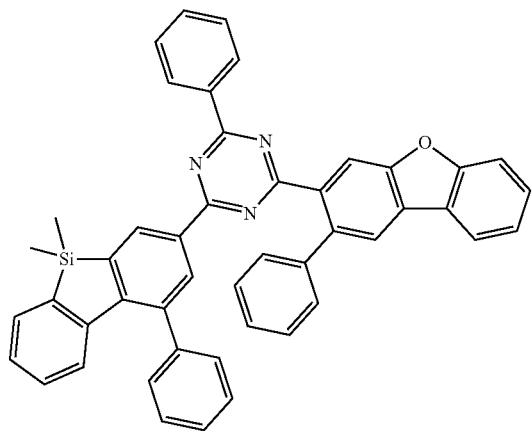

-continued
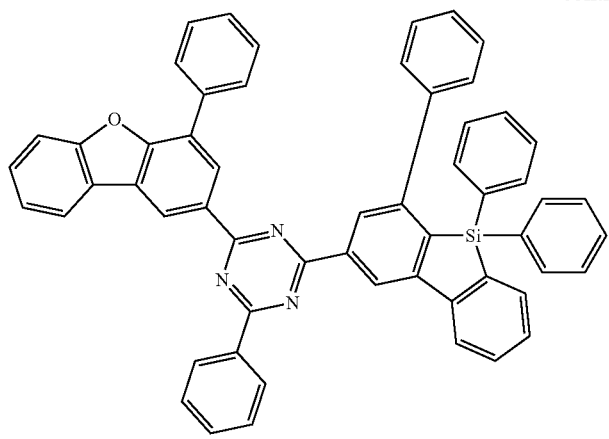
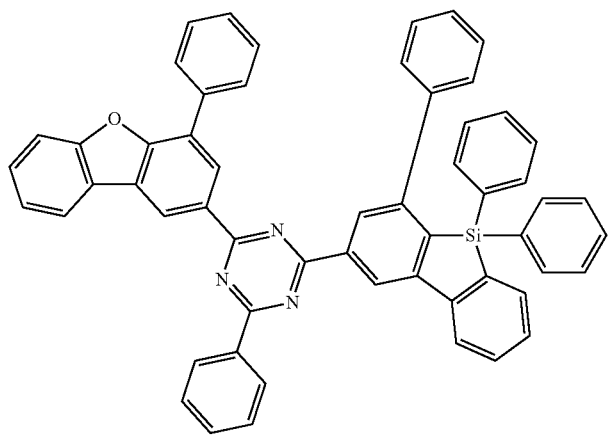
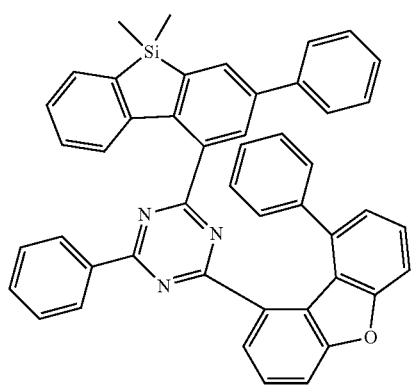
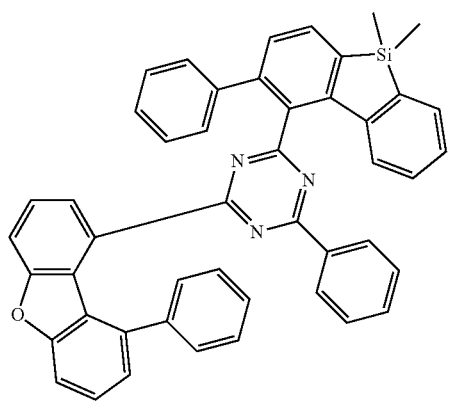

-continued
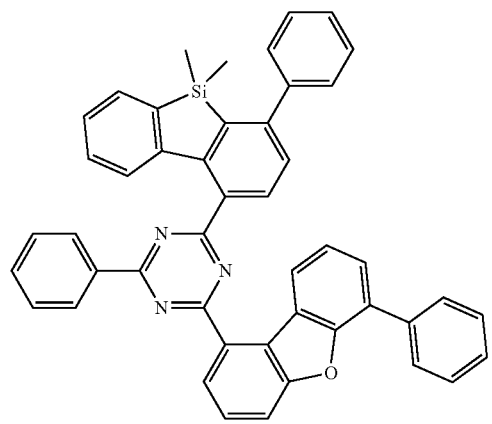
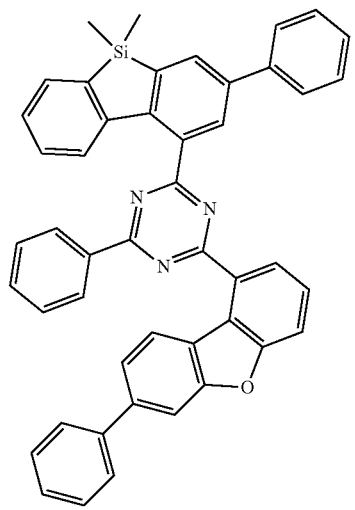
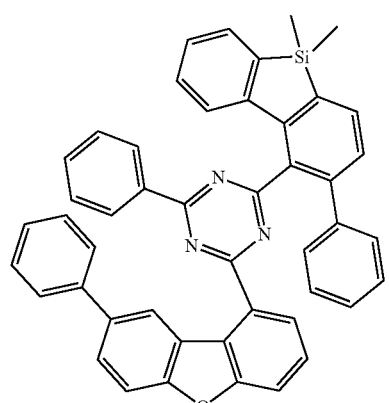
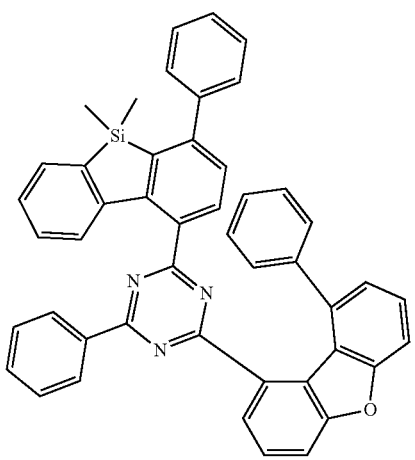
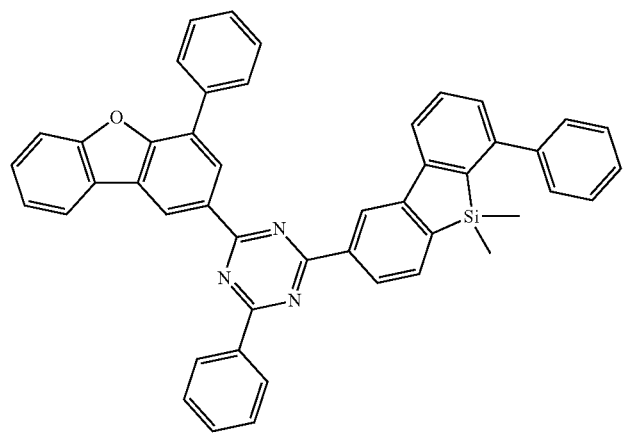
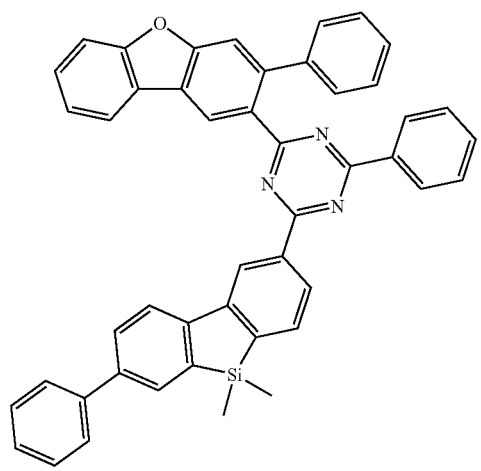

-continued
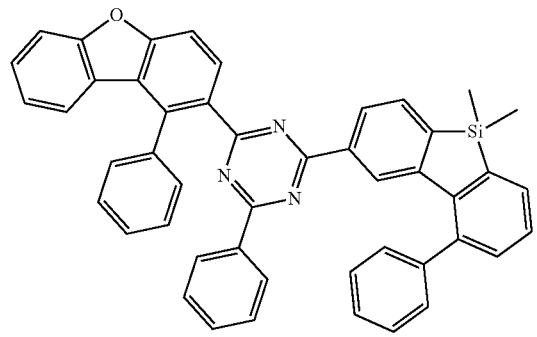
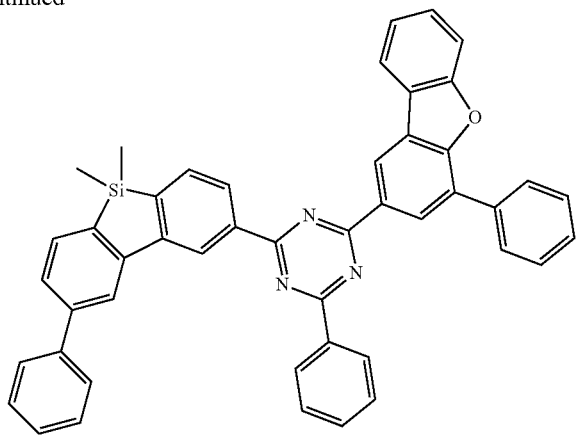
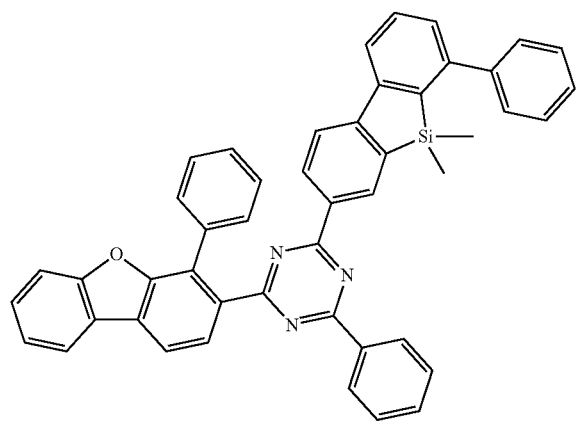
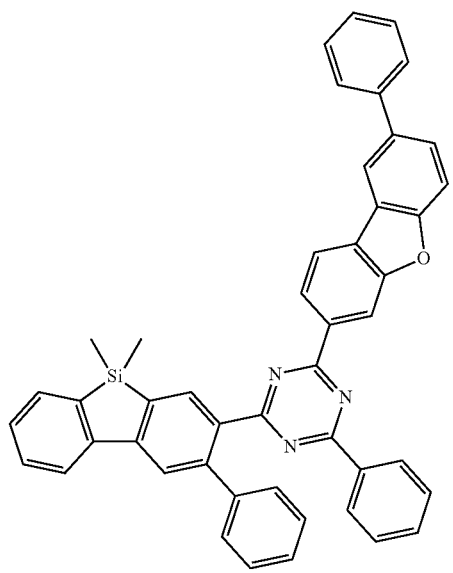
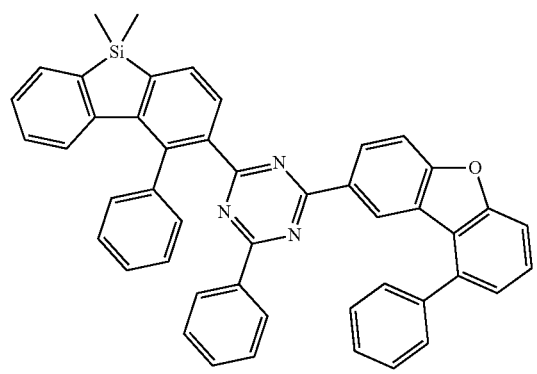
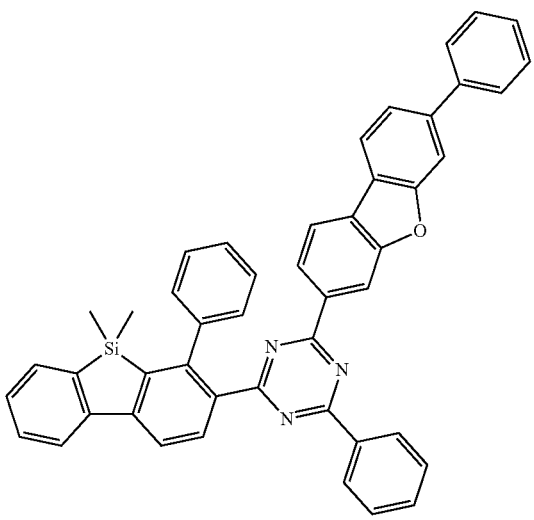

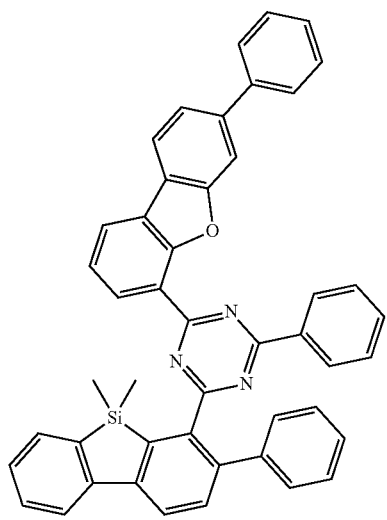
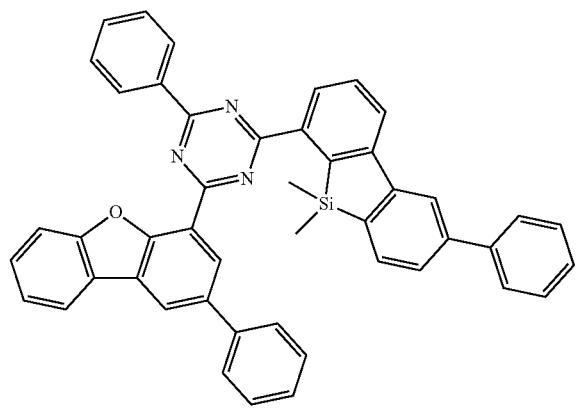
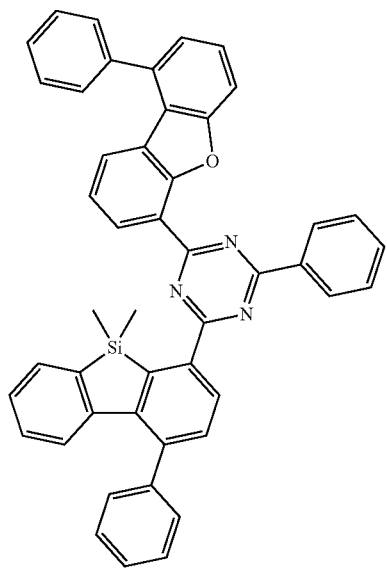
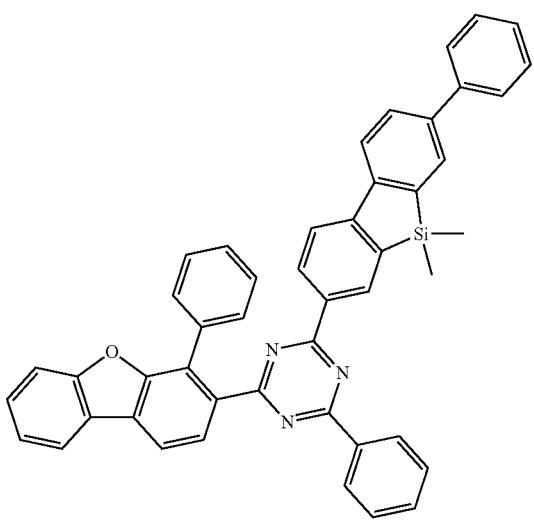
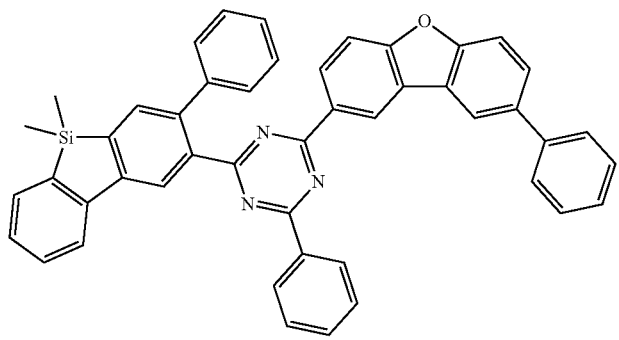

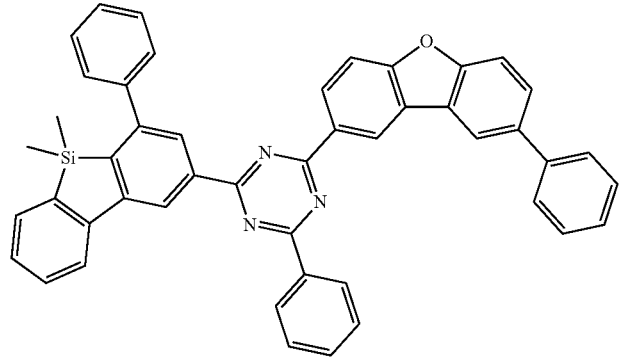
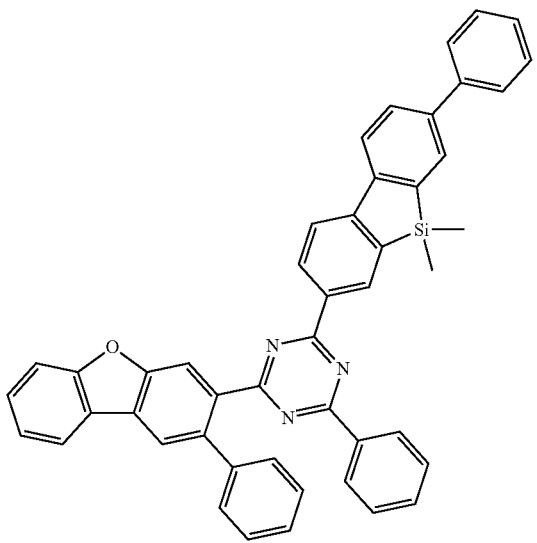
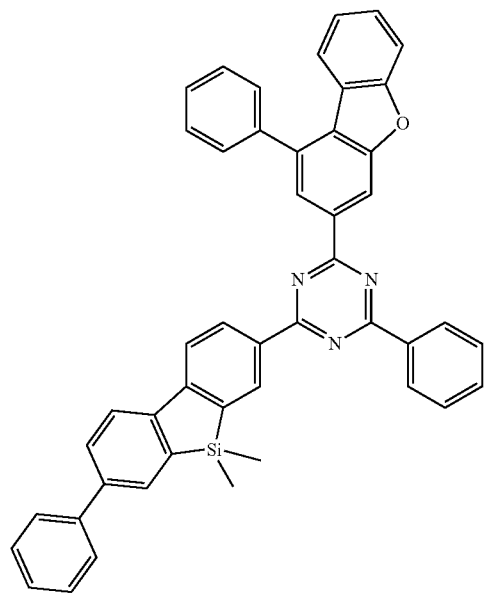
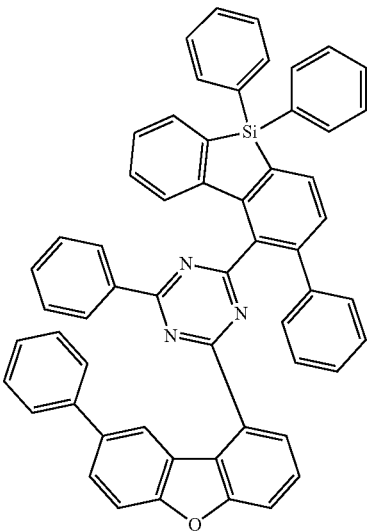

-continued
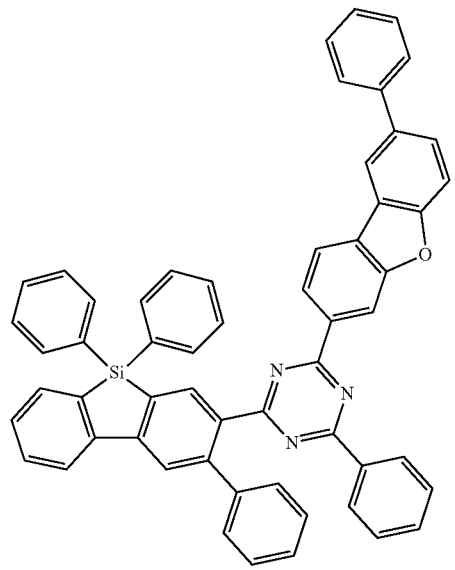
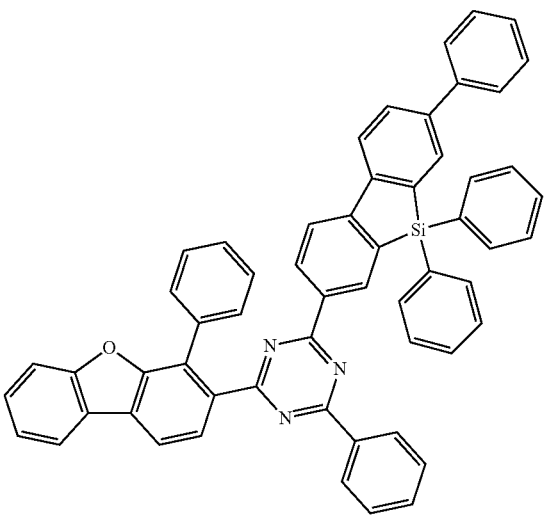
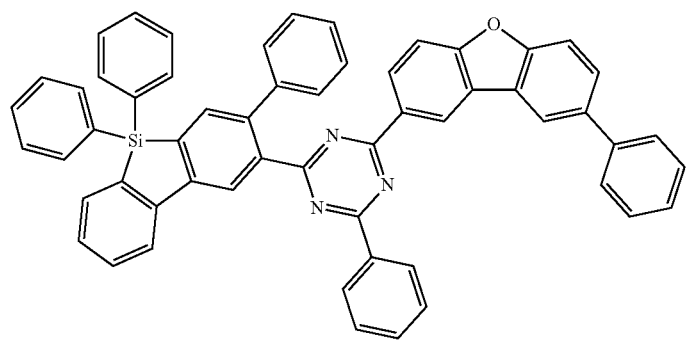
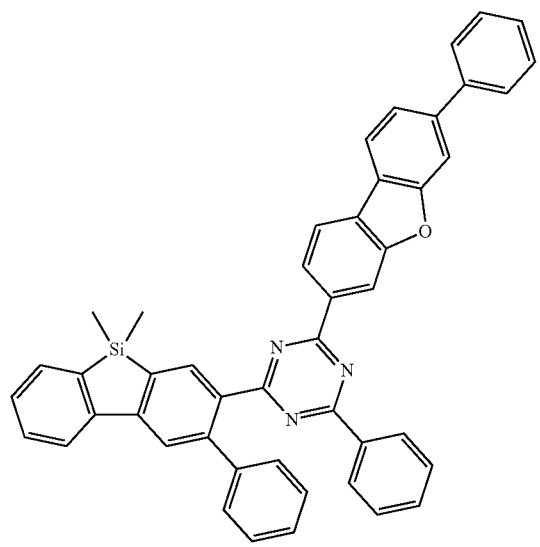

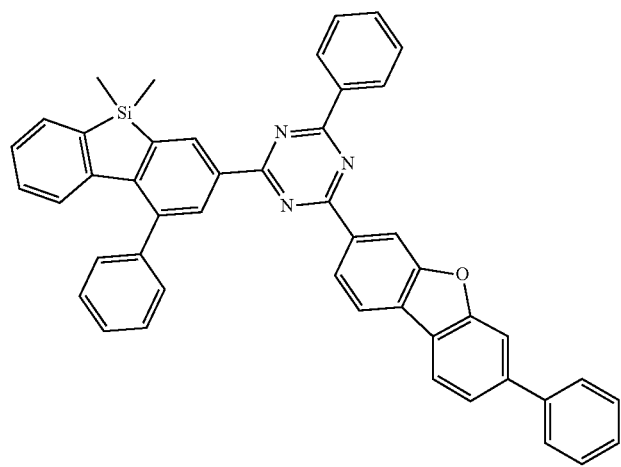
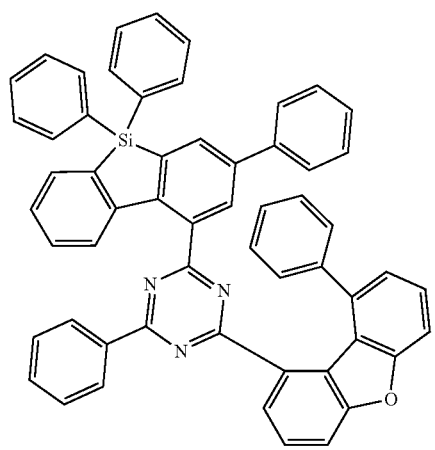
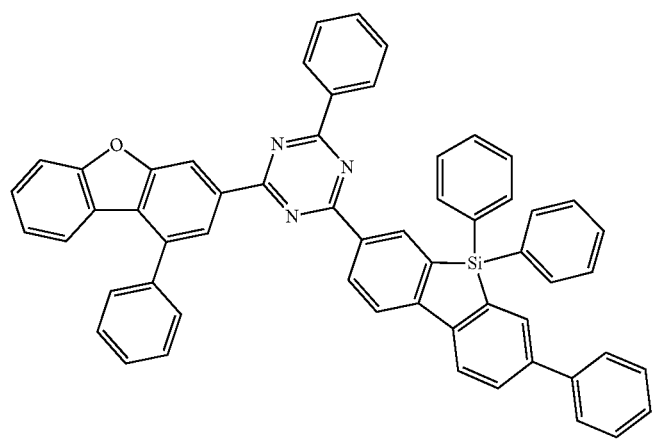
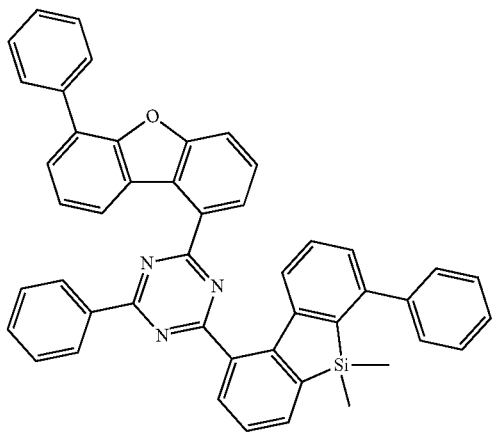
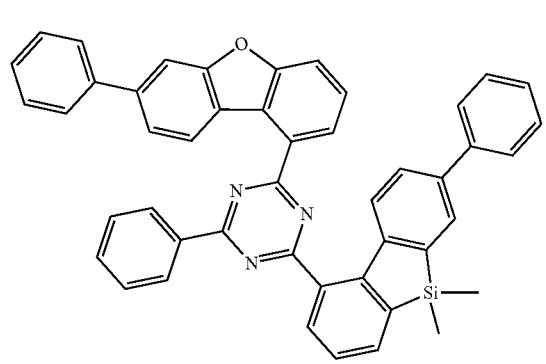
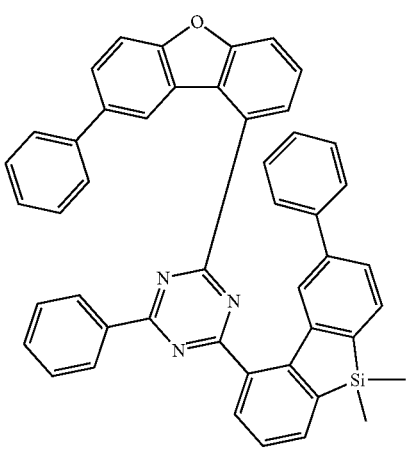

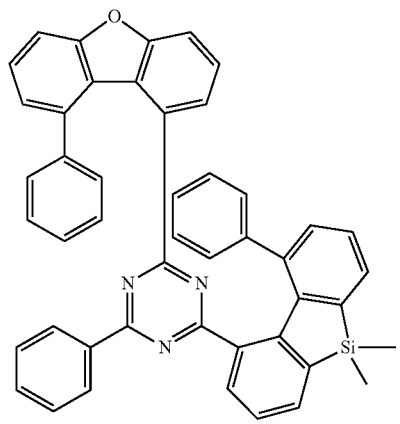
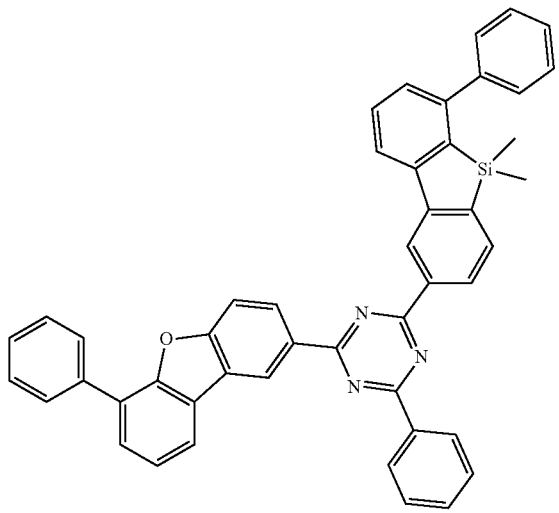
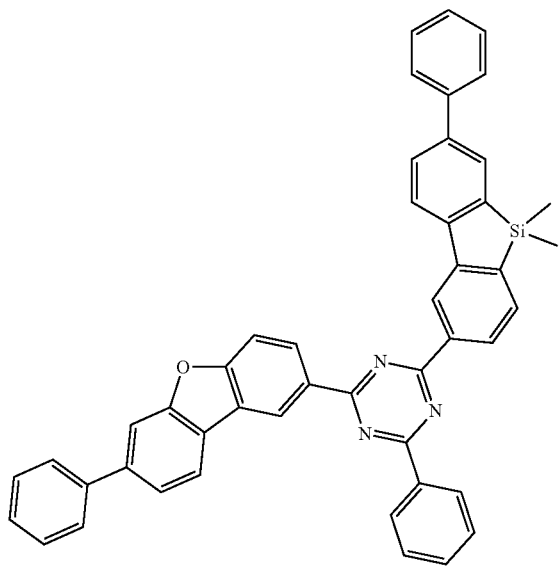
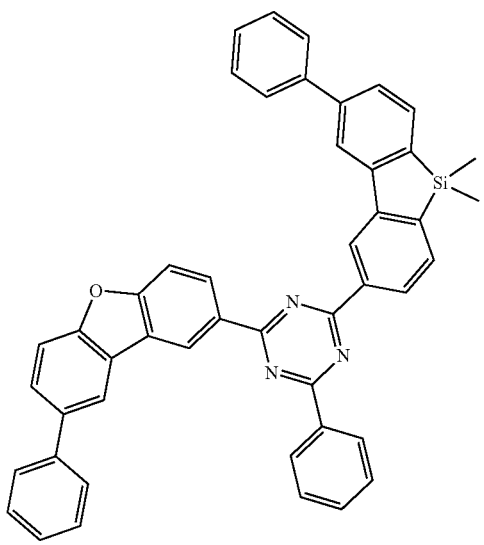
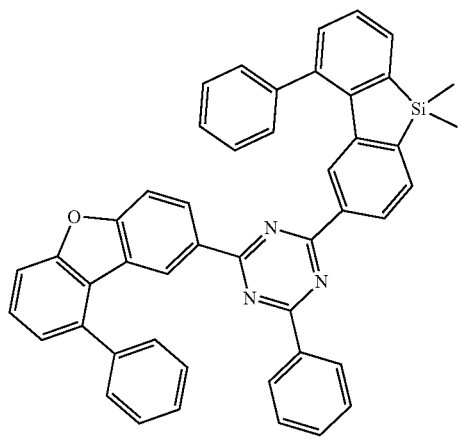
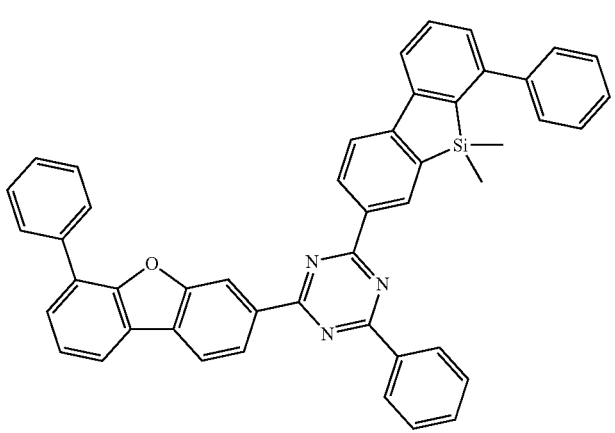

-continued
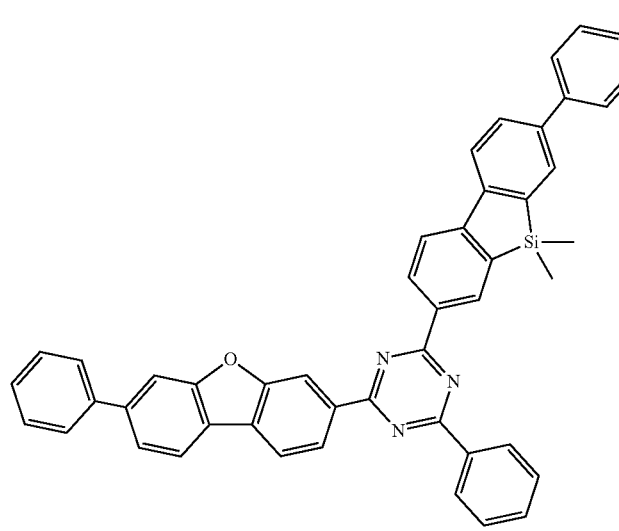
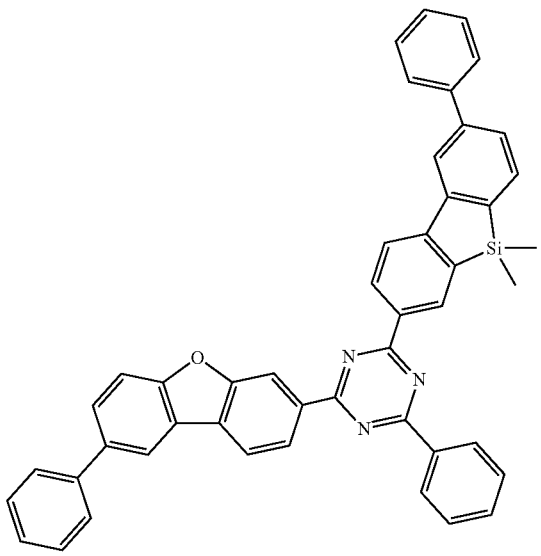
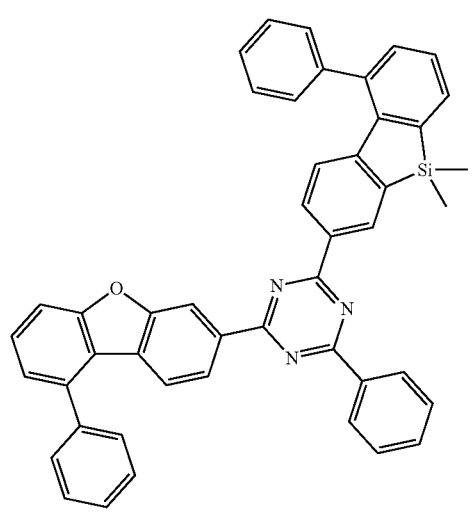
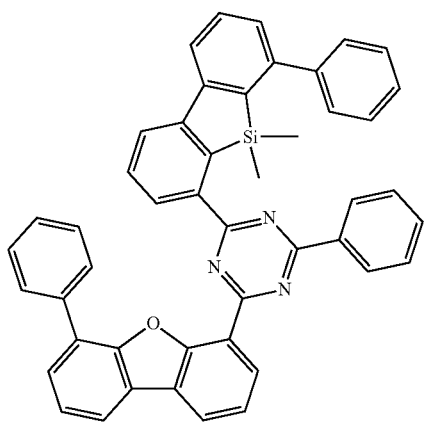
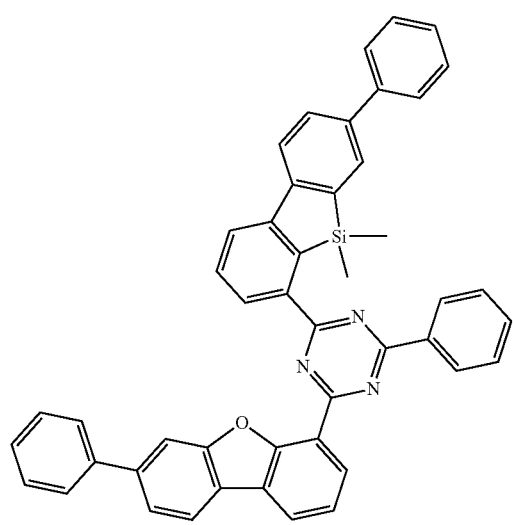
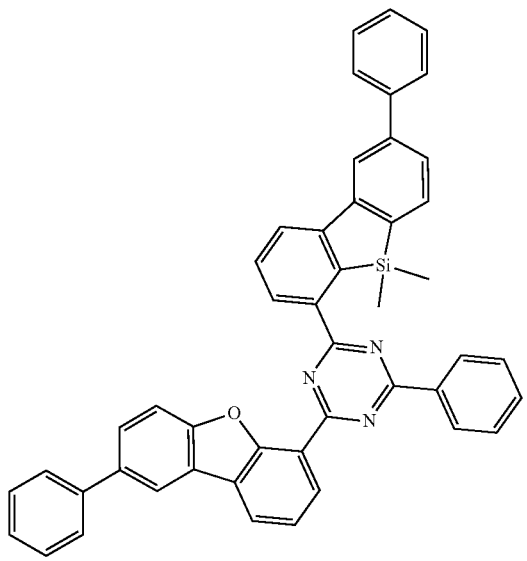

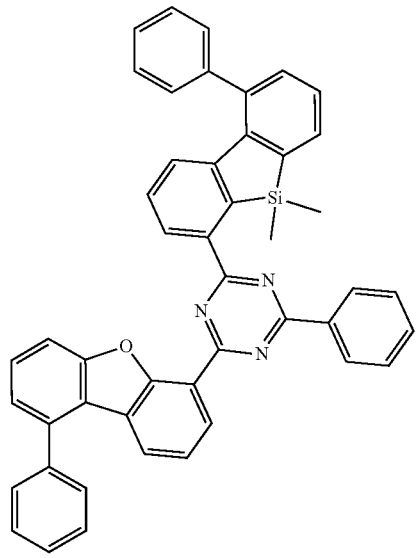
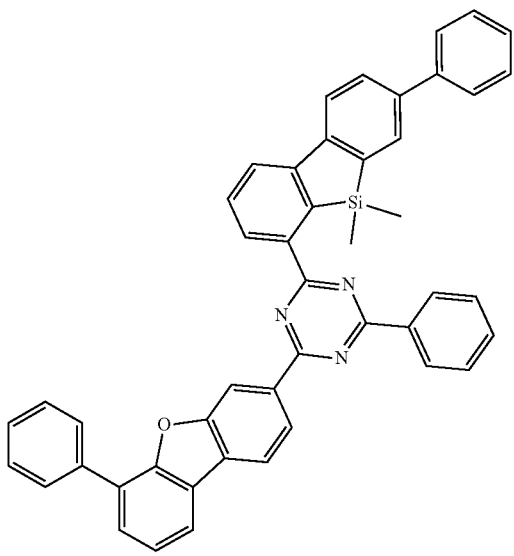
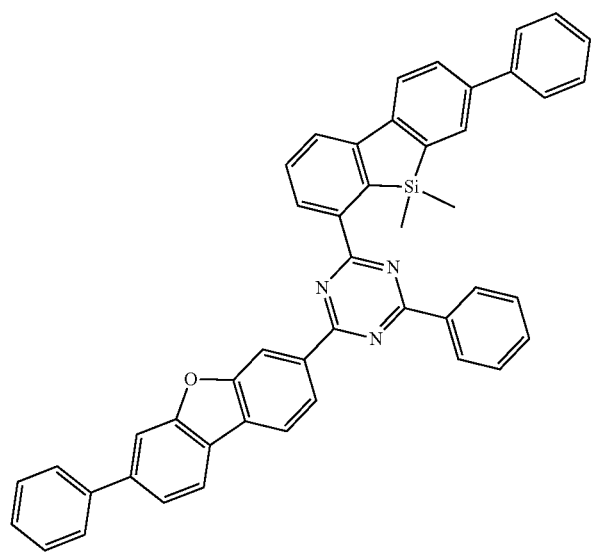
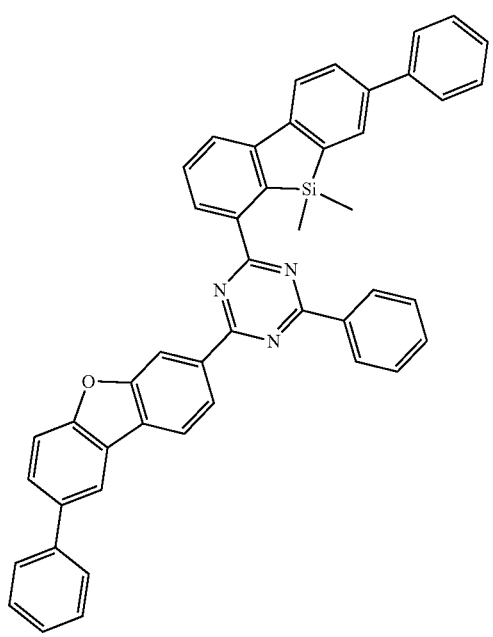

-continued
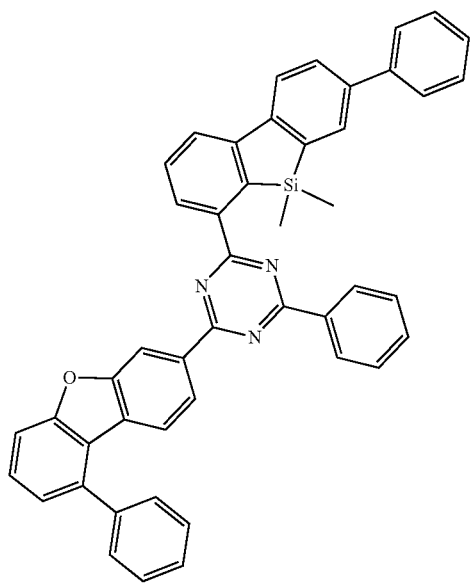
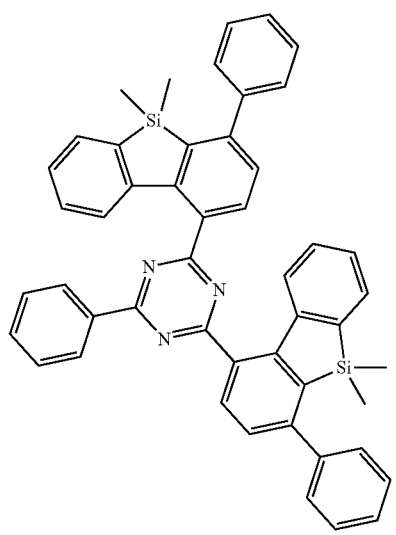
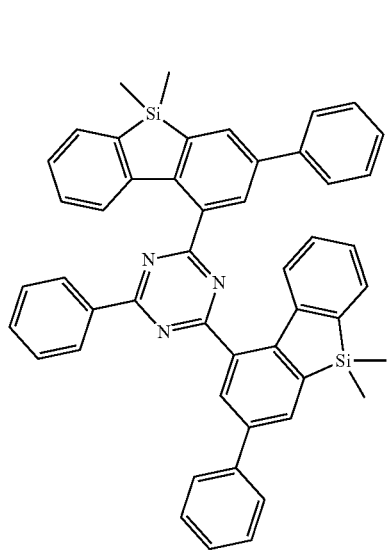
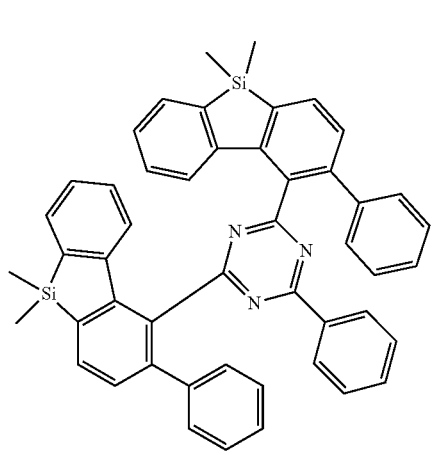
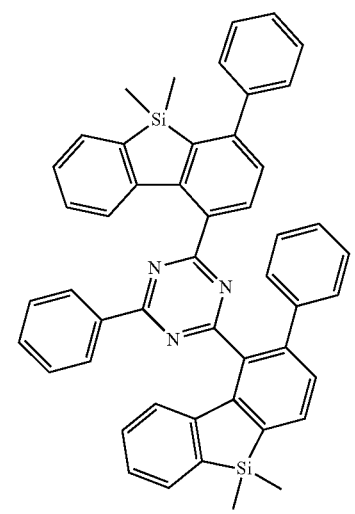
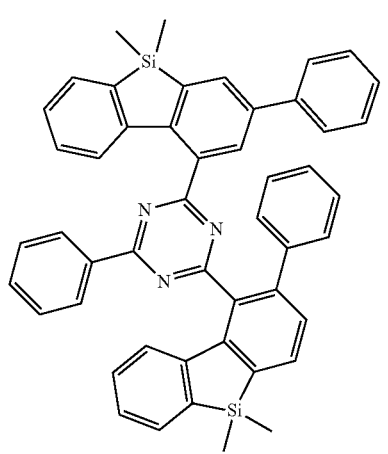
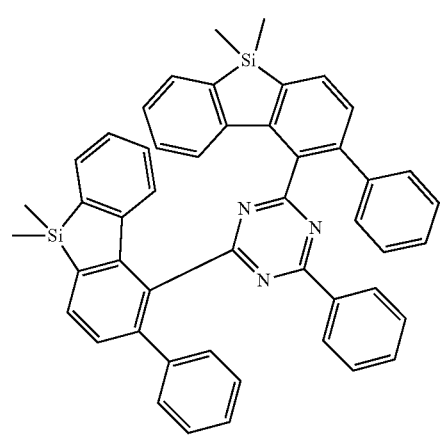

-continued
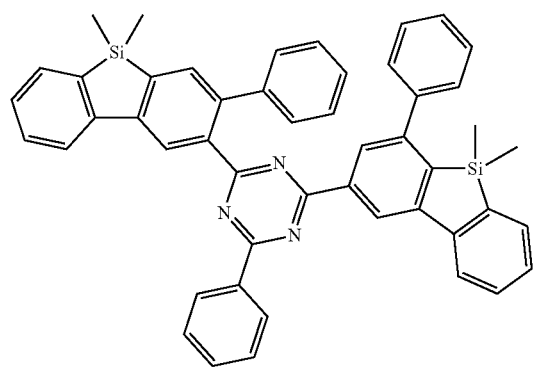
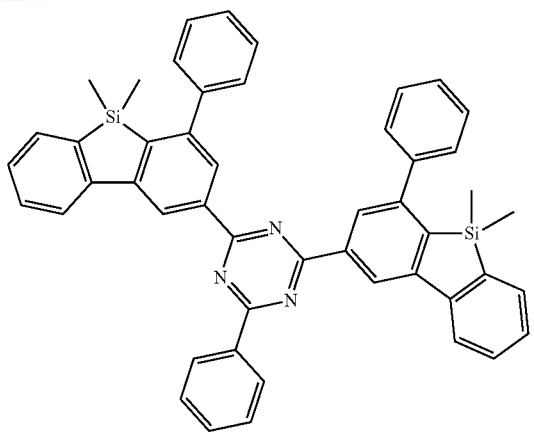
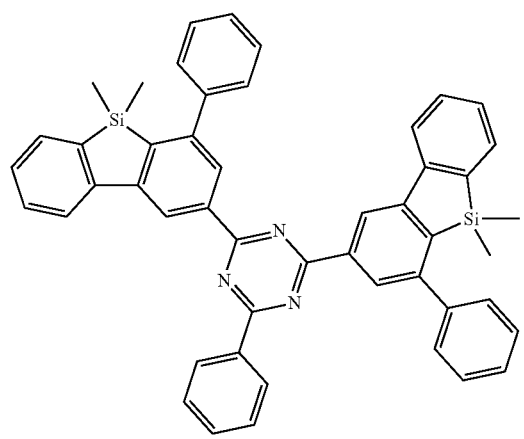
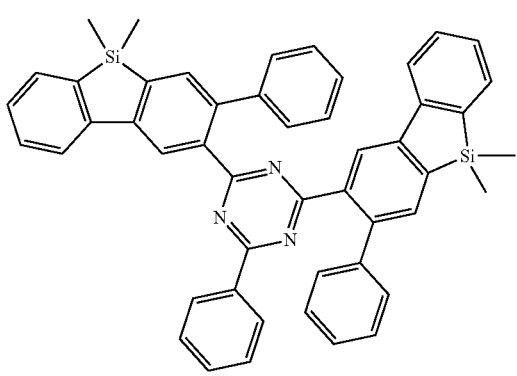
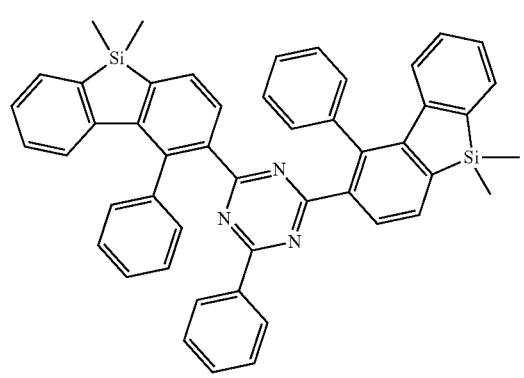
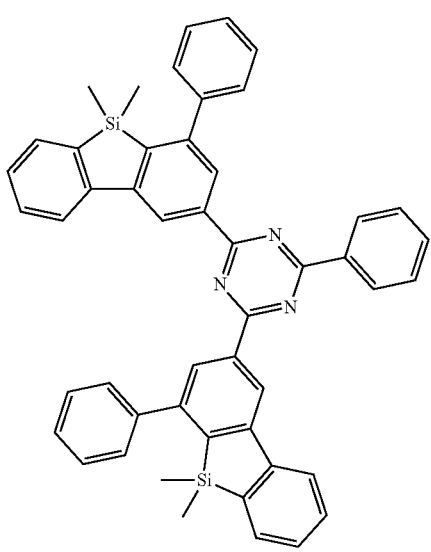

-continued
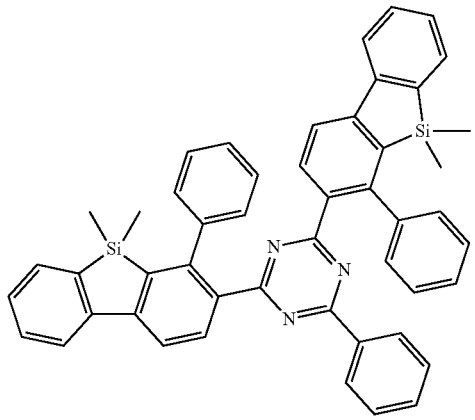
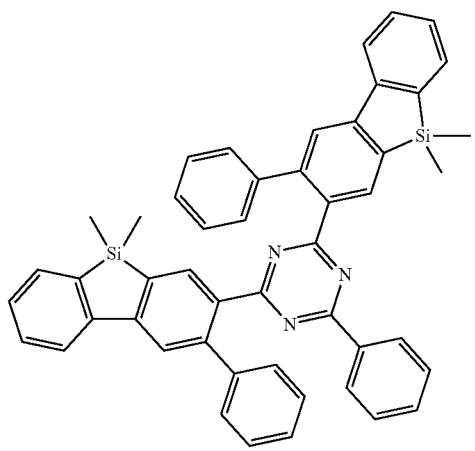
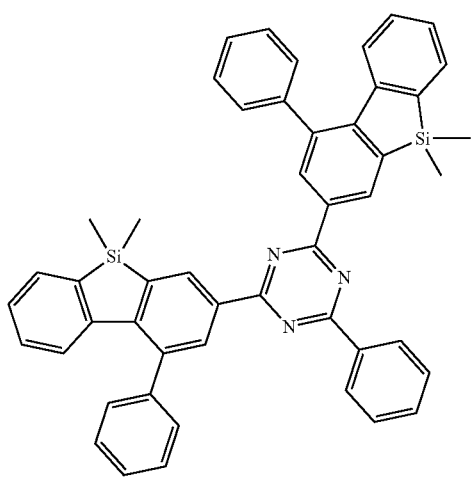
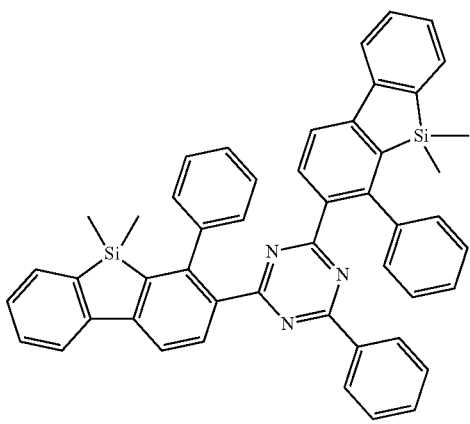
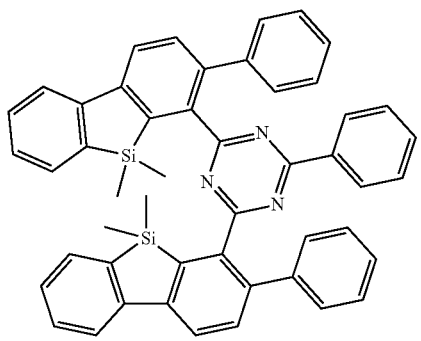
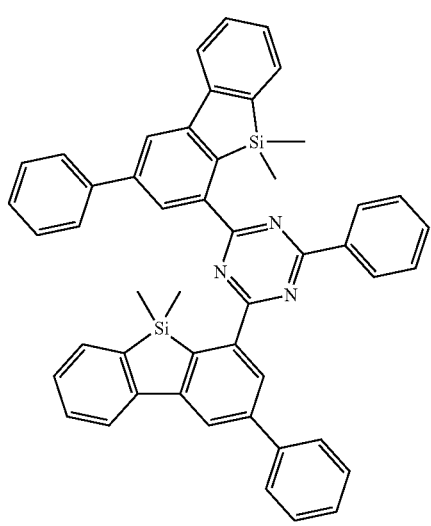

-continued
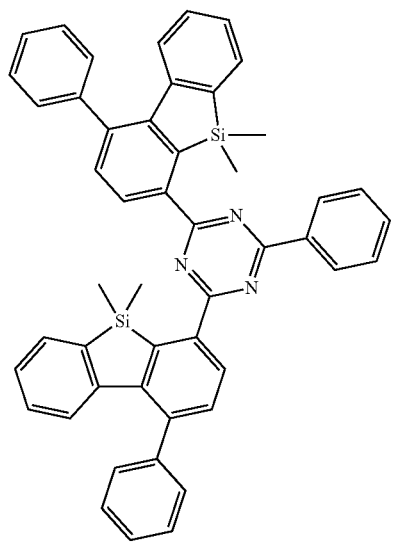
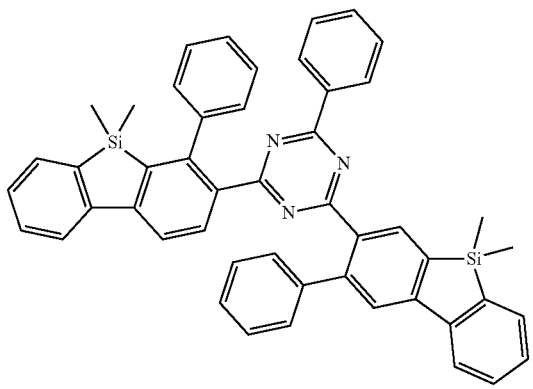
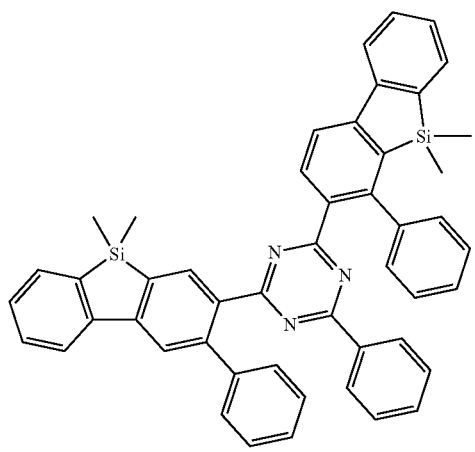
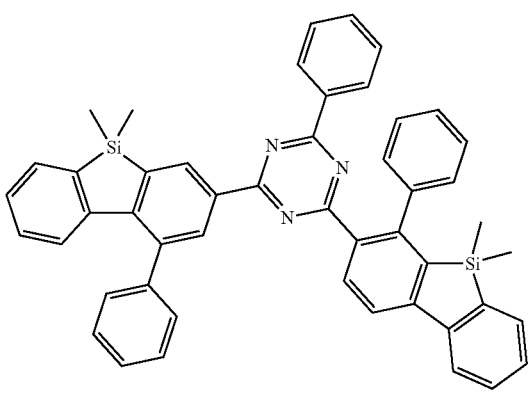
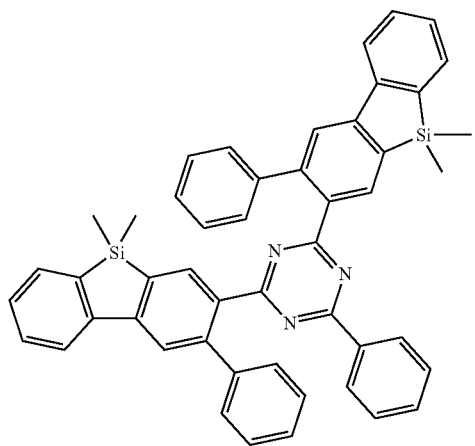
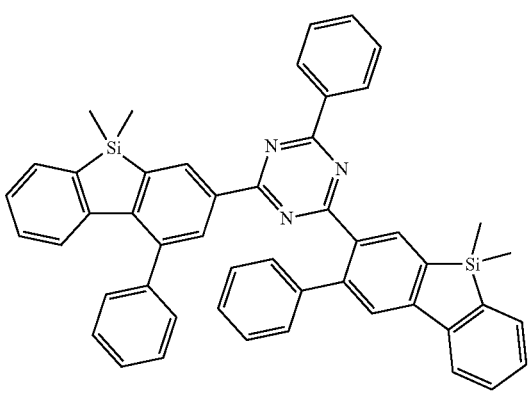

-continued
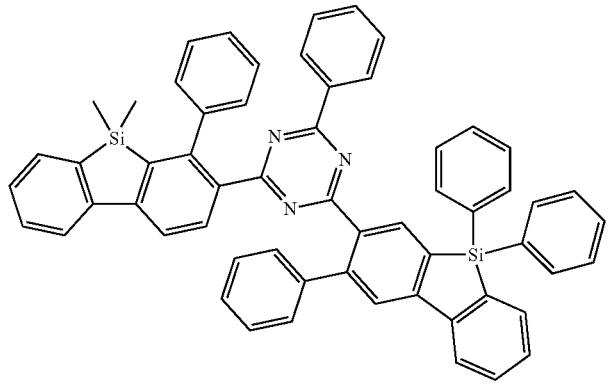
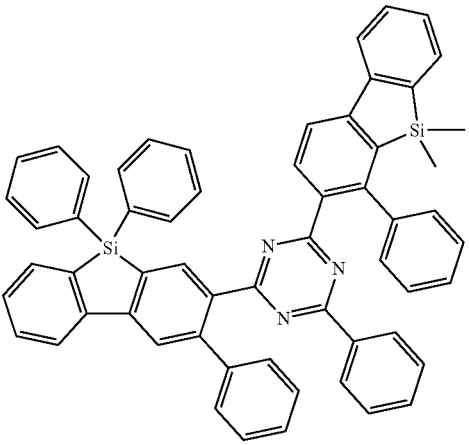
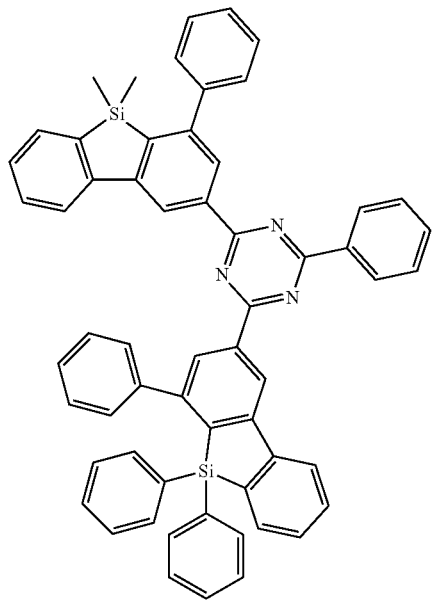
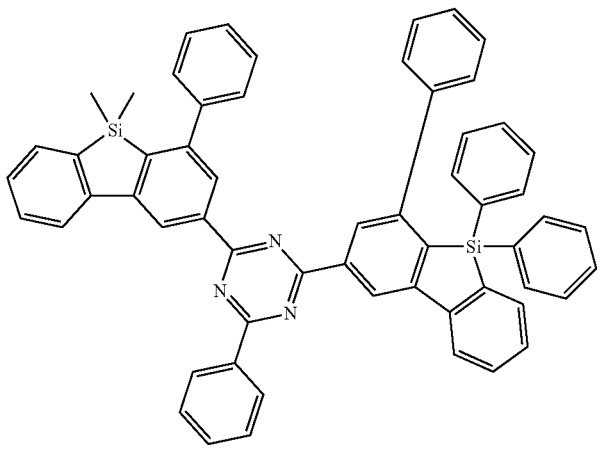
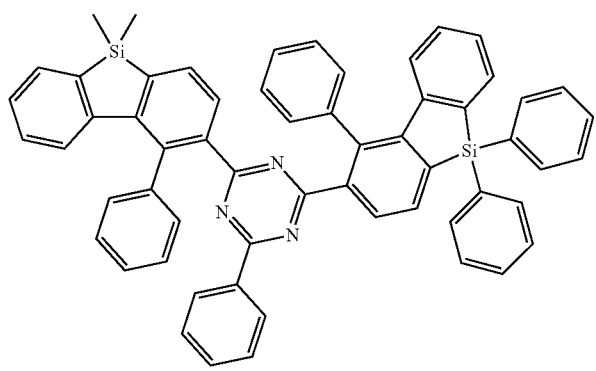
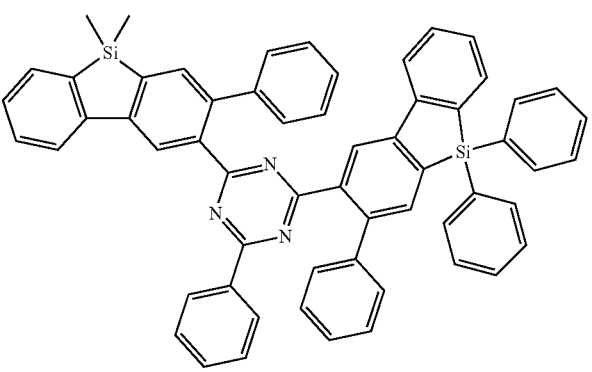

-continued
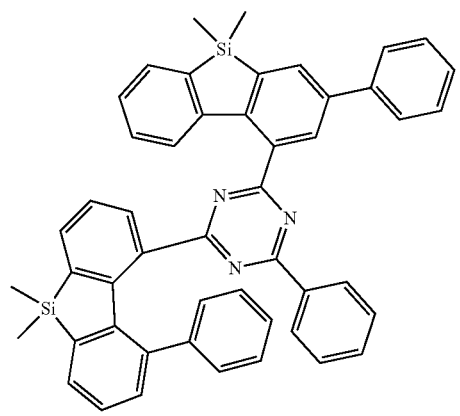
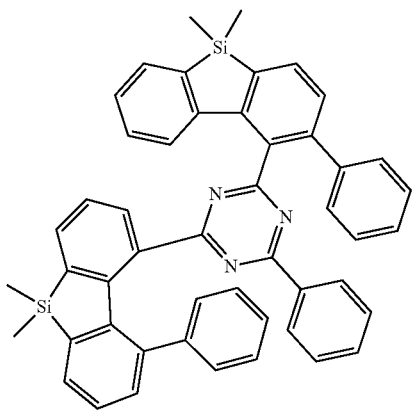
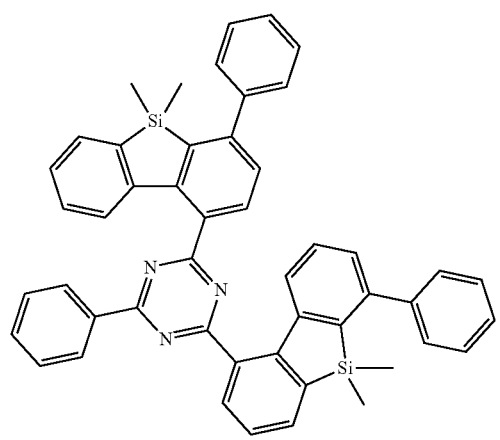
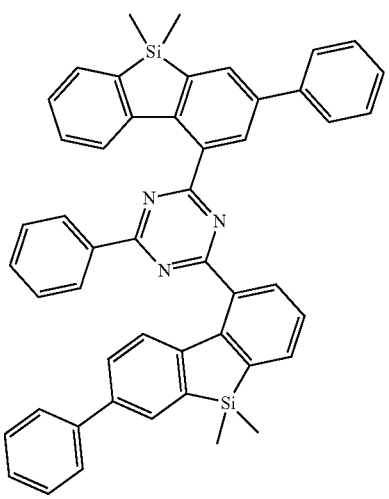
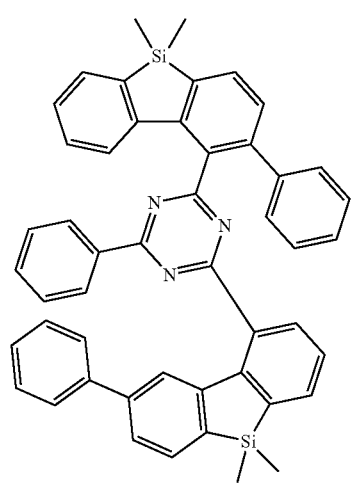
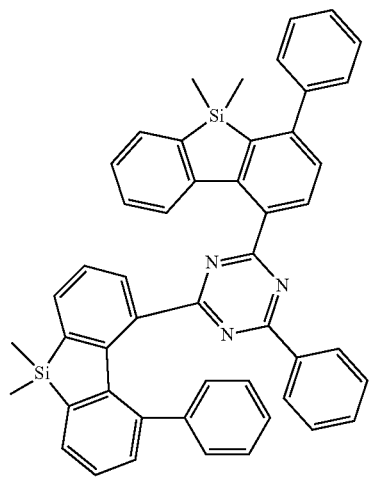

-continued
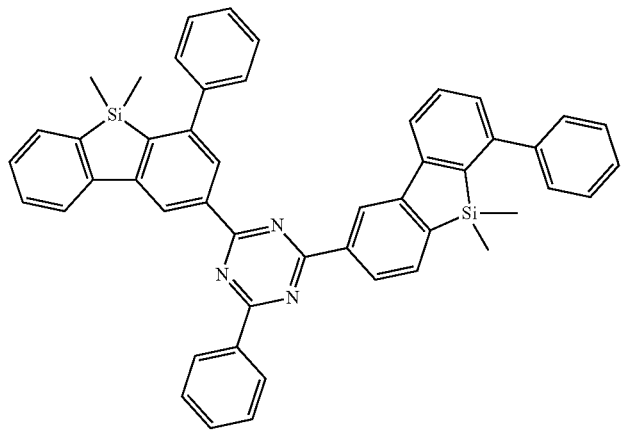
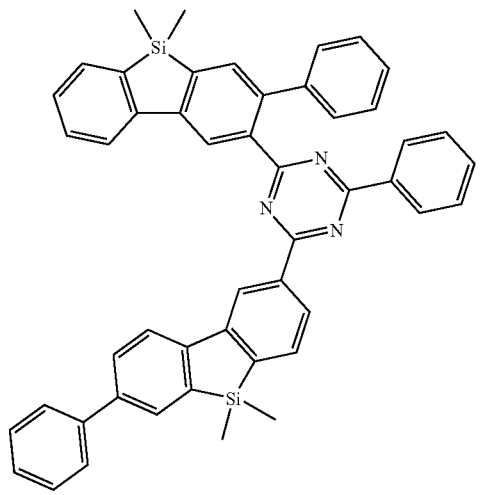
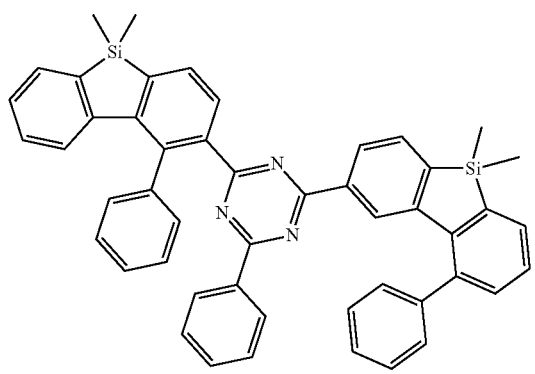
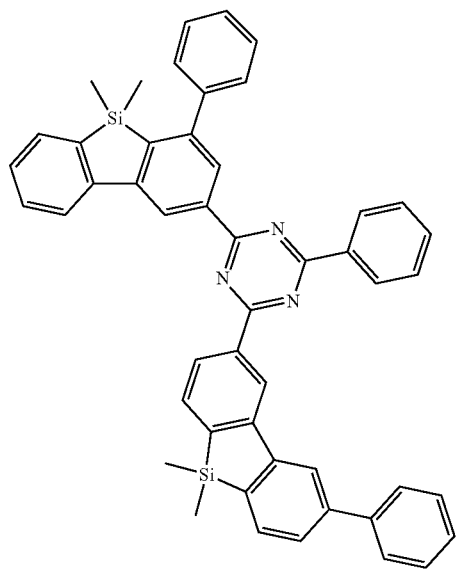
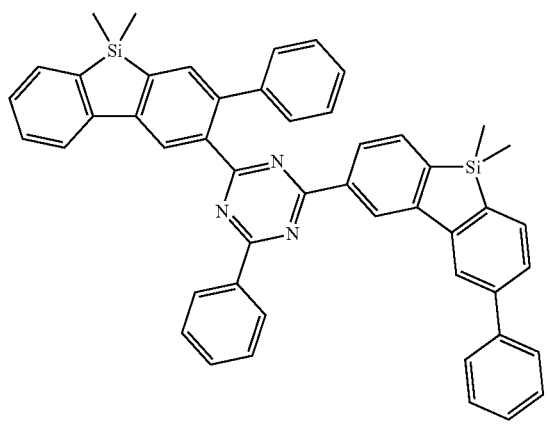
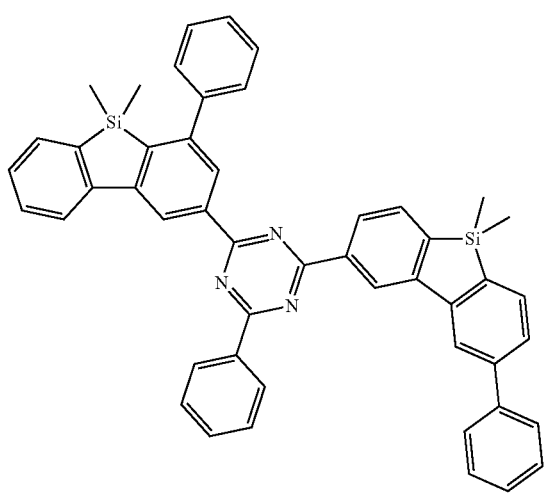

-continued
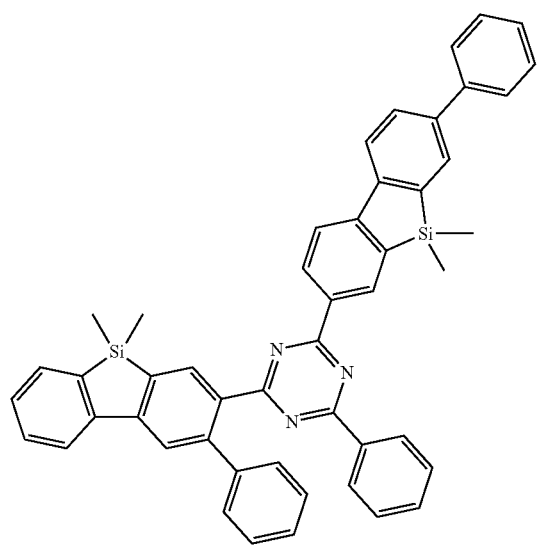
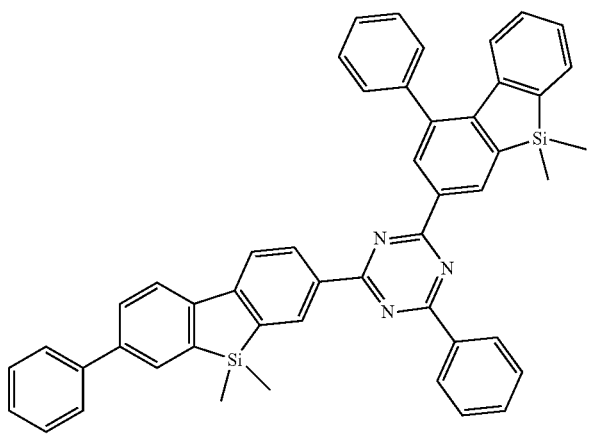
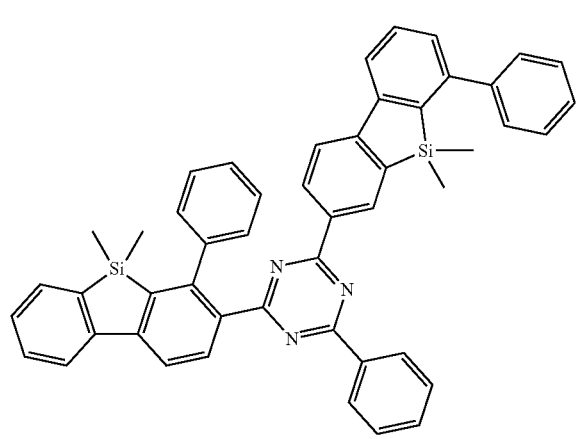
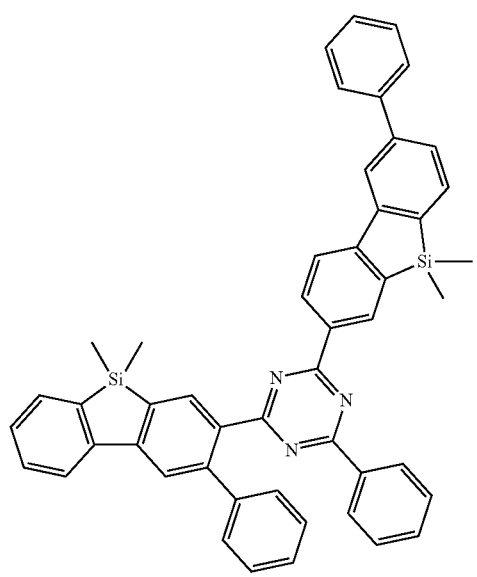
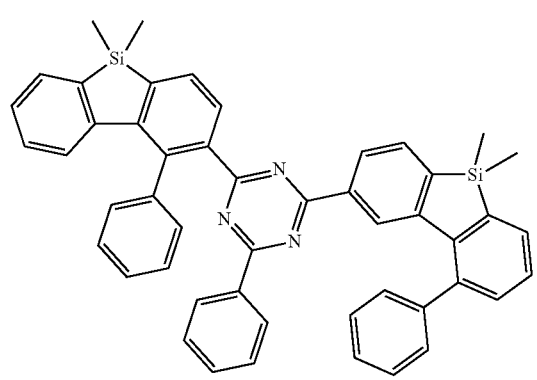
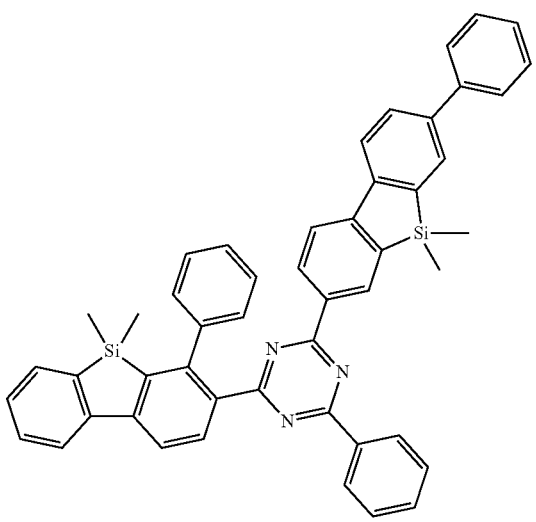

-continued
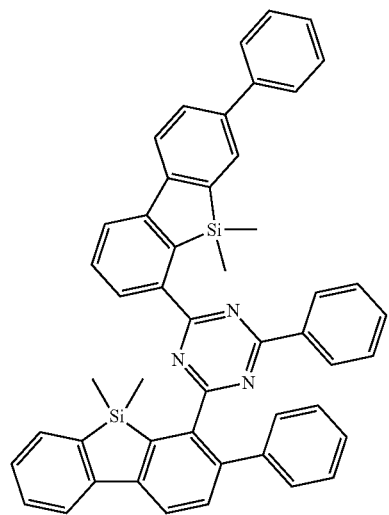
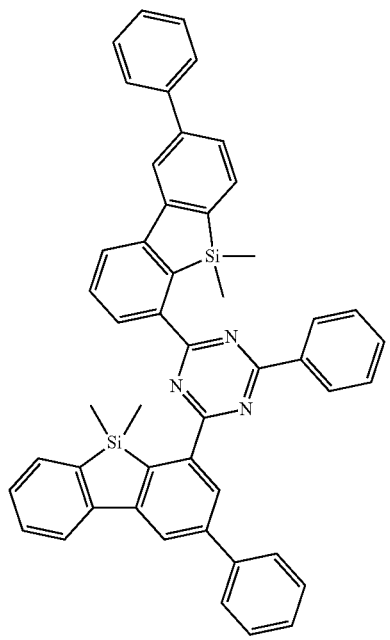
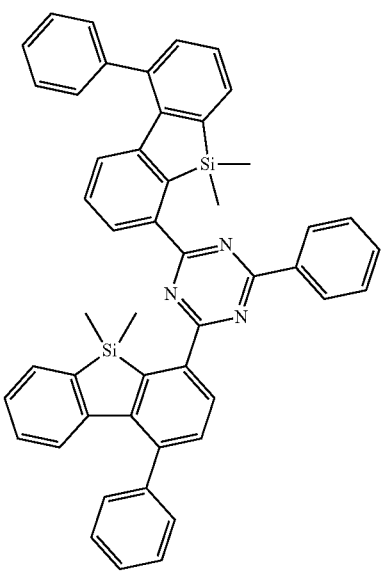
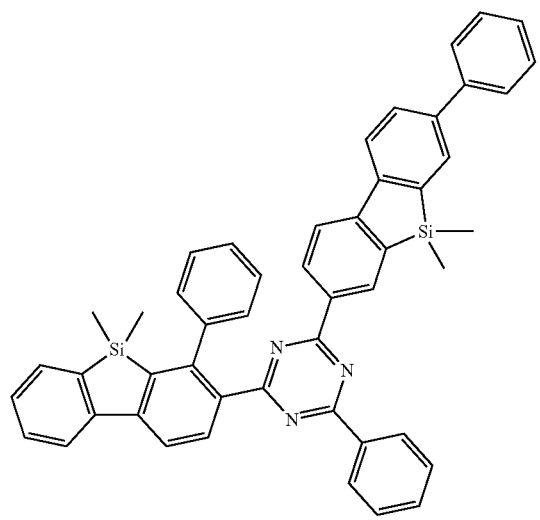
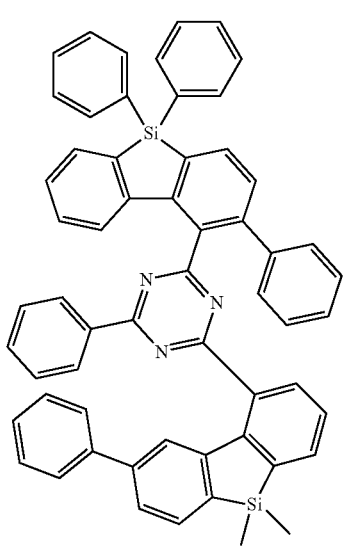
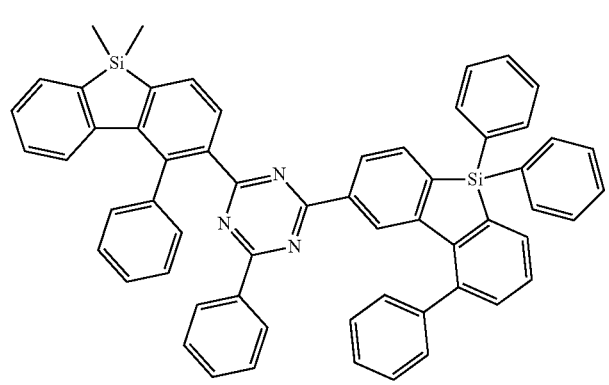
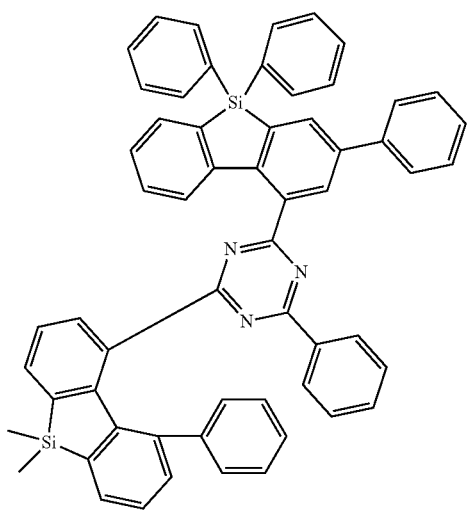

-continued
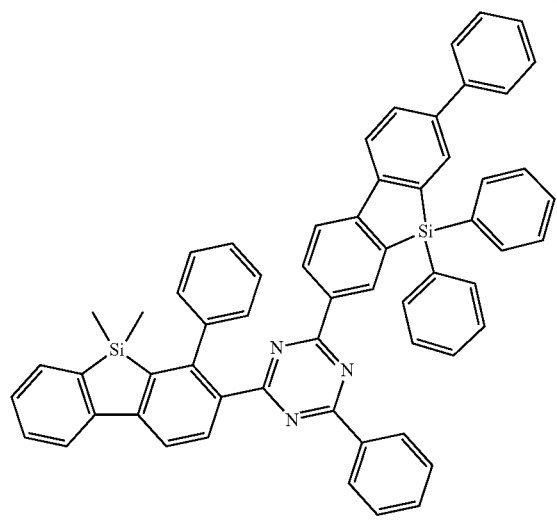 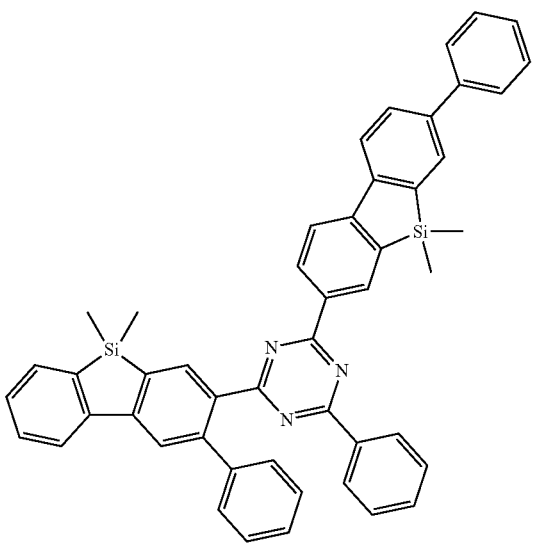
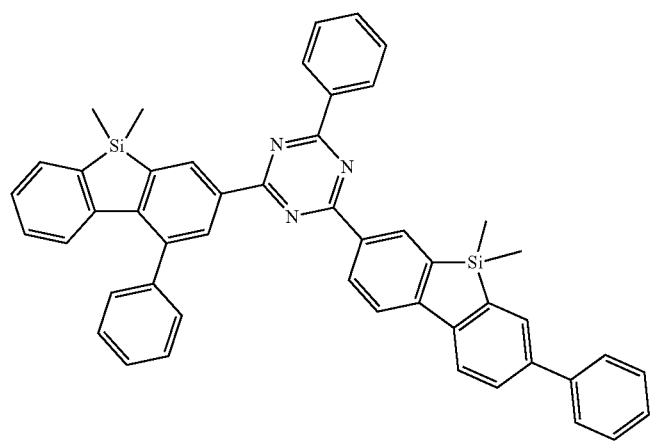 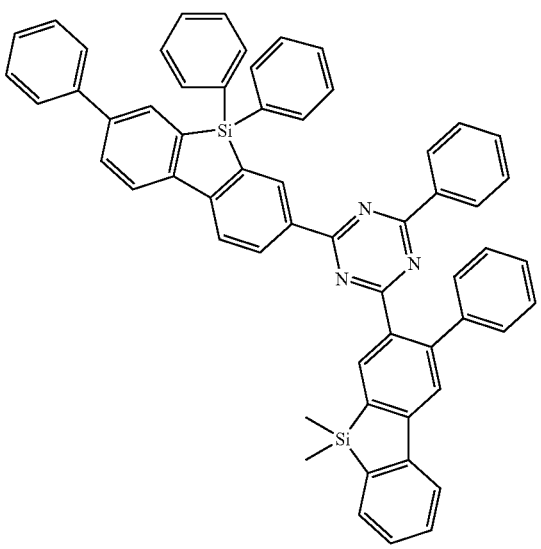
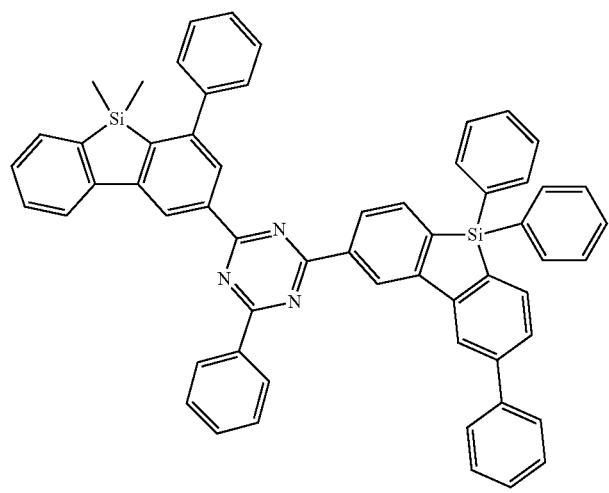 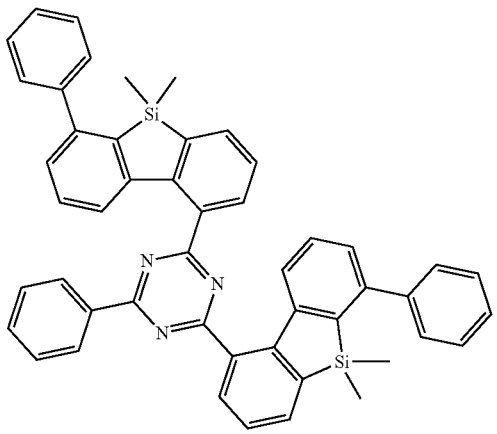

-continued
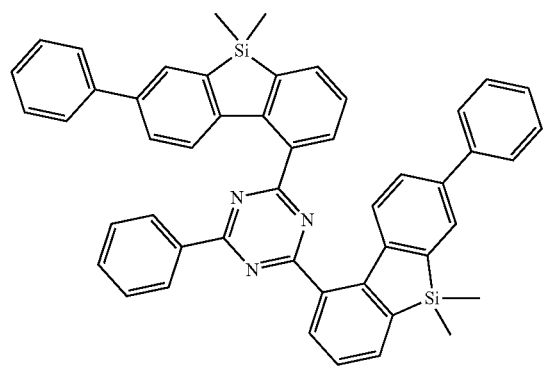
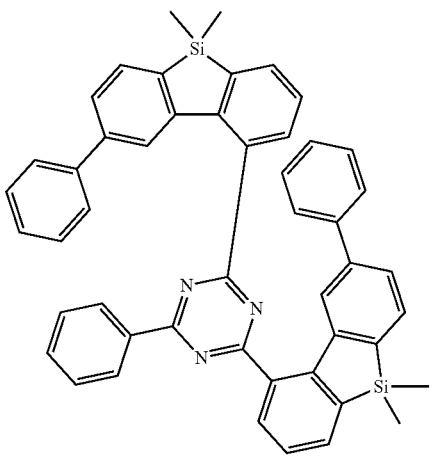
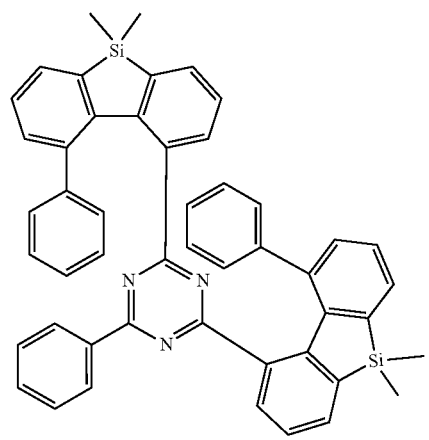
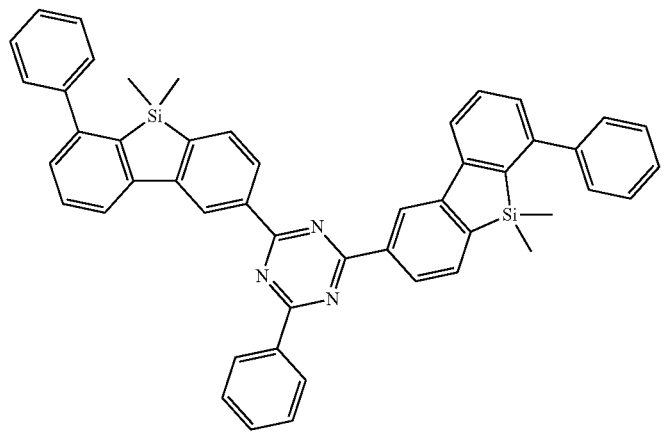
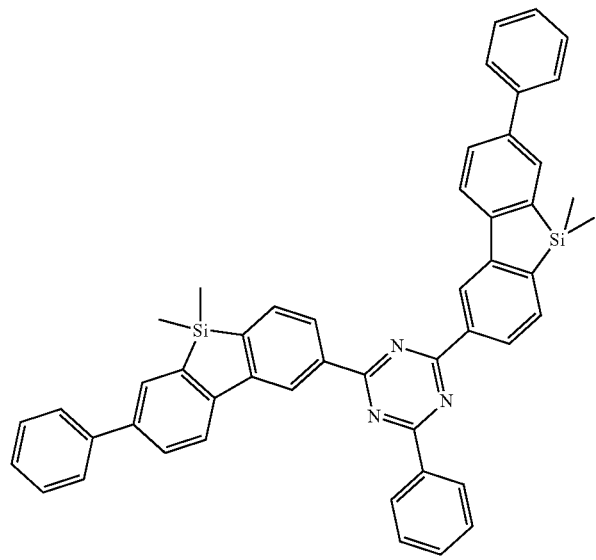
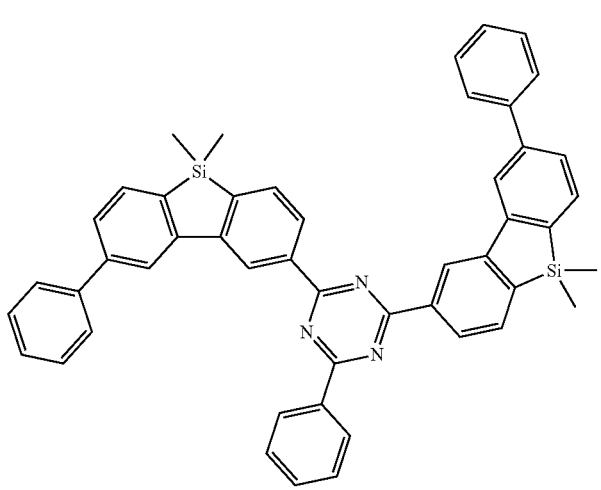

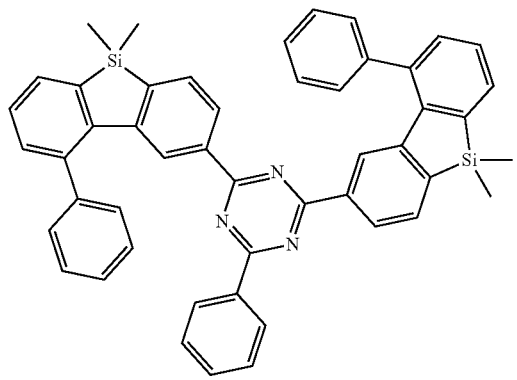
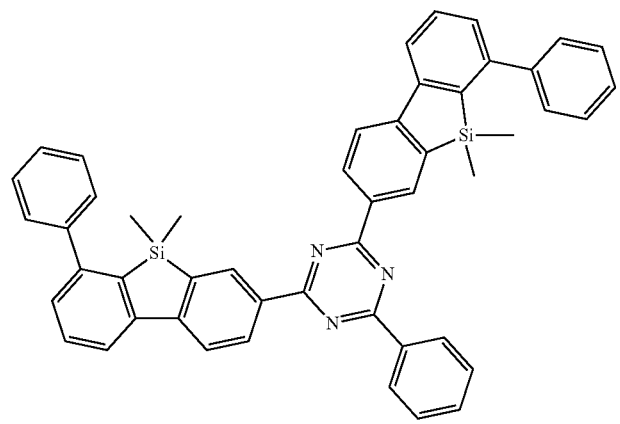
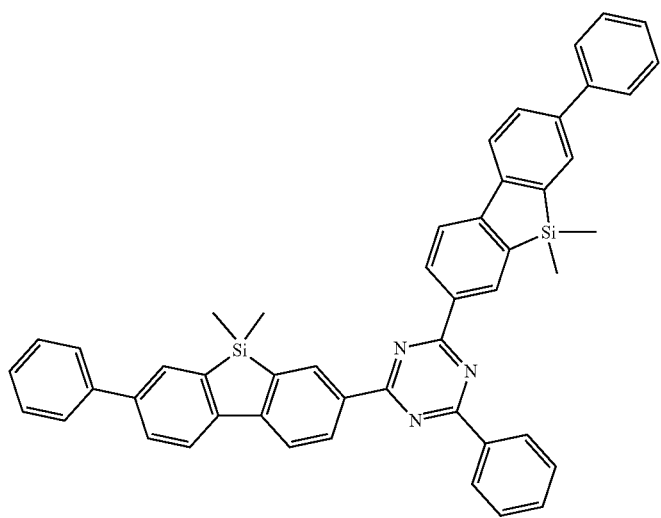
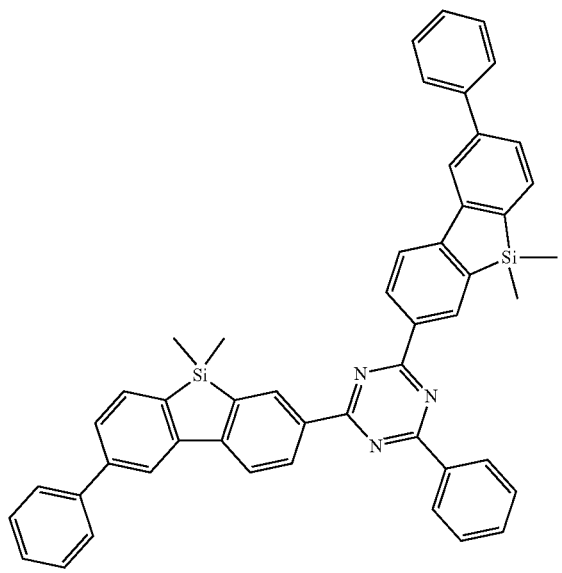

65
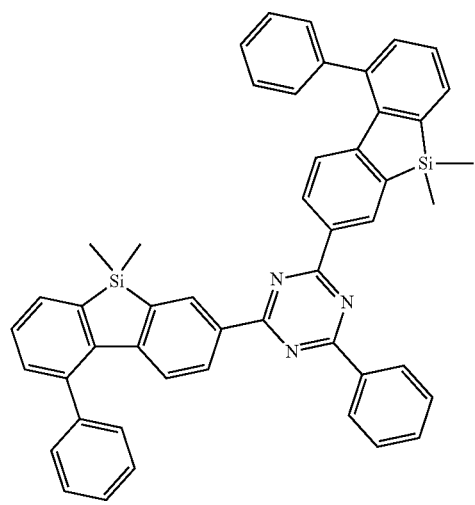
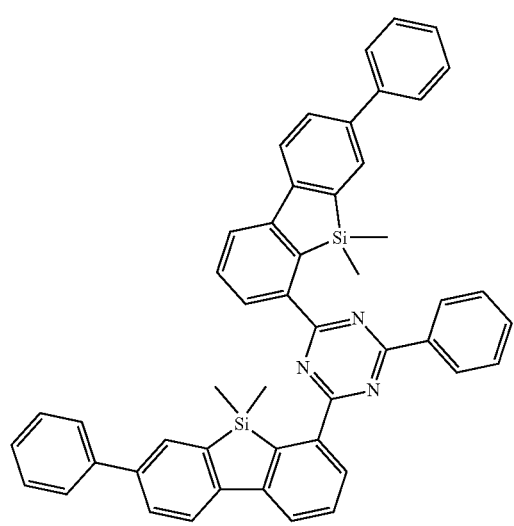
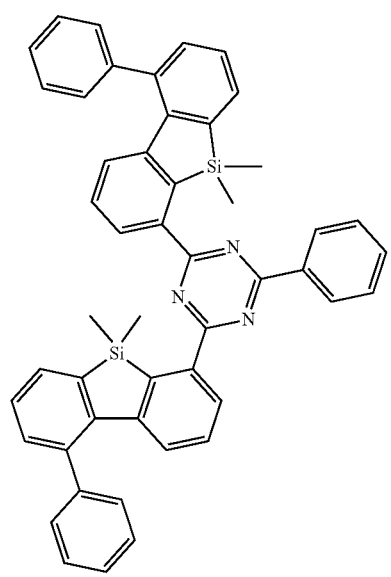
-continued
66
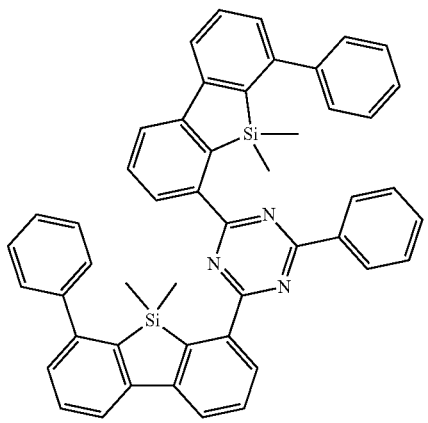
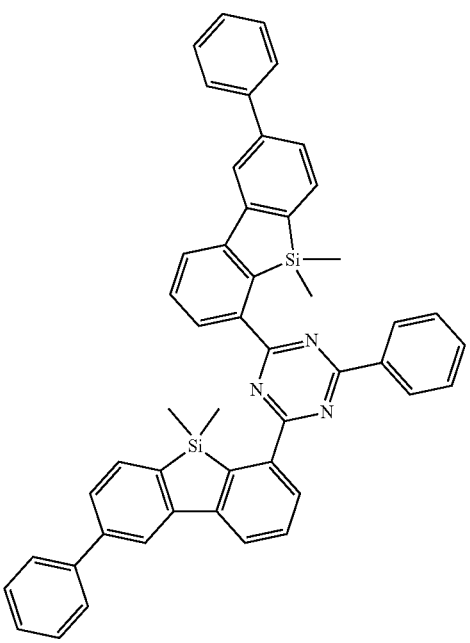
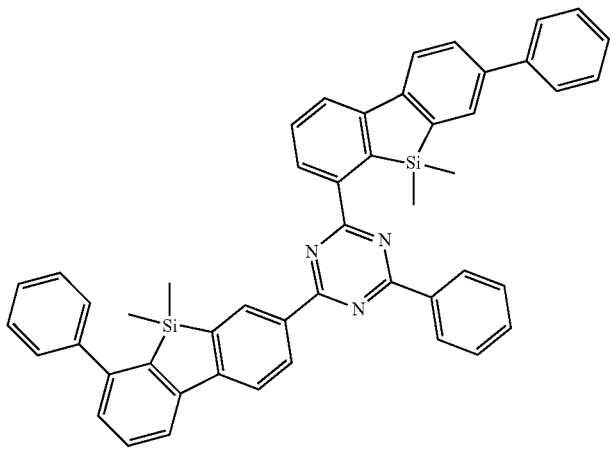

-continued
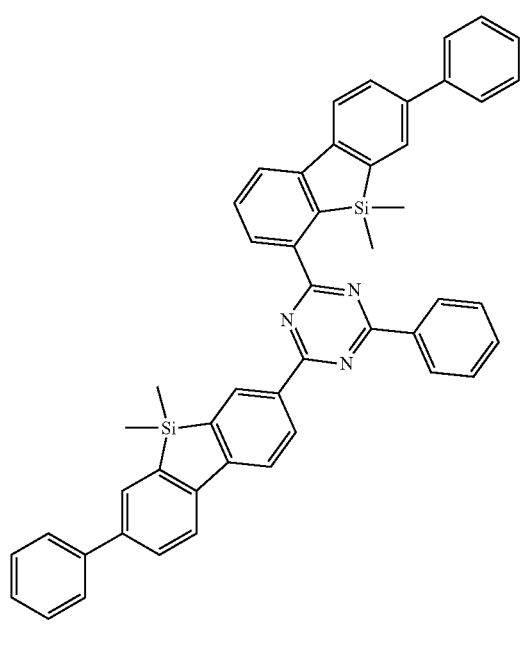
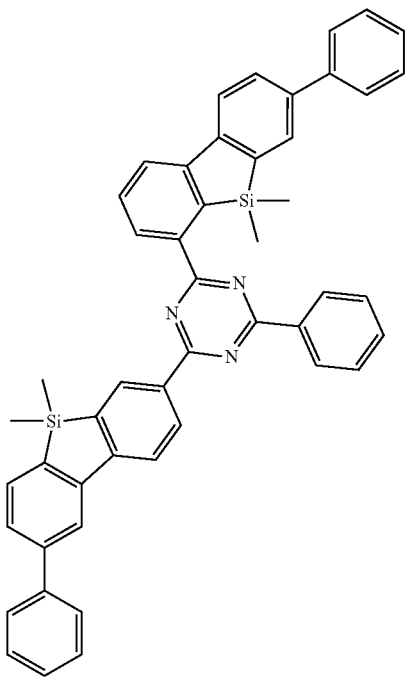
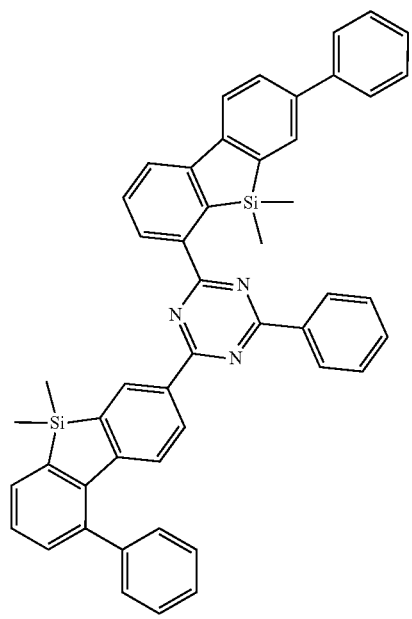
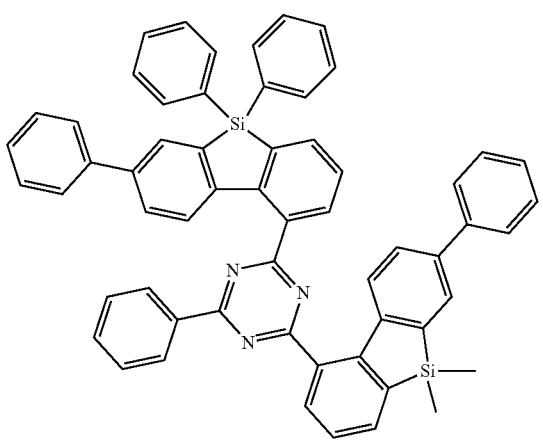
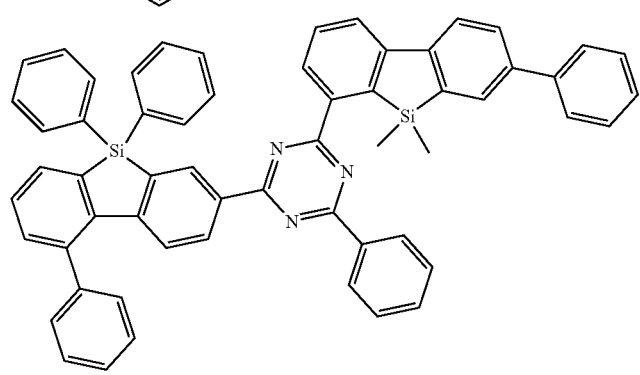

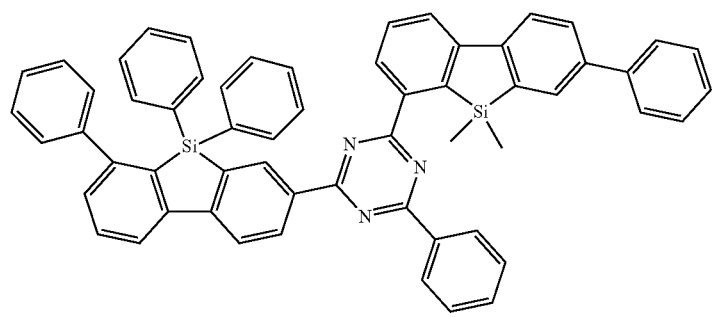
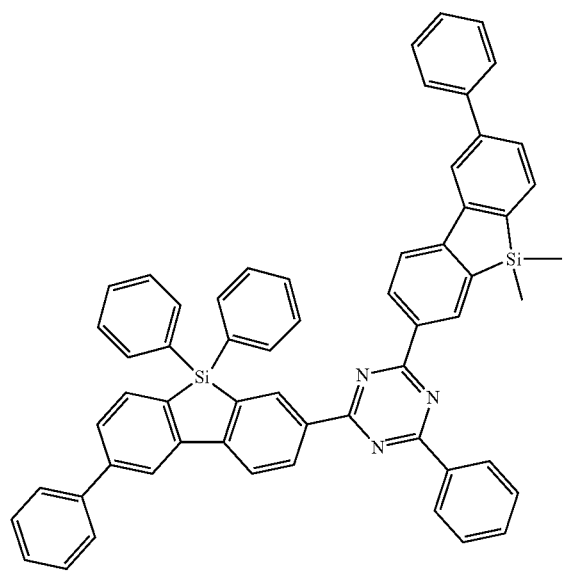
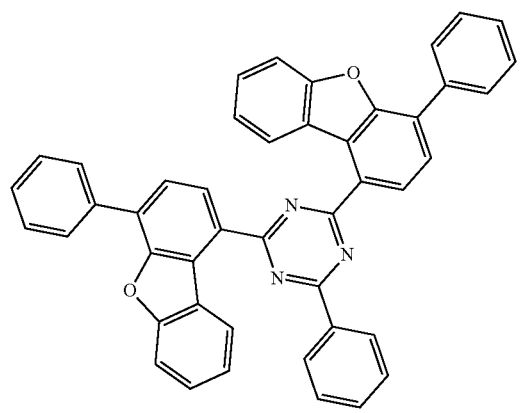
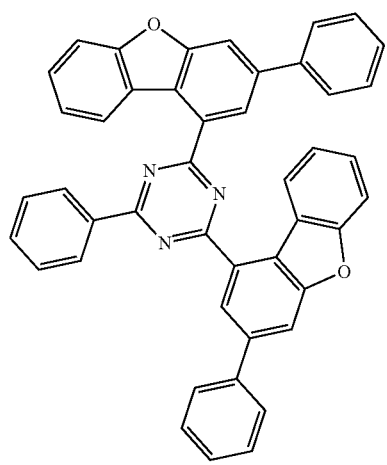

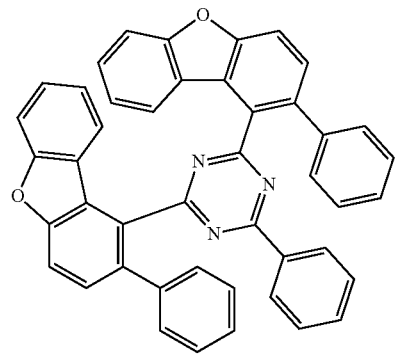
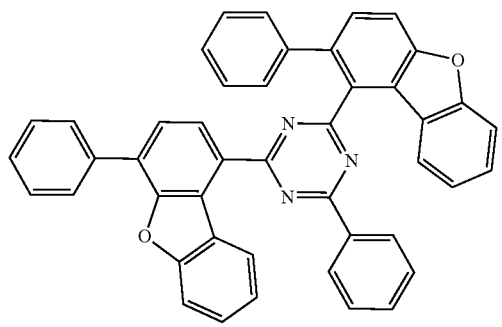
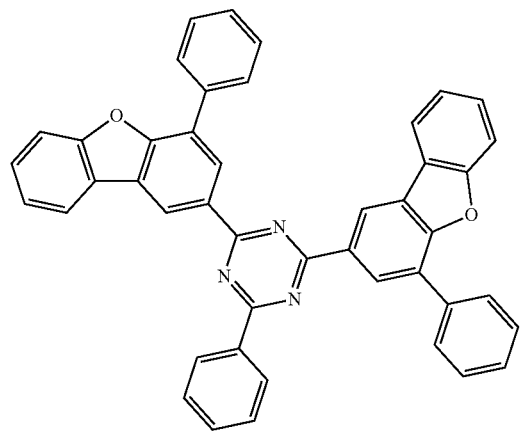
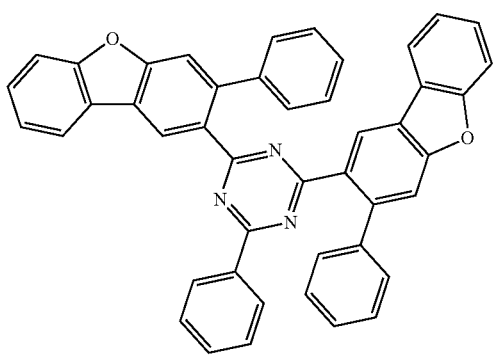
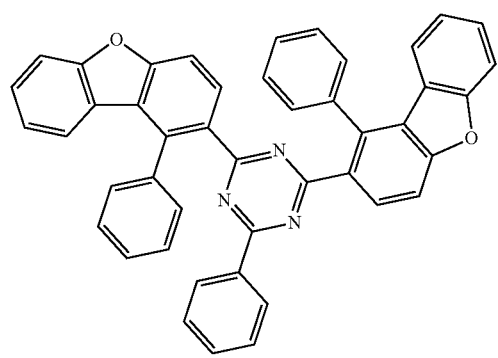
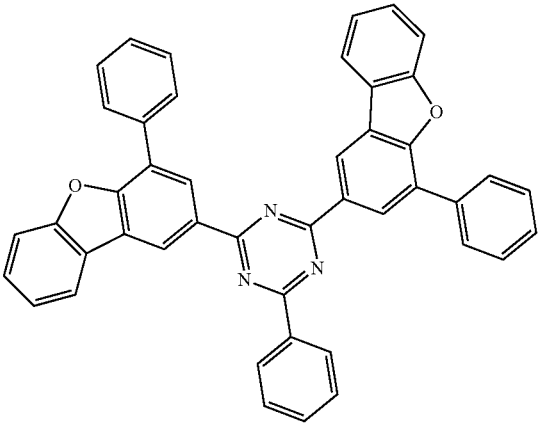
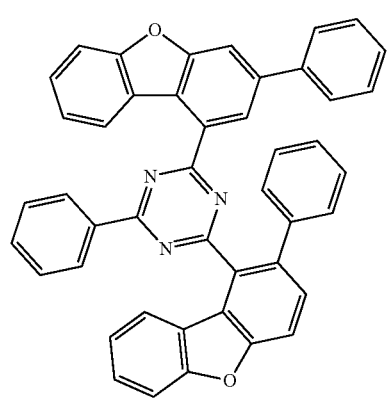
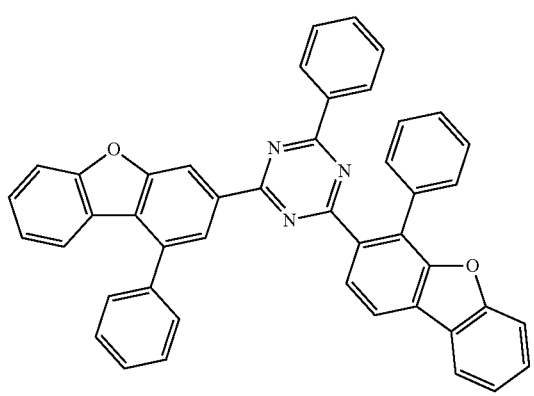

-continued
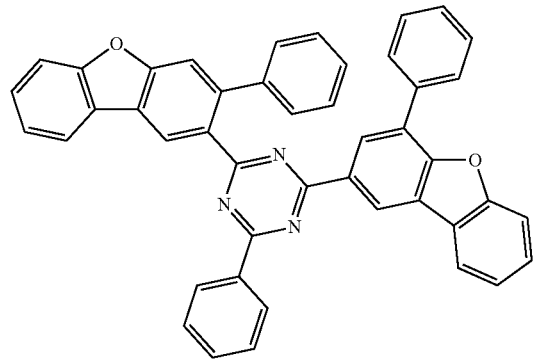
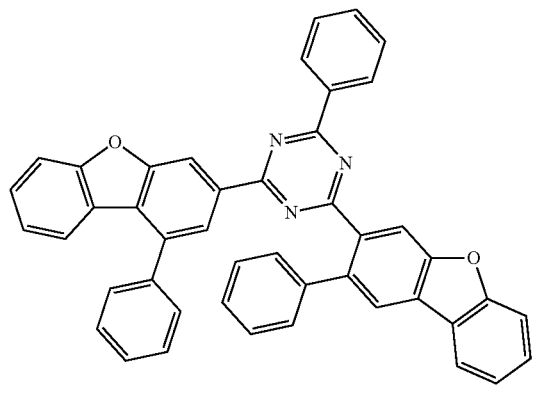
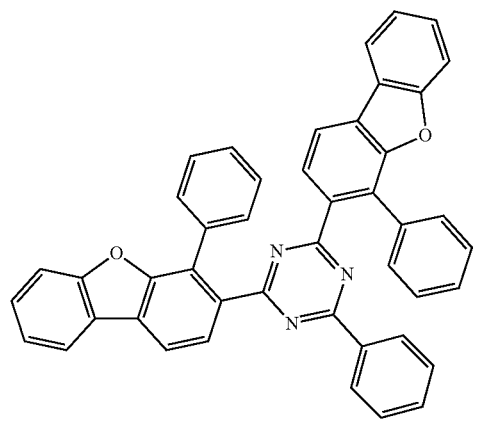
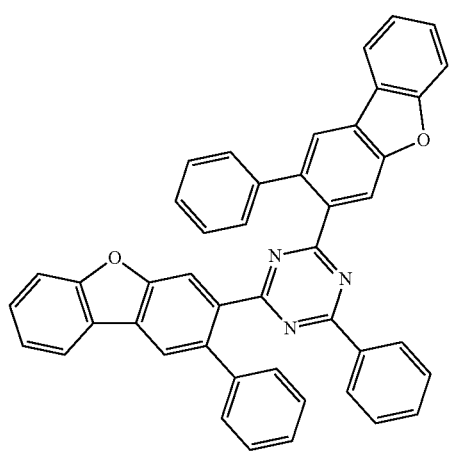
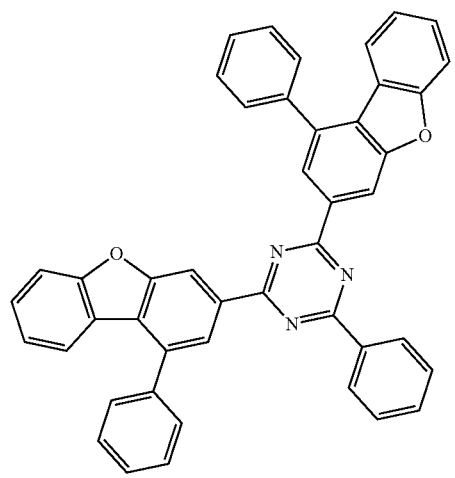
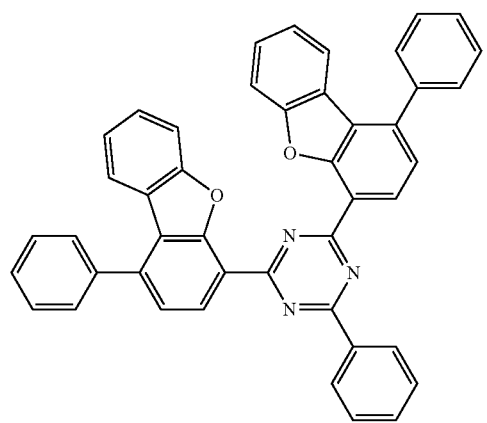

-continued
75
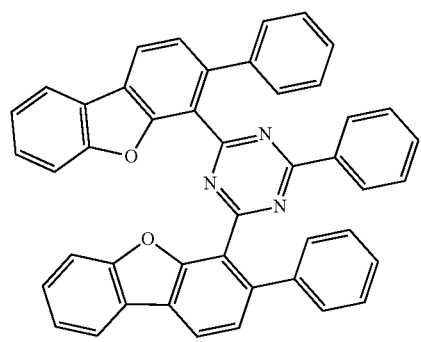
76
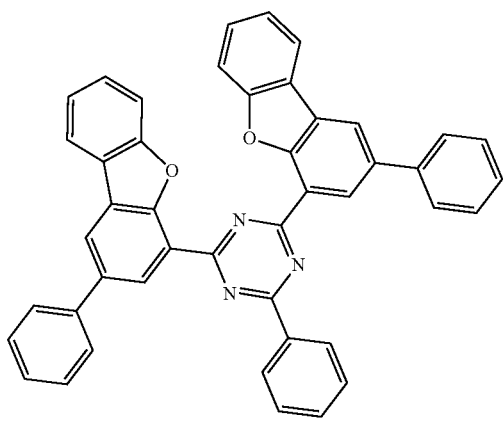
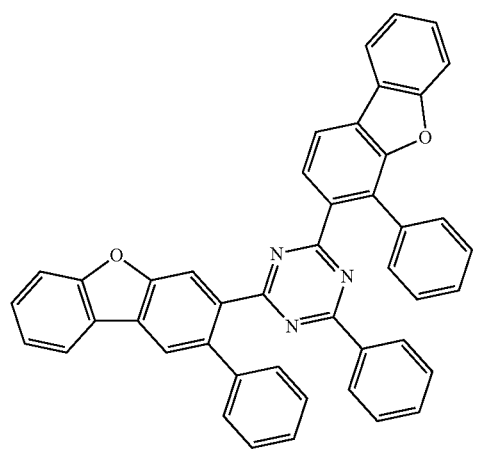
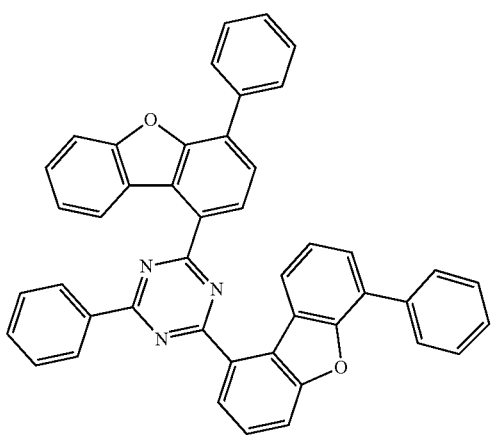
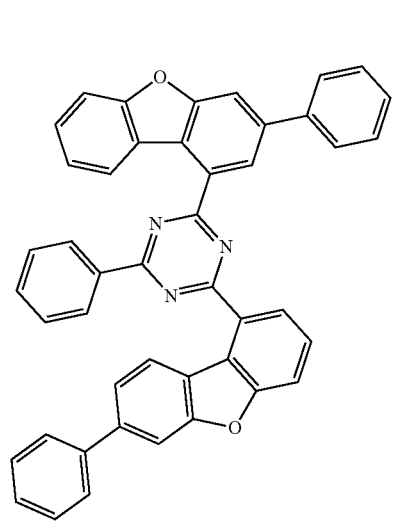
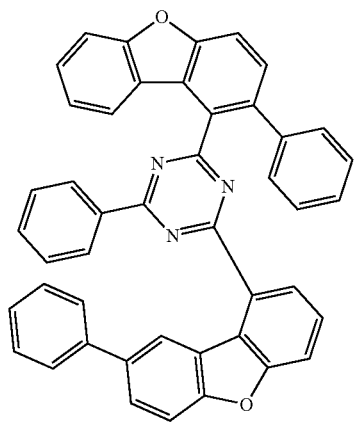
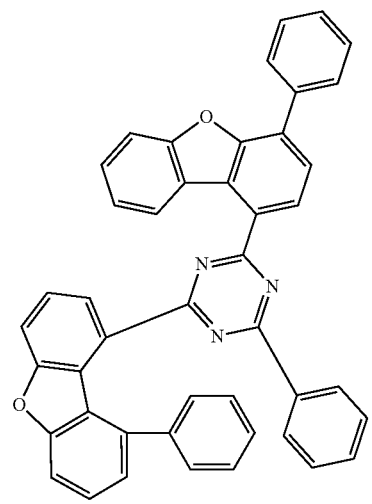

-continued
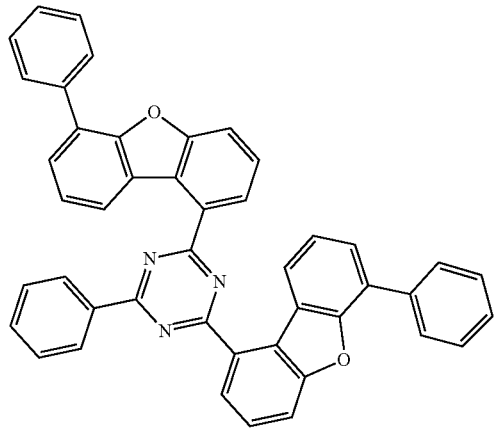
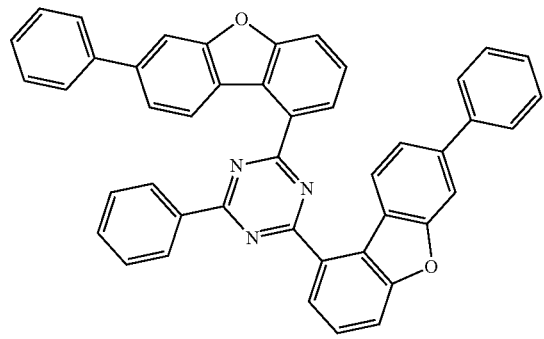
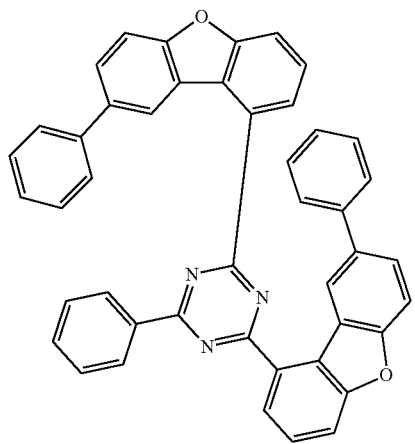
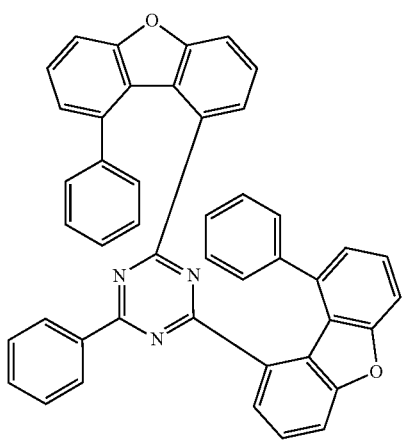
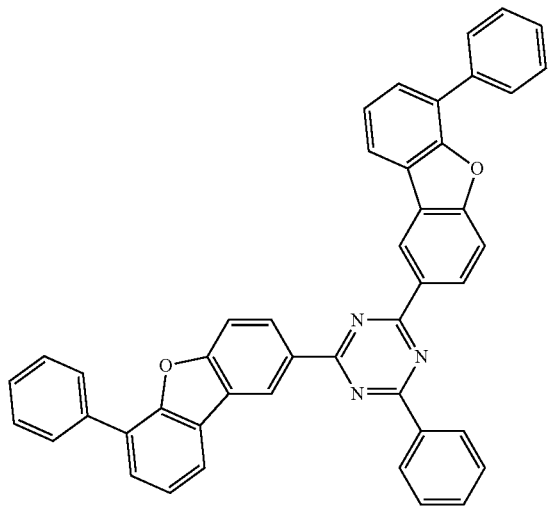
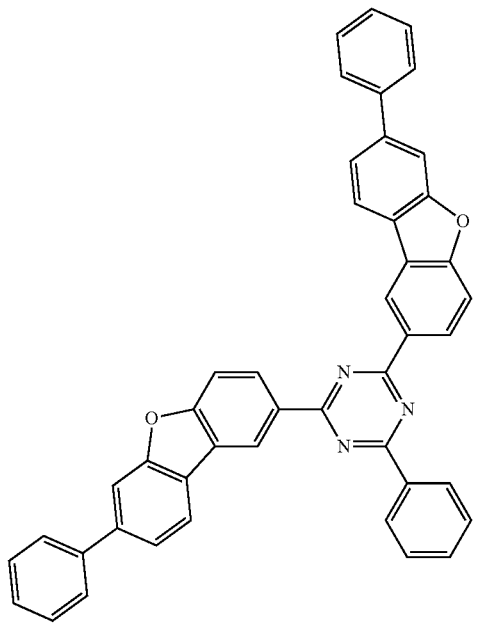

79
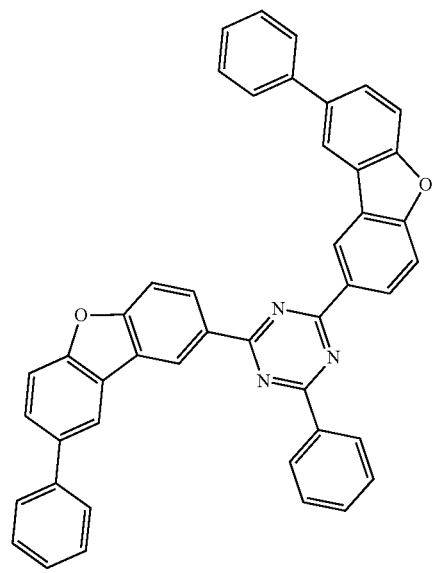
80
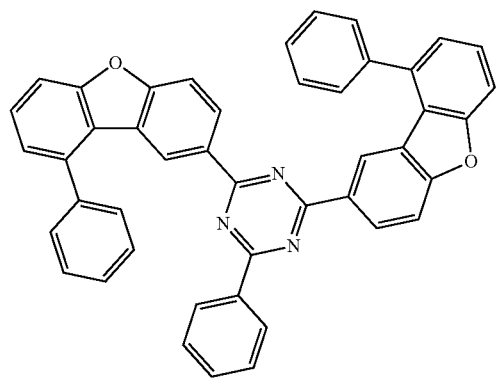
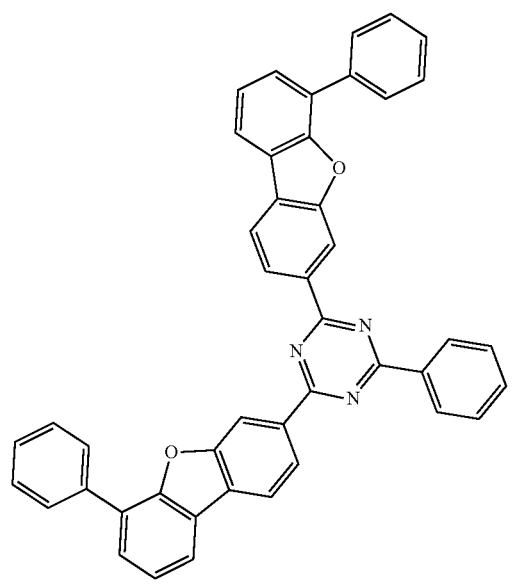
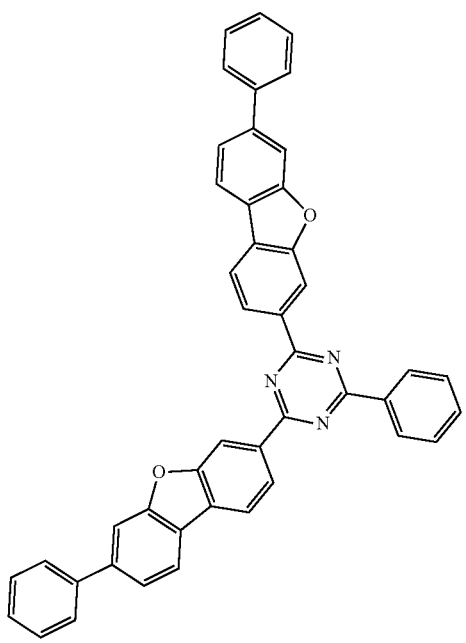

81
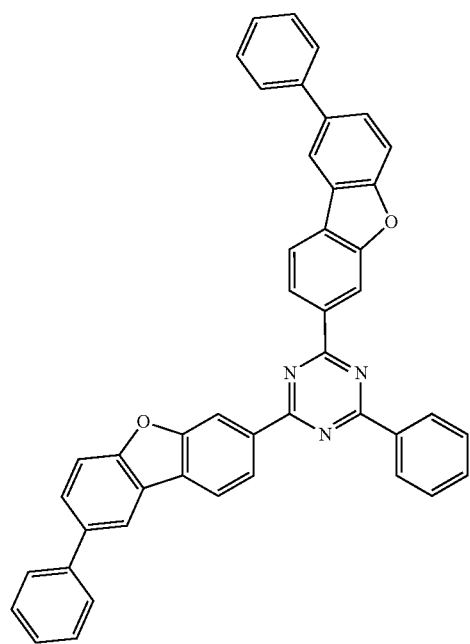
82
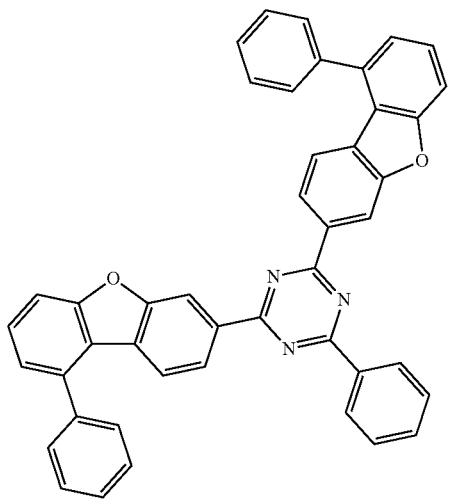
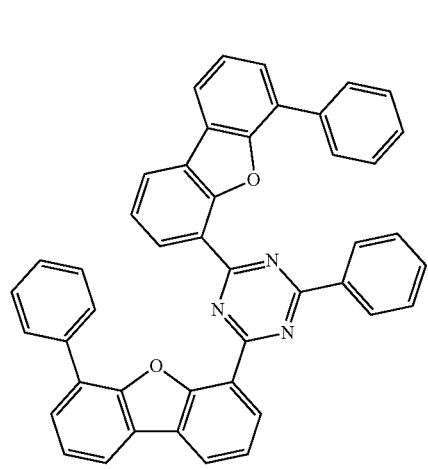
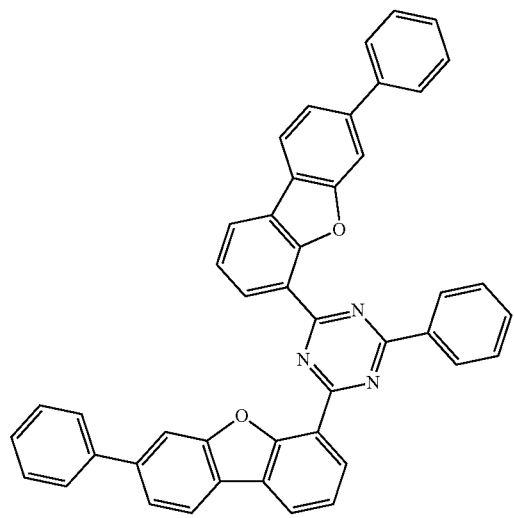

-continued
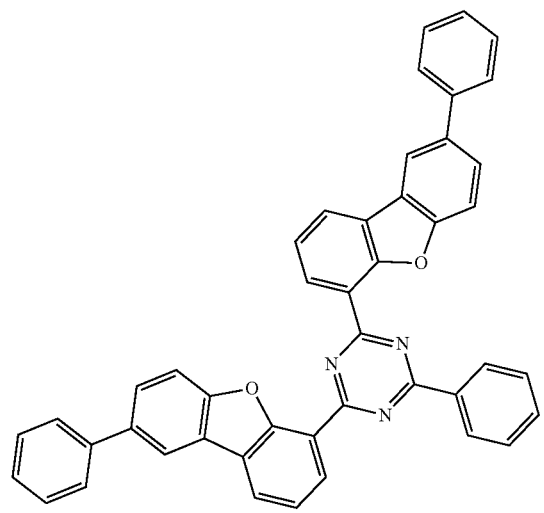
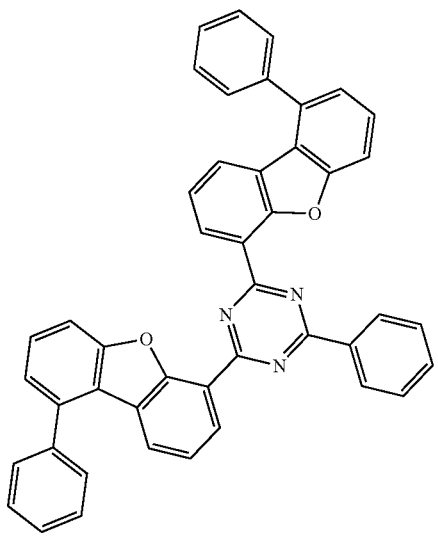
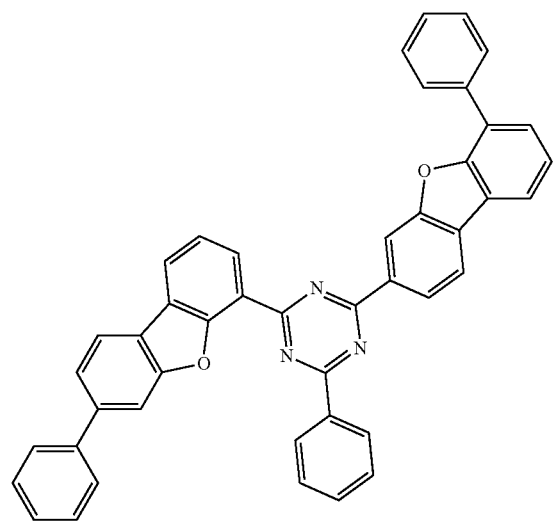
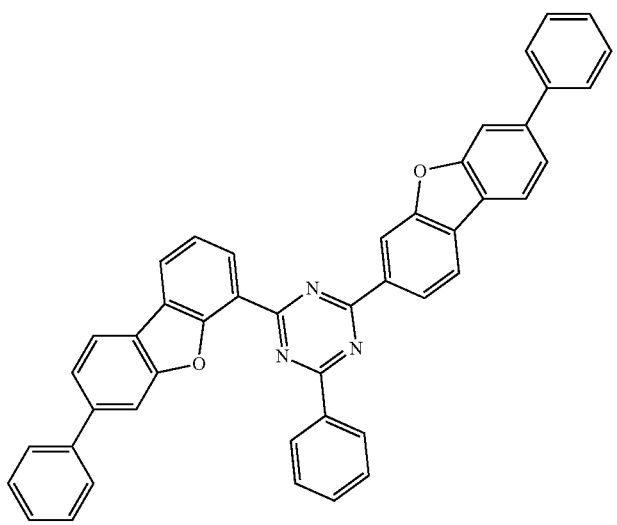
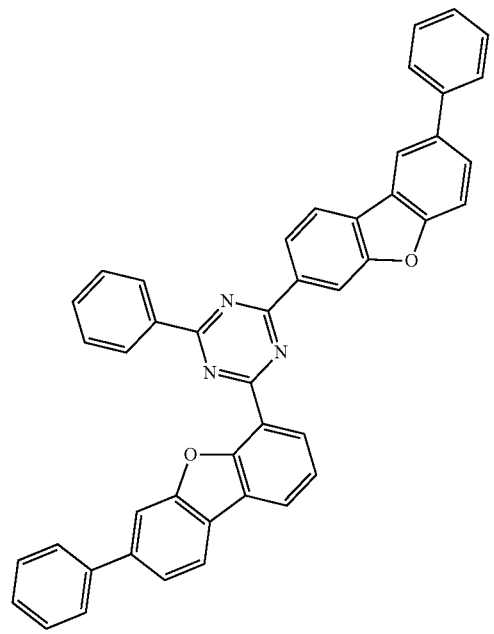
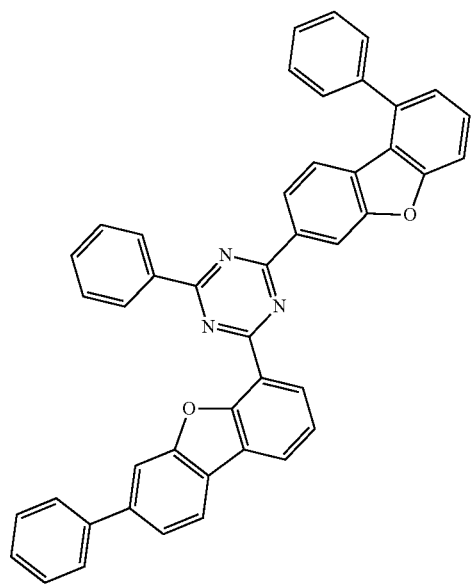

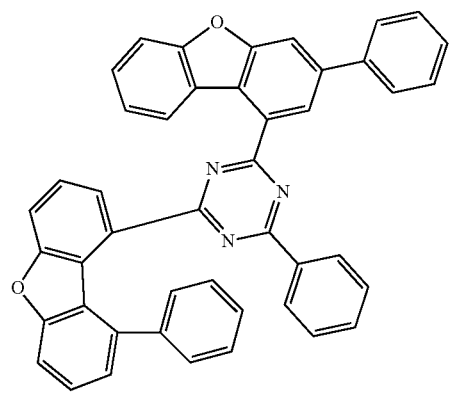
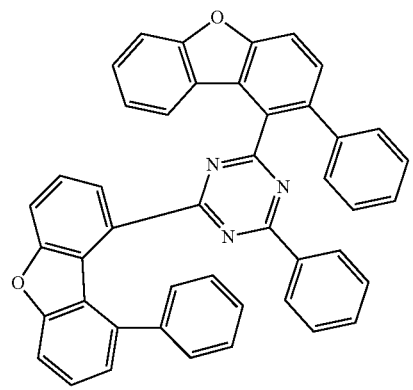
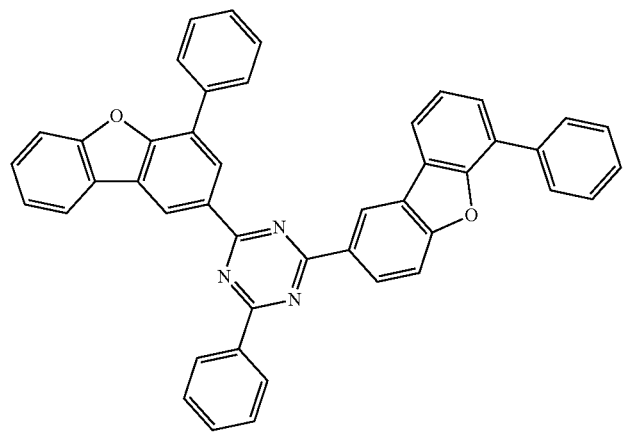
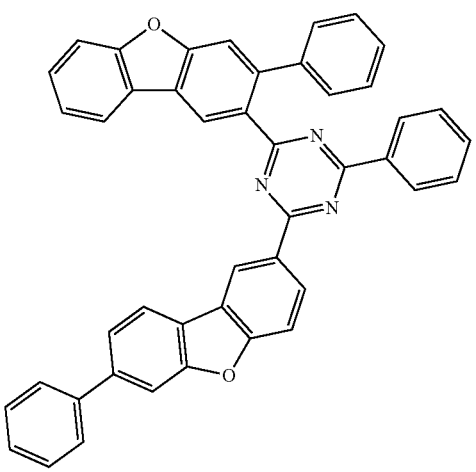
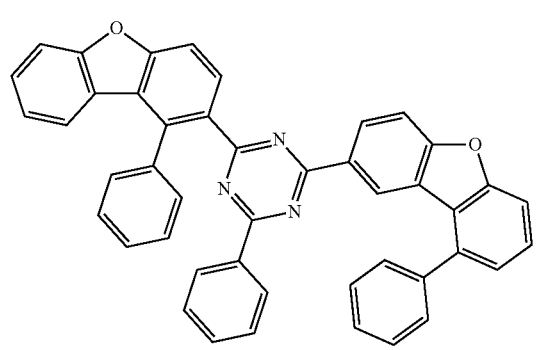
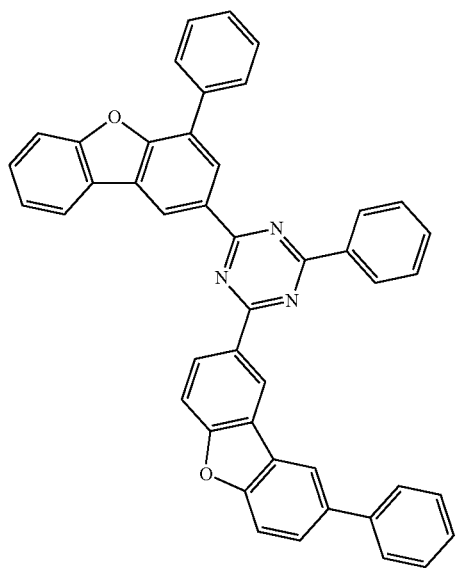

-continued
87
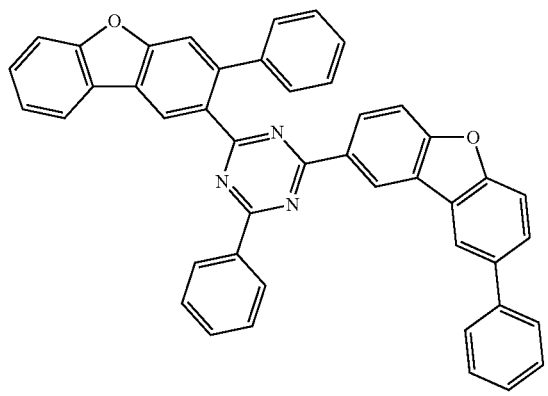
88
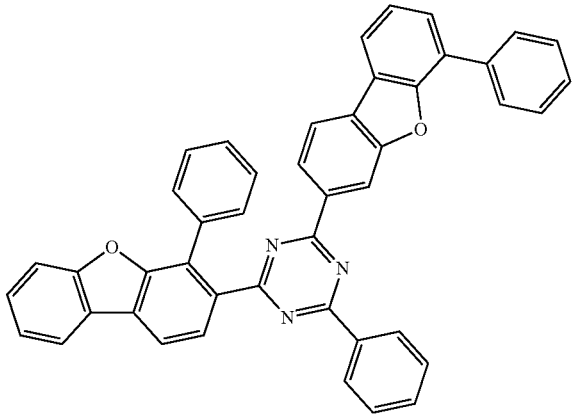
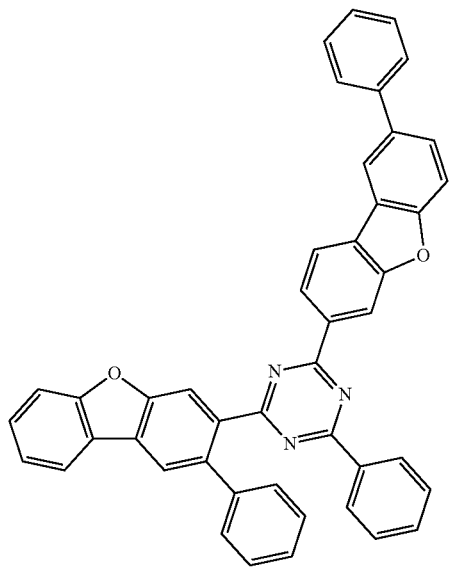
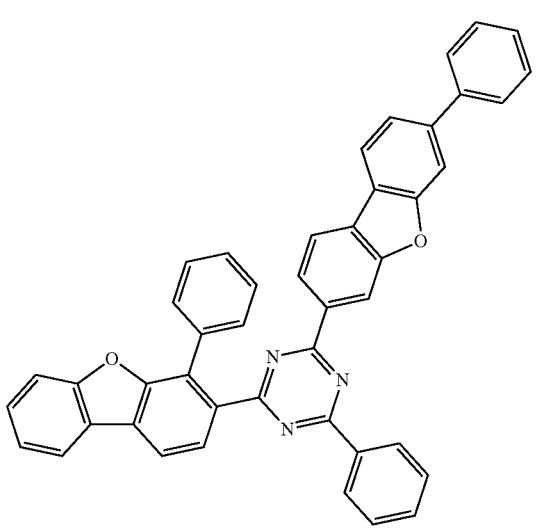
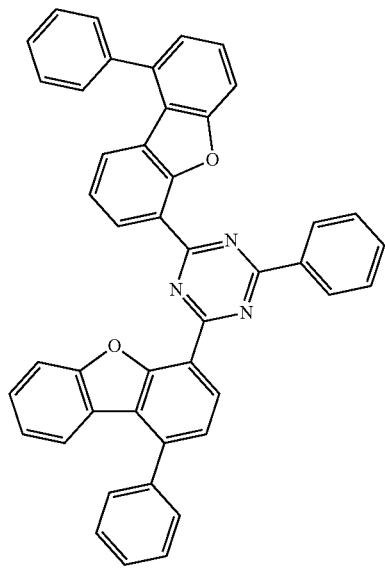
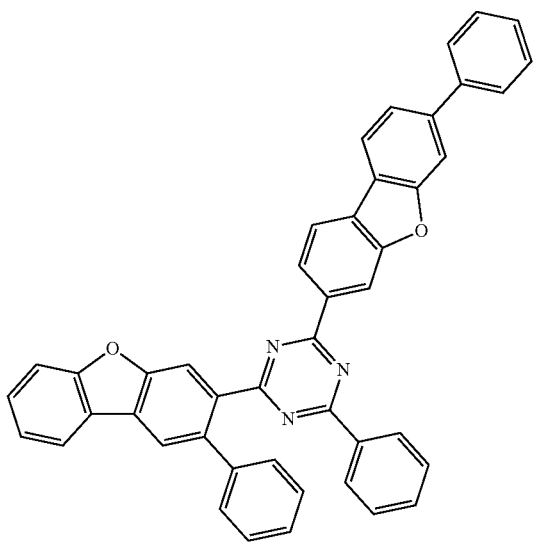

-continued
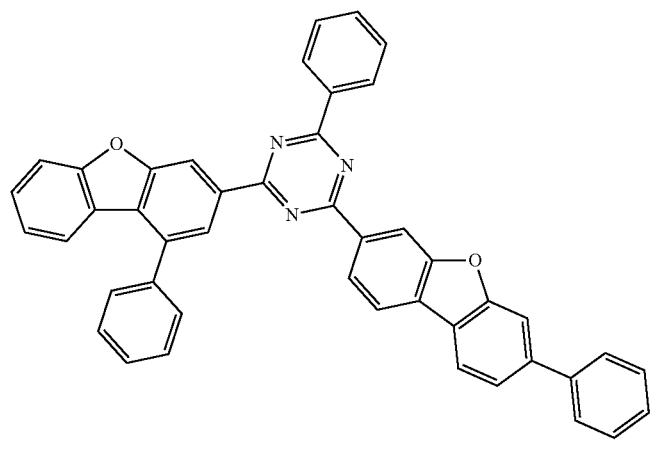
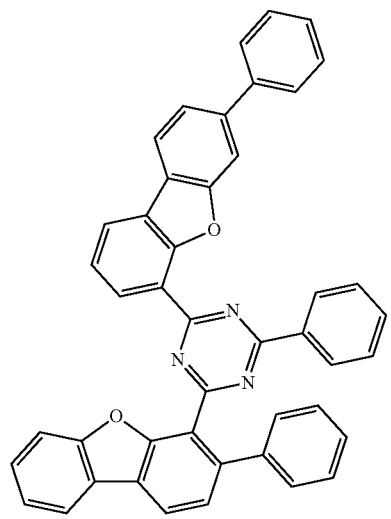
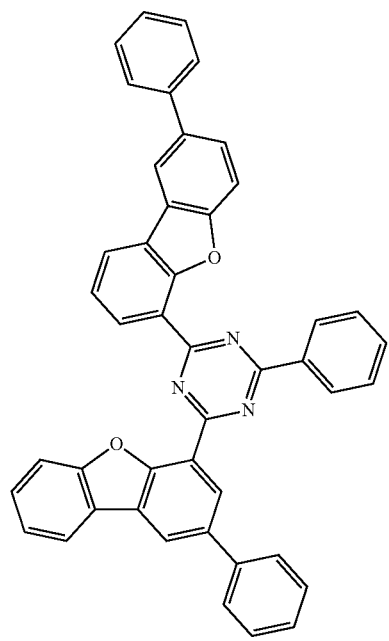
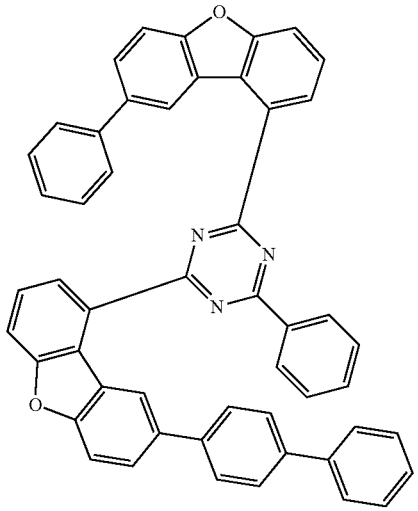
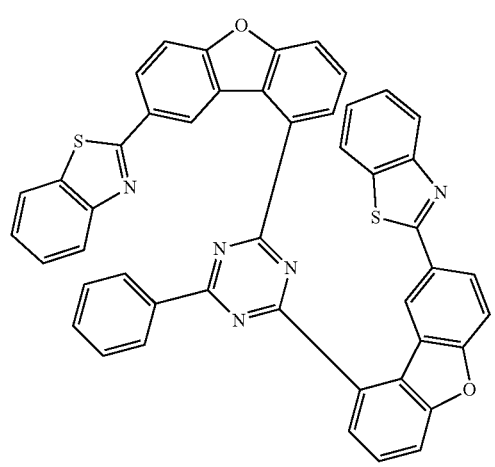

-continued
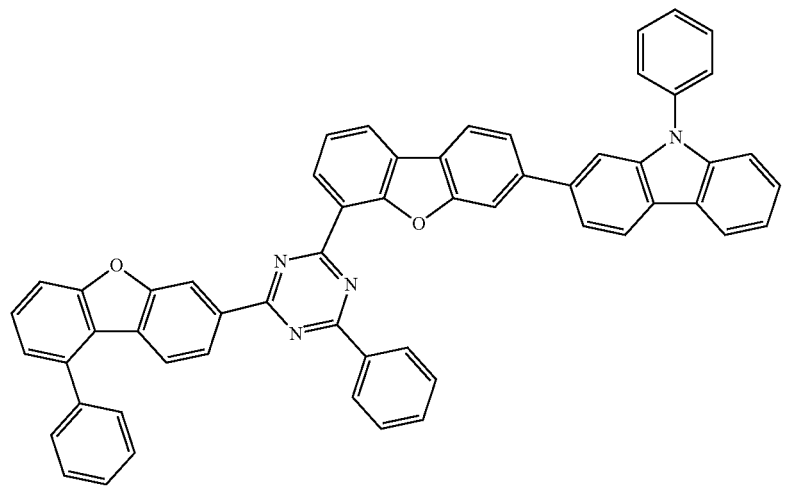
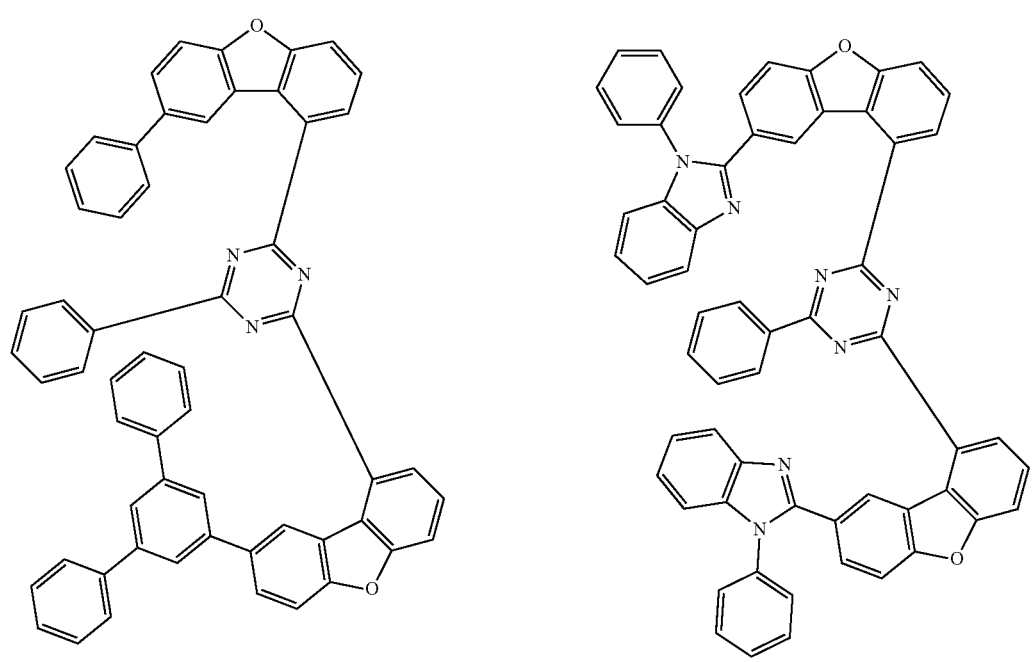

-continued
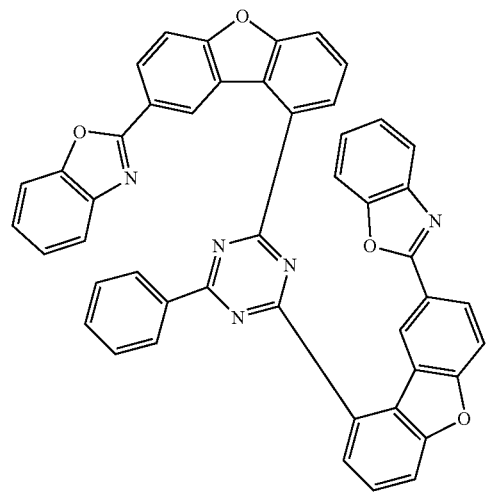
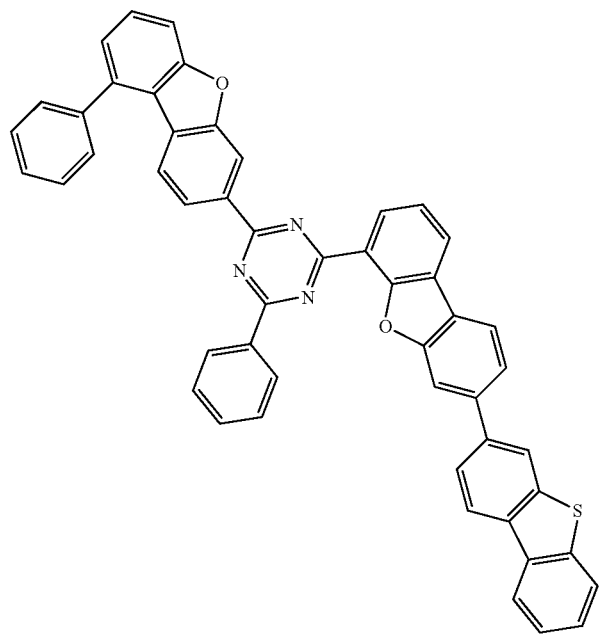
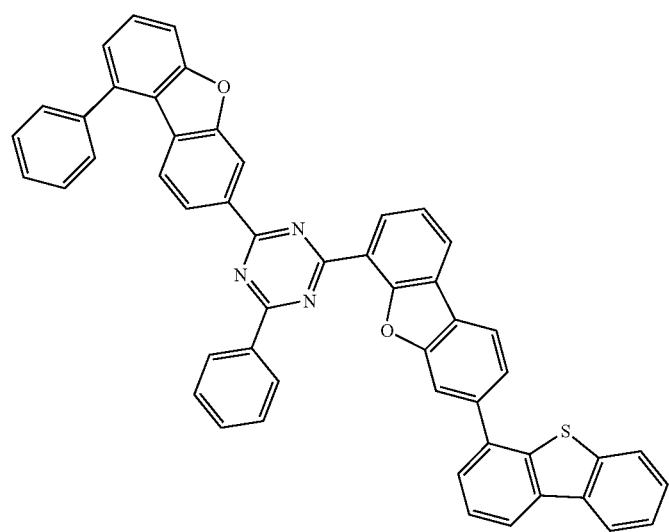
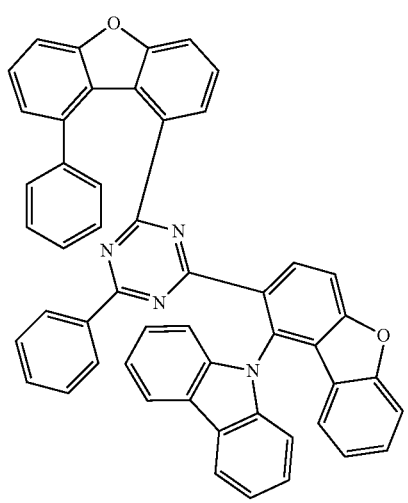

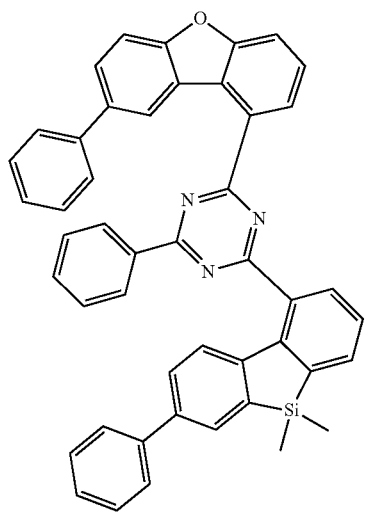
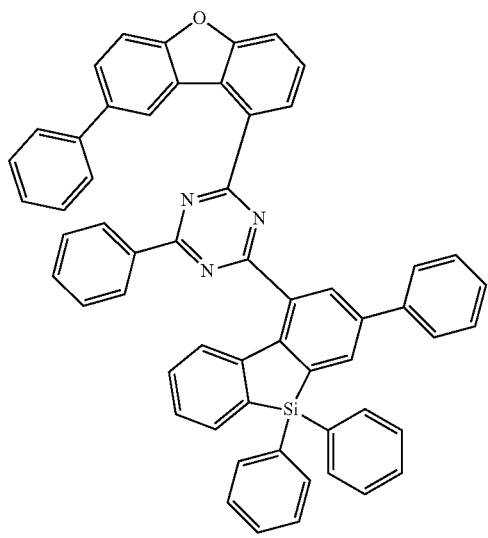
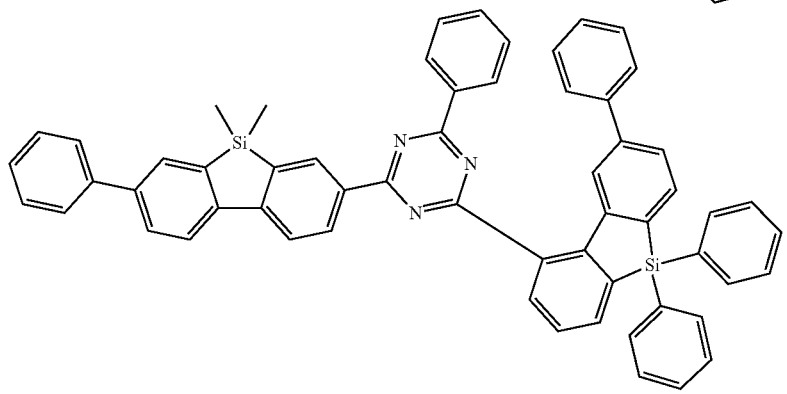
According to one embodiment of the present specification, the compound of Chemical Formula 1 described above may be prepared according to the following General Formula 1 or General Formula 2.
[General Formula 1]
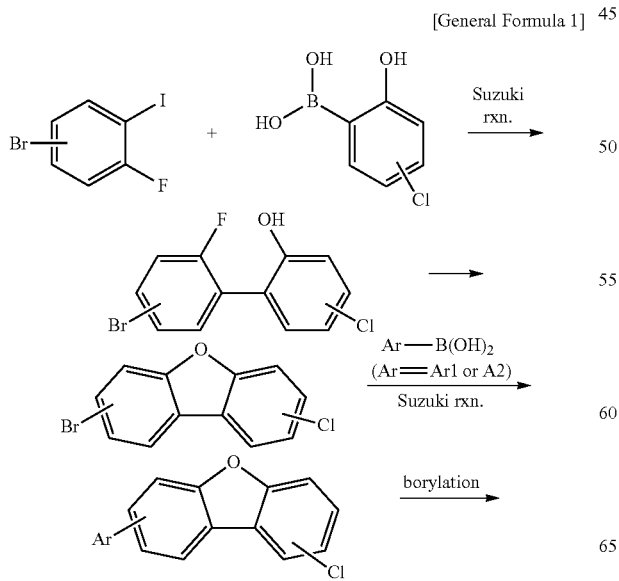
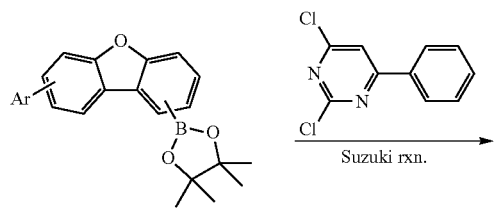
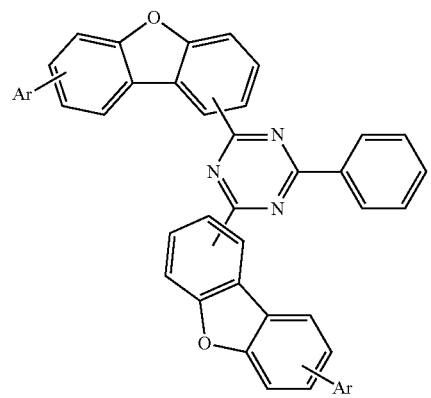

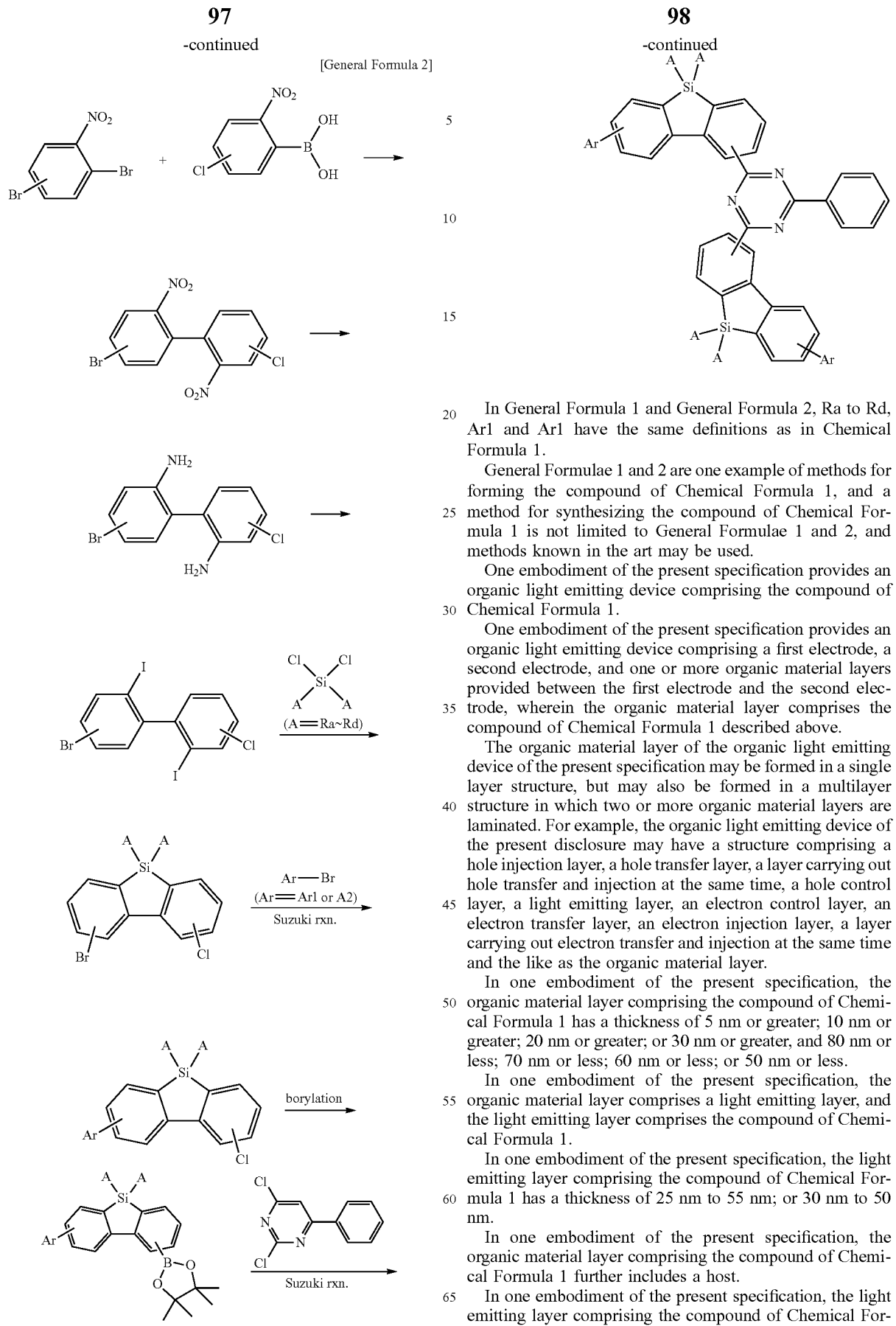

In General Formula 1 and General Formula 2, Ra to Rd, Ar1 and Ar1 have the same definitions as in Chemical Formula 1.

General Formulae 1 and 2 are one example of methods for forming the compound of Chemical Formula 1, and a method for synthesizing the compound of Chemical Formula 1 is not limited to General Formulae 1 and 2, and methods known in the art may be used.

One embodiment of the present specification provides an organic light emitting device comprising the compound of Chemical Formula 1.

One embodiment of the present specification provides an organic light emitting device comprising a first electrode, a second electrode, and one or more organic material layers provided between the first electrode and the second electrode, wherein the organic material layer comprises the compound of Chemical Formula 1 described above.

The organic material layer of the organic light emitting device of the present specification may be formed in a single layer structure, but may also be formed in a multilayer structure in which two or more organic material layers are laminated. For example, the organic light emitting device of the present disclosure may have a structure comprising a hole injection layer, a hole transfer layer, a layer carrying out hole transfer and injection at the same time, a hole control layer, a light emitting layer, an electron control layer, an electron transfer layer, an electron injection layer, a layer carrying out electron transfer and injection at the same time and the like as the organic material layer.

In one embodiment of the present specification, the organic material layer comprising the compound of Chemical Formula 1 has a thickness of 5 nm or greater; 10 nm or greater; 20 nm or greater; or 30 nm or greater, and 80 nm or less; 70 nm or less; 60 nm or less; or 50 nm or less.

In one embodiment of the present specification, the organic material layer comprises a light emitting layer, and the light emitting layer comprises the compound of Chemical Formula 1.

In one embodiment of the present specification, the light emitting layer comprising the compound of Chemical Formula 1 has a thickness of 25 nm to 55 nm; or 30 nm to 50 nm.

In one embodiment of the present specification, the organic material layer comprising the compound of Chemical Formula 1 further includes a host.

In one embodiment of the present specification, the light emitting layer comprising the compound of Chemical Formula 1 further comprises a host. When the light emitting layer including the compound of Chemical Formula 1 further comprises a host, device lifetime properties may be greatly enhanced.

In one embodiment of the present specification, the host is a carbazole derivative; or a biscarbazole derivative.

In one embodiment of the present specification, the host is a substituted or unsubstituted biscarbazole.

In one embodiment of the present specification, the host is a compound of the following Chemical Formula H.

[Chemical Formula H]

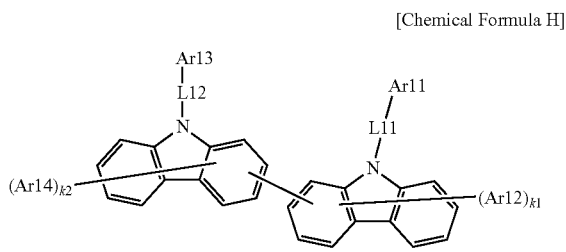

In Chemical Formula H,
Ar11 to Ar14 are the same as or different from each other, and each independently hydrogen; deuterium; a substituted or unsubstituted alkyl group; a substituted or unsubstituted aryl group; or a substituted or unsubstituted heteroaryl group,
L11 and L12 are the same as or different from each other, and each independently a direct bond; a substituted or unsubstituted divalent aryl group; or a substituted or unsubstituted divalent heteroaryl group,
k1 and k2 are each independently an integer of 0 to 7,
when k1 is 2 or greater, Ar12s are the same as or different from each other, and
when k2 is 2 or greater, Ar14s are the same as or different from each other.

In one embodiment of the present specification, Ar11 and Ar12 are the same as or different from each other, and each independently a substituted or unsubstituted aryl group; or a substituted or unsubstituted heteroaryl group.

In one embodiment of the present specification, Ar11 and Ar12 are the same as or different from each other, and each independently a substituted or unsubstituted aryl group having 6 to 30 carbon atoms; or a substituted or unsubstituted heteroaryl group having 2 to 30 carbon atoms.

In one embodiment of the present specification, Ar11 and Ar12 are the same as or different from each other, and each independently a substituted or unsubstituted aryl group having 6 to 18 carbon atoms; or a substituted or unsubstituted heteroaryl group having 2 to 15 carbon atoms.

In one embodiment of the present specification, Ar11 and Ar12 are the same as or different from each other, and each independently an aryl group unsubstituted or substituted with an aryl group or a heteroaryl group; or a heteroaryl group unsubstituted or substituted with an aryl group or a heteroaryl group.

In one embodiment of the present specification, Ar11 and Ar12 are the same as or different from each other, and each independently a phenyl group; a biphenyl group; or a triazinyl group unsubstituted or substituted with a phenyl group or a biphenyl group.

In one embodiment of the present specification, Ar13 and Ar14 are the same as or different from each other, and each independently hydrogen; deuterium; an alkyl group; an aryl group unsubstituted or substituted with an aryl group or a heteroaryl group; or a heteroaryl group unsubstituted or substituted with an aryl group or a heteroaryl group.

In one embodiment of the present specification, Ar13 and Ar14 are the same as or different from each other, and each independently hydrogen; a methyl group; a phenyl group; a biphenyl group; or a carbazolyl group unsubstituted or substituted with a phenyl group.

In one embodiment of the present specification, Ar13 and Ar14 are the same as or different from each other, and each independently hydrogen; or deuterium.

In one embodiment of the present specification, L11 and L12 are the same as or different from each other, and each independently a direct bond; a substituted or unsubstituted divalent aryl group having 6 to 20 carbon atoms; or a substituted or unsubstituted divalent heteroaryl group having 2 to 20 carbon atoms.

In one embodiment of the present specification, L11 and L12 are the same as or different from each other, and each independently a direct bond; a divalent aryl group unsubstituted or substituted with an aryl group; or a divalent heteroaryl group unsubstituted or substituted with an aryl group.

In one embodiment of the present specification, L11 and L12 are the same as or different from each other, and each independently a direct bond; or a phenylene group.

In one embodiment of the present specification, the light emitting layer comprising the compound of Chemical Formula 1 further comprises a dopant.

In one embodiment of the present specification, the light emitting layer comprising the compound of Chemical Formula 1 further comprises a dopant, and a content of the dopant is greater than or equal to 0.1 parts by weight and less than or equal to 20 parts by weight; or greater than or equal to 1 parts by weight and less than or equal to 15 parts by weight with respect to a total 100 parts by weight of the light emitting layer.

In one embodiment of the present specification, the dopant is an iridium complex.

In one embodiment of the present specification, the dopant is a compound of the following Chemical Formula Dp.

[Chemical Formula Dp]

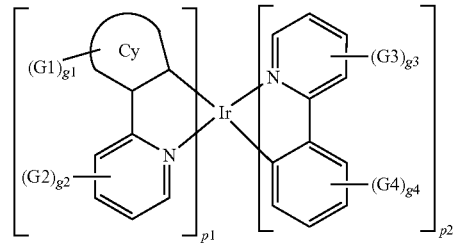

In Chemical Formula Dp,
G1 to G4 are the same as or different from each other, and each independently hydrogen; deuterium; a halogen group; an alkyl group; an aryl group; —OR$_{11}$; —C(=O)R$_{12}$; an aryl group; or a heteroaryl group, and adjacent G1s; adjacent G2s; adjacent G3s; or adjacent G4s can bond to each other to form a ring unsubstituted or substituted with deuterium; a halogen group; an alkyl group; an aryl group; —OR$_{13}$; —C(=O)R$_{14}$; an aryl group; or a heteroaryl group,
R$_{11}$ to R$_{14}$ are the same as or different from each other, and each independently an alkyl group; or an aryl group, Cy is an aromatic ring, g1 is an integer of 0 or greater, and when g1 is 2 or greater, G1s are the same as or different from each other, g2 is an integer of 0 to 4, and when g2 is 2 or greater, G2s are the same as or different from each other, g3 is an integer of 0 to 4, and when g3 is 2 or greater, G3s are the same as or different from each other, g4 is an integer of 0 to 4, and when g4 is 2 or greater, G4s are the same as or different from each other, p1 is 1 or 2, p2 is 1 or 2, a sum of p1 and p2 is 3, when p1 is 2,

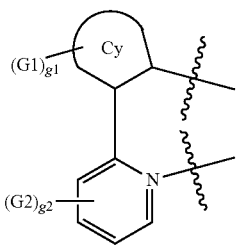

s are the same as or different from each other, and when p2 is 2,

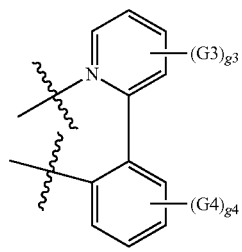

s are the same as or different from each other.

In one embodiment of the present specification, Cy is an aromatic hydrocarbon ring; or an aromatic heteroring.

In one embodiment of the present specification, Cy is an aromatic hydrocarbon ring; or an aromatic heteroring comprising at least one element selected form the group consisting of N, S and O.

In one embodiment of the present specification, Cy is an aromatic ring having 3 to 14 carbon atoms.

In one embodiment of the present specification, Cy is an aromatic ring having 3 to 10 carbon atoms.

In one embodiment of the present specification, Cy is benzene; thiophene; or benzothiophene.

In one embodiment of the present specification, Chemical Formula Dp is of the following Chemical Formula Dp'.

[Chemical Formula Dp']

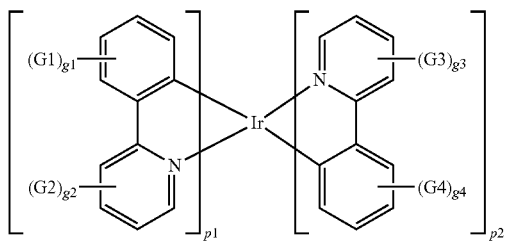

In Chemical Formula Dp',

G1 to G4, g2, g3, g4, p1 and p2 have the same definitions as in Chemical Formula Dp, and g1 is an integer of 0 to 4, and when g1 is 2 or greater, G1s are the same as or different from each other.

In one embodiment of the present specification, G1 to G4 are the same as or different from each other, and each independently hydrogen; deuterium; a halogen group; an alkyl group; an aryl group; $-OR_{11}$; $-C(=O)R_{12}$; an aryl group; or a heteroaryl group, and adjacent G1s; adjacent G2s; adjacent G3s; or adjacent G4s can bond to each other to form a benzene ring unsubstituted or substituted with deuterium; a halogen group; an alkyl group; an aryl group; $-OR_{13}$; $-C(=O)RN$; an aryl group; or a heteroaryl group.

In one embodiment of the present specification, the organic material layer comprises a hole injection layer; a hole transfer layer; a layer carrying out hole transfer and injection at the same time; a hole control layer; an electron control layer; an electron injection layer; an electron transfer layer; or a layer carrying out electron transfer and injection at the same time, and the hole injection layer; the hole transfer layer; the layer carrying out hole transfer and injection at the same time; the hole control layer; the electron control layer; the electron injection layer; the electron transfer layer; or the layer carrying out electron transfer and injection at the same time comprises the compound of Chemical Formula 1.

In one embodiment of the present specification, the organic light emitting device may be an organic light emitting device having a normal structure in which an anode, one or more organic material layers and a cathode are consecutively laminated on a substrate (normal type).

In one embodiment of the present specification, the organic light emitting device may be an organic light emitting device having a structure in a reverse direction in which a cathode, one or more organic material layers and an anode are consecutively laminated on a substrate (inverted type).

In one embodiment of the present specification, the first electrode is an anode, and the second electrode is a cathode.

In another embodiment, the first electrode is a cathode, and the second electrode is an anode.

The organic light emitting device according to one embodiment of the present specification may have structures as illustrated in FIGS. 1 and 2.

As illustrated in FIG. 1, the organic light emitting device according to one embodiment of the present disclosure may be formed with a substrate (1), an anode (2), an organic material layer (3) and a cathode (4). In one embodiment, the compound of Chemical Formula 1 is included in the organic material layer (3).

As illustrated in FIG. 2, the organic light emitting device according to one embodiment of the present disclosure may be formed with a substrate (1), an anode (2), a hole injection layer (5), a hole transfer layer (6), a hole control layer (7), a light emitting layer (8), an electron transfer layer (9), an electron injection layer (10) and a cathode (4). In one embodiment, the compound of Chemical Formula 1 is included in the light emitting layer (8). In another embodiment, the compound of Chemical Formula 1 is included in any one of the hole transfer layer (5), the hole transfer layer (6) and the hole control layer (7). In still another embodiment, the compound of Chemical Formula 1 is included in the electron transfer layer (9) or the electron injection layer (10).

However, the structure of the organic light emitting device according to one embodiment of the present specification is not limited to FIG. 1 and FIG. 2, and may be any one of the following structures.

(1) an anode/a hole transfer layer/a light emitting layer/a cathode
(2) an anode/a hole injection layer/a hole transfer layer/a light emitting layer/a cathode
(3) an anode/a hole transfer layer/a light emitting layer/an electron transfer layer/a cathode
(4) an anode/a hole transfer layer/a light emitting layer/an electron transfer layer/an electron injection layer/a cathode
(5) an anode/a hole injection layer/a hole transfer layer/a light emitting layer/an electron transfer layer/a cathode
(6) an anode/a hole injection layer/a hole transfer layer/a light emitting layer/an electron transfer layer/an electron injection layer/a cathode
(7) an anode/a hole transfer layer/a hole control layer/a light emitting layer/an electron transfer layer/a cathode
(8) an anode/a hole transfer layer/a hole control layer/a light emitting layer/an electron transfer layer/an electron injection layer/a cathode
(9) an anode/a hole injection layer/a hole transfer layer/a hole control layer/a light emitting layer/an electron transfer layer/a cathode
(10) an anode/a hole injection layer/a hole transfer layer/a hole control layer/a light emitting layer/an electron transfer layer/an electron injection layer/a cathode
(11) an anode/a hole transfer layer/a light emitting layer/an electron control layer/an electron transfer layer/a cathode
(12) an anode/a hole transfer layer/a light emitting layer/an electron control layer/an electron transfer layer/an electron injection layer/a cathode
(13) an anode/a hole injection layer/a hole transfer layer/a light emitting layer/an electron control layer/an electron transfer layer/a cathode
(14) an anode/a hole injection layer/a hole transfer layer/a light emitting layer/an electron control layer/an electron transfer layer/an electron injection layer/a cathode When the organic light emitting device includes a plurality of organic material layers, the organic material layers may be formed with materials the same as or different from each other.

For example, the organic light emitting device of the present specification may be manufactured by consecutively laminating a first electrode, an organic material layer and a second electrode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon.

In addition, the compound of Chemical Formula 1 may be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such a method, the organic light emitting device may also be manufactured by consecutively depositing a cathode material, an organic material layer and an anode material on a substrate (International Patent Application Laid-Open Publication No. 2003/012890). However, the manufacturing method is not limited thereto.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer injecting holes received from an electrode to a light emitting layer or an adjacent layer provided on a light emitting layer side. As the hole injection material, compounds having an ability to transfer holes, therefore, having a hole injection effect in an anode, having an excellent hole injection effect for a light emitting layer or a light emitting material, preventing excitons generated in the light emitting layer from moving to an electron injection layer or an electron injection material, and in addition thereto, having an excellent thin film forming ability are preferably used. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer receiving holes from a hole injection layer and transferring the holes to a light emitting layer or an adjacent layer provided on a light emitting layer side. As the hole transfer material, materials capable of receiving holes from an anode or a hole injection layer, moving the holes to a light emitting layer, and having high mobility for the holes are suited. Specific examples the hole transfer material include arylamine-based organic materials, conductive polymers, block copolymers having conjugated parts and non-conjugated parts together, and the like, but are not limited thereto.

The hole control layer is a layer controlling performance of a whole device by preventing electrons inflowing from a light emitting layer to an anode and by controlling a flow of holes inflowing to the light emitting layer. As the hole control material, compounds having abilities of preventing electrons inflowing from a light emitting layer to an anode, and controlling a flow of holes injected to the light emitting layer or the light emitting material are preferred. In one embodiment, arylamine-based organic materials may be used as the hole control layer, however, the hole control layer is not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes (Alq$_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene; rubrene, and the like, but are not limited thereto.

The light emitting layer may include a host material and a dopant material. The host material may include fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like may be included, and as the heteroring-containing compound, carbazole derivatives, dibenzofuran derivatives, ladder-type furan compounds, pyrimidine derivatives and the like may be included, however, the host material is not limited thereto.

The dopant material of the light emitting layer may include aromatic amine derivatives, styrylamine compounds, boron complexes, fluoranthene compounds, metal complexes and the like. The aromatic amine derivative is a fused aromatic ring derivative having a substituted or unsubstituted arylamine group, and arylamine group-including pyrene, anthracene, chrysene, peryflanthene and the like may be used. As the styrylamine compound, compounds in which substituted or unsubstituted arylamine is substituted with at least one arylvinyl group may be used. Examples of the styralamine compound may include styrylamine, styryldiamine, styryltriamine, styryltetramine and the like, but are not limited thereto. As the metal complex, iridium complexes, platinum complexes and the like may be used, however, the metal complex is not limited thereto.

The electron control layer is a layer controlling performance of a whole device by blocking holes inflowing from a light emitting layer to a cathode and by controlling electrons inflowing to the light emitting layer. As the electron control material, compounds having abilities of preventing holes inflowing from a light emitting layer to a cathode, and controlling electrons injected to the light emitting layer or the light emitting material are preferred. As the electron control material, proper materials may be used depending on the constitution of the organic material layers used in a device. The electron control layer is placed between a light emitting layer and a cathode, and is preferably provided directly in contact with a light emitting layer.

The electron transfer layer is a layer receiving electrons from an electron injection layer and transferring the electrons to a light emitting layer. As the electron transfer material, materials capable of favorably receiving electrons from a cathode, moving the electrons to a light emitting layer, and having high mobility for the electrons are suited. Examples of the electron transfer material may include Al complexes of 8-hydroxyquinoline; complexes including Alq$_3$; organic radical compounds; hydroxyflavon-metal complexes, and the like, but are not limited thereto. The electron transfer layer may be used together with any desired cathode material as used in the art. In one embodiment, as the cathode material, materials having low work function; and an aluminum layer or a silver layer may be used. Examples of the material having low work function may include cesium, barium, calcium, ytterbium, samarium and the like, and after forming a layer with the above-mentioned material, an aluminum layer or a silver layer may be formed on the layer.

The electron injection layer is a layer injecting electrons received from an electrode to a light emitting layer. As the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferably used. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(O-cresolato)gallium, bis(2-methyl-8-quinolinato) (1-naphtholato)aluminum, bis(2-methyl-8-quinolinato) (2-naphtholato)gallium and the like, but is not limited thereto.

The organic light emitting device according to the present specification may be a top-emission type, a bottom-emission type or a dual-emission type depending on the materials used.

MODE FOR CARRYING OUT THE INVENTION

A method for preparing the compound of Chemical Formula 1 and a method for manufacturing an organic light emitting device including the same will be specifically described in the following examples. However, the following examples are for illustrative purposes only, and the scope of the present disclosure is not limited thereto.

PREPARATION EXAMPLE

Preparation Example 1: Preparation of Compound A1

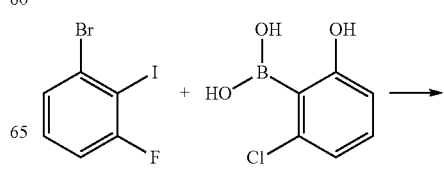

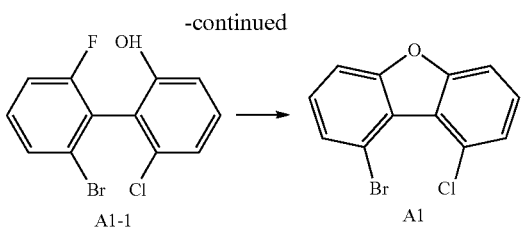

Preparation of Compound A1-1

1-Bromo-3-fluoro-2-iodobenzene (100 g, 332.34 mmol) and (2-chloro-6-hydroxyphenyl)boronic acid (57.3 g, 332.34 mmol) were dissolved in tetrahydrofuran (THF) (800 ml). A 2 M sodium carbonate (Na$_2$CO$_3$) solution (500 mL) and tetrakis(triphenylphosphine)palladium(0) [Pd(PPh$_3$)$_4$] (11.5 g, 9.97 mmol) were introduced thereto, and the result was refluxed for 12 hours. After the reaction was finished, the result was cooled to room temperature, and a produced mixture was extracted three times with water and toluene. The toluene layer was separated and dried with magnesium sulfate, and a mixture obtained by vacuum distilling the filtered filtrate was recrystallized three times using chloroform and ethanol to obtain Compound A1-1 (62.1 g, yield 52%; MS: [M+H]$^+$=301).

Preparation of Compound A1

Compound A1-1 (40 g, 199 mmol) was dissolved in dimethylformamide (DMF) (400 ml). Potassium carbonate (82.5 g, 596.9 mmol) was introduced thereto, and the result was stirred for 1 hour at 100° C. After the reaction was finished, the result was cooled to room temperature, and ethanol (100 ml) was slowly introduced thereto. A mixture obtained by vacuum distilling the above-described mixture was recrystallized with chloroform and ethyl acetate to obtain Compound A1 (43.7 g, yield 78%; MS: [M+H]$^+$=282).

Preparation Example 2: Preparation of Compound A2

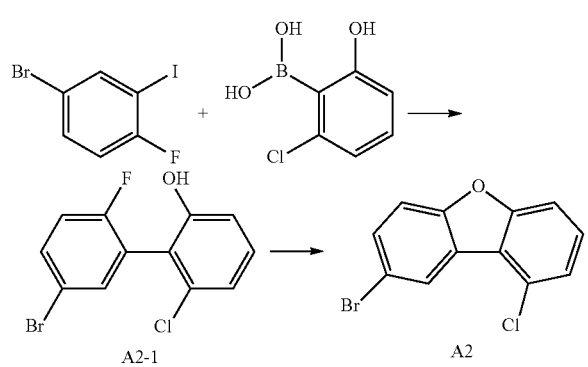

Preparation of Compound A2-1

4-Bromo-1-fluoro-2-iodobenzene (100 g, 332.34 mmol) and (2-chloro-6-hydroxyphenyl)boronic acid (57.3 g, 332.34 mmol) were dissolved in tetrahydrofuran (THF) (800 ml). A 2 M sodium carbonate (Na$_2$CO$_3$) solution (500 mL) and tetrakis(triphenylphosphine)palladium(0) [Pd(PPh$_3$)$_4$] (11.5 g, 9.97 mmol) were introduced thereto, and the result was refluxed for 12 hours. After the reaction was finished, the result was cooled to room temperature, and a produced mixture was extracted three times with water and toluene. The toluene layer was separated and dried with magnesium sulfate, and a mixture obtained by vacuum distilling the filtered filtrate was recrystallized three times using chloroform and ethanol to obtain Compound A2-1 (68.1 g, yield 68%; MS: [M+H]$^+$=301).

Preparation of Compound A2

Compound A2-1 (40 g, 132.65 mmol) was dissolved in dimethylformamide (DMF) (400 ml). Potassium carbonate (55 g, 398 mmol) was introduced thereto, and the result was stirred for 1 hour at 100° C. After the reaction was finished, the result was cooled to room temperature, and ethanol (100 ml) was slowly introduced thereto. A mixture obtained by vacuum distilling the above-described mixture was recrystallized with chloroform and ethyl acetate to obtain Compound A2 (26.5 g, yield 71%; MS: [M+H]$^+$=282).

Preparation Example 3: Preparation of Compound A3

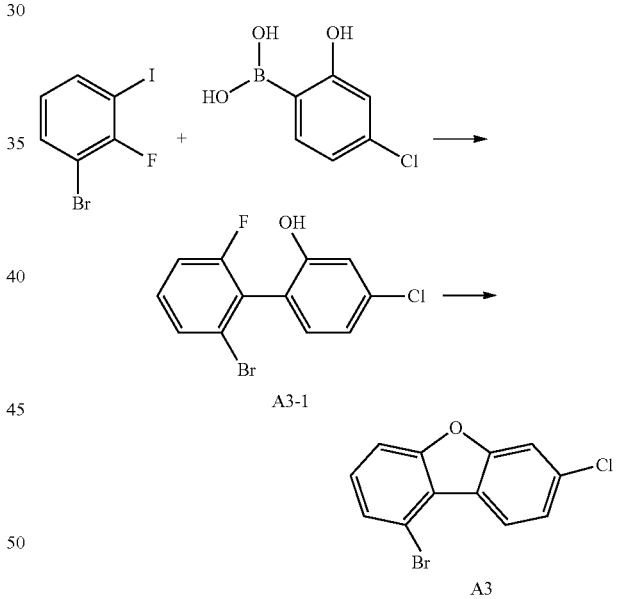

Preparation of Compound A3-1

1-Bromo-3-fluoro-2-iodobenzene (100 g, 332.34 mmol) and 4-chloro-2-hydroxyphenyl)boronic acid (57.3 g, 332.34 mmol) were dissolved in tetrahydrofuran (THF) (800 ml). A 2 M sodium carbonate (Na$_2$CO$_3$) solution (500 mL) and tetrakis(triphenylphosphine)palladium(0) [Pd(PPh$_3$)$_4$] (11.5 g, 9.97 mmol) were introduced thereto, and the result was refluxed for 12 hours. After the reaction was finished, the result was cooled to room temperature, and a produced mixture was extracted three times with water and toluene. The toluene layer was separated and dried with magnesium sulfate, and a mixture obtained by vacuum distilling the filtered filtrate was recrystallized three times using chloroform and ethanol to obtain Compound A3-1 (71.2 g, yield 71%; MS: [M+H]⁺=301).

Preparation of Compound A3

Compound A3-1 (40 g, 132.6 mmol) was dissolved in dimethylformamide (DMF) (400 ml). Potassium carbonate (55 g, 398 mmol) was introduced thereto, and the result was stirred for 1 hour at 100° C. After the reaction was finished, the result was cooled to room temperature, and ethanol (100 ml) was slowly introduced thereto. A mixture obtained by vacuum distilling the above-described mixture was recrystallized with chloroform and ethyl acetate to obtain Compound A3 (24.3 g, yield 65%; MS: [M+H]⁺=282).

Preparation Example 4: Preparation of Compound A4

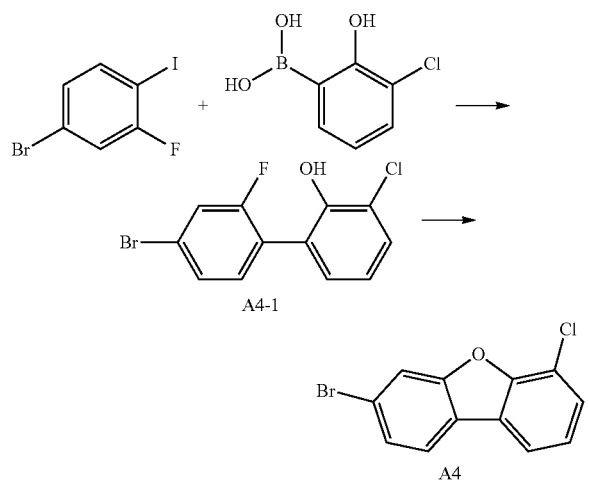

Preparation of Compound A4-1

4-Bromo-2-fluoro-1-iodobenzene (100 g, 332.34 mmol) and (3-chloro-2-hydroxyphenyl)boronic acid (57.3 g, 332.34 mmol) were dissolved in tetrahydrofuran (THF) (800 ml). A 2 M sodium carbonate (Na₂CO₃) solution (500 mL) and tetrakis(triphenylphosphine)palladium(0) [Pd(PPh₃)₄] (11.5 g, 9.97 mmol) were introduced thereto, and the result was refluxed for 12 hours. After the reaction was finished, the result was cooled to room temperature, and a produced mixture was extracted three times with water and toluene. The toluene layer was separated and dried with magnesium sulfate, and a mixture obtained by vacuum distilling the filtered filtrate was recrystallized three times using chloroform and ethanol to obtain Compound A4-1 (78.2 g, yield 78%; MS: [M+H]⁺=301).

Preparation of Compound A4

Compound A4-1 (40 g, 132.6 mmol) was dissolved in dimethylformamide (DMF) (400 ml). Potassium carbonate (55 g, 398 mmol) was introduced thereto, and the result was stirred for 1 hour at 100° C. After the reaction was finished, the result was cooled to room temperature, and ethanol (100 ml) was slowly introduced thereto. A mixture obtained by vacuum distilling the above-described mixture was recrystallized with chloroform and ethyl acetate to obtain Compound A4 (23.9 g, yield 64%; MS: [M+H]⁺=282).

Preparation Example 5: Preparation of Compound A5

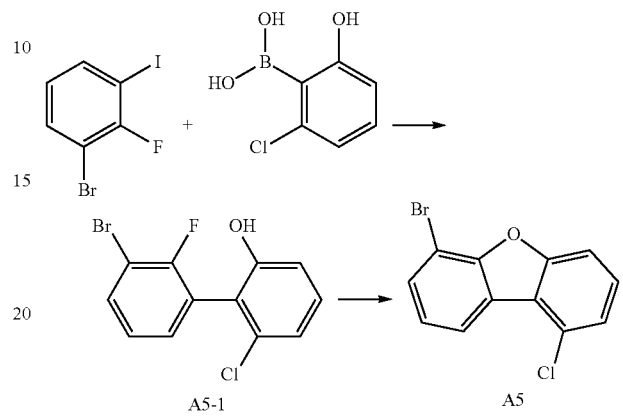

Preparation of Compound A5-1

1-Bromo-2-fluoro-3-iodobenzene (100 g, 332.34 mmol) and (2-chloro-6-hydroxyphenyl)boronic acid (57.3 g, 332.34 mmol) were dissolved in tetrahydrofuran (THF) (800 ml). A 2 M sodium carbonate (Na₂CO₃) solution (500 mL) and tetrakis(triphenylphosphine)palladium(0) [Pd(PPh₃)₄] (11.5 g, 9.97 mmol) were introduced thereto, and the result was refluxed for 12 hours. After the reaction was finished, the result was cooled to room temperature, and a produced mixture was extracted three times with water and toluene. The toluene layer was separated and dried with magnesium sulfate, and a mixture obtained by vacuum distilling the filtered filtrate was recrystallized three times using chloroform and ethanol to obtain Compound A5-1 (64.1 g, yield 64%; MS: [M+H]⁺=301).

Preparation of Compound A5

Compound A5-1 (40 g, 132.65 mmol) was dissolved in dimethylformamide (DMF) (400 ml). Potassium carbonate (55 g, 398 mmol) was introduced thereto, and the result was stirred for 1 hour at 100° C. After the reaction was finished, the result was cooled to room temperature, and ethanol (100 ml) was slowly introduced thereto. A mixture obtained by vacuum distilling the above-described mixture was recrystallized with chloroform and ethyl acetate to obtain Compound A5 (28 g, yield 75%; MS: [M+H]⁺=282).

Preparation Example 6: Preparation of Compound A6

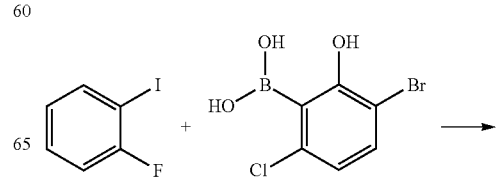

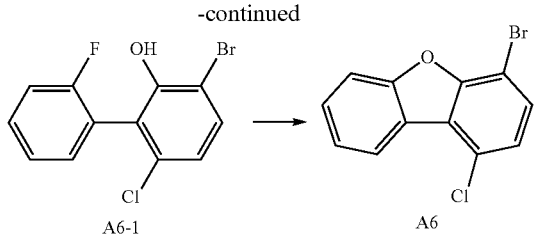

Preparation of Compound A6-1

Fluoro-2-iodobenzene (66 g, 299.99 mmol) and (3-bromo-6-chloro-2-hydroxyphenyl)boronic acid (75.38 g, 299.99 mmol) were dissolved in tetrahydrofuran (THF) (800 ml). A 2 M sodium carbonate (Na$_2$CO$_3$) solution (500 mL) and tetrakis(triphenylphosphine)palladium(0) [Pd(PPh$_3$)$_4$] (10.4 g, 9 mmol) were introduced thereto, and the result was refluxed for 12 hours. After the reaction was finished, the result was cooled to room temperature, and a produced mixture was extracted three times with water and toluene. The toluene layer was separated and dried with magnesium sulfate, and a mixture obtained by vacuum distilling the filtered filtrate was recrystallized three times using chloroform and ethanol to obtain Compound A6-1 (64.1 g, yield 64%; MS: [M+H]$^+$=301)

Preparation of Compound A6

Compound A6-1 (40 g, 132.65 mmol) was dissolved in dimethylformamide (DMF) (400 ml). Potassium carbonate (55 g, 397.96 mmol) was introduced thereto, and the result was stirred for 1 hour at 100° C. After the reaction was finished, the result was cooled to room temperature, and ethanol (100 ml) was slowly introduced thereto. A mixture obtained by vacuum distilling the above-described mixture was recrystallized with chloroform and ethyl acetate to obtain Compound A6 (29.5 g, yield 79%; MS: [M+H]$^+$=282).

Preparation Example 7: Preparation of Compound A7

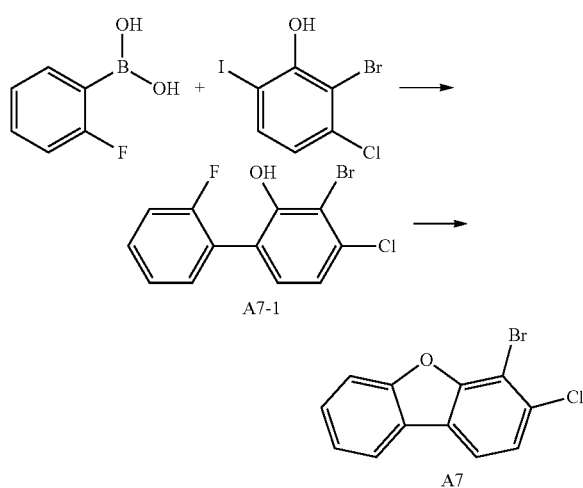

Preparation of Compound A7-1

2-Bromo-3-chloro-6-iodophenol (42 g, 299.99 mmol) and (2-fluorophenyl)boronic acid (100 g, 299.99 mmol) were dissolved in tetrahydrofuran (THF) (800 ml). A 2 M sodium carbonate (Na$_2$CO$_3$) solution (500 mL) and tetrakis(triphenylphosphine)palladium(0) [Pd(PPh$_3$)$_4$] (10.4 g, 9 mmol) were introduced thereto, and the result was refluxed for 12 hours. After the reaction was finished, the result was cooled to room temperature, and a produced mixture was extracted three times with water and toluene. The toluene layer was separated and dried with magnesium sulfate, and a mixture obtained by vacuum distilling the filtered filtrate was recrystallized three times using chloroform and ethanol to obtain Compound A7-1 (46.1 g, yield 51%; MS: [M+H]$^+$=301).

Preparation of Compound A7

Compound A7-1 (40 g, 132.65 mmol) was dissolved in dimethylformamide (DMF) (400 ml). Potassium carbonate (55 g, 397.96 mmol) was introduced thereto, and the result was stirred for 1 hour at 100° C. After the reaction was finished, the result was cooled to room temperature, and ethanol (100 ml) was slowly introduced thereto. A mixture obtained by vacuum distilling the above-described mixture was recrystallized with chloroform and ethyl acetate to obtain Compound A7 (29.9 g, yield 80%; MS: [M+H]$^+$=282).

Preparation Example 8: Preparation of Compound A8

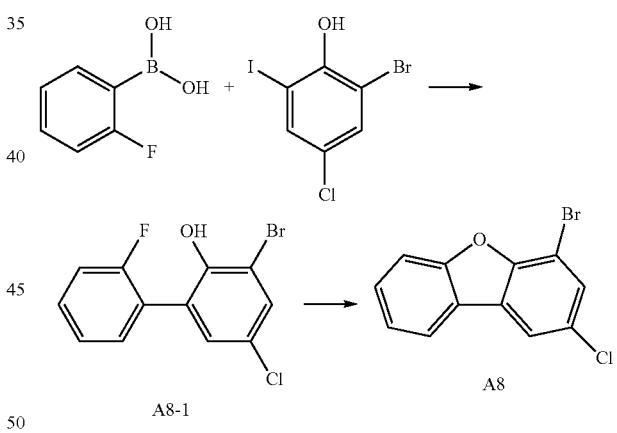

Preparation of Compound A8-1

2-Bromo-4-chloro-6-iodophenol (100 g, 299.99 mmol) and (2-fluorophenyl)boronic acid (42 g, 299.99 mmol) were dissolved in tetrahydrofuran (THF) (800 ml). A 2 M sodium carbonate (Na$_2$CO$_3$) solution (500 mL) and tetrakis(triphenylphosphine)palladium(0) [Pd(PPh$_3$)$_4$] (10.4 g, 9 mmol) were introduced thereto, and the result was refluxed for 12 hours. After the reaction was finished, the result was cooled to room temperature, and a produced mixture was extracted three times with water and toluene. The toluene layer was separated and dried with magnesium sulfate, and a mixture obtained by vacuum distilling the filtered filtrate was recrystallized three times using chloroform and ethanol to obtain Compound A8-1 (41.6 g, yield 46%; MS: [M+H]$^+$=301).

Preparation of Compound A8

Compound A8-1 (40 g, 132.65 mmol) was dissolved in dimethylformamide (DMF) (400 ml). Potassium carbonate (55 g, 397.96 mmol) was introduced thereto, and the result was stirred for 1 hour at 100° C. After the reaction was finished, the result was cooled to room temperature, and ethanol (100 ml) was slowly introduced thereto. A mixture obtained by vacuum distilling the above-described mixture was recrystallized with chloroform and ethyl acetate to obtain Compound A8 (26.5 g, yield 71%; MS: [M+H]$^+$=282).

Preparation Example 9: Preparation of Compound A9

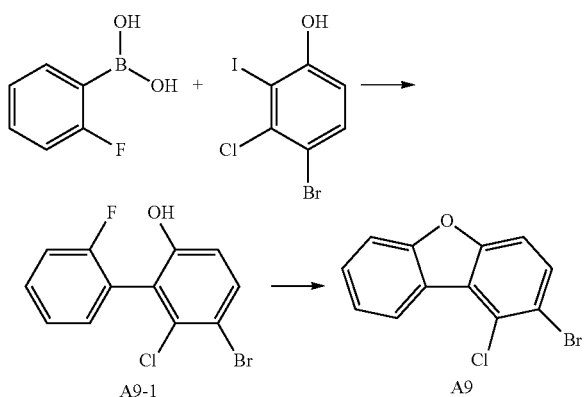

Preparation of Compound A9-1

4-Bromo-3-chloro-2-iodophenol (100 g, 299.99 mmol) and (2-fluorophenyl)boronic acid (42 g, 299.99 mmol) were dissolved in tetrahydrofuran (THF) (800 ml). A 2 M sodium carbonate (Na$_2$CO$_3$) solution (500 mL) and tetrakis(triphenylphosphine)palladium(0) [Pd(PPh$_3$)$_4$] (10.4 g, 9 mmol) were introduced thereto, and the result was refluxed for 12 hours. After the reaction was finished, the result was cooled to room temperature, and a produced mixture was extracted three times with water and toluene. The toluene layer was separated and dried with magnesium sulfate, and a mixture obtained by vacuum distilling the filtered filtrate was recrystallized three times using chloroform and ethanol to obtain Compound A9-1 (43.4 g, yield 48%; MS: [M+H]$^+$=301).

Preparation of Compound A9

Compound A9-1 (40 g, 132.65 mmol) was dissolved in dimethylformamide (DMF) (400 ml). Potassium carbonate (55 g, 397.96 mmol) was introduced thereto, and the result was stirred for 1 hour at 100° C. After the reaction was finished, the result was cooled to room temperature, and ethanol (100 ml) was slowly introduced thereto. A mixture obtained by vacuum distilling the above-described mixture was recrystallized with chloroform and ethyl acetate to obtain Compound A9 (24.3 g, yield 65%; MS: [M+H]$^+$=282).

Preparation Example 10: Preparation of Compound A10

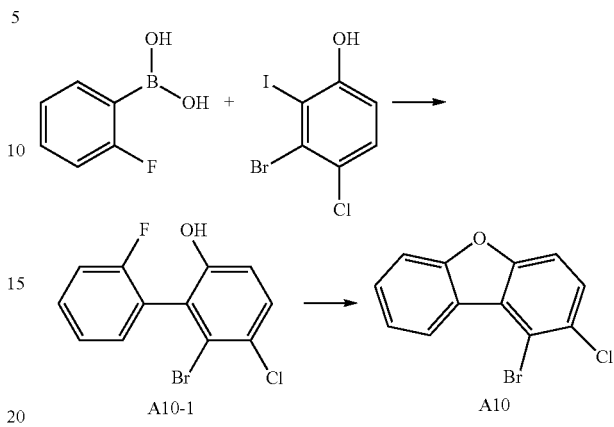

Preparation of Compound A10-1

3-Bromo-4-chloro-2-iodophenol (100 g, 299.99 mmol) and (2-fluorophenyl)boronic acid (42 g, 299.99 mmol) were dissolved in tetrahydrofuran (THF) (800 ml). A 2 M sodium carbonate (Na$_2$CO$_3$) solution (500 mL) and tetrakis(triphenylphosphine)palladium(0) [Pd(PPh$_3$)$_4$] (10.4 g, 9 mmol) were introduced thereto, and the result was refluxed for 12 hours. After the reaction was finished, the result was cooled to room temperature, and a produced mixture was extracted three times with water and toluene. The toluene layer was separated and dried with magnesium sulfate, and a mixture obtained by vacuum distilling the filtered filtrate was recrystallized three times using chloroform and ethanol to obtain Compound A10-1 (46.1 g, yield 51%; MS: [M+H]$^+$=301).

Preparation of Compound A10

Compound A10-1 (40 g, 132.65 mmol) was dissolved in dimethylformamide (DMF) (400 ml). Potassium carbonate (55 g, 397.96 mmol) was introduced thereto, and the result was stirred for 1 hour at 100° C. After the reaction was finished, the result was cooled to room temperature, and ethanol (100 ml) was slowly introduced thereto. A mixture obtained by vacuum distilling the above-described mixture was recrystallized with chloroform and ethyl acetate to obtain Compound A10 (21.3 g, yield 57%; MS: [M+H]$^+$=282).

Preparation Example 11: Preparation of Compound B1

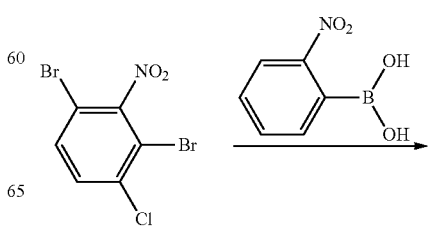

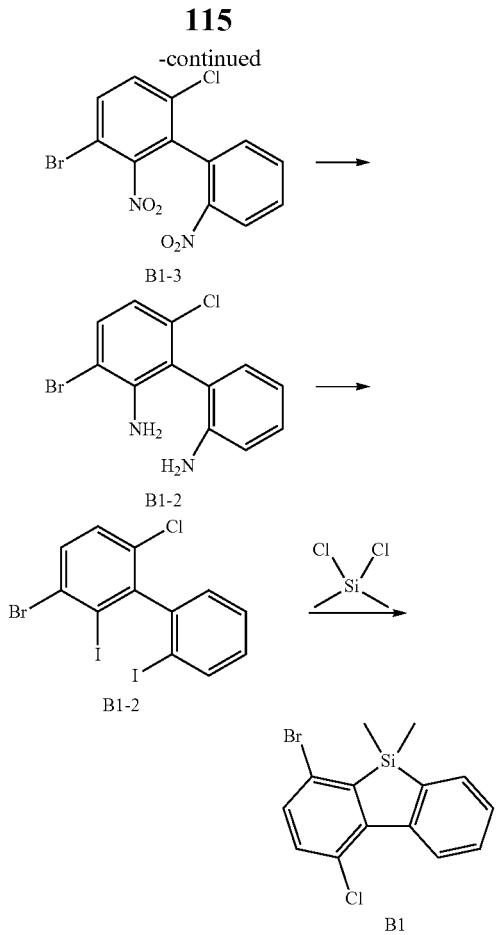

Preparation of Compound B1-3

1,3-Dibromo-4-chloro-2-nitrobenzene (87.03 g, 275.98 mmol) and (2-nitrophenyl)boronic acid (46.1 g, 275.98 mmol) were dissolved in tetrahydrofuran (THF) (800 ml). A 2 M sodium carbonate ($Na_2CO_3$) solution (500 mL) and tetrakis(triphenylphosphine)palladium(0) [$Pd(PPh_3)_4$] (9.6 g, 8.28 mmol) were introduced thereto, and the result was refluxed for 6 hours at 50° C. After the reaction was finished, the result was cooled to room temperature, and a produced mixture was extracted three times with water and toluene. The toluene layer was separated and dried with magnesium sulfate, and a mixture obtained by vacuum distilling the filtered filtrate was recrystallized three times using chloroform and ethanol to obtain Compound B1-3 (50.3 g, yield 51%; MS: $[M+H]^+$=358).

Preparation of Compound B1-2

After dissolving Compound B1-3 (20 g, 55.93 mmol) in ethanol (200 mL), a 32% (w/w) aqueous HCl solution (120 mL) was slowly added thereto. Tin powder (26.8 g, 223 mmol) was added portion-wise thereto over 10 minutes, and the result was stirred for 2 hours at 100° C. After cooling the result to room temperature, the reaction mixture was reversely added dropwise to ice water. The result was made basic using a 20% (w/w) aqueous NaOH solution (150 mL), extracted with diethyl ether, washed with brine, then dried and then recrystallized with ethanol to obtain Compound B1-2 (12.5 g, yield 75%; MS: $[M+H]^+$=298).

Preparation of Compound B1-1

After adding a 17% (w/w) aqueous HCl solution (85 mL) to Compound B1-2 (12 g, 40.33 mmol) at 0° C., $NaNO_2$ (7 g) and $H_2O$ (15 mL) were added thereto. The result was stirred for 1 hour at room temperature, and stirred for 3 hours at 80° C. The result was cooled to room temperature, and then neutralized with a saturated aqueous potassium hydroxide (KOH) solution. The result was extracted with ethyl acetate and washed with a saturated aqueous sodium sulfite ($Na_2SO_3$) solution. A mixture obtained by vacuum distilling the organic layer solution was recrystallized using chloroform and ethanol to obtain B1-1 (17 g, yield 81%; MS: $[M+H]^+$=520).

Preparation of Compound B1

After dissolving Compound B1-1 (15 g, 28.88 mmol) in tetrahydrofuran (30 mL) under nitrogen gas, the result was cooled to −78° C. n-Butyl lithium (2.5 M in hexane) (21.4 mL, 63.54 mmol) was slowly added thereto, and the result was stirred for 30 minutes. Dichlorodimethylsilane (8.1 g, 63.54 mmol) was added thereto, and after slowly raising the temperature to room temperature while stirring the result for 12 hours, ethanol was added thereto, and the result was stirred for 10 minutes. The result was extracted with ethyl acetate and washed with water. A mixture obtained by vacuum distilling the organic layer solution was recrystallized using chloroform and ethanol to obtain B1 (7 g, yield 75%; MS: $[M+H]^+$=324).

Preparation Example 12: Preparation of Compound B2

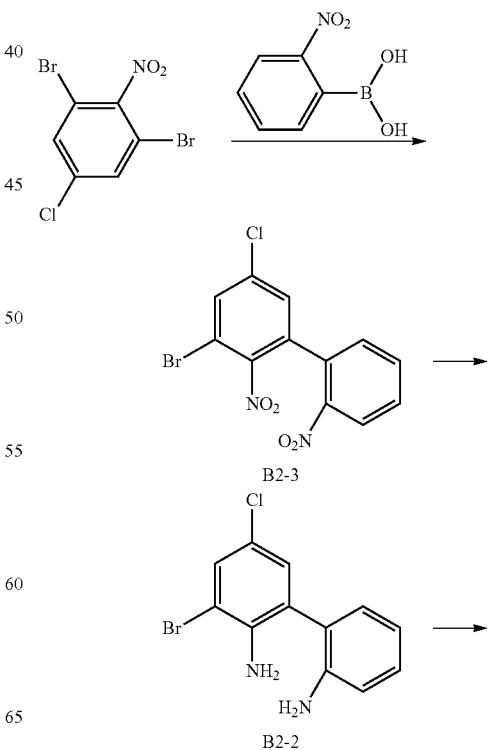

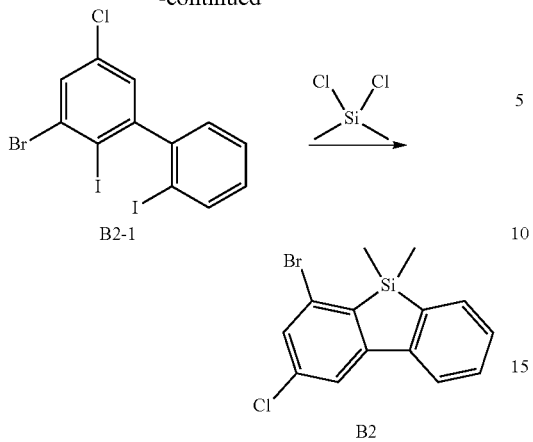

B2-1

B2

Preparation of Compound B2-3

Compound B2-3 was prepared in the same manner as in the method of preparing Compound B1-3 except that 1,3-dibromo-5-chloro-2-nitrobenzene was used instead of 1,3-dibromo-4-chloro-2-nitrobenzene. (62.2 g, yield 63%; MS: [M+H]$^+$=358)

Preparation of Compound B2-2

Compound B2-2 was prepared in the same manner as in the method of preparing Compound B1-2 except that Compound B2-3 was used instead of Compound B1-3. (11.8 g, yield 71%; MS: [M+H]$^+$=298)

Preparation of Compound B2-1

Compound B2-1 was prepared in the same manner as in the method of preparing Compound B1-1 except that Compound B2-2 was used instead of Compound B1-2. (18.6 g, yield 89%; MS: [M+H]$^+$=520)

Preparation of Compound B2

Compound B2 was prepared in the same manner as in the method of preparing Compound B1 except that Compound B2-1 was used instead of Compound B1-1. (6.6 g, yield 71%; MS: [M+H]$^+$=324)

Preparation Example 13: Preparation of Compound B3

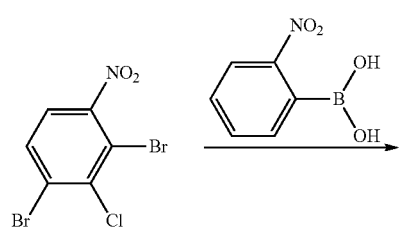

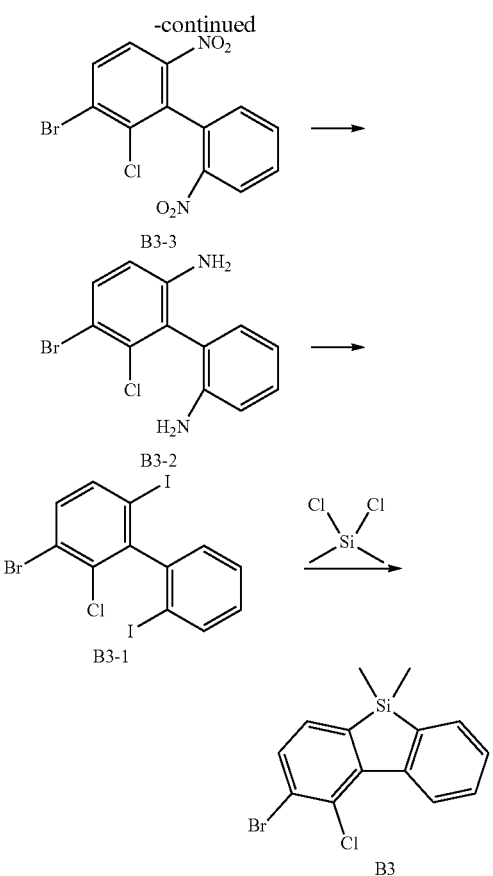

Preparation of Compound B3-3

Compound B3-3 was prepared in the same manner as in the method of preparing Compound B1-3 except that 1,3-dibromo-2-chloro-4-nitrobenzene was used instead of 1,3-dibromo-4-chloro-2-nitrobenzene. (80.9 g, yield 82%; MS: [M+H]$^+$=358)

Preparation of Compound B3-2

Compound B3-2 was prepared in the same manner as in the method of preparing Compound B1-2 except that Compound B3-3 was used instead of Compound B1-3. (13.2 g, yield 84%; MS: [M+H]$^+$=298)

Preparation of Compound B3-1

Compound B3-1 was prepared in the same manner as in the method of preparing Compound B1-1 except that Compound B3-2 was used instead of Compound B1-2. (16.5 g, yield 79%; MS: [M+H]$^+$=520)

Preparation of Compound B3

Compound B3 was prepared in the same manner as in the method of preparing Compound B1 except that Compound B3-1 was used instead of Compound B1-1. (7.9 g, yield 85%; MS: [M+H]$^+$=324)

Preparation Example 14: Preparation of Compound B4

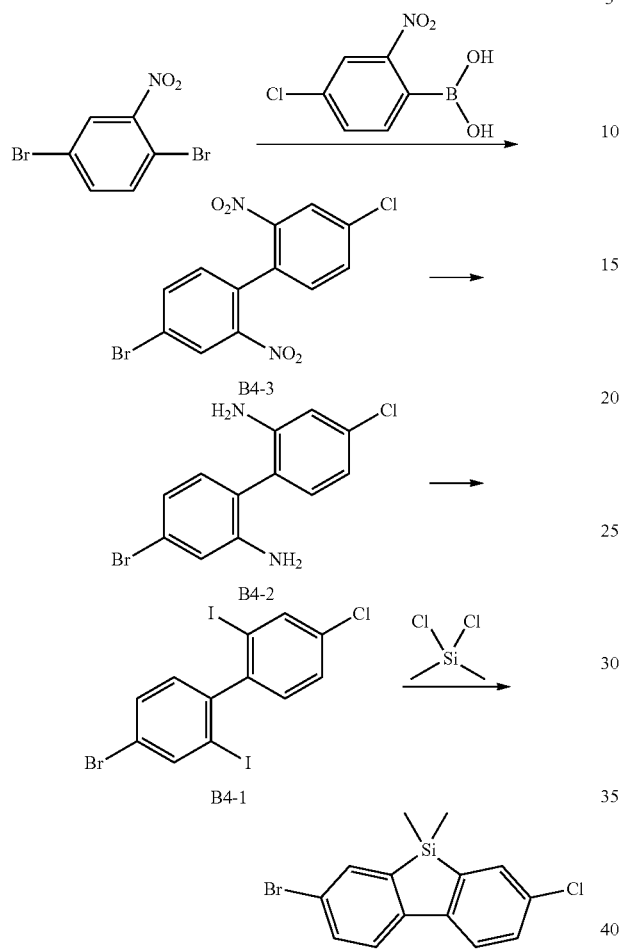

Preparation of Compound B4-3

Compound B4-3 was prepared in the same manner as in the method of preparing Compound B1-3 except that 1,4-dibromo-2-nitrobenzene and (4-chloro-2-nitrophenyl)boronic acid were respectively used instead of 1,3-dibromo-4-chloro-2-nitrobenzene and (2-nitrophenyl)boronic acid. (75 g, yield 76%; MS: [M+H]$^+$=358)

Preparation of Compound B4-2

Compound B4-2 was prepared in the same manner as in the method of preparing Compound B1-2 except that Compound B4-3 was used instead of Compound B1-3. (13.2 g, yield 79%; MS: [M+H]$^+$=298)

Preparation of Compound B4-1

Compound B4-1 was prepared in the same manner as in the method of preparing Compound B1-1 except that Compound B4-2 was used instead of Compound B1-2. (17 g, yield 81%; MS: [M+H]$^+$=520)

Preparation of Compound B4

Compound B4 was prepared in the same manner as in the method of preparing Compound B1 except that Compound B4-1 was used instead of Compound B1-1. (7.3 g, yield 78%; MS: [M+H]$^+$=324)

Preparation Example 15: Preparation of Compound B5

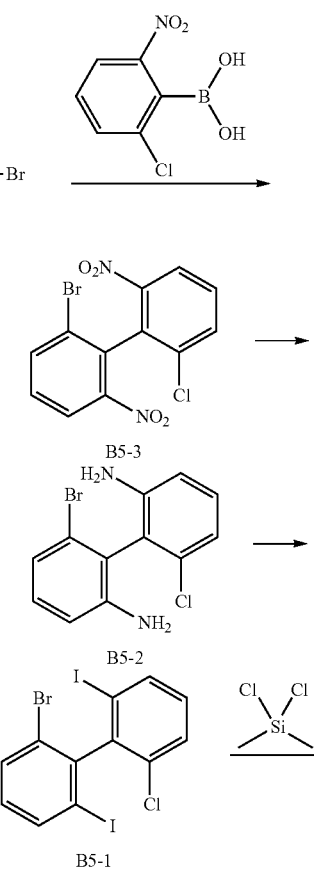

Preparation of Compound B5-3

Compound B5-3 was prepared in the same manner as in the method of preparing Compound B1-3 except that 1,2-dibromo-3-nitrobenzene and (2-chloro-6-nitrophenyl)boronic acid were respectively used instead of 1,3-dibromo-4-chloro-2-nitrobenzene and (2-nitrophenyl)boronic acid. (87.8 g, yield 89%; MS: [M+H]$^+$=358)

Preparation of Compound B5-2

Compound B5-2 was prepared in the same manner as in the method of preparing Compound B1-2 except that Compound B5-3 was used instead of Compound B1-3. (13.5 g, yield 81%; MS: [M+H]$^+$=298)

Preparation of Compound B5-1

Compound B5-1 was prepared in the same manner as in the method of preparing Compound B1-1 except that Compound B5-2 was used instead of Compound B1-2. (15.5 g, yield 74%; MS: [M+H]$^+$=520)

Preparation of Compound B5

Compound B5 was prepared in the same manner as in the method of preparing Compound B1 except that Compound B5-1 was used instead of Compound B1-1. (7.6 g, yield 81%; MS: [M+H]$^+$=324)

Preparation Example 16: Preparation of Compound B6

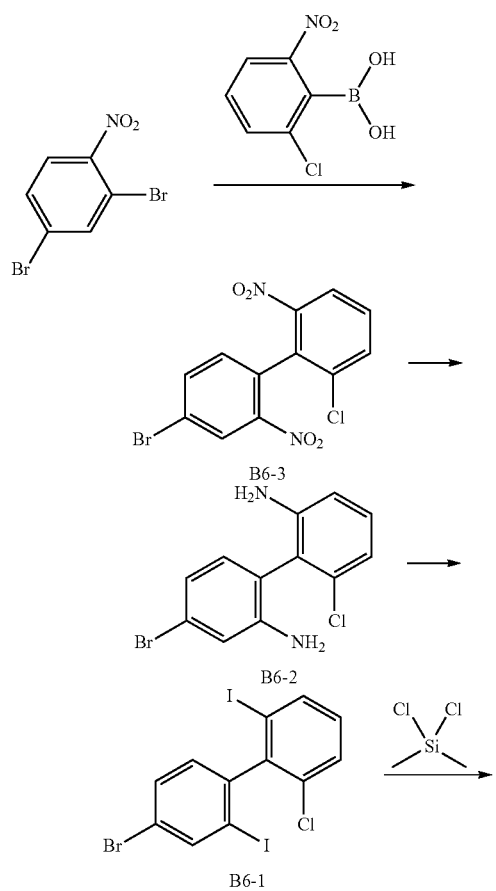

Preparation of Compound B6-3

Compound B6-3 was prepared in the same manner as in the method of preparing Compound B1-3 except that 2,4-dibromo-1-nitrobenzene and (2-chloro-6-nitrophenyl)boronic acid were respectively used instead of 1,3-dibromo-4-chloro-2-nitrobenzene and (2-nitrophenyl)boronic acid. (77 g, yield 78%; MS: [M+H]$^+$=358)

Preparation of Compound B6-2

Compound B6-2 was prepared in the same manner as in the method of preparing Compound B1-2 except that Compound B6-3 was used instead of Compound B1-3. (12.5 g, yield 75%; MS: [M+H]$^+$=298)

Preparation of Compound B6-1

Compound B6-1 was prepared in the same manner as in the method of preparing Compound B1-1 except that Compound B6-2 was used instead of Compound B1-2. (18.6 g, yield 89%; MS: [M+H]$^+$=520)

Preparation of Compound B6

Compound B6 was prepared in the same manner as in the method of preparing Compound B1 except that Compound B6-1 was used instead of Compound B1-1. (8.4 g, yield 90%; MS: [M+H]$^+$=324)

Preparation Example 17: Preparation of Compound B7

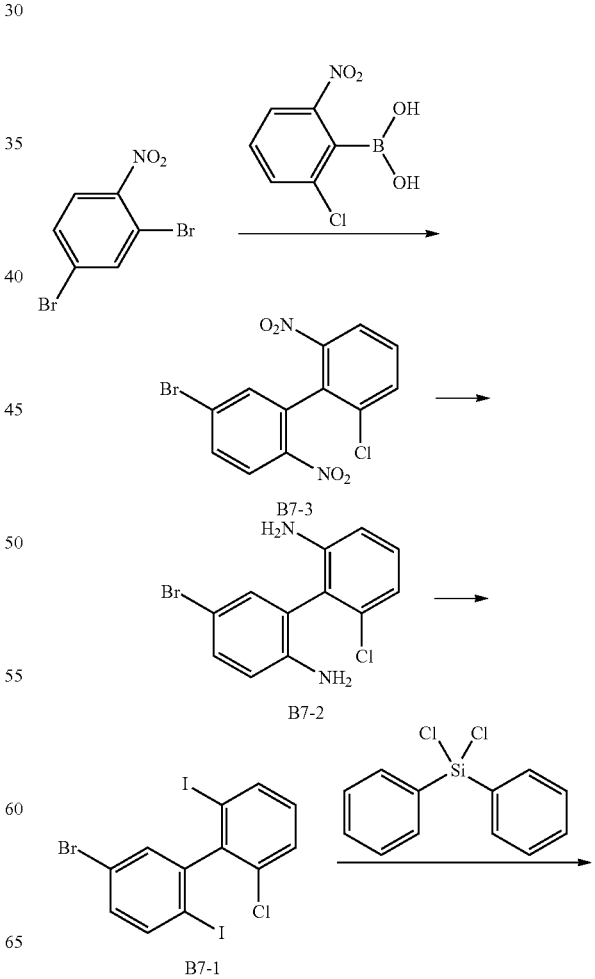

-continued

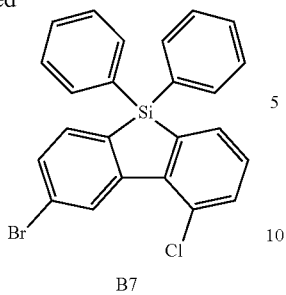

B7

Preparation of Compound B7-3

Compound B7-3 was prepared in the same manner as in the method of preparing Compound B1-3 except that 2,4-dibromo-1-nitrobenzene and (2-chloro-6-nitrophenyl)boronic acid were respectively used instead of 1,3-dibromo-4-chloro-2-nitrobenzene and (2-nitrophenyl)boronic acid. (77 g, yield 78%; MS: [M+H]$^+$=358)

Preparation of Compound B7-2

Compound B7-2 was prepared in the same manner as in the method of preparing Compound B1-2 except that Compound B7-3 was used instead of Compound B1-3. (12.5 g, yield 75%; MS: [M+H]+=298)

Preparation of Compound B7-1

Compound B7-1 was prepared in the same manner as in the method of preparing Compound B1-1 except that Compound B7-2 was used instead of Compound B1-2. (18.6 g, yield 89%; MS: [M+H]$^+$=520)

Preparation of Compound B7

Compound B7 was prepared in the same manner as in the method of preparing Compound B1 except that Compound B7-1 and dichlorodiphenylsilane were respectively used instead of Compound B1-1 and dichlorodimethylsilane. (8.4 g, yield 90%; MS: [M+H]$^+$=324)

Preparation Example 18: Preparation of Compound B8

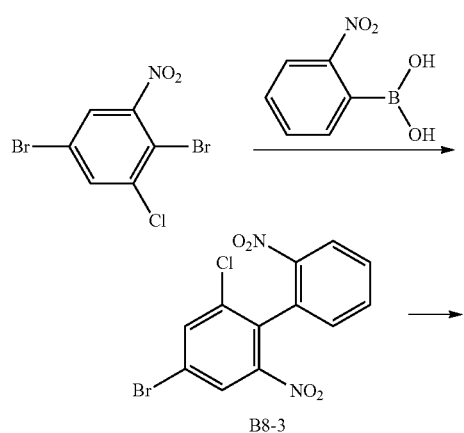

B8-3

-continued

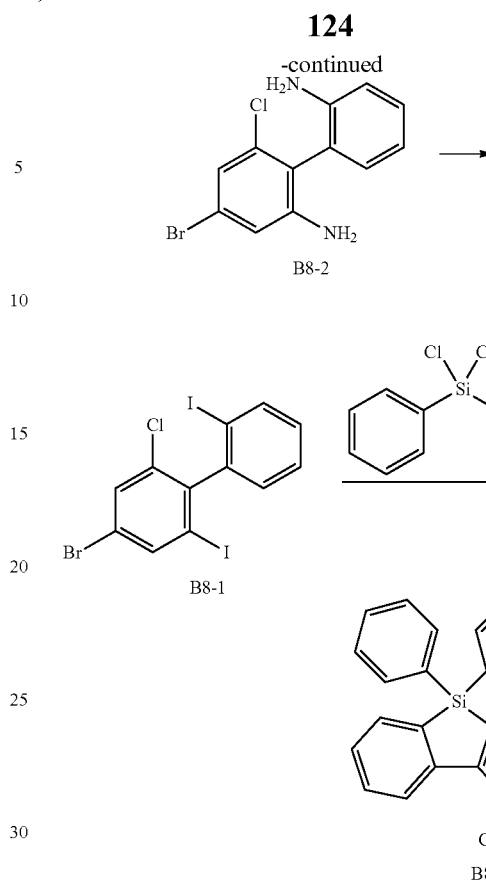

B8

Preparation of Compound B8-3

Compound B8-3 was prepared in the same manner as in the method of preparing Compound B1-3 except that 2,5-dibromo-1-chloro-3-nitrobenzene was used instead of 1,3-dibromo-4-chloro-2-nitrobenzene. (77 g, yield 78%; MS: [M+H]$^+$=358)

Preparation of Compound B8-2

Compound B8-2 was prepared in the same manner as in the method of preparing Compound B1-2 except that Compound B8-3 was used instead of Compound B1-3. (12.5 g, yield 75%; MS: [M+H]$^+$=298)

Preparation of Compound B8-1

Compound B8-1 was prepared in the same manner as in the method of preparing Compound B1-1 except that Compound B8-2 was used instead of Compound B1-2. (18.6 g, yield 89%; MS: [M+H]$^+$=520)

Preparation of Compound B8

Compound B8 was prepared in the same manner as in the method of preparing Compound B1 except that Compound B8-1 and dichlorodiphenylsilane were respectively used instead of Compound B1-1 and dichlorodimethylsilane. (8.4 g, yield 90%; MS: [M+H]$^+$=324)

Preparation Example 19: Preparation of Compound C1

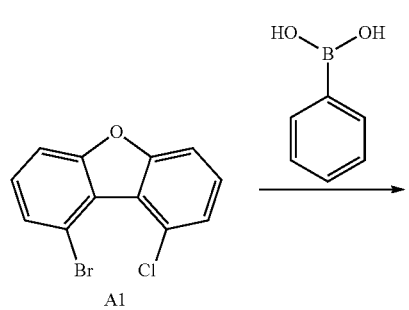

A1

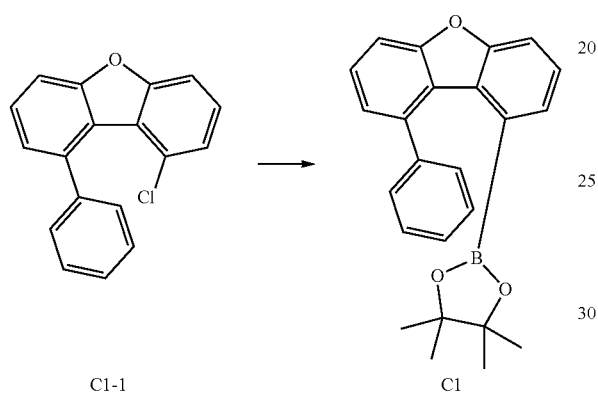

C1-1   C1

Preparation of Compound C1-1

Compound A1 (20 g, 71.04 mmol) and phenylboronic acid (8.66 g, 71.04 mmol) were dissolved in tetrahydrofuran (THF) (200 ml). A 2 M potassium carbonate ($K_2CO_3$) solution (100 mL) and tetrakis(triphenylphosphine)palladium(0) [$Pd(PPh_3)_4$] (2.5 g, 2.13 mmol) were introduced thereto, and the result was refluxed for 12 hours. After the reaction was finished, the result was cooled to room temperature, and a produced mixture was extracted three times with water and toluene. The toluene layer was separated and dried with magnesium sulfate, and a mixture obtained by vacuum distilling the filtered filtrate was recrystallized three times using chloroform and ethanol to obtain Compound C1-1 (15.4 g, yield 78%; MS: $[M+H]^+=279$).

Preparation of Compound C1

Compound C1-1 (20 g, 55.2 mmol) was dissolved in 1,4-dioxane (200 ml). Bis(pinacolato)diboron (14 g, 55.2 mmol), potassium acetate (16.3 g, 165.6 mmol) and $Pd(dppf)_2$ (1.2 g, 1.66 mmol) were introduced thereto, and the result was stirred for 6 hours at 120° C. After the reaction was finished, the result was cooled to room temperature, and the solvent was removed through distillation. The result was extracted with chloroform and water, and the organic layer was dried with $MgSO_4$, concentrated, and then recrystallized with ethyl acetate to obtain Compound C1 (18.2 g, yield 89%; MS: $[M+H]^+=371$).

Preparation Example 20: Preparation of Compound C2

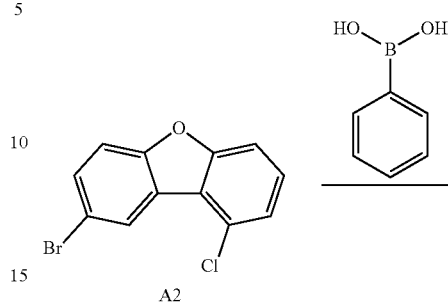

A2

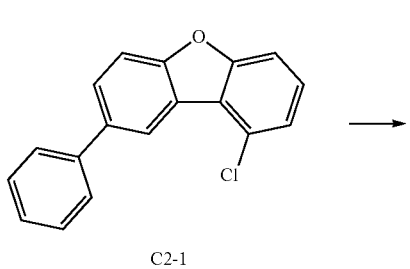

C2-1

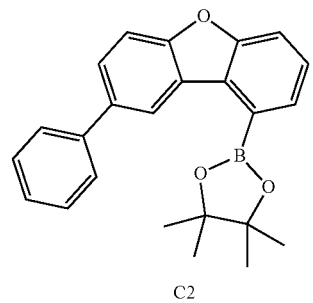

C2

Preparation of Compound C2-1

Compound C2-1 was prepared in the same manner as in the method of preparing Compound C1-1 except that Compound A2 was used instead of Compound A1. (16.8 g, yield 85%; MS: $[M+H]^+=279$)

Preparation of Compound C2

Compound C2 was prepared in the same manner as in the method of preparing Compound C1 except that Compound C2-1 was used instead of Compound C1-1. (19.2 g, yield 94%; MS: $[M+H]^+=371$)

Preparation Example 21: Preparation of Compound C3

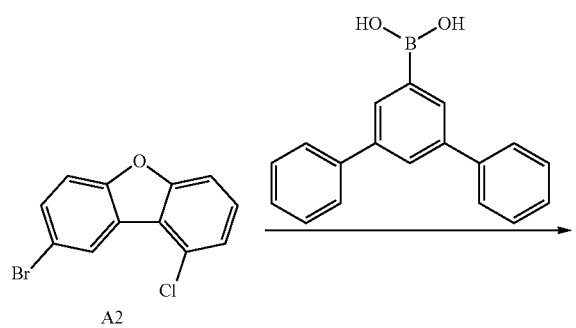

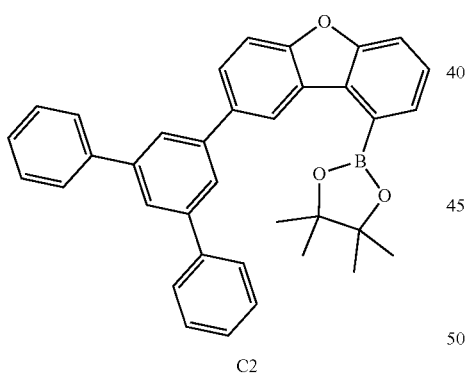

Preparation of Compound C3-1

Compound C3-1 was prepared in the same manner as in the method of preparing Compound C1-1 except that Compound A2 and [1,1':3',1''-terphenyl]-5'-ylboronic acid were respectively used instead of Compound A1 and phenylboronic acid. (17.8 g, yield 84%; MS: [M+H]$^+$=431)

Preparation of Compound C3

Compound C3 was prepared in the same manner as in the method of preparing Compound C1 except that Compound C3-1 was used instead of Compound C1-1. (19.5 g, yield 84%; MS: [M+H]$^+$=522)

Preparation Example 22: Preparation of Compound C4

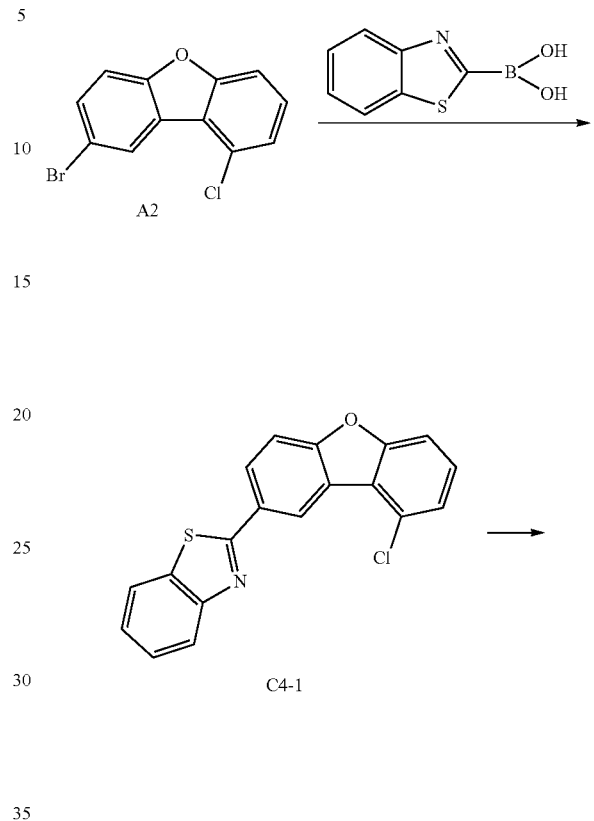

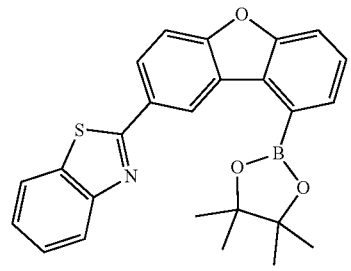

Preparation of Compound C4-1

Compound C4-1 was prepared in the same manner as in the method of preparing Compound C1-1 except that Compound A2 and benzo[d]thiazol-2-ylboronic acid were respectively used instead of Compound A1 and phenylboronic acid. (18.5 g, yield 85%; MS: [M+H]$^+$=336)

Preparation of Compound C4

Compound C4 was prepared in the same manner as in the method of preparing Compound C1 except that Compound C4-1 was used instead of Compound C1-1. (21.7 g, yield 91%; MS: [M+H]$^+$=428)

Preparation Example 23: Preparation of Compound C5

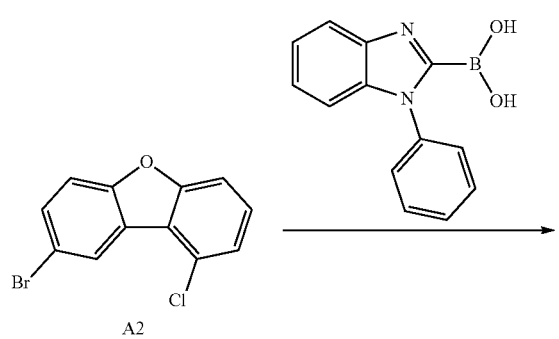

Preparation Example 24: Preparation of Compound C6

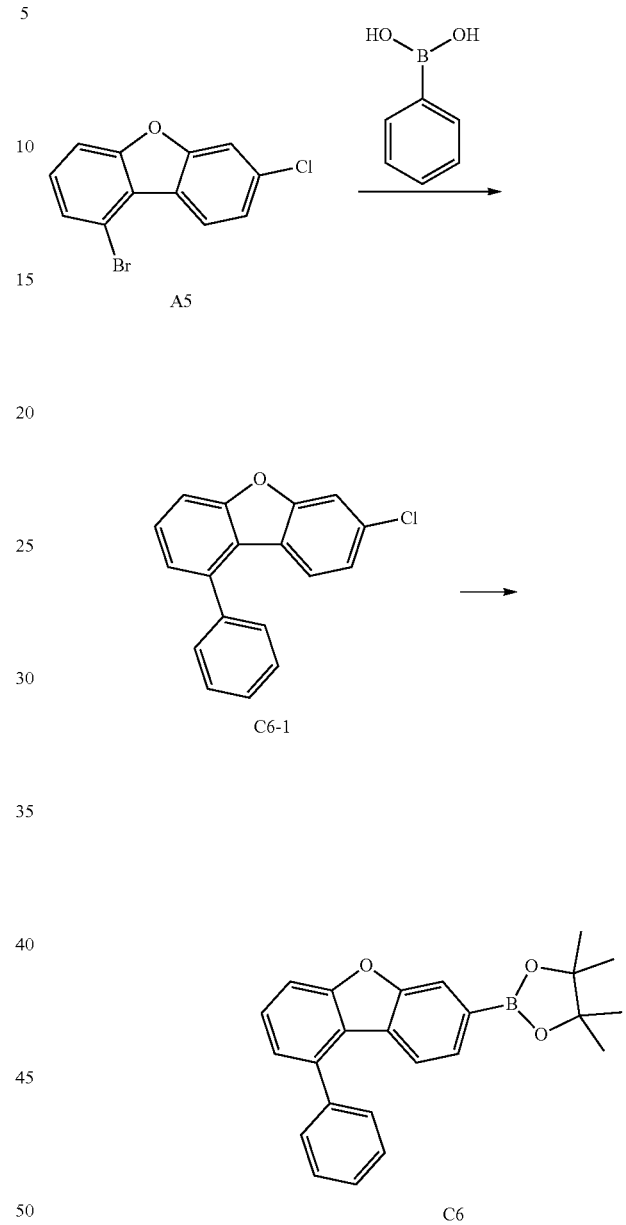

Preparation of Compound C5-1

Compound C5-1 was prepared in the same manner as in the method of preparing Compound C1-1 except that Compound A2 and (1-phenyl-1H-benzo[d]imidazol-2-yl)boronic acid were respectively used instead of Compound A1 and phenylboronic acid. (21.5 g, yield 89%; MS: $[M+H]^+=336$)

Preparation of Compound C5

Compound C5 was prepared in the same manner as in the method of preparing Compound C1 except that Compound C5-1 was used instead of Compound C1-1. (15.6 g, yield 74%; MS: $[M+H]^+=487$)

Preparation of Compound C6-1

Compound C6-1 was prepared in the same manner as in the method of preparing Compound C1-1 except that Compound A5 was used instead of Compound A1. (12.8 g, yield 74%; MS: $[M+H]^+=279$)

Preparation of Compound C6

Compound C6 was prepared in the same manner as in the method of preparing Compound C1 except that Compound C6-1 was used instead of Compound C1-1. (18.5 g, yield 91%; MS: $[M+H]^+=371$)

Preparation Example 25: Preparation of Compound C7

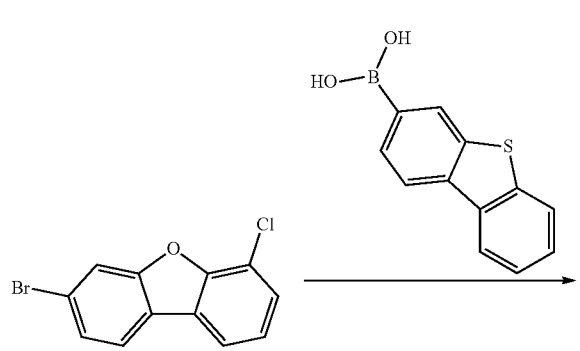

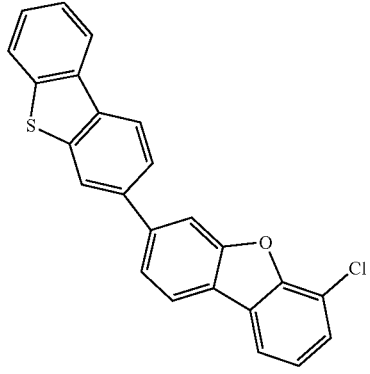

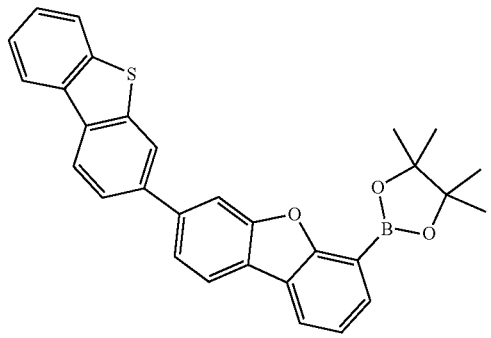

Preparation of Compound C7-1

Compound C7-1 was prepared in the same manner as in the method of preparing Compound C1-1 except that Compound A4 and dibenzo[b,d]thiophen-3-ylboronic acid were respectively used instead of Compound A1 and phenylboronic acid. (17.1 g, yield 74%; MS: [M+H]$^+$=385)

Preparation of Compound C7

Compound C7 was prepared in the same manner as in the method of preparing Compound C1 except that Compound C7-1 was used instead of Compound C1-1. (18.6 g, yield 73%; MS: [M+H]$^+$=477)

Preparation Example 26: Preparation of Compound C8

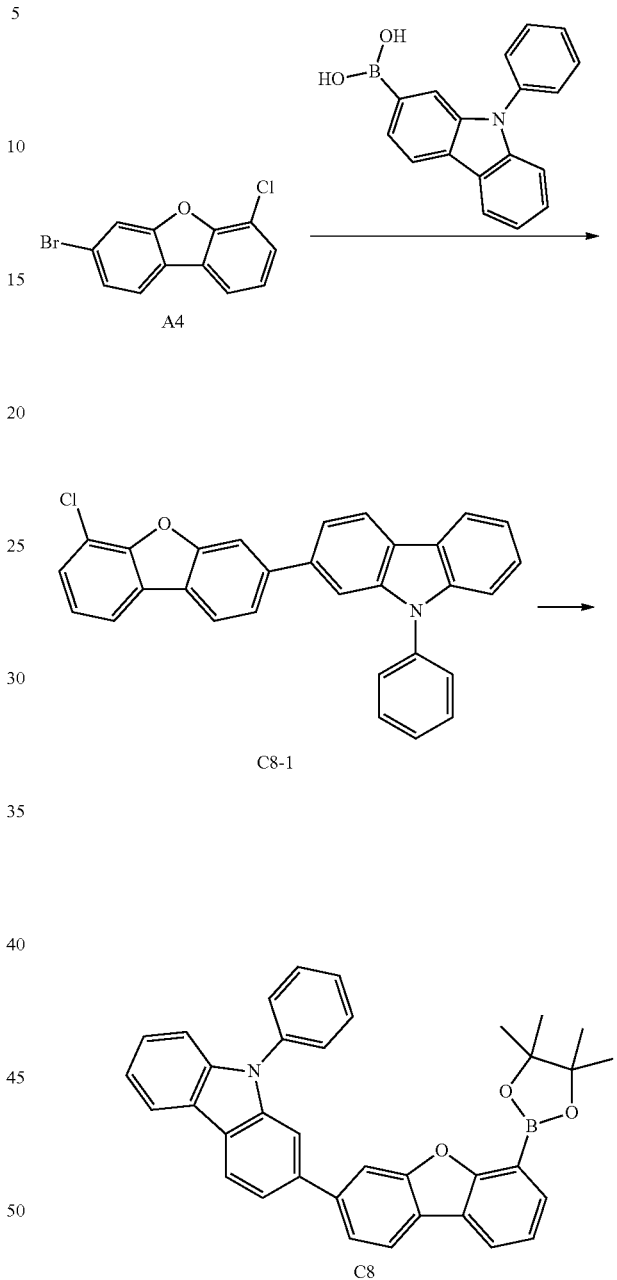

Preparation of Compound C8-1

Compound C8-1 was prepared in the same manner as in the method of preparing Compound C1-1 except that Compound A4 and (9-phenyl-9H-carbazol-2-yl)boronic acid were respectively used instead of Compound A1 and phenylboronic acid. (18.5 g, yield 69%; MS: [M+H]$^+$=444)

Preparation of Compound C8

Compound C8 was prepared in the same manner as in the method of preparing Compound C1 except that Compound C8-1 was used instead of Compound C1-1. (20.6 g, yield 84%; MS: [M+H]$^+$=536)

Preparation Example 27: Preparation of Compound C9

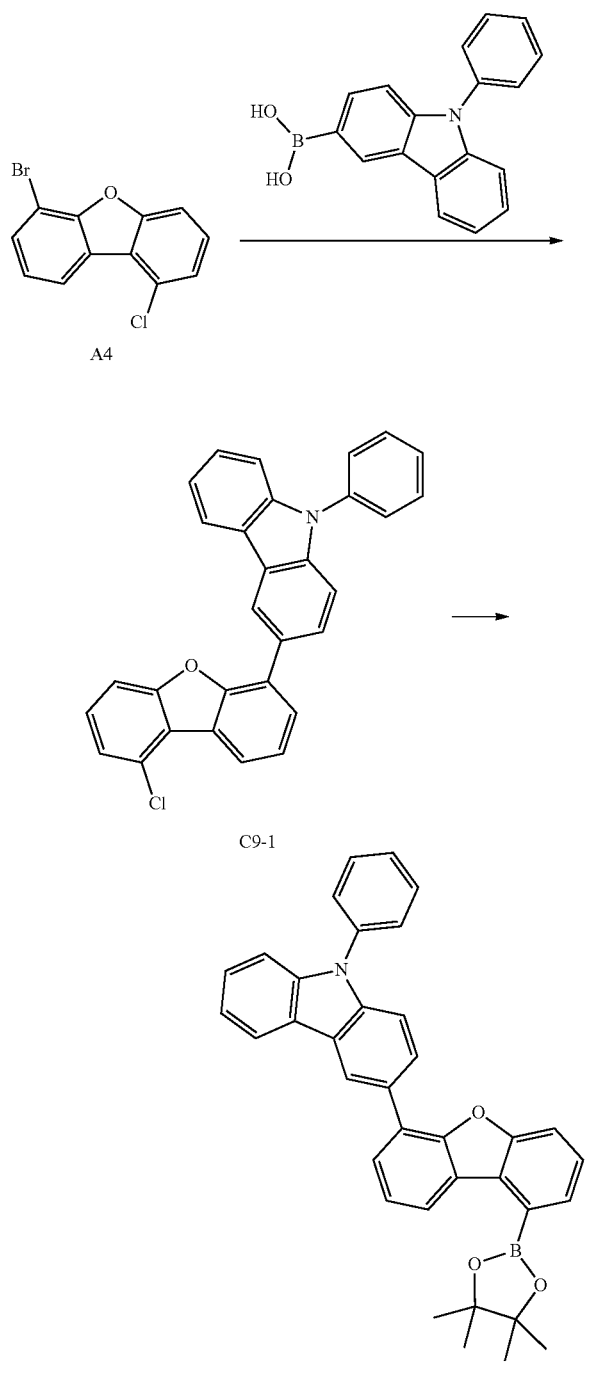

Preparation of Compound C9-1

Compound C9-1 was prepared in the same manner as in the method of preparing Compound C1-1 except that Compound A4 and (9-phenyl-9H-carbazol-3-yl)boronic acid were respectively used instead of Compound A1 and phenylboronic acid. (17.4 g, yield 67%; MS: [M+H]$^+$=444)

Preparation of Compound C9

Compound C9 was prepared in the same manner as in the method of preparing Compound C1 except that Compound C9-1 was used instead of Compound C1-1. (18.1 g, yield 79%; MS: [M+H]$^+$=536)

Preparation Example 28: Preparation of Compound C10

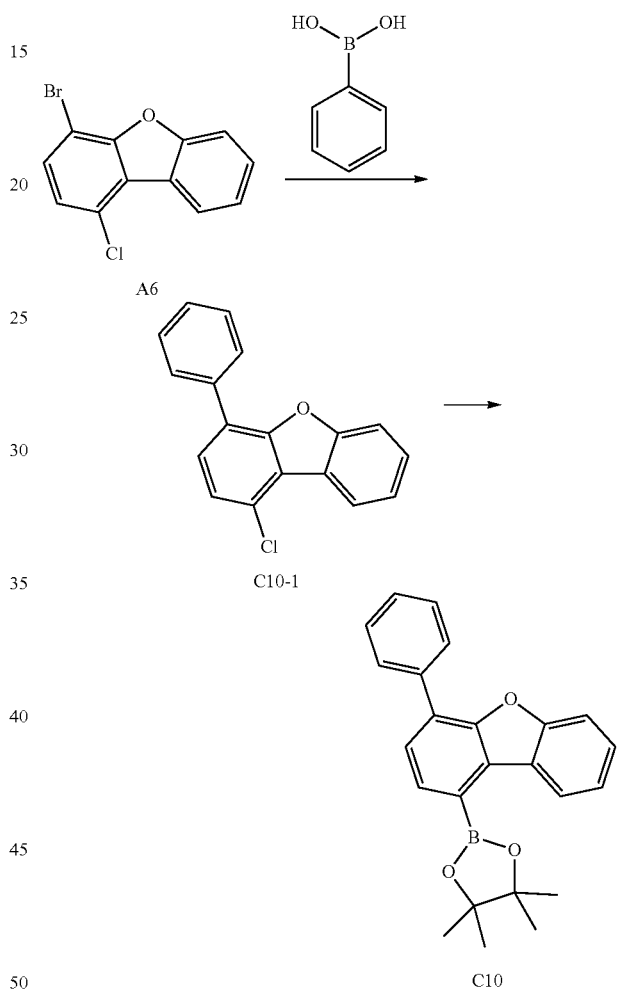

Preparation of Compound C10-1

Compound C10-1 was prepared in the same manner as in the method of preparing Compound C1-1 except that Compound A6 was used instead of Compound A1. (18.4 g, yield 89%; MS: [M+H]$^+$=279)

Preparation of Compound C10

Compound C10 was prepared in the same manner as in the method of preparing Compound C1 except that Compound C10-1 was used instead of Compound C1-1. (16.7 g, yield 84%; MS: [M+H]$^+$=371)

Preparation Example 29: Preparation of Compound C11

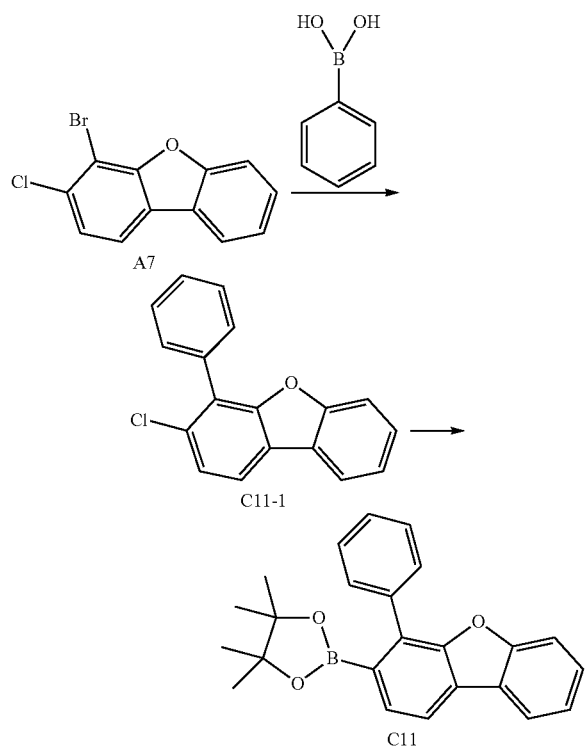

Preparation of Compound C11-1

Compound C11-1 was prepared in the same manner as in the method of preparing Compound C1-1 except that Compound A7 was used instead of Compound A1. (17.1 g, yield 81%; MS: [M+H]$^+$=279)

Preparation of Compound C11

Compound C11 was prepared in the same manner as in the method of preparing Compound C1 except that Compound C11-1 was used instead of Compound C1-1. (18.6 g, yield 92%; MS: [M+H]$^+$=371)

Preparation Example 30: Preparation of Compound C12

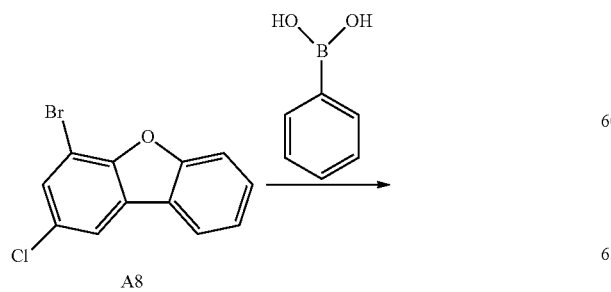

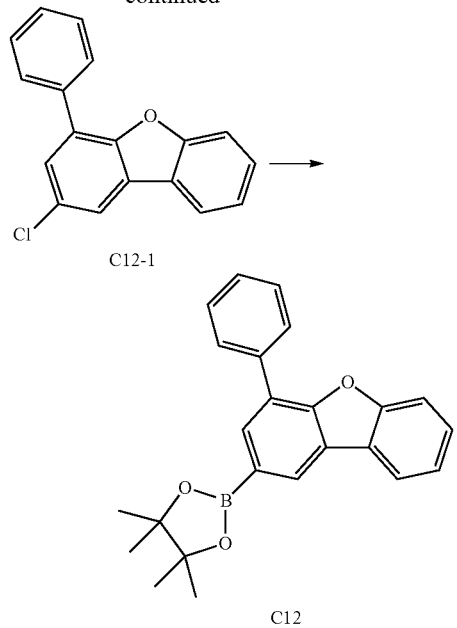

Preparation of Compound C12-1

Compound C12-1 was prepared in the same manner as in the method of preparing Compound C1-1 except that Compound A8 was used instead of Compound A1. (18.2 g, yield 87%; MS: [M+H]$^+$=279)

Preparation of Compound C12

Compound C12 was prepared in the same manner as in the method of preparing Compound C1 except that Compound C12-1 was used instead of Compound C1-1. (15.8 g, yield 81%; MS: [M+H]$^+$=371)

Preparation Example 31: Preparation of Compound C13

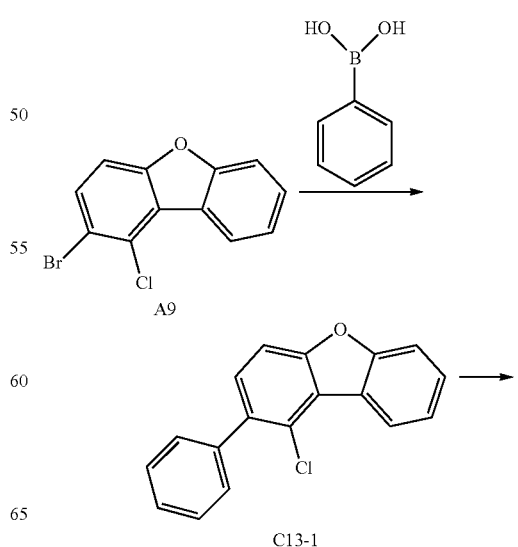

-continued

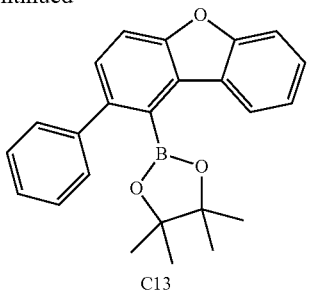
C13

Preparation of Compound C13-1

Compound C13-1 was prepared in the same manner as in the method of preparing Compound C1-1 except that Compound A9 was used instead of Compound A1. (17.2 g, yield 81%; MS: [M+H]$^+$=279)

Preparation of Compound C13

Compound C13 was prepared in the same manner as in the method of preparing Compound C1 except that Compound C13-1 was used instead of Compound C1-1. (15.4 g, yield 80%; MS: [M+H]$^+$=371)

Preparation Example 32: Preparation of Compound C14

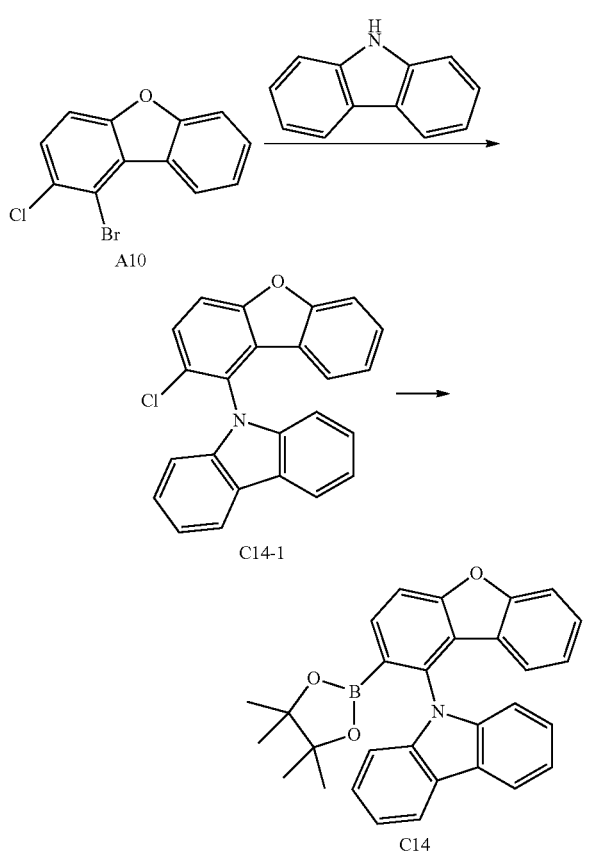

Preparation of Compound C14-1

Compound A10 (20 g, 71.04 mmol), sodium t-butoxide (NaOt-Bu) (20.5 g, 85.25 mmol), 9H-carbazole (11.9 g, 71.04 mmol) and bis(tri-tert-butylphosphine)palladium(0) (1.1 g, 2.13 mmol) were mixed with toluene (200 ml), and heated for 12 hours under a nitrogen environment. The temperature was lowered to room temperature, and after adding ethanol (400 ml) thereto, the result was crystallized, filtered and then dried to prepare Compound C14-1. (17.2 g, yield 81%; MS: [M+H]$^+$=368)

Preparation of Compound C14

Compound C14 was prepared in the same manner as in the method of preparing Compound C1 except that Compound C14-1 was used instead of Compound C1-1. (15.4 g, yield 80%; MS: [M+H]$^+$=460)

Preparation Example 33: Preparation of Compound D1

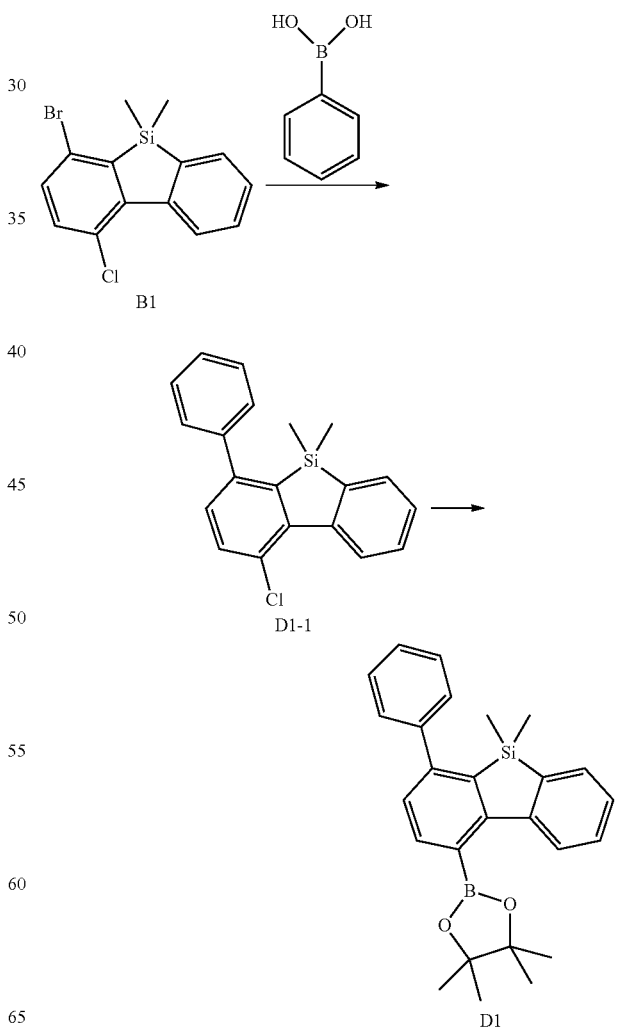

Preparation of Compound D1-1

Compound D1-1 was prepared in the same manner as in the method of preparing Compound C1-1 except that Compound B1 was used instead of Compound A1. (14.7 g, yield 74%; MS: [M+H]$^+$=279)

Preparation of Compound D1

Compound D1 was prepared in the same manner as in the method of preparing Compound C1 except that Compound D1-1 was used instead of Compound C1-1. (17.2 g, yield 89%; MS: [M+H]$^+$=371)

Preparation Example 34: Preparation of Compound D2

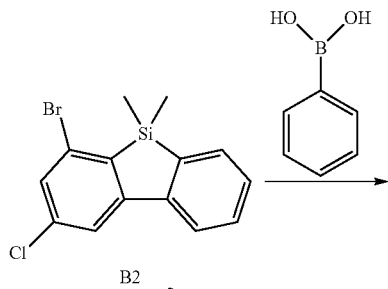

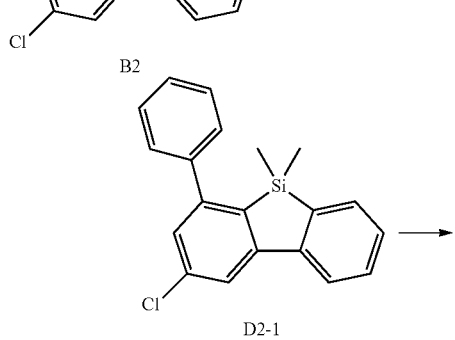

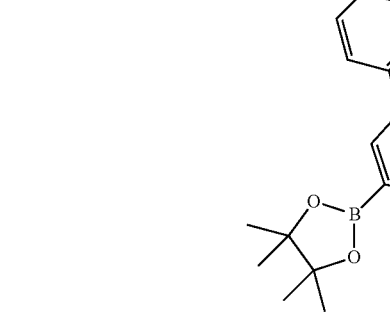

Preparation of Compound D2-1

Compound D2-1 was prepared in the same manner as in the method of preparing Compound C1-1 except that Compound B2 was used instead of Compound A1. (14.1 g, yield 71%; MS: [M+H]$^+$=279)

Preparation of Compound D2

Compound D2 was prepared in the same manner as in the method of preparing Compound C1 except that Compound D2-1 was used instead of Compound C1-1. (15.4 g, yield 80%; MS: [M+H]$^+$=371)

Preparation Example 35: Preparation of Compound D3

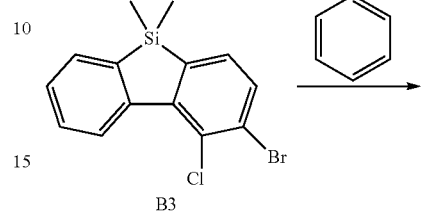

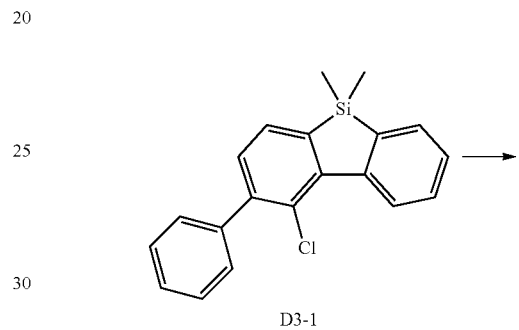

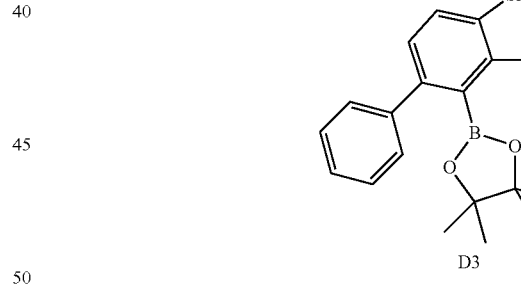

Preparation of Compound D3-1

Compound D3-1 was prepared in the same manner as in the method of preparing Compound C1-1 except that Compound B3 was used instead of Compound A1. (12.9 g, yield 65%; MS: [M+H]$^+$=279)

Preparation of Compound D3

Compound D3 was prepared in the same manner as in the method of preparing Compound C1 except that Compound D3-1 was used instead of Compound C1-1. (17.2 g, yield 89%; MS: [M+H]$^+$=371)

Preparation Example 36: Preparation of Compound D4

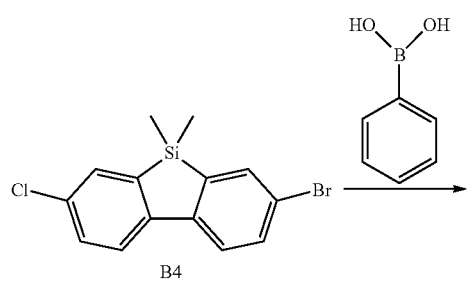

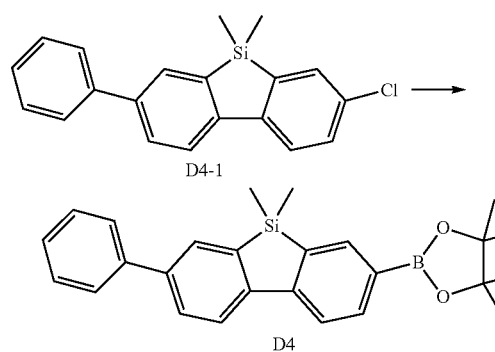

Preparation of Compound D4-1

Compound D4-1 was prepared in the same manner as in the method of preparing Compound C1-1 except that Compound B4 was used instead of Compound A1. (16.7 g, yield 84%; MS: [M+H]$^+$=279)

Preparation of Compound D4

Compound D4 was prepared in the same manner as in the method of preparing Compound C1 except that Compound D4-1 was used instead of Compound C1-1. (14.3 g, yield 74%; MS: [M+H]$^+$=371)

Preparation Example 37: Preparation of Compound D5

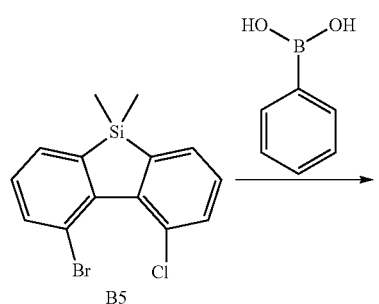

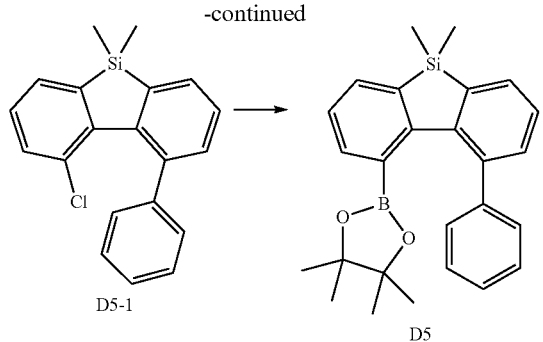

Preparation of Compound D5-1

Compound D5-1 was prepared in the same manner as in the method of preparing Compound C1-1 except that Compound B5 was used instead of Compound A1. (15.7 g, yield 79%; MS: [M+H]$^+$=279)

Preparation of Compound D5

Compound D5 was prepared in the same manner as in the method of preparing Compound C1 except that Compound D5-1 was used instead of Compound C1-1. (14.3 g, yield 70%; MS: [M+H]$^+$=371)

Preparation Example 38: Preparation of Compound D6

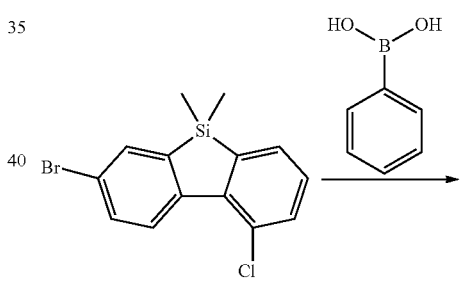

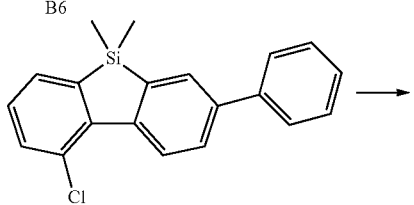

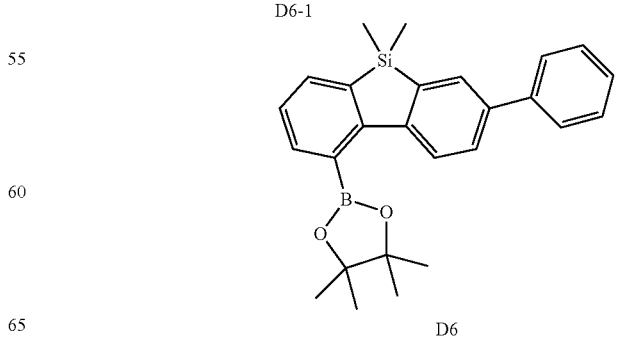

Preparation of Compound D6-1

Compound D6-1 was prepared in the same manner as in the method of preparing Compound C1-1 except that Compound B6 was used instead of Compound A1. (16.7 g, yield 84%; MS: [M+H]$^+$=279)

Preparation of Compound D6

Compound D6 was prepared in the same manner as in the method of preparing Compound C1 except that Compound D6-1 was used instead of Compound C1-1. (16.2 g, yield 84%; MS: [M+H]$^+$=371)

Preparation Example 39: Preparation of Compound D7

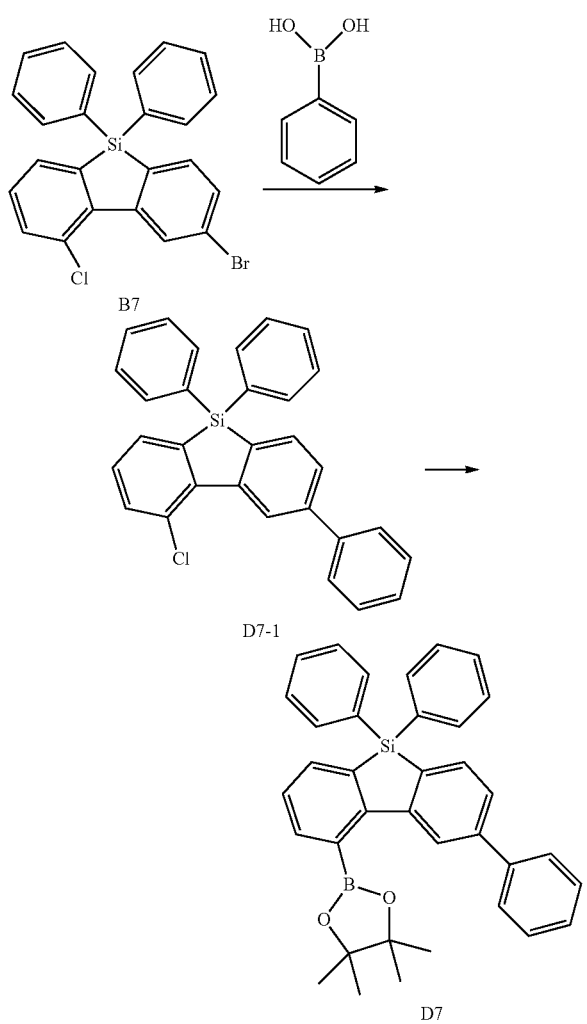

Preparation of Compound D7-1

Compound D7-1 was prepared in the same manner as in the method of preparing Compound C1-1 except that Compound B7 was used instead of Compound A1. (17.7 g, yield 89%; MS: [M+H]$^+$=446)

Preparation of Compound D7

Compound D7 was prepared in the same manner as in the method of preparing Compound C1 except that Compound D7-1 was used instead of Compound C1-1. (14.3 g, yield 79%; MS: [M+H]$^+$=537)

Preparation Example 40: Preparation of Compound D8

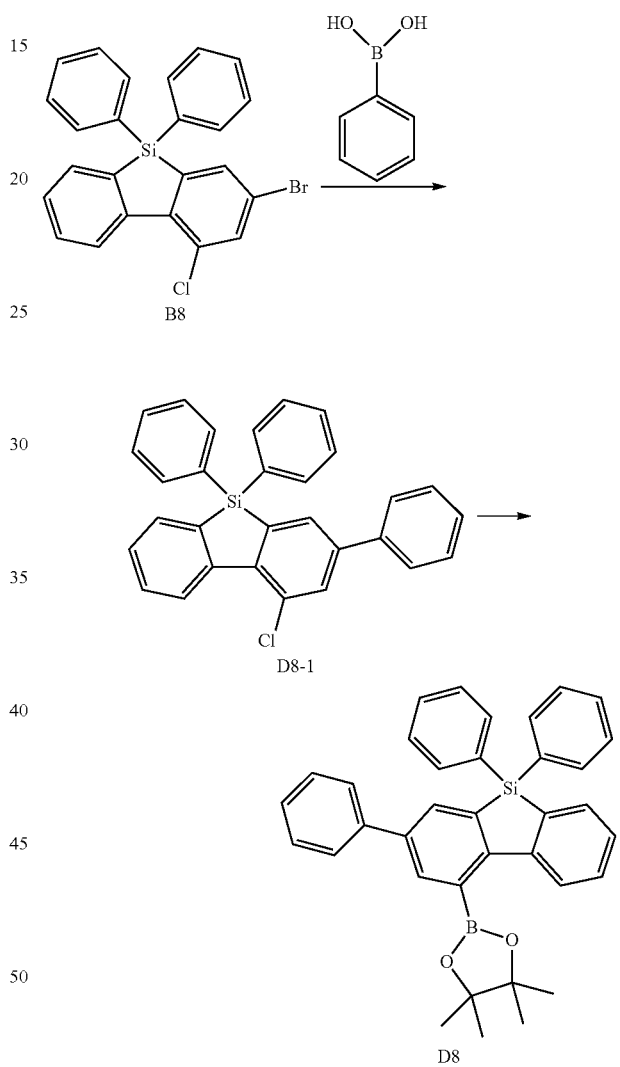

Compound D8-1 was prepared in the same manner as in the method of preparing Compound C1-1 except that Compound B8 was used instead of Compound A1. (18.7 g, yield 94%; MS: [M+H]$^+$=446)

Preparation of Compound D8

Compound D8 was prepared in the same manner as in the method of preparing Compound C1 except that Compound D8-1 was used instead of Compound C1-1. (15.7 g, yield 87%; MS: [M+H]$^+$=537)

[Preparation of Compounds 1 to 18]

Preparation of Compound 1

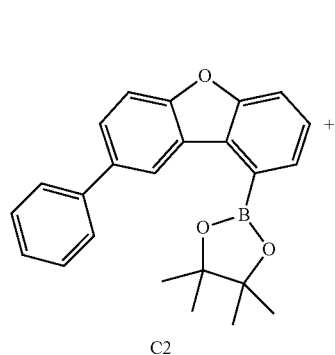

C2

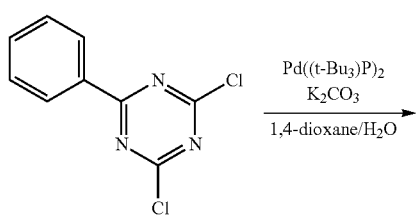

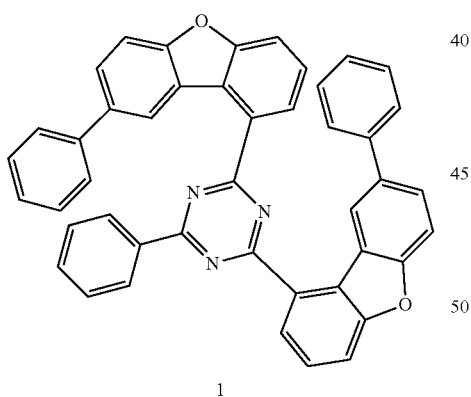

1

After dissolving Compound C2 (32.7 g, 88.47 mmol) and 2,4-dichloro-6-phenyl-1,3,5-triazine (10 g, 44.26 mmol) in dioxane (100 mL), a 2 M potassium carbonate (K$_2$CO$_3$) solution (130 mL) and then tetrakis(triphenylphosphine)palladium(0) [Pd(PPh$_3$)$_4$] (1.5 g, 1.33 mmol) were added thereto, and the result was heated and stirred for 7 hours. After lowering the temperature to room temperature, the water layer was separated and removed, and the result was dried with anhydrous magnesium sulfate, then vacuum concentrated, recrystallized using chloroform and ethyl acetate, and dried to prepare Compound 1 (21.3 g, yield 75%, MS: [M+H]$^+$=642).

Preparation of Compound 2

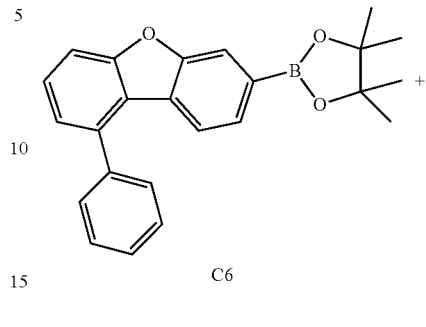

C6

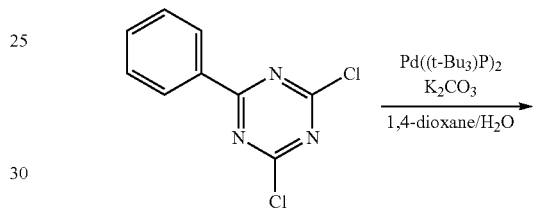

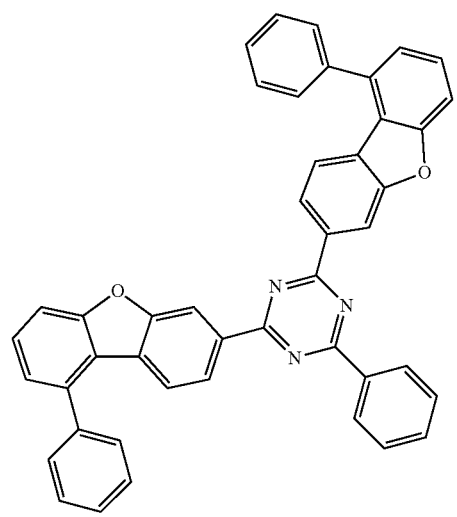

2

Compound 2 was prepared in the same manner as in the method of preparing Compound 1 except that Compound C6 was used instead of Compound C2. (23.8 g, yield 84%, MS: [M+H]$^+$=642).

Preparation of Compound 3

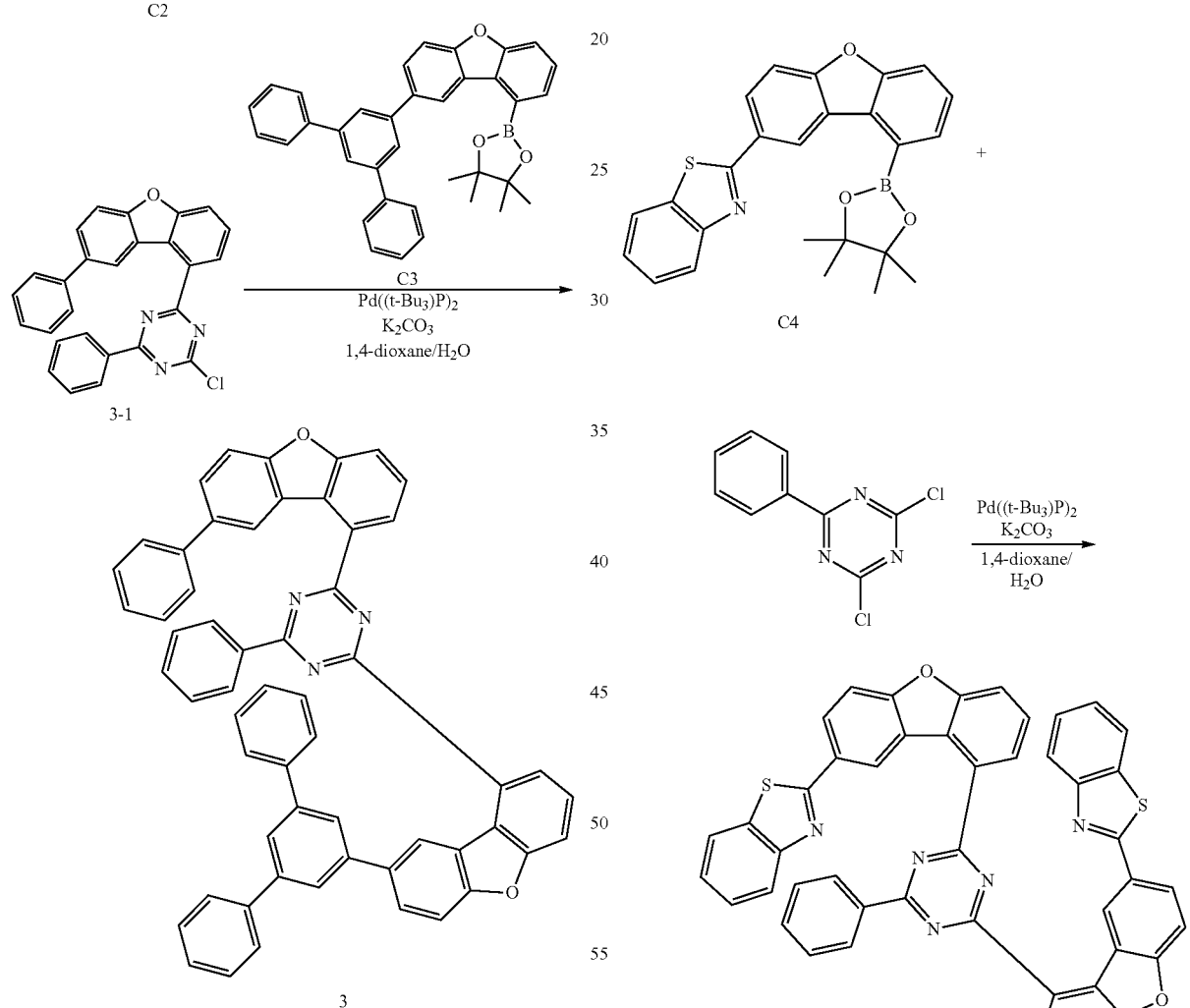

Preparation of Compound 3

After dissolving Compound 3-1 (15 g, 34.57 mmol) and Compound C3 (18.1 g, 34.57 mmol) in 1,4-dioxane (100 mL), a 2 M potassium carbonate ($K_2CO_3$) solution (50 mL) and then bis(tri-tert-butylphosphine)palladium(0) (0.5 g, 1.04 mmol) were added thereto, and the result was heated and stirred for 7 hours. After lowering the temperature to room temperature, the water layer was separated and removed, and the result was dried with anhydrous magnesium sulfate, then vacuum concentrated, recrystallized using chloroform and ethyl acetate, and dried to prepare Compound 3 (23 g, yield 84%, MS: $[M+H]^+=794$).

Preparation of Compound 4

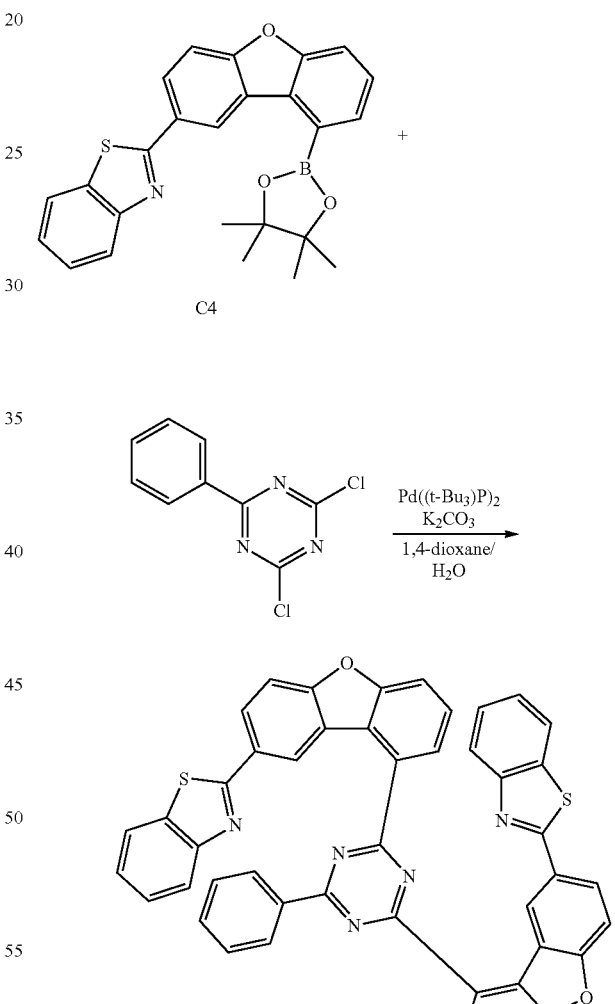

Preparation of Compound 3-1

Compound 3-1 was prepared in the same manner as in the method of preparing Compound C1-1 except that Compound C2 and 2,4-dichloro-6-phenyl-1,3,5-triazine were respectively used instead of Compound A1 and phenylboronic acid. (15.3 g, yield 87%, MS: $[M+H]^+=434$).

Compound 4 was prepared in the same manner as in the method of preparing Compound 1 except that Compound C4 was used instead of Compound C2. (23.4 g, yield 70%, MS: $[M+H]^+=756$).

Preparation of Compound 5
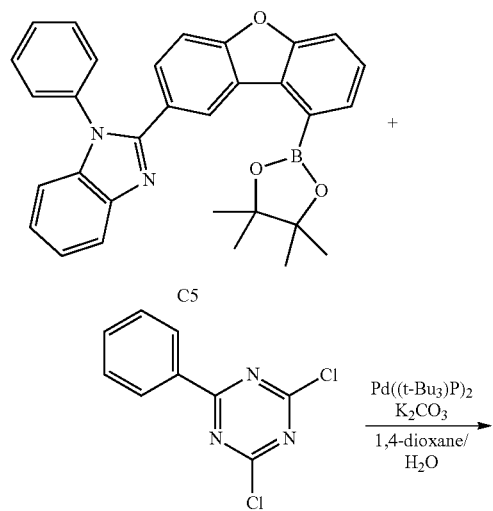
C5
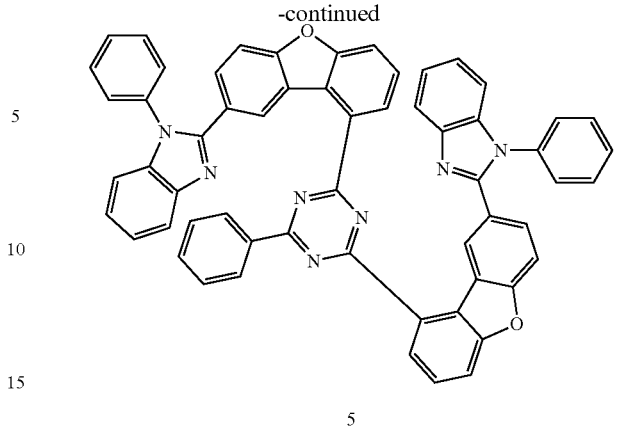
5
Compound 5 was prepared in the same manner as in the method of preparing Compound 1 except that Compound C5 was used instead of Compound C2. (25.1 g yield 65%, MS: [M+H]$^+$=784).
Preparation of Compound 6
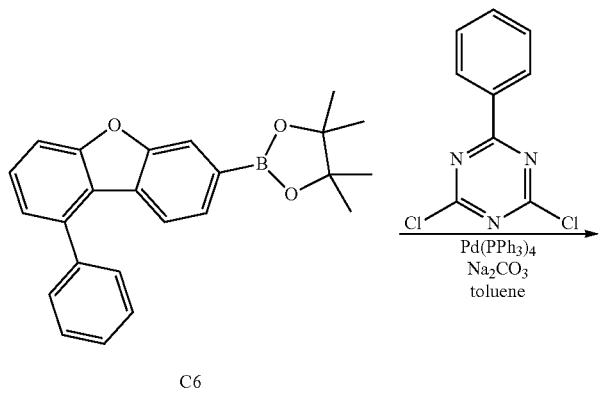
C6
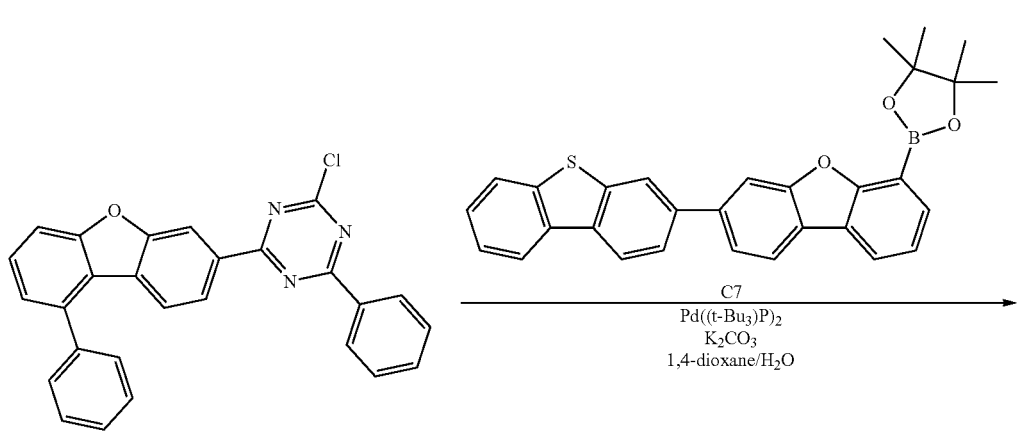
6-1

-continued

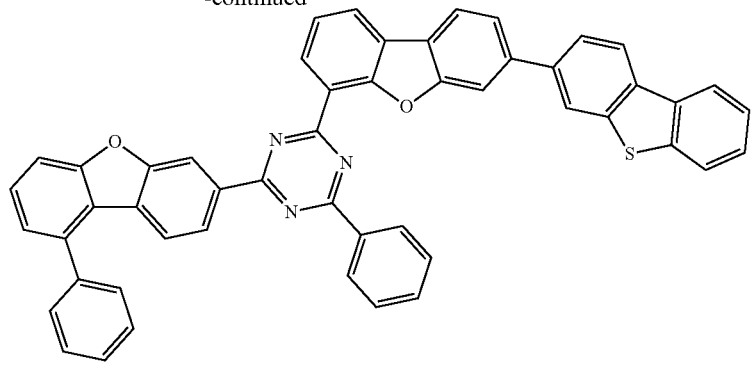

6

Preparation of Compound 6-1

Compound 6-1 was prepared in the same manner as in the method of preparing Compound C1-1 except that Compound C6 and 2,4-dichloro-6-phenyl-1,3,5-triazine were respectively used instead of Compound A1 and phenylboronic acid. (14.8 g, yield 84%, MS: [M+H]$^+$=434).

Preparation of Compound 6

Compound 6 was prepared in the same manner as in the method of preparing Compound 3 except that Compound 6-1 and Compound C7 were respectively used instead of Compound 3-1 and Compound C3. (20.7 g, yield 80%, MS: [M+H]$^+$=748).

Preparation of Compound 7

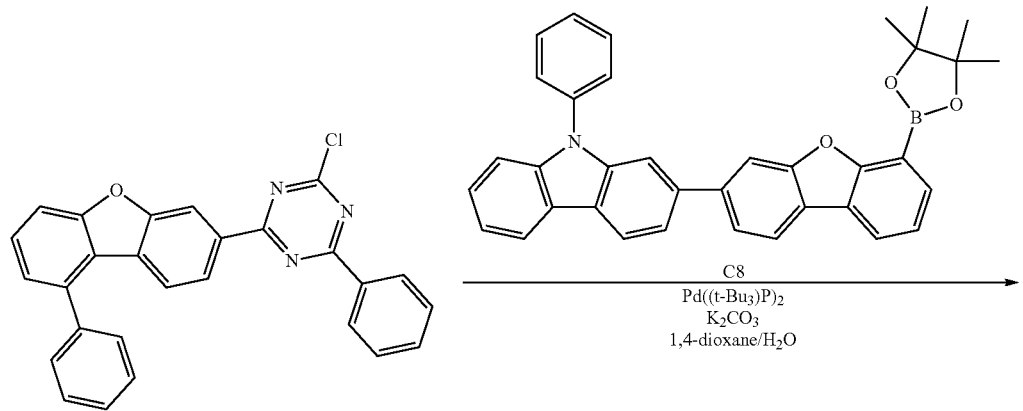

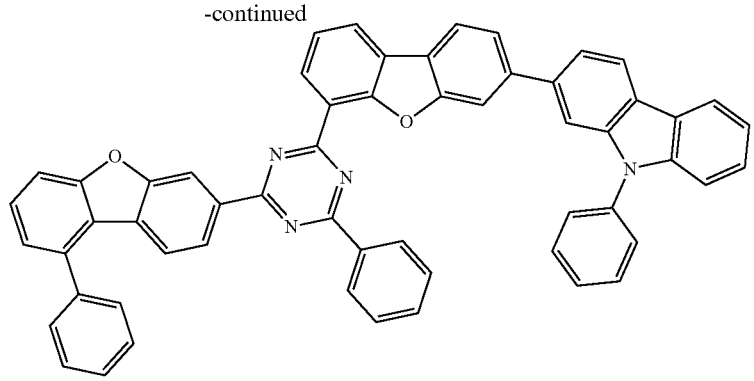

7

Compound 7 was prepared in the same manner as in the method of preparing Compound 3 except that Compound 6-1 and Compound C8 were respectively used instead of Compound 3-1 and Compound C3. (20.1 g, yield 72%, MS: [M+H]⁺=807).

Preparation of Compound 8

Compound 8 was prepared in the same manner as in the method of preparing Compound 3 except that Compound 3-1 and Compound C13 were respectively used instead of Compound 3-1 and Compound C3. (13.8 g, yield 62%, MS: [M+H]⁺=807).

Preparation of Compound 9

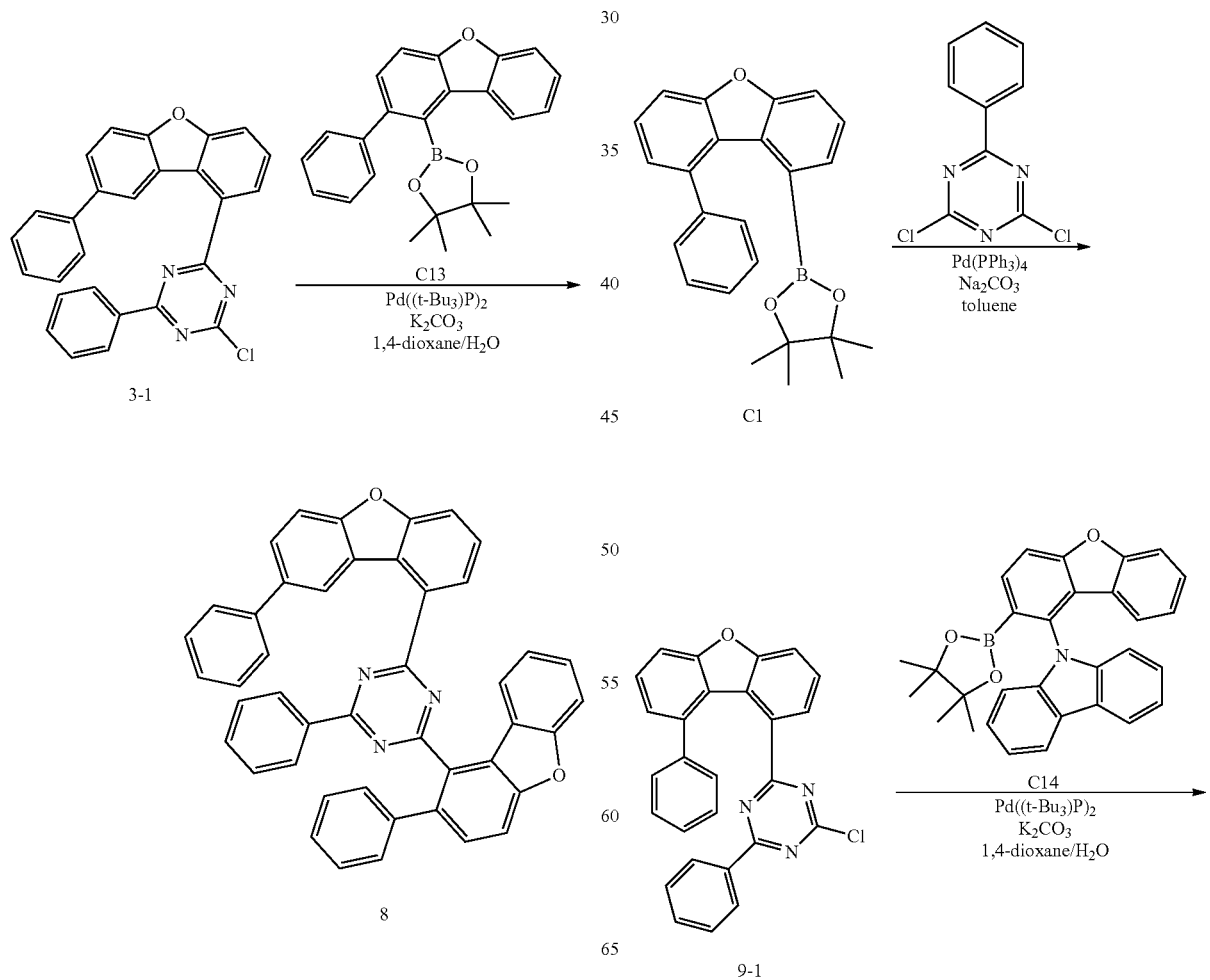

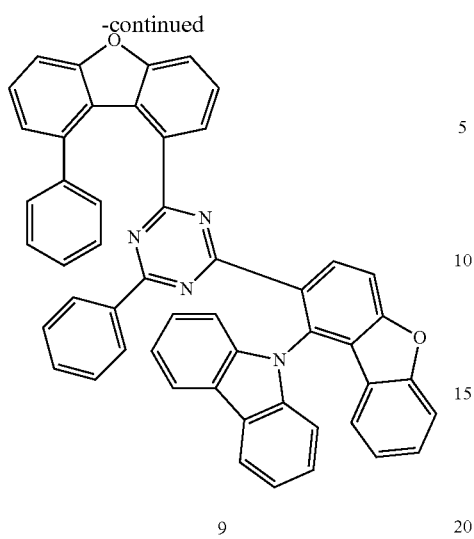

9

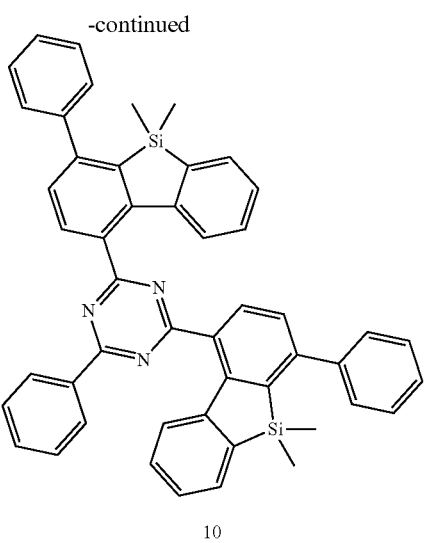

10

Preparation of Compound 9-1

Compound 9-1 was prepared in the same manner as in the method of preparing Compound C1-1 except that Compound C1 and 2,4-dichloro-6-phenyl-1,3,5-triazine were respectively used instead of Compound A1 and phenylboronic acid. (13.9 g, yield 80%, MS: [M+H]$^+$=434).

Preparation of Compound 9

Compound 9 was prepared in the same manner as in the method of preparing Compound 3 except that Compound 9-1 and Compound C14 were respectively used instead of Compound 3-1 and Compound C3. (18.2 g, yield 72%, MS: [M+H]$^+$=731).

Preparation of Compound 10

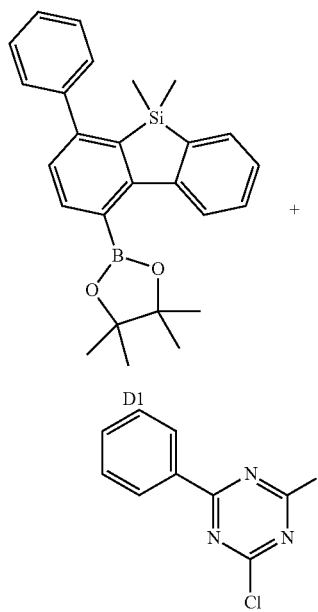

Compound 10 was prepared in the same manner as in the method of preparing Compound 1 except that Compound D1 was used instead of Compound C1. (19.9 g yield 62%, MS: [M+H]$^+$=726).

Preparation of Compound 11

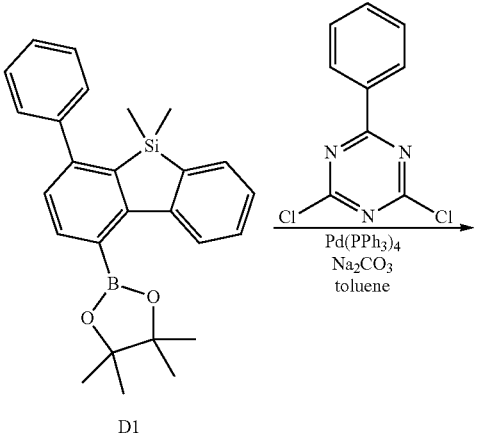

D1

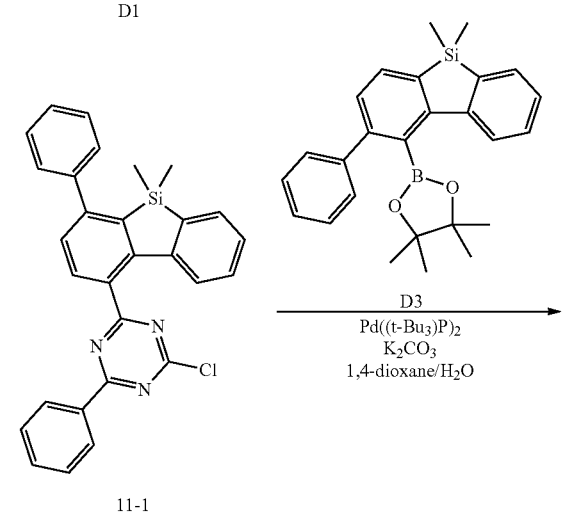

11-1

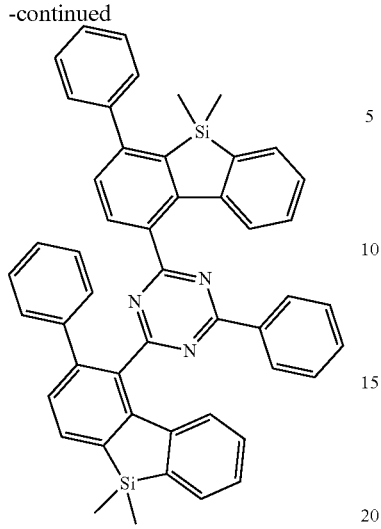

11

Preparation of Compound 11-1

Compound 11-1 was prepared in the same manner as in the method of preparing Compound C1-1 except that Compound D1 and 2,4-dichloro-6-phenyl-1,3,5-triazine were respectively used instead of Compound A1 and phenylboronic acid. (13.1 g, yield 62%, MS: [M+H]$^+$=476).

Preparation of Compound 11

Compound 11 was prepared in the same manner as in the method of preparing Compound 3 except that Compound 11-1 and Compound D3 were respectively used instead of Compound 3-1 and Compound C3. (19.5 g, yield 74%, MS: [M+H]$^+$=726).

Preparation of Compound 12

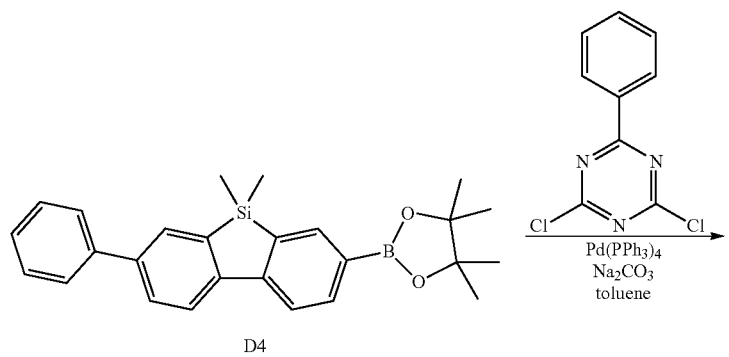

D4

-continued

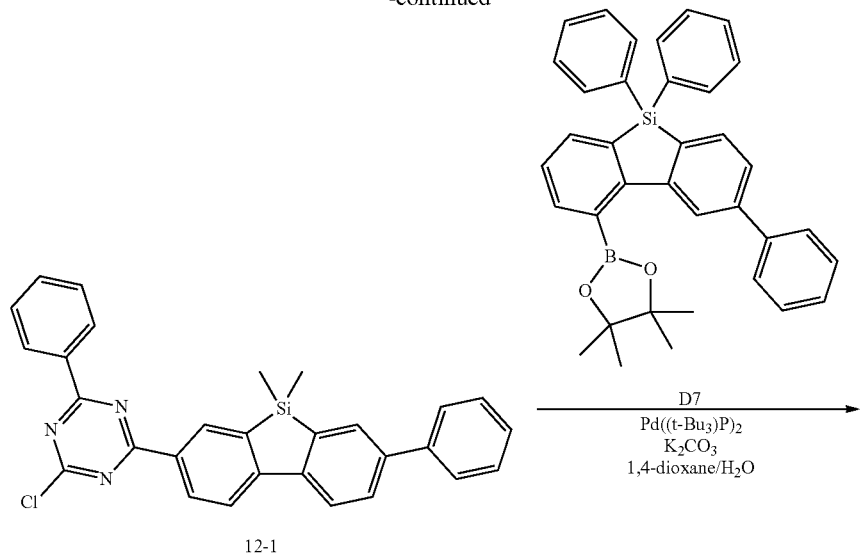
12-1

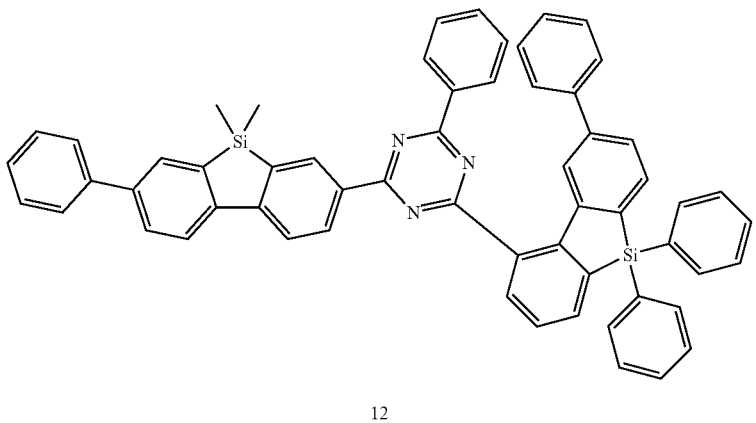
12

Preparation of Compound 12-1

Compound 12-1 was prepared in the same manner as in the method of preparing Compound C1-1 except that Compound D4 and 2,4-dichloro-6-phenyl-1,3,5-triazine were respectively used instead of Compound A1 and phenylboronic acid. (14.3 g, yield 68%, MS: $[M+H]^+=476$).

Preparation of Compound 12

Compound 12 was prepared in the same manner as in the method of preparing Compound 3 except that Compound 12-1 and Compound D7 were respectively used instead of Compound 3-1 and Compound C3. (23.8 g, yield 84%, MS: $[M+H]^+=850$).

Preparation of Compound 13

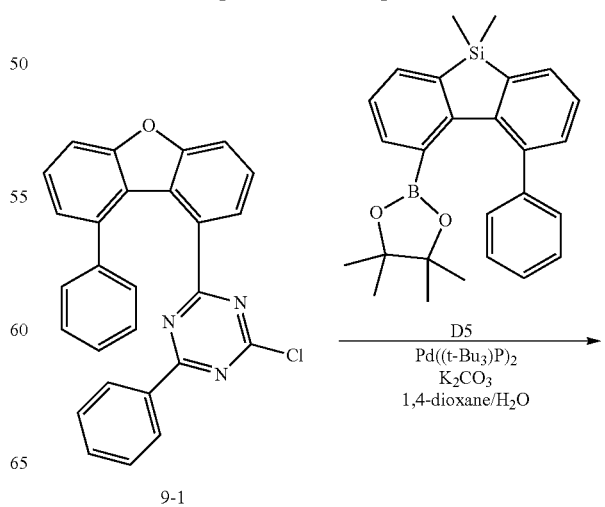
9-1

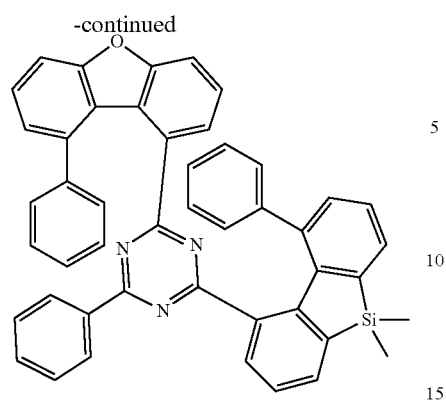
13
Compound 13 was prepared in the same manner as in the method of preparing Compound 3 except that Compound 9-1 and Compound D5 were respectively used instead of Compound 3-1 and Compound C3. (17.7 g, yield 80%, MS: [M+H]$^+$=684).
Preparation of Compound 14
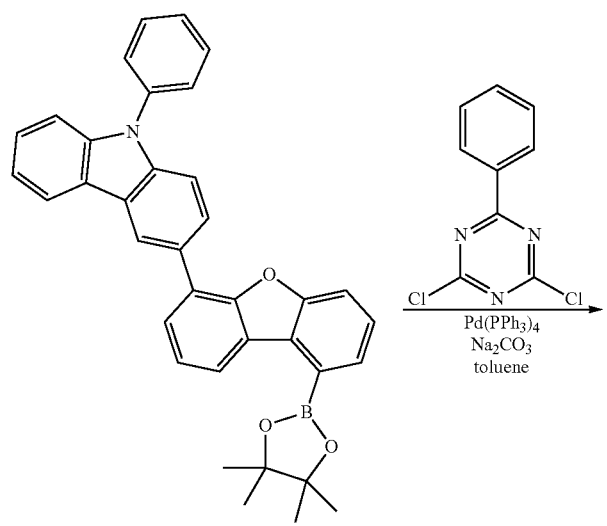
C9

-continued
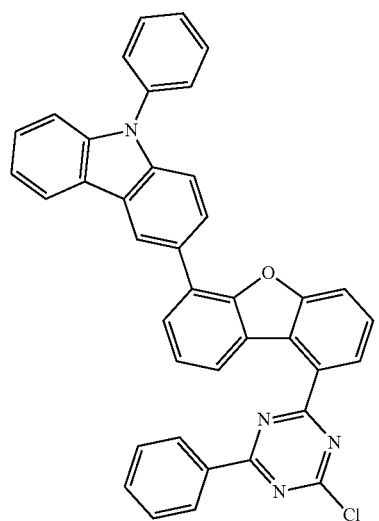
14-1
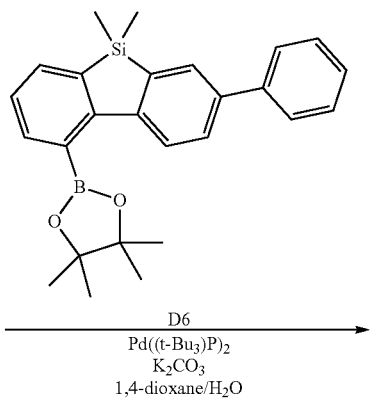
D6
Pd((t-Bu₃)P)₂
K₂CO₃
1,4-dioxane/H₂O
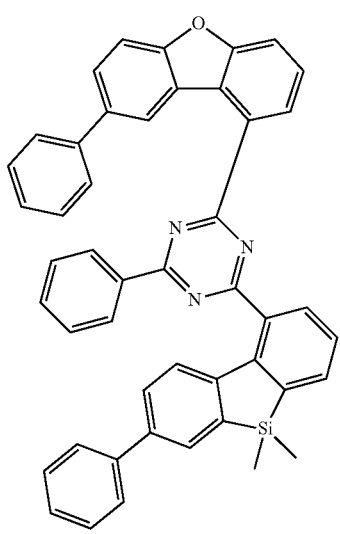
14

Preparation of Compound 14-1

Compound 14-1 was prepared in the same manner as in the method of preparing Compound C1-1 except that Compound C9 and 2,4-dichloro-6-phenyl-1,3,5-triazine were respectively used instead of Compound A1 and phenylboronic acid. (11.9 g, yield 69%, MS: [M+H]$^+$=599).

Preparation of Compound 14

Compound 14 was prepared in the same manner as in the method of preparing Compound 3 except that Compound 14-1 and Compound D6 were respectively used instead of Compound 3-1 and Compound C3. (12.2 g, yield 71%, MS: [M+H]$^+$=684).

Preparation of Compound 15

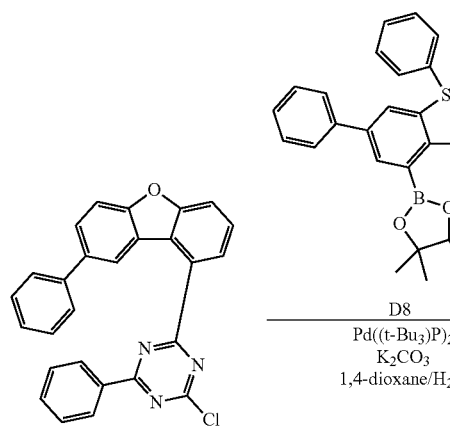

Compound 15 was prepared in the same manner as in the method of preparing Compound 3 except that Compound D8 was used instead of Compound C3. (22.1 g, yield 79%, MS: [M+H]$^+$=809).

Preparation of Compound 16

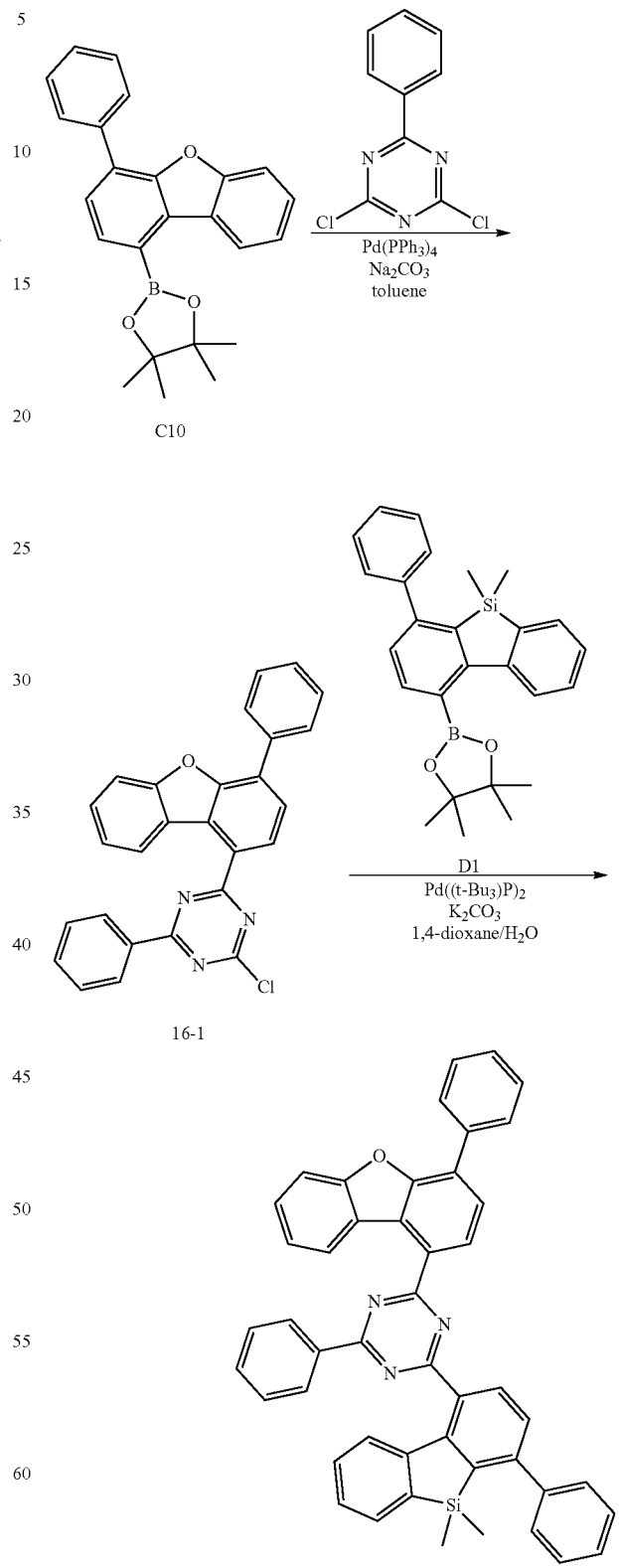

Preparation of Compound 16-1

Compound 16-1 was prepared in the same manner as in the method of preparing Compound C1-1 except that Compound C10 and 2,4-dichloro-6-phenyl-1,3,5-triazine were respectively used instead of Compound A1 and phenylboronic acid. (12.5 g, yield 71%, MS: [M+H]$^+$=434).

Preparation of Compound 16

Compound 16 was prepared in the same manner as in the method of preparing Compound 3 except that Compound 16-1 and Compound D1 were respectively used instead of Compound 3-1 and Compound C3. (19.4 g, yield 82%, MS: [M+H]$^+$=684).

Preparation of Compound 17

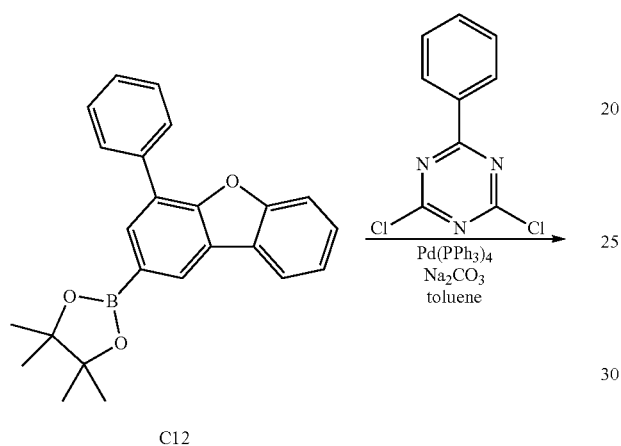

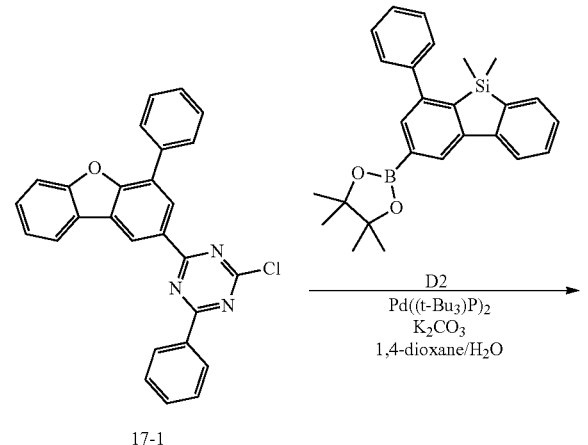

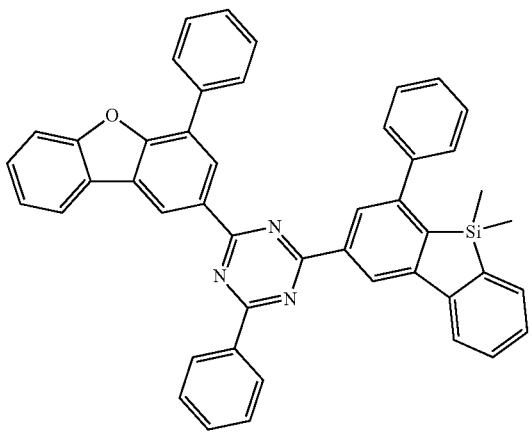

17

Preparation of Compound 17-1

Compound 17-1 was prepared in the same manner as in the method of preparing Compound C1-1 except that Compound C12 and 2,4-dichloro-6-phenyl-1,3,5-triazine were respectively used instead of Compound A1 and phenylboronic acid. (12 g, yield 68%, MS: [M+H]$^+$=434)

Preparation of Compound 17

Compound 17 was prepared in the same manner as in the method of preparing Compound 3 except that Compound 17-1 and Compound D2 were respectively used instead of Compound 3-1 and Compound C3. (18.7 g, yield 79%, MS: [M+H]$^+$=684).

Preparation of Compound 18

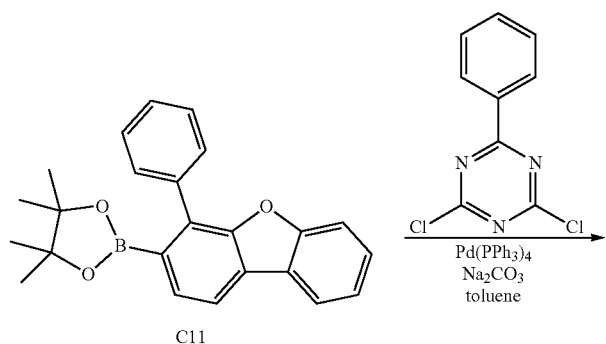

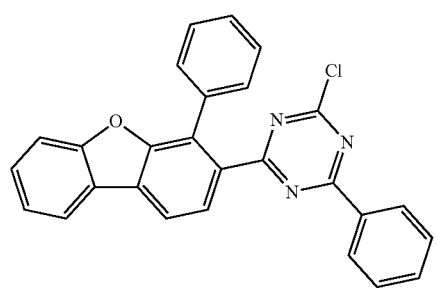
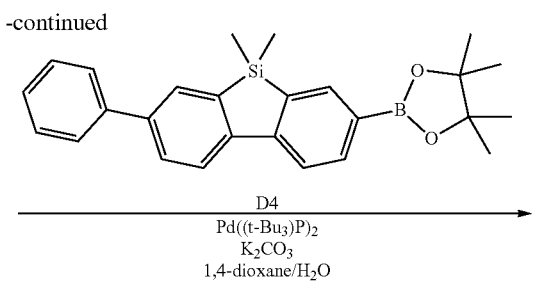

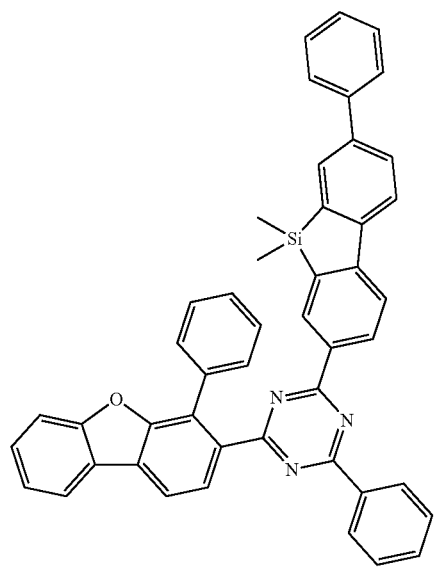

Preparation of Compound 18-1

Compound 18-1 was prepared in the same manner as in the method of preparing Compound C1-1 except that Compound C11 and 2,4-dichloro-6-phenyl-1,3,5-triazine were respectively used instead of Compound A1 and phenylboronic acid. (14.8 g, yield 84%, MS: [M+H]$^+$=434).

Preparation of Compound 18

Compound 18 was prepared in the same manner as in the method of preparing Compound 3 except that Compound 18-1 and Compound D4 were respectively used instead of Compound 3-1 and Compound C3. (19.2 g, yield 81%, MS: [M+H]$^+$=684).

Example 1

A glass substrate on which indium tin oxide (ITO) was coated as a thin film to a thickness of 130 nm was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing the following Compound HI-1 to a thickness of 5 nm. A hole transfer layer was formed on the hole injection layer by thermal vacuum depositing the following Compound HT-1 to a thickness of 25 nm, and on the HT-1 deposited film, a hole control layer was formed by vacuum depositing the following Compound HT-2 to a thickness of 5 nm. Subsequently, a light emitting layer having a thickness of 40 nm was formed on the HT-2 deposited film by co-depositing Compound 1 prepared above and the following Compound Dp-25 in a weight ratio of 88:12. On the light emitting layer, an electron transfer layer was formed by vacuum depositing the following Compound ET-1 to a thickness of 25 nm, and an electron injection layer was formed thereon by vacuum depositing (thickness 10 nm) the following Compound ET-2 and LiQ in a weight ratio of 98:2. On the electron injection layer, a cathode was formed by depositing aluminum to a thickness of 100 nm.

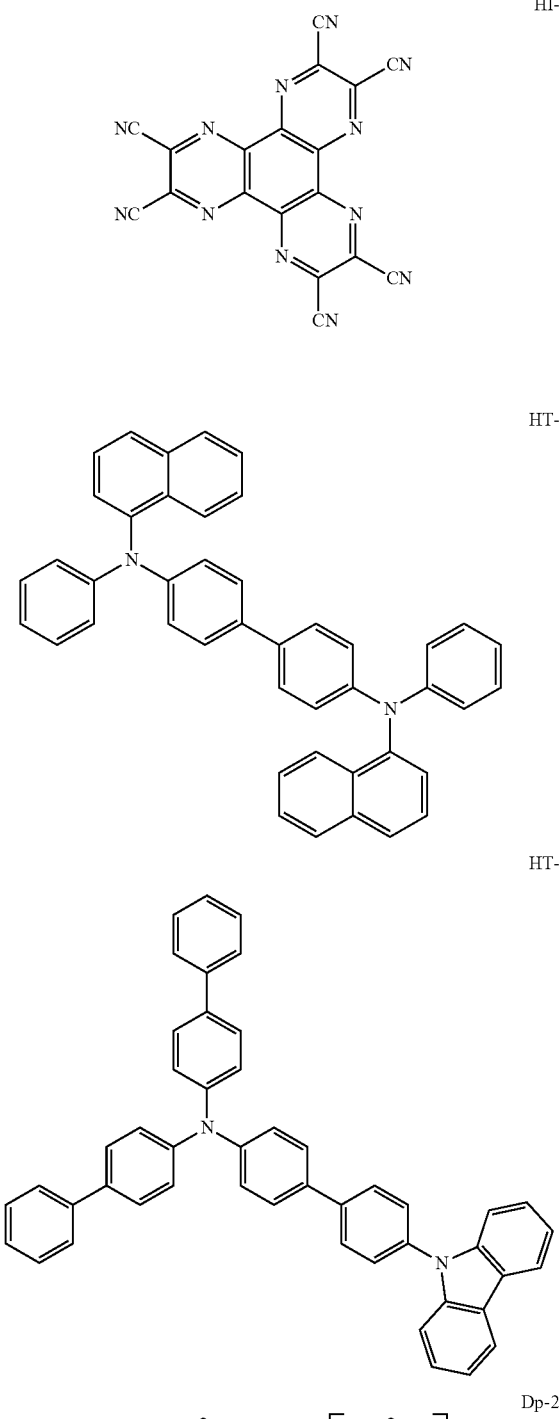
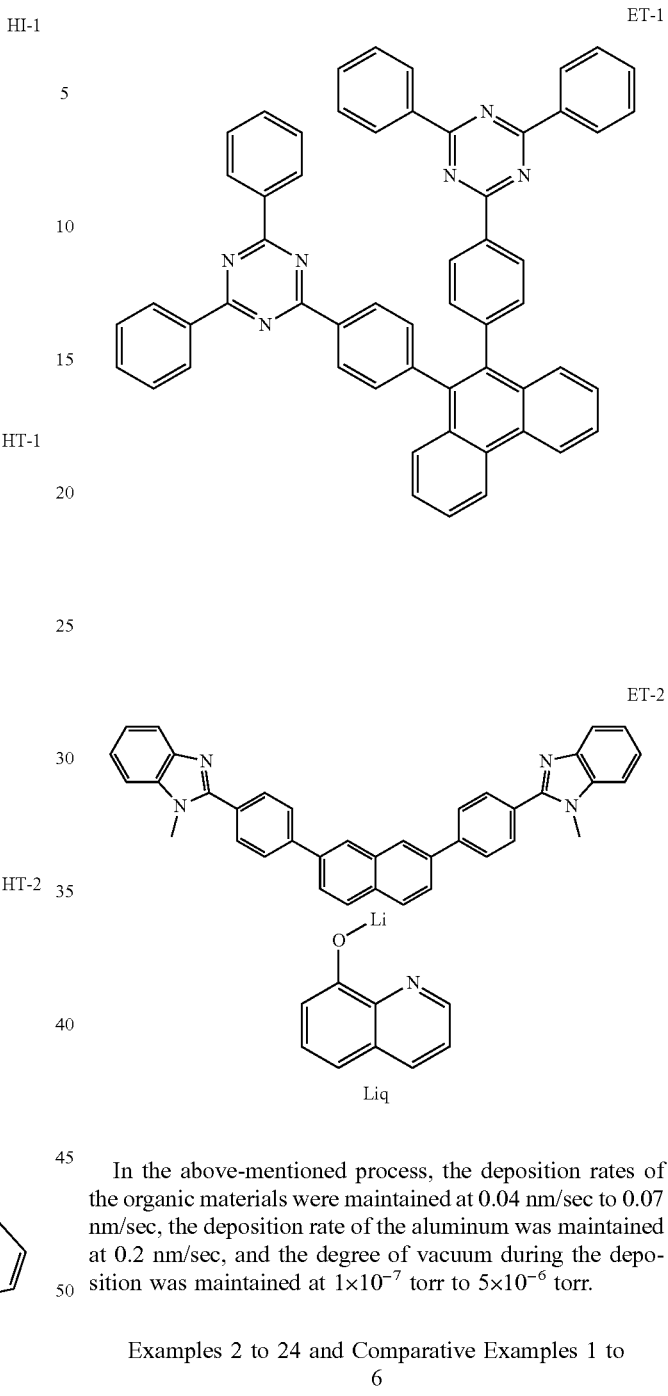
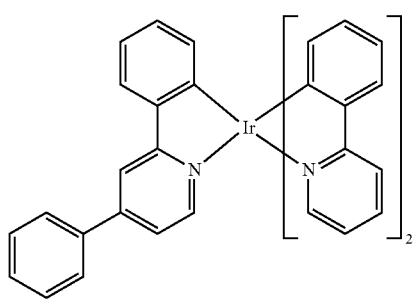

In the above-mentioned process, the deposition rates of the organic materials were maintained at 0.04 nm/sec to 0.07 nm/sec, the deposition rate of the aluminum was maintained at 0.2 nm/sec, and the degree of vacuum during the deposition was maintained at $1\times10^{-7}$ torr to $5\times10^{-6}$ torr.

Examples 2 to 24 and Comparative Examples 1 to 6

Organic light emitting devices of Examples 2 to 18 and Comparative Examples 1 to 4 were manufactured in the same manner as in Example 1 except that compounds described in the following Table 1 were used instead of Compound 1.

In Examples 19 to 24 and Comparative Examples 5 and 6, organic light emitting devices were manufactured in the same manner as in Example 1 except that compounds described in the following Table 1 were used in a weight ratio of 1:1 instead of Compound 1. Taking Example 19 as an example, Compound 1 and Compound H-2 were used in a weight ratio of 1:1 instead of Compound 1 in Example 1.

173
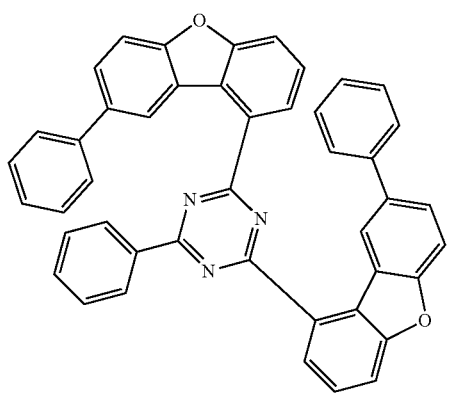
1
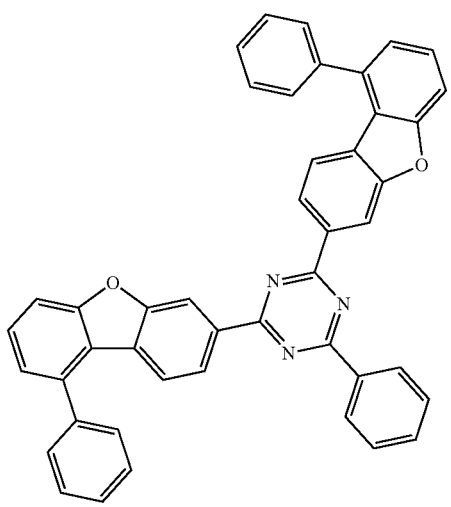
2
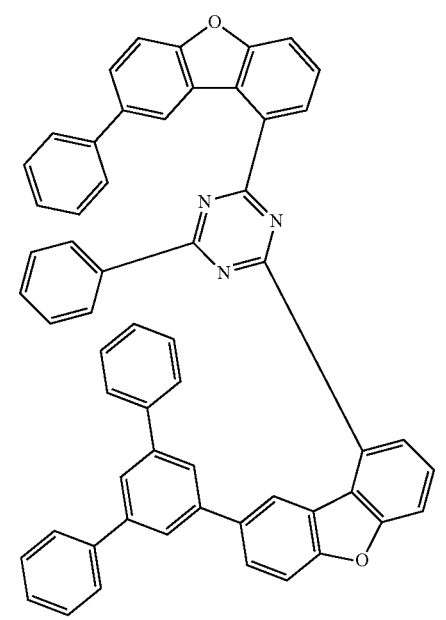
3
174
-continued
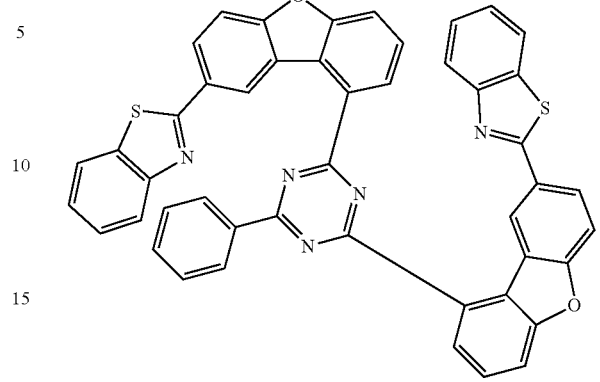
4
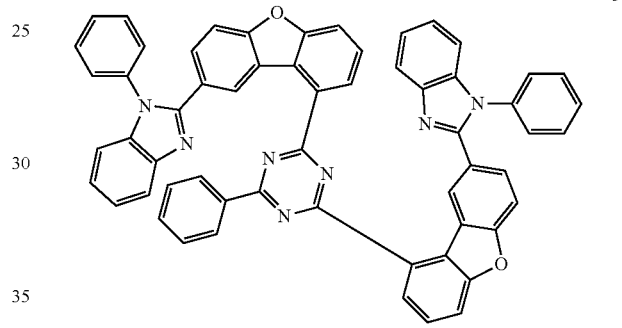
5
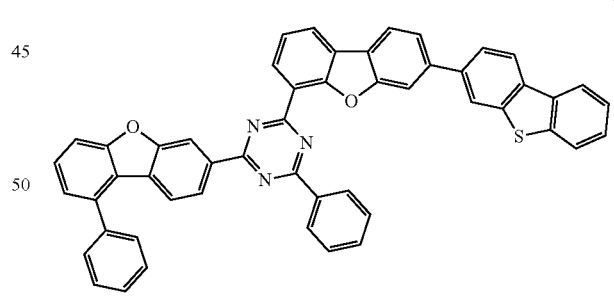
6
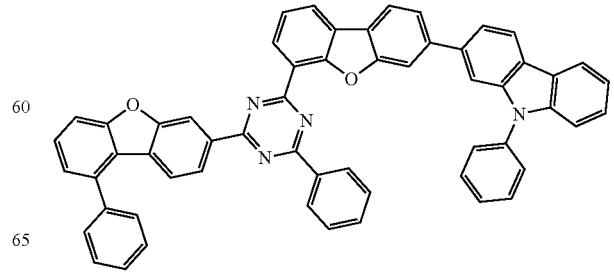
7

-continued
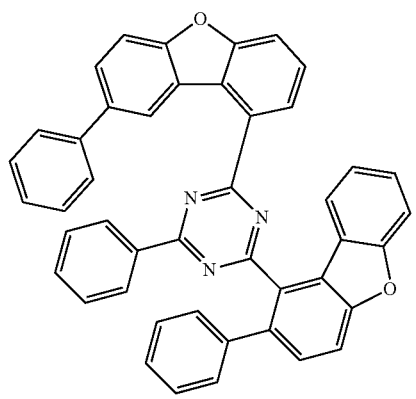
8
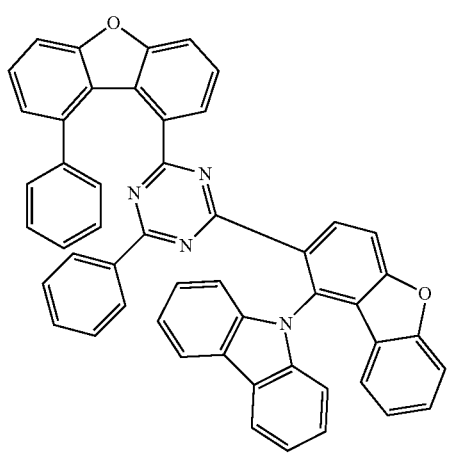
9
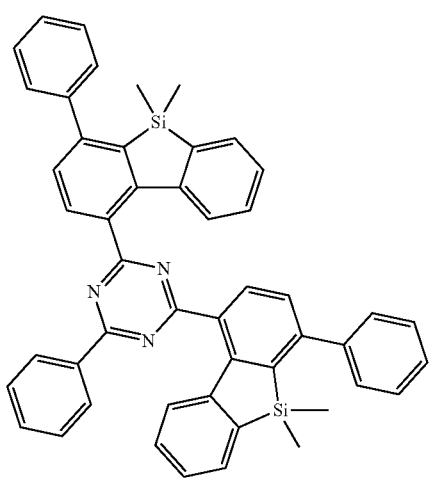
10
-continued
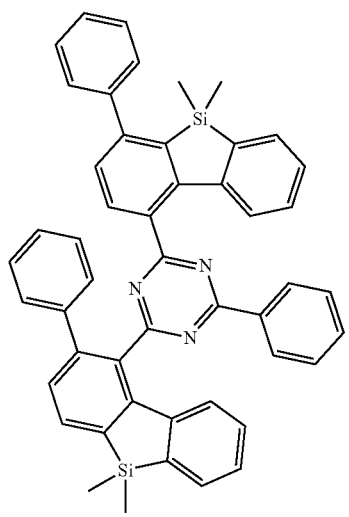
11
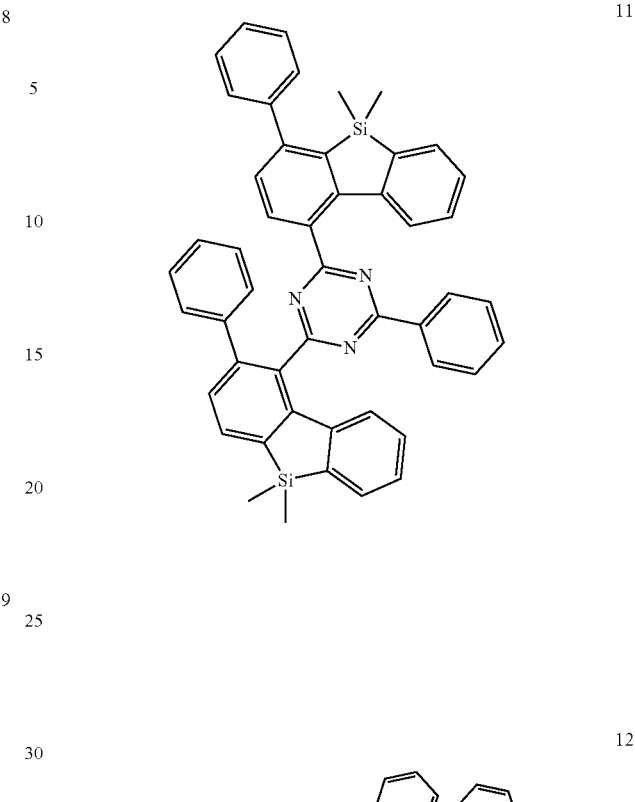
12
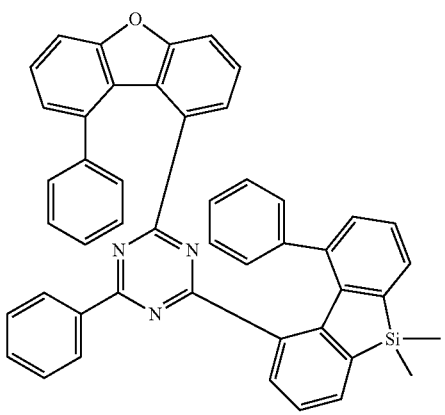
13

14
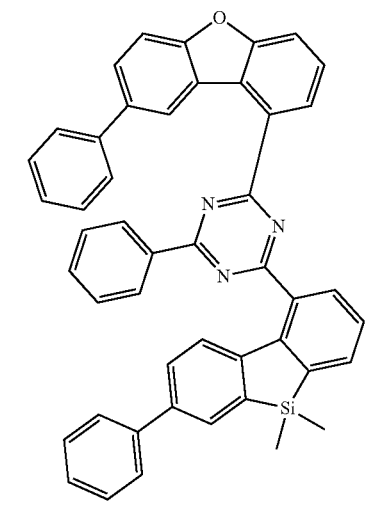
15
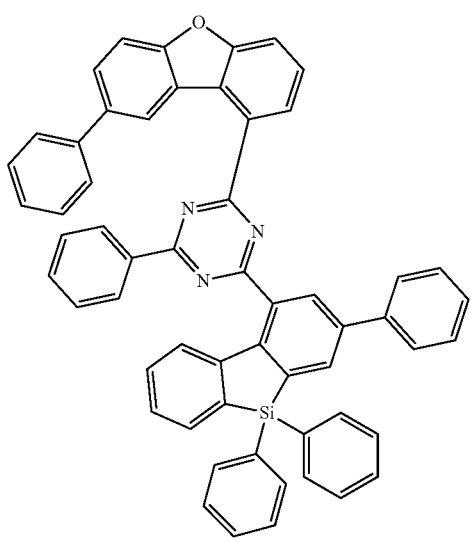
16
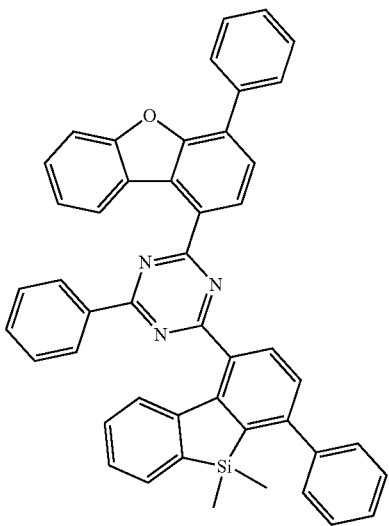
17
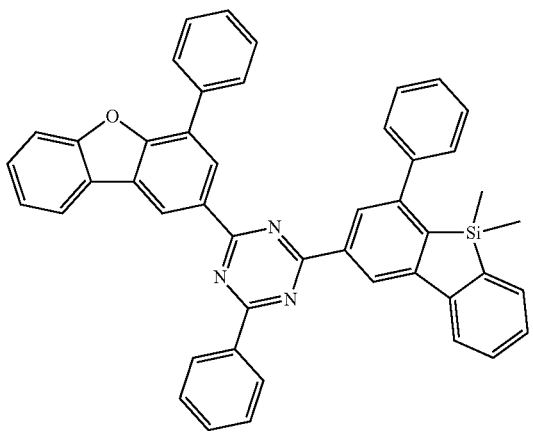
18
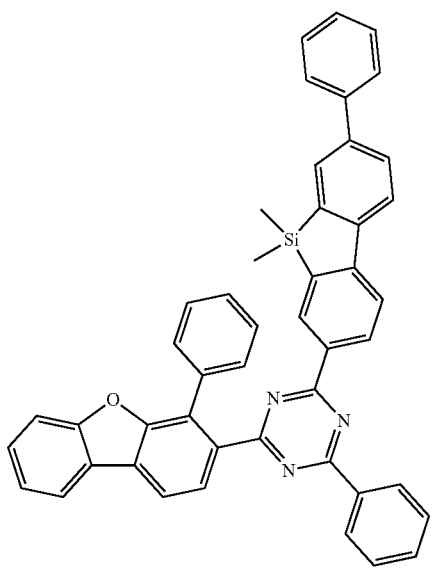
H-1
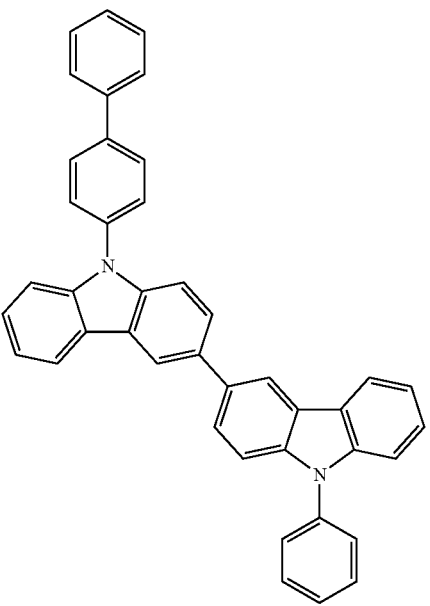

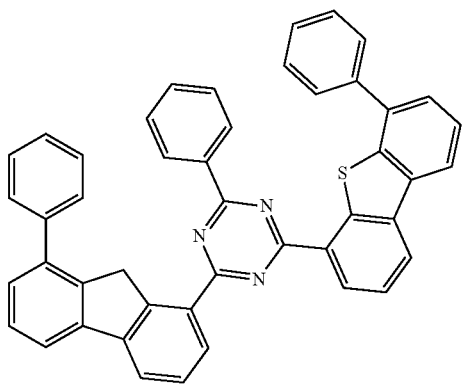

C1

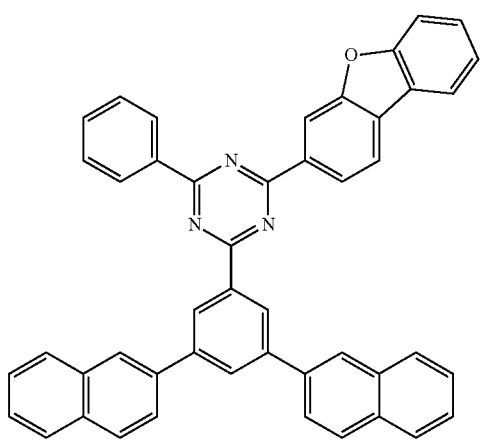

C2

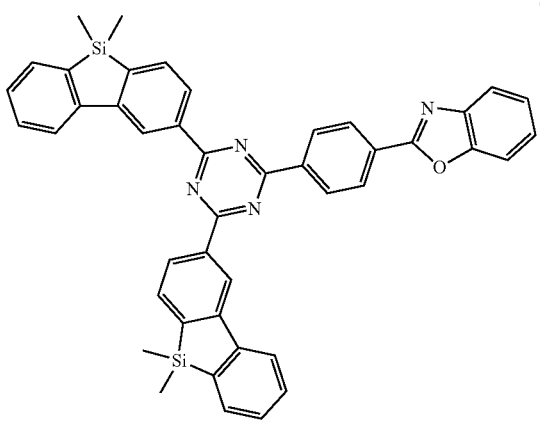

C3

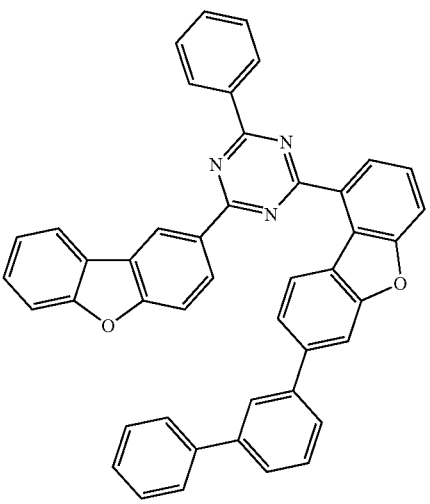

C4

Voltage, current efficiency, light emission color and lifetime were measured when applying current density of 10 mA/cm² to each of the organic light emitting devices of the examples and the comparative examples, and the results are shown in the following Table 1. Herein, $T_{95}$ means time taken for luminance decreasing to 95% when employing initial luminance at current density of 20 mA/cm² as 100%.

TABLE 1

| | Compound | Voltage (V) (@10 mA/cm²) | Efficiency (cd/A) (@10 mA/cm²) | Light Emission Color | $T_{95}$ (@20 mA/cm²) |
|---|---|---|---|---|---|
| Example 1 | 1 | 3.01 | 65.9 | Green | 59 |
| Example 2 | 2 | 3.00 | 65.8 | Green | 60 |
| Example 3 | 3 | 3.06 | 66.6 | Green | 69 |
| Example 4 | 4 | 3.13 | 62.1 | Green | 71 |
| Example 5 | 5 | 3.15 | 62.3 | Green | 69 |
| Example 6 | 6 | 3.11 | 63.6 | Green | 72 |
| Example 7 | 7 | 3.17 | 64.5 | Green | 75 |
| Example 8 | 8 | 2.97 | 66.1 | Green | 59 |
| Example 9 | 9 | 2.89 | 64.0 | Green | 66 |
| Example 10 | 10 | 2.84 | 66.1 | Green | 69 |
| Example 11 | 11 | 3.11 | 67.2 | Green | 68 |
| Example 12 | 12 | 2.98 | 67.9 | Green | 60 |
| Example 13 | 13 | 2.92 | 66.9 | Green | 65 |
| Example 14 | 14 | 3.05 | 68.0 | Green | 58 |
| Example 15 | 15 | 3.03 | 65.9 | Green | 70 |
| Example 16 | 16 | 3.10 | 66.5 | Green | 68 |
| Example 17 | 17 | 3.09 | 68.8 | Green | 66 |
| Example 18 | 18 | 2.97 | 66.8 | Green | 62 |
| Comparative Example 1 | C1 | 3.01 | 60.0 | Green | 40 |
| Comparative Example 2 | C2 | 3.07 | 62.5 | Green | 43 |
| Comparative Example 3 | C3 | 3.11 | 59.5 | Green | 62 |
| Comparative Example 4 | C4 | 3.14 | 58.9 | Green | 66 |
| Example 19 | 1, H-1 | 3.29 | 72.1 | Green | 160 |
| Example 20 | 4, H-1 | 3.20 | 74.8 | Green | 169 |
| Example 21 | 6, H-1 | 3.28 | 74.0 | Green | 161 |
| Example 22 | 11, H-1 | 3.32 | 74.7 | Green | 165 |
| Example 23 | 12, H-1 | 3.48 | 74.9 | Green | 169 |
| Example 24 | 16, H-1 | 3.26 | 74.1 | Green | 171 |
| Comparative Example 5 | C1, H-1 | 3.50 | 65.0 | Green | 138 |
| Comparative Example 6 | C4, H-1 | 3.48 | 65.9 | Green | 141 |

Examples 1 to 18 and Comparative Examples 1 and 2 are examples of a device using a single host in a light emitting layer.

Compound C1 used in Comparative Example 1 is a compound in which triazine is substituted with two dibenzothiophenyl groups. From Table 1, it was identified that the devices of Examples 1 to 18 had lifetime properties enhanced by approximately 55% to 88% compared to the device of Comparative Example 1.

Compound C2 used in Comparative Example 2 is a compound in which triazine is substituted with one dibenzofuranyl group and two aryl groups. From Table 1, it was identified that the devices of Examples 1 to 18 had lifetime properties enhanced by approximately 37% to 75% compared to the device of Comparative Example 2.

Compound C3 used in Comparative Example 3 is a compound in which a phenyl group, one of substituents of the triazine, is substituted with a heteroaryl group. From Table 1, it was identified that the devices of Examples 1 to 18 had current efficiency enhanced by approximately 4.3% to 15.5% compared to the device of Comparative Example 3.

Compound C4 used in Comparative Example 4 is a compound in which one dibenzofuranyl group of the two dibenzofuranyl groups, a substituent of the triazine, is unsubstituted. From Table 1, it was identified that the devices of Examples 1 to 18 had current efficiency enhanced by approximately 4.7% to 17% compared to the device of Comparative Example 4.

Examples 19 to 24 are examples of a device using two types of hosts in a light emitting layer. When comparing Examples 19 to 24 and Examples 1 to 18, it was identified that, when using two types of hosts in a light emitting layer, current efficiency increased more, and particularly, lifetime properties were significantly enhanced.

It was identified that, when using two types of hosts in the light emitting layer, the devices of Examples 19 to 24 using the compound of the present disclosure also had excellent current efficiency and lifetime properties compared to the devices of Comparative Examples 5 and 6.

In the compound of Chemical Formula 1 of the present disclosure, a dibenzofuranyl group and/or a dibenzosilole group directly bond to triazine having strong electron properties, and the dibenzofuranyl group and/or the dibenzosilole group are substituted with an aryl group and a heteroaryl group having strong hole properties. By the above-described structural characteristics, the compound of Chemical Formula 1 of the present disclosure may be understood to have advantages in terms of device efficiency and lifetime since holes and electros are smoothly inflowing, and holes and electrons are well balanced.

The invention claimed is:

1. A compound of the following Chemical Formula 1:

[Chemical Formula 1]

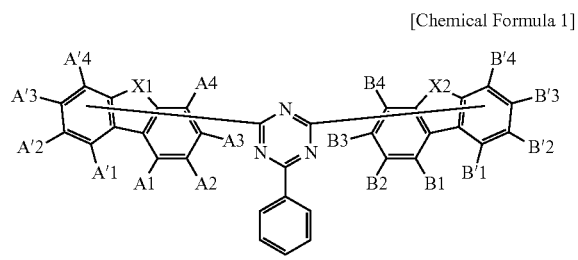

wherein, in Chemical Formula 1,

X1 is SiRaRb;

X2 is O or SiRcRd;

Ra to Rd are the same as or different from each other, and each independently hydrogen; deuterium; an alkyl group; or an aryl group;

any one of A1 to A4 and A'1 to A'4 is a linking group bonding to triazine, any one is Ar1, and the rest are hydrogen;

any one of B1 to B4 and B'1 to B'4 is a linking group bonding to triazine, any one is Ar2, and the rest are hydrogen; and Ar1 and Ar2 are the same as or different from each other, and each independently an aryl group; or a heteroaryl group unsubstituted or substituted with an aryl group.

2. The compound of claim 1, wherein Chemical Formula 1 is any one of the following Chemical Formula 2 to Chemical Formula 4:

in the following Chemical Formula 2 to Chemical Formula 4, X1, X2, Ar1 and Ar2 have the same definitions as in Chemical Formula 1,

[Chemical Formula 2]

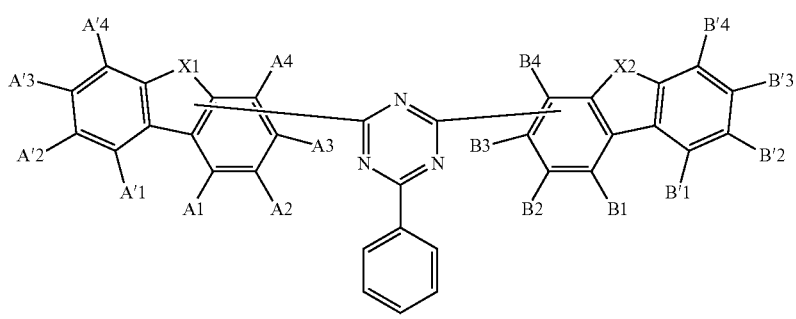

in Chemical Formula 2,
any one of A1 to A4 is a linking group bonding to triazine, and the rest are hydrogen;
any one of A'1 to A'4 is Ar1, and the rest are hydrogen;
any one of B1 to B4 is a linking group bonding to triazine, and the rest are hydrogen; and
any one of B'1 to B'4 is Ar2, and the rest are hydrogen,

[Chemical Formula 3]

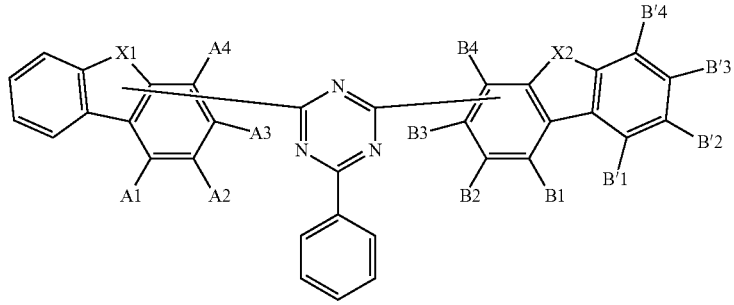

in Chemical Formula 3,
any one of A1 to A4 is a linking group bonding to triazine, any one is Ar1, and the rest are hydrogen;
any one of B1 to B4 is a linking group bonding to triazine, and the rest are hydrogen; and
any one of B'1 to B'4 is Ar2, and the rest are hydrogen,

[Chemical Formula 4]

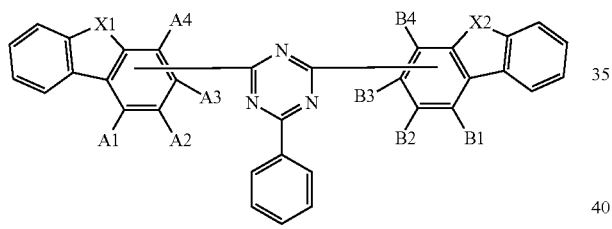

in Chemical Formula 4,
any one of A1 to A4 is a linking group bonding to triazine, any one is Ar1, and the rest are hydrogen; and
any one of B1 to B4 is a linking group bonding to triazine, any one is Ar2, and the rest are hydrogen.

3. The compound of claim 1, wherein Chemical Formula 1 is represented by any one of the following Chemical Formula 1-B and Chemical Formula 1-C:

[Chemical Formula 1-A]

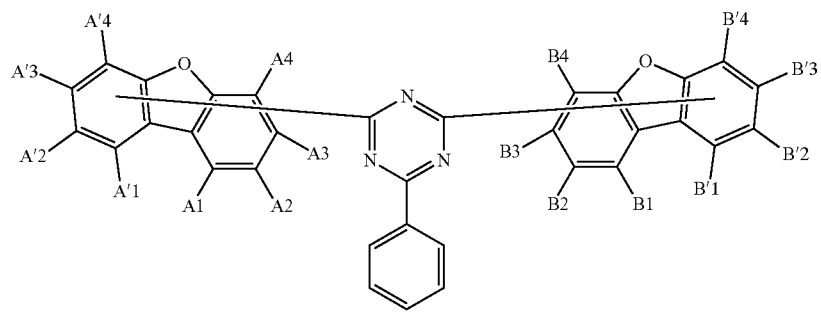

-continued

[Chemical Formula 1-B]

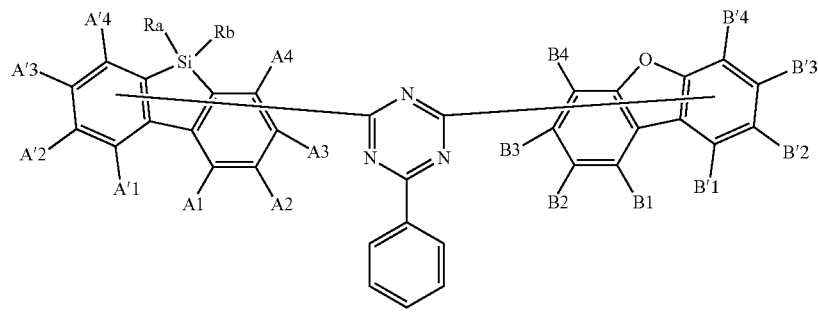

[Chemical Formula 1-C]

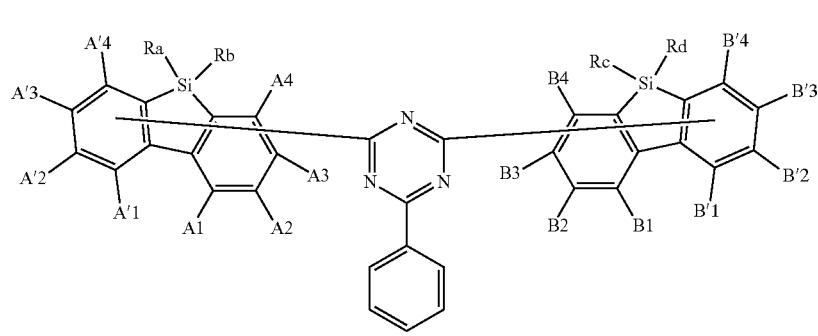

in Chemical Formula 1-B and Chemical Formula 1-C,
Ra to Rd, A1 to A4, A'1 to A'4, B1 to B4 and B'1 to B'4 have the same definitions as in Chemical Formula 1.

4. The compound of claim 1, wherein Ar1 and Ar2 are the same as or different from each other, and each independently an aryl group having 6 to 25 carbon atoms; or a heteroaryl group having 2 to 25 carbon atoms unsubstituted or substituted with an aryl group.

5. The compound of claim 1, wherein the compound of Chemical Formula 1 is any one selected from among the following compounds:

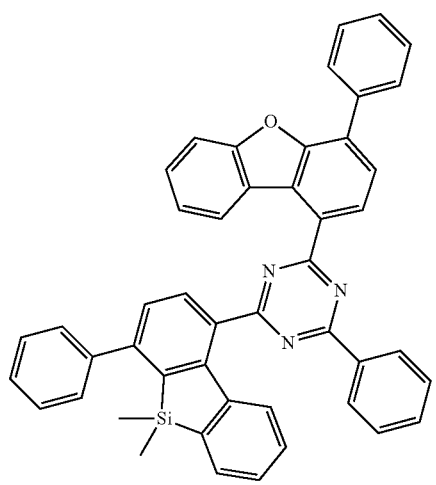

-continued

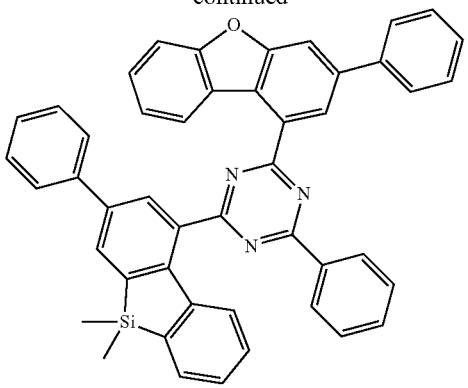

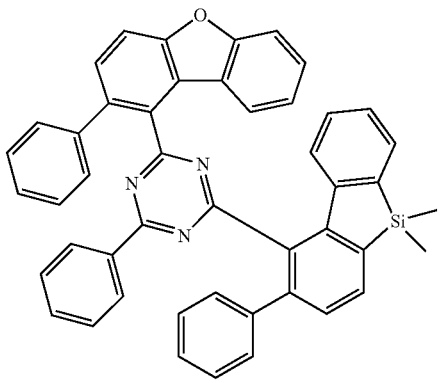

-continued
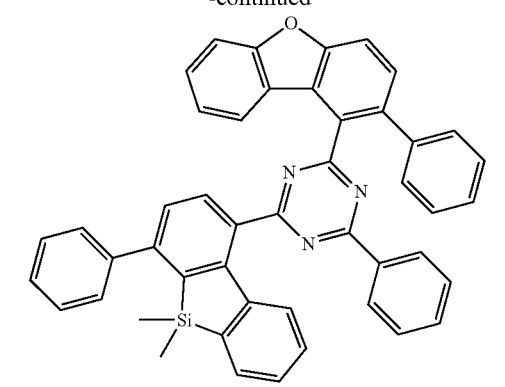
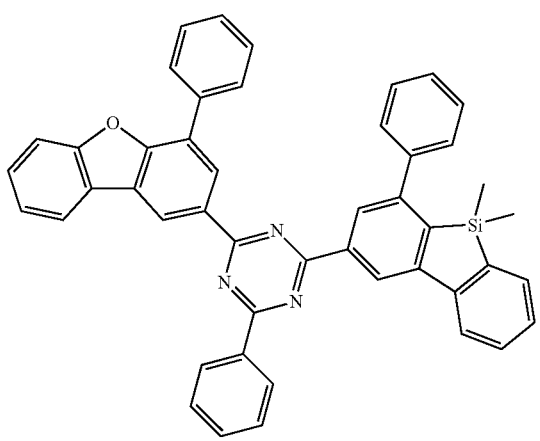
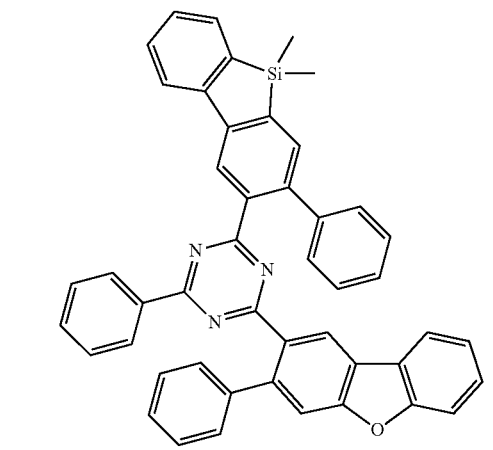
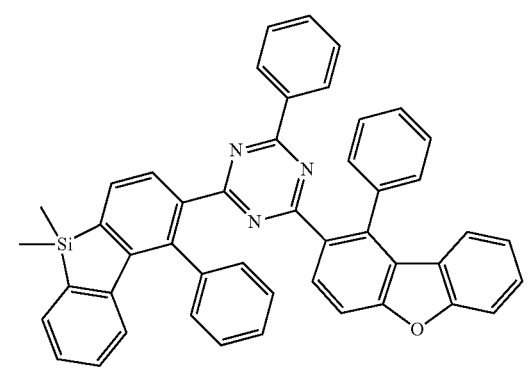
-continued
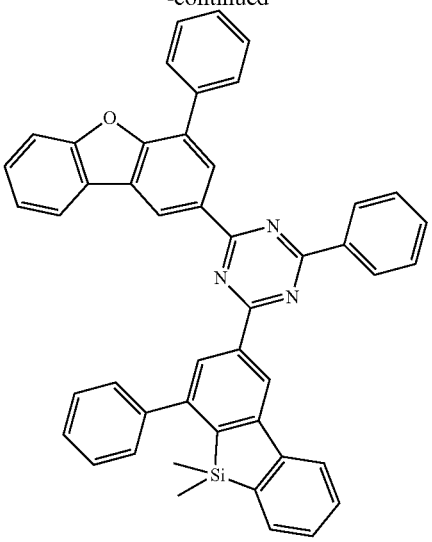
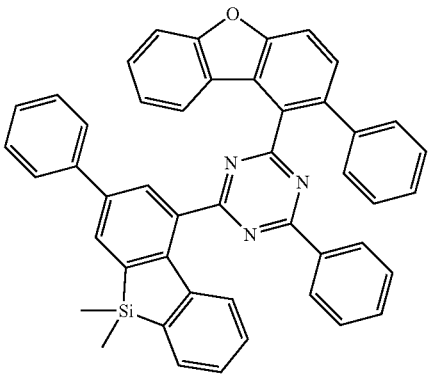
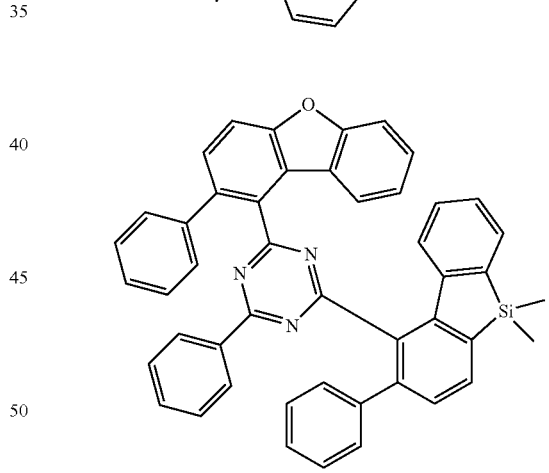
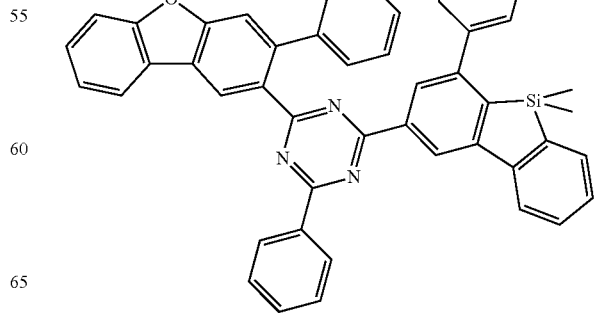

189
-continued
190
-continued
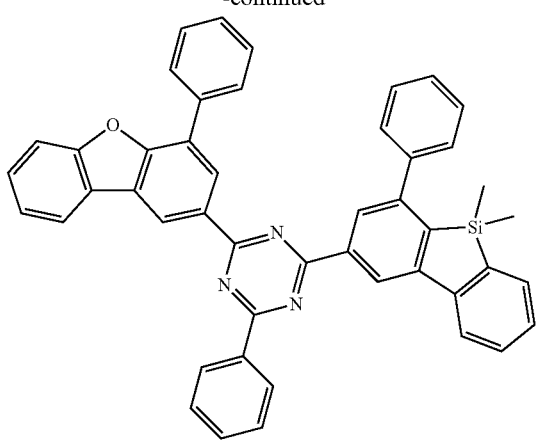
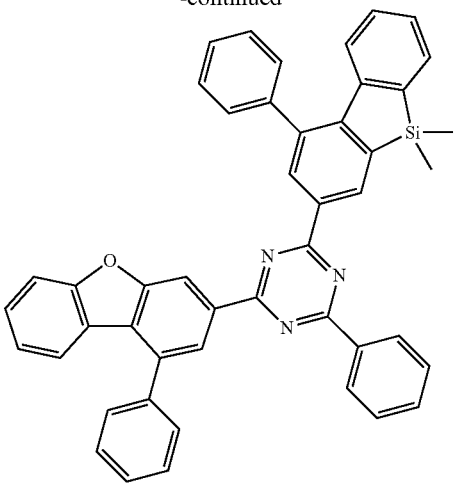
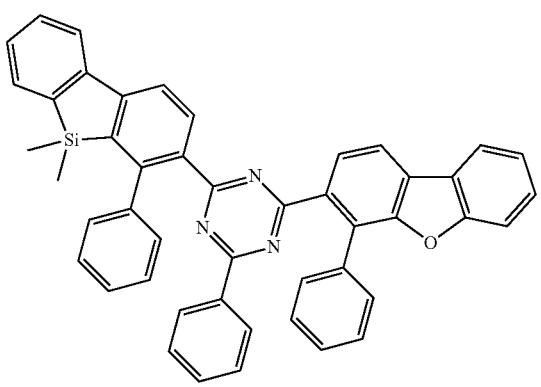
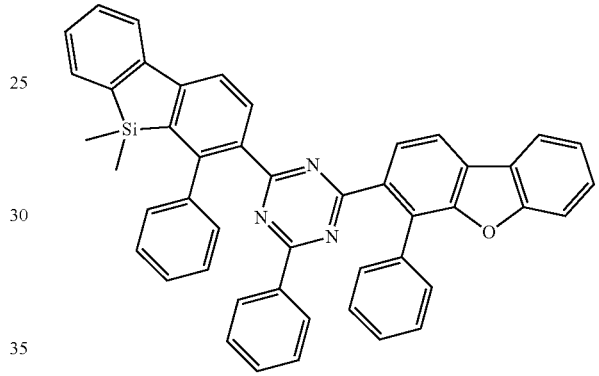
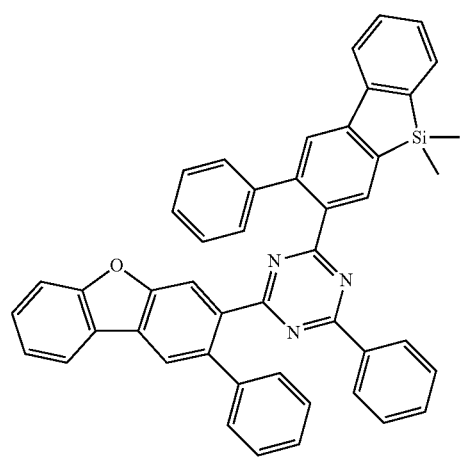
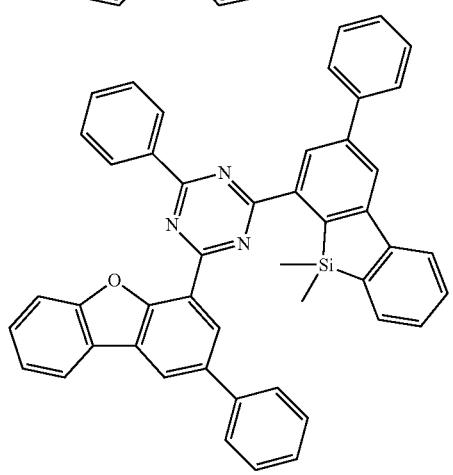

191
-continued
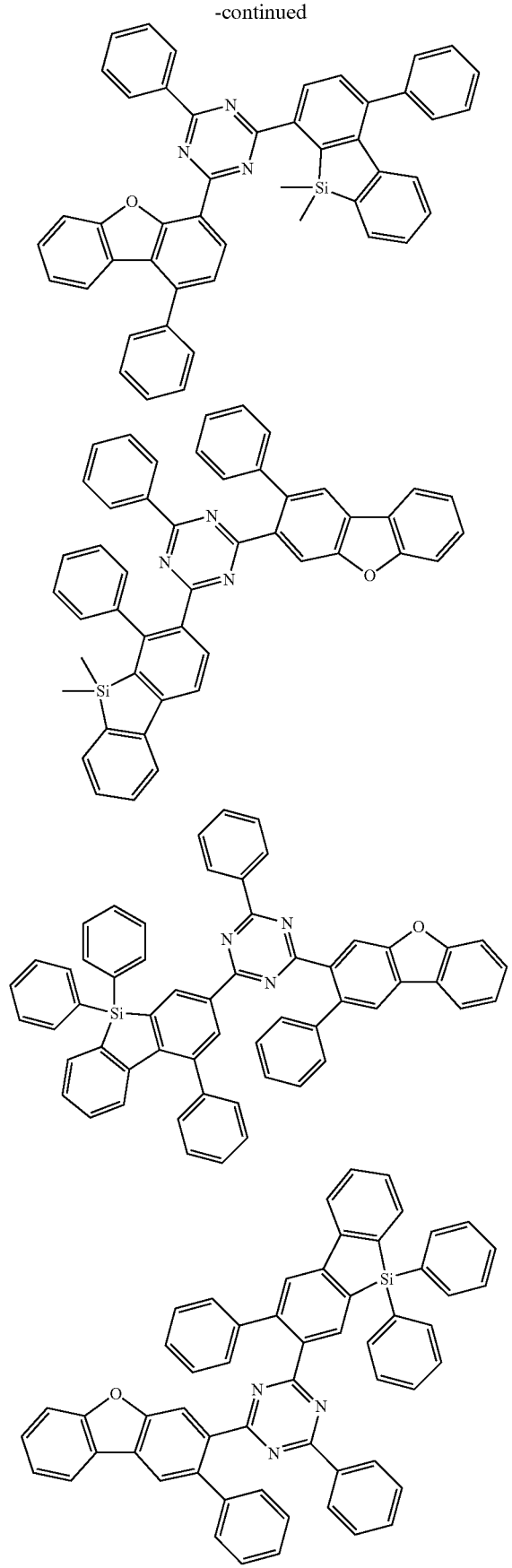
192
-continued
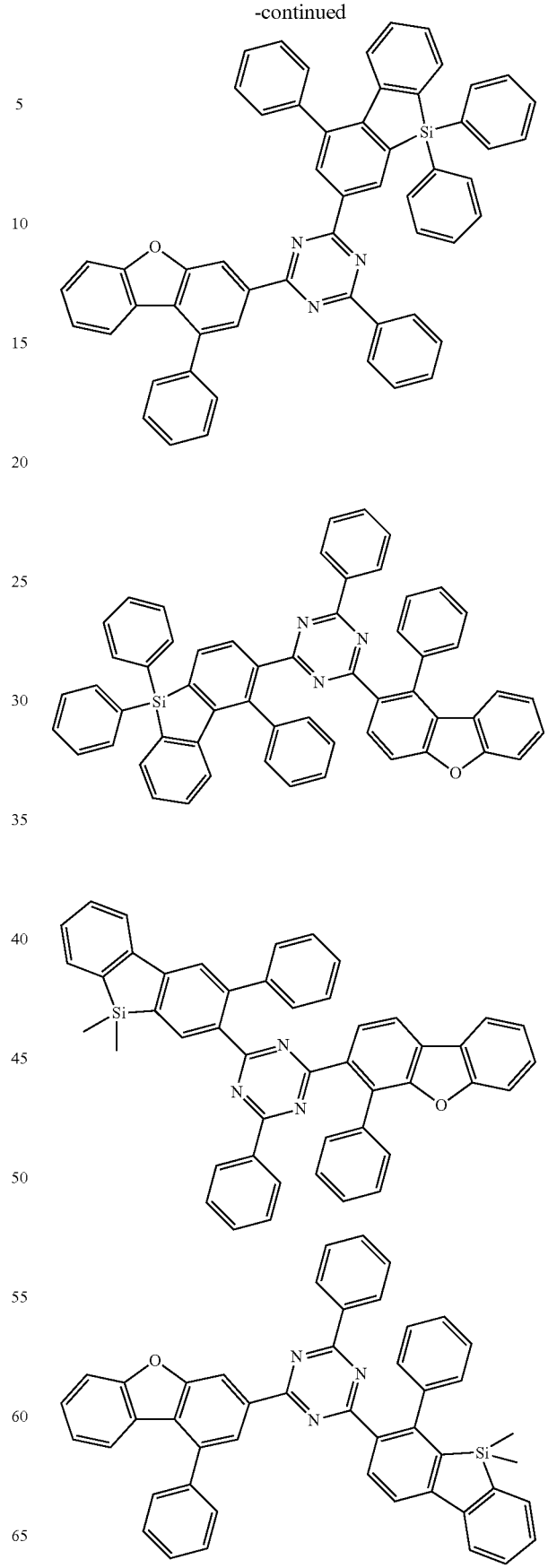

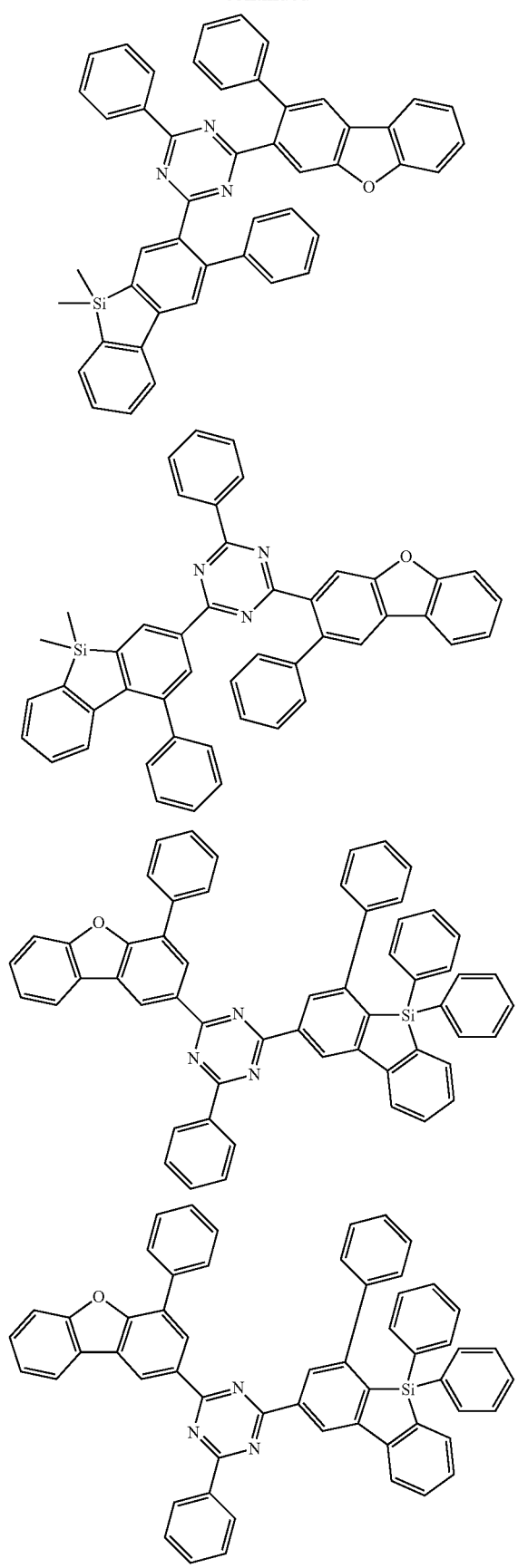
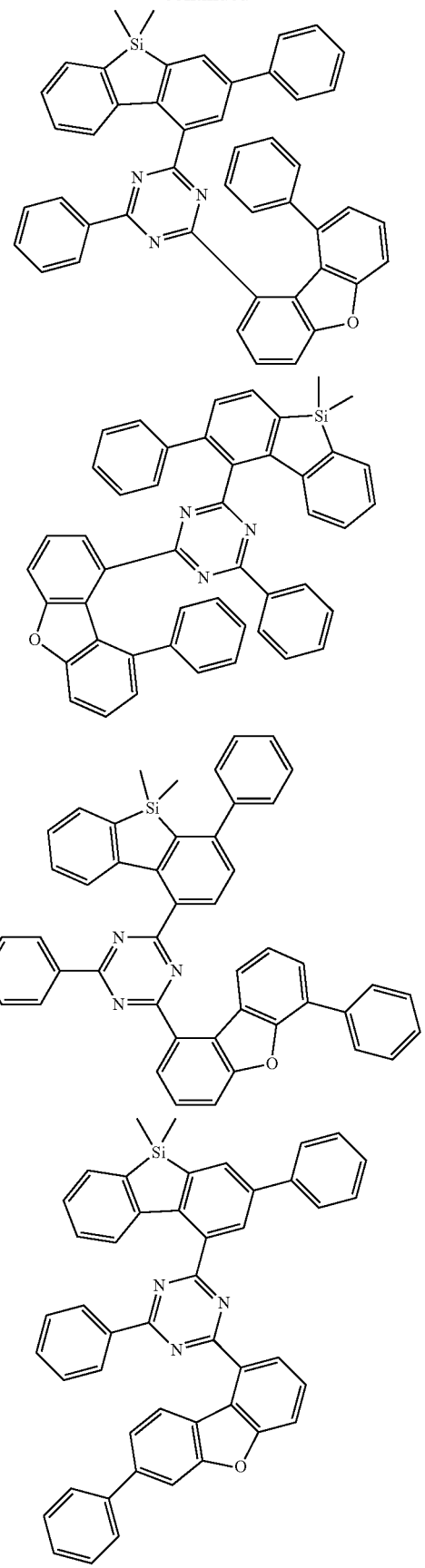

195
-continued
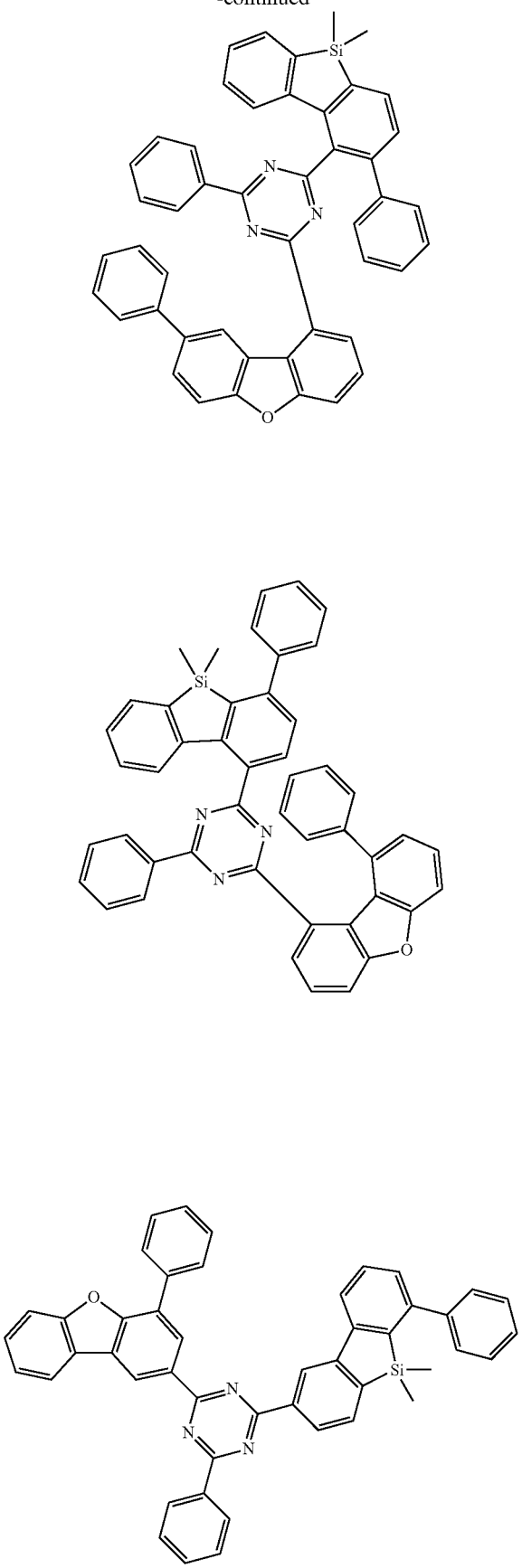
196
-continued
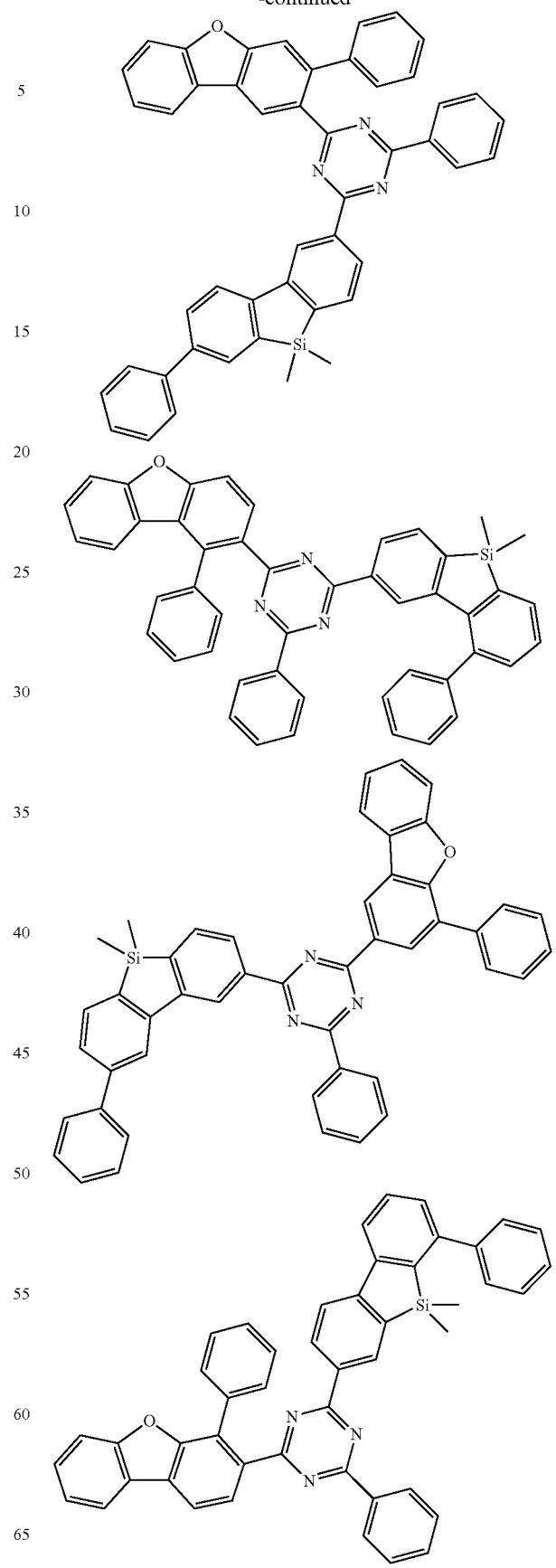

197
-continued
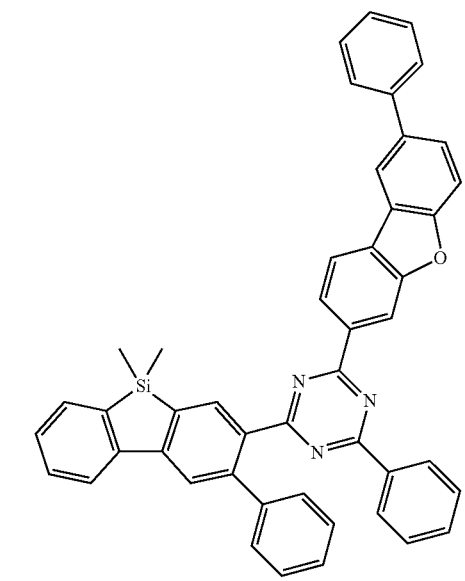
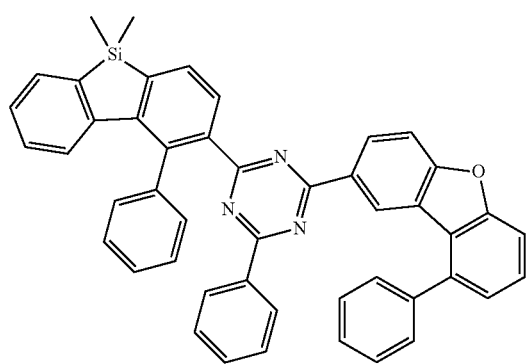
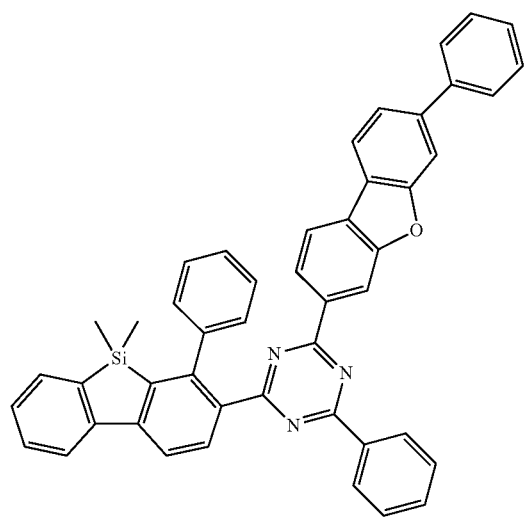
198
-continued
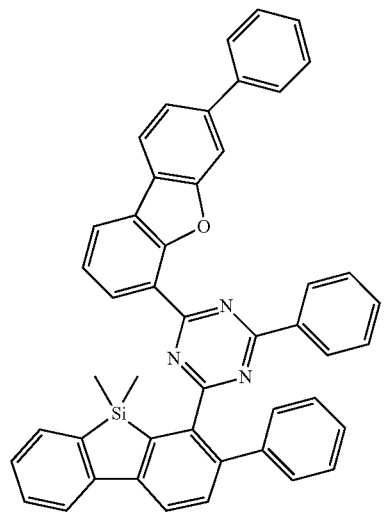
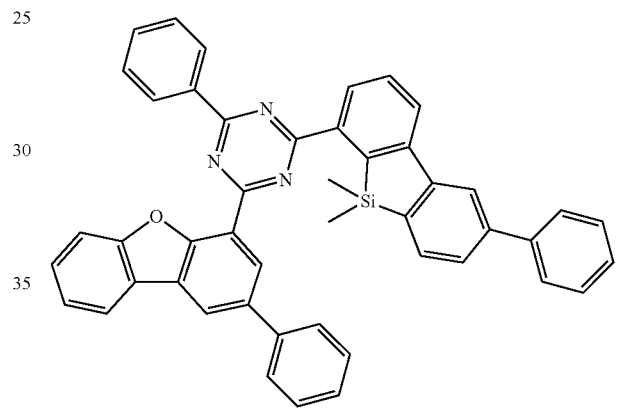
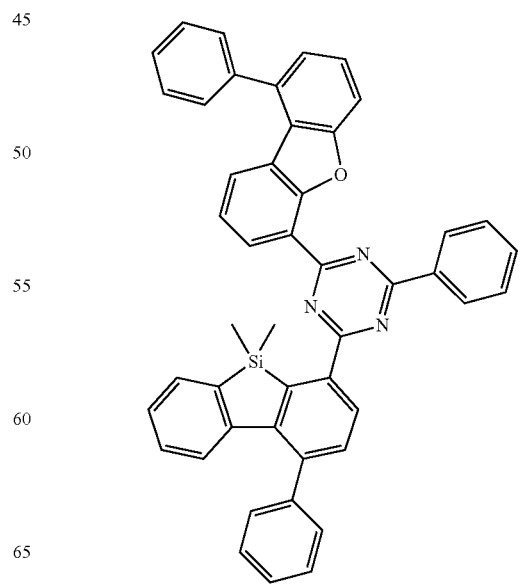

199
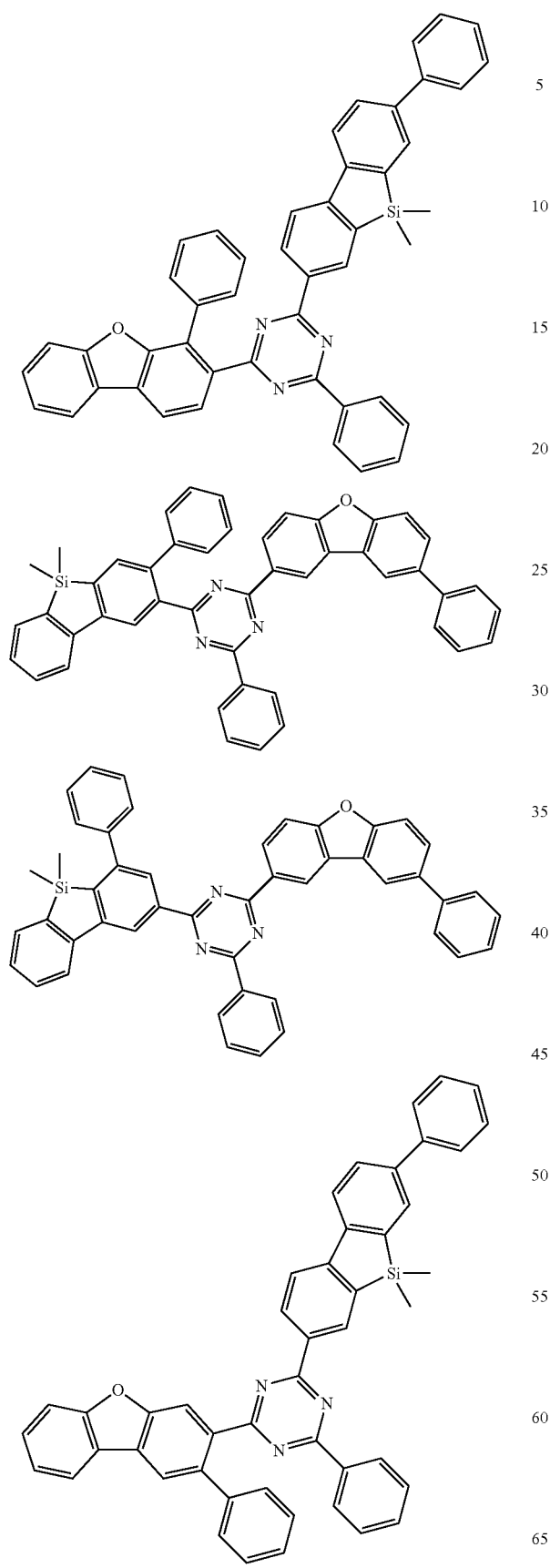
200
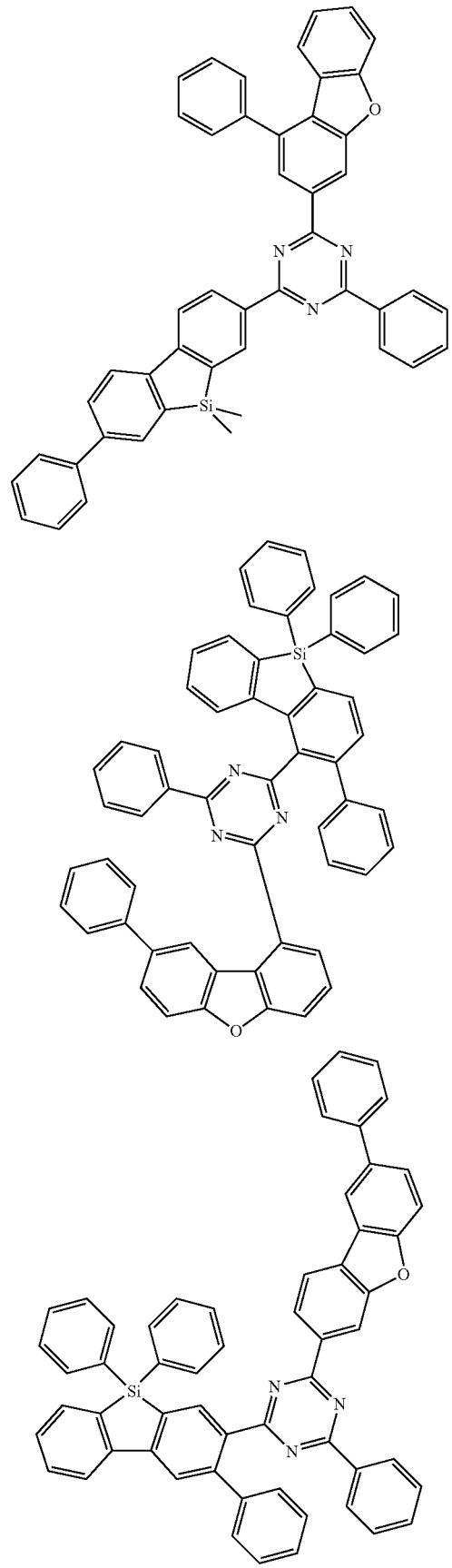

201
-continued
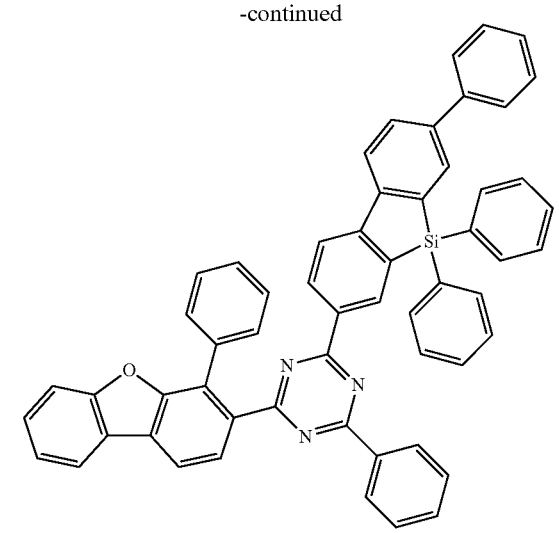
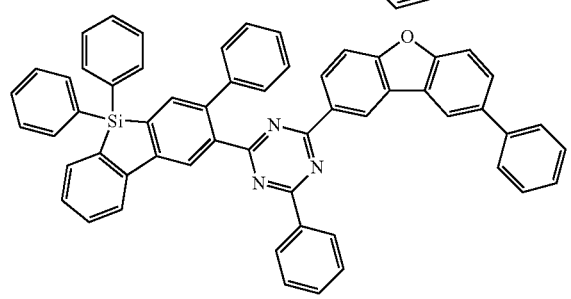
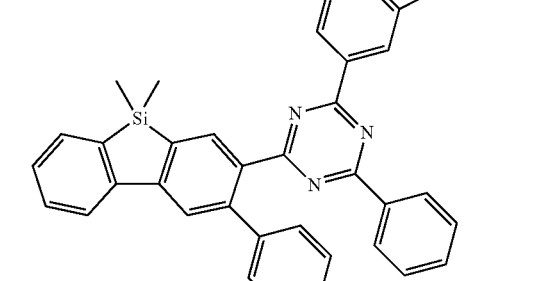
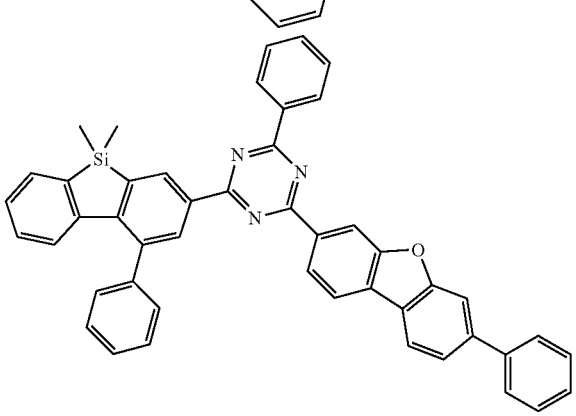
202
-continued
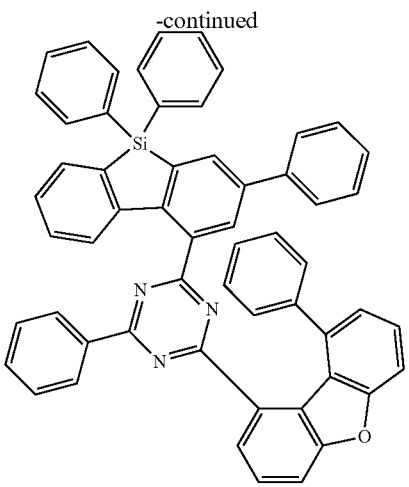
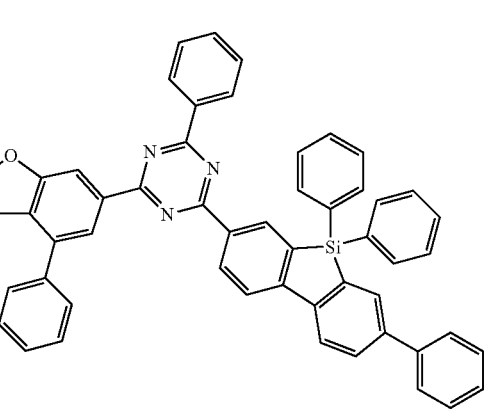
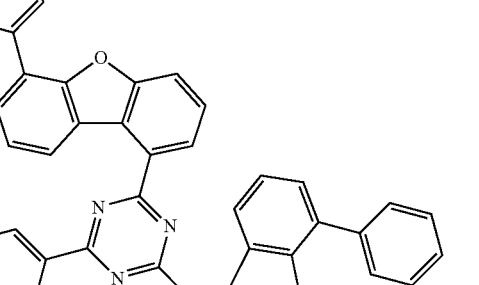
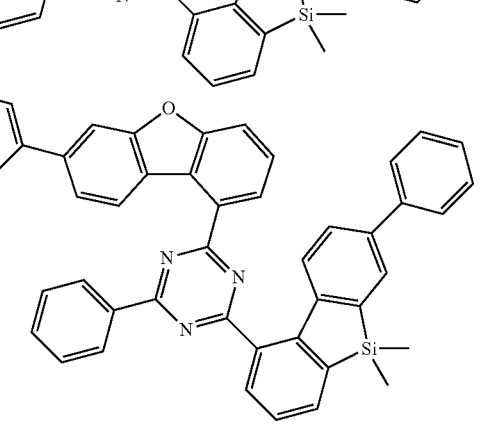

203
-continued
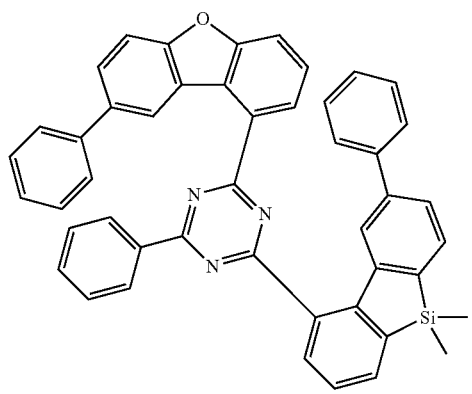
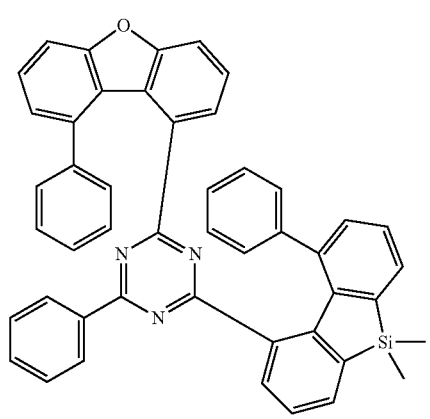
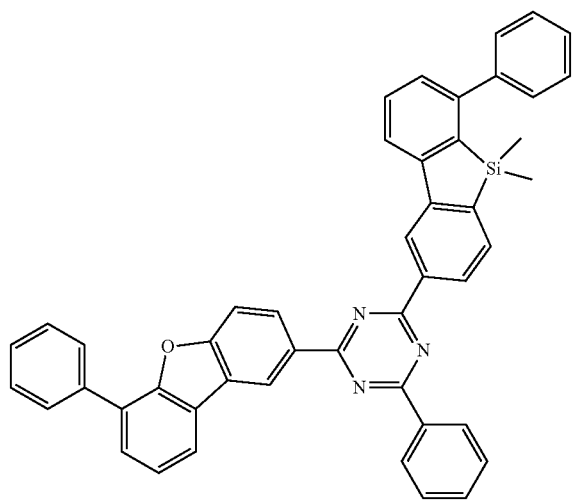
204
-continued
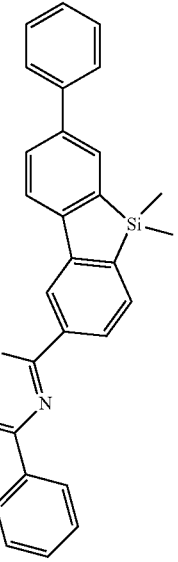
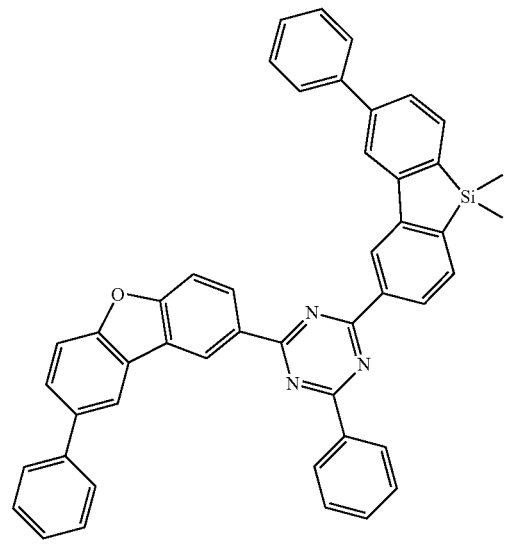
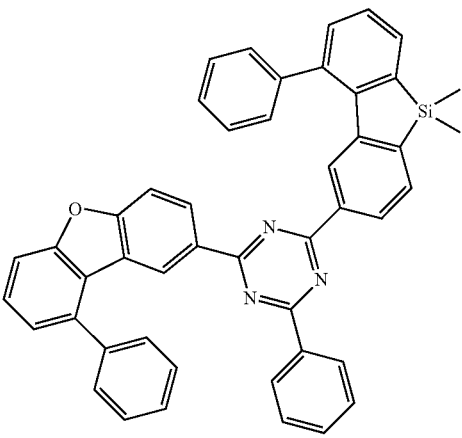

205
-continued
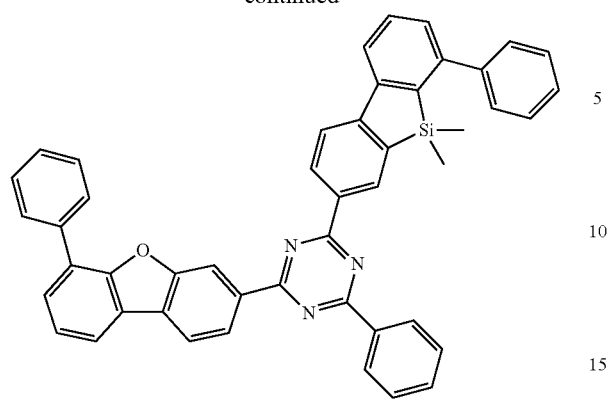
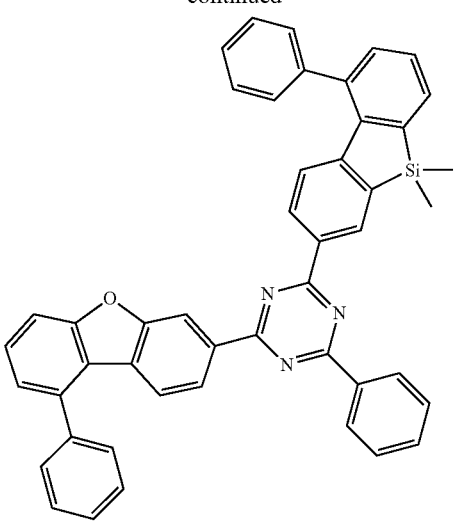
206
-continued
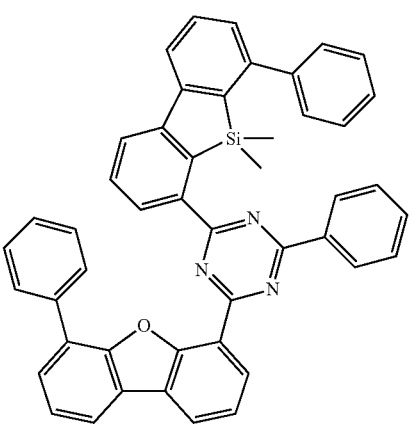
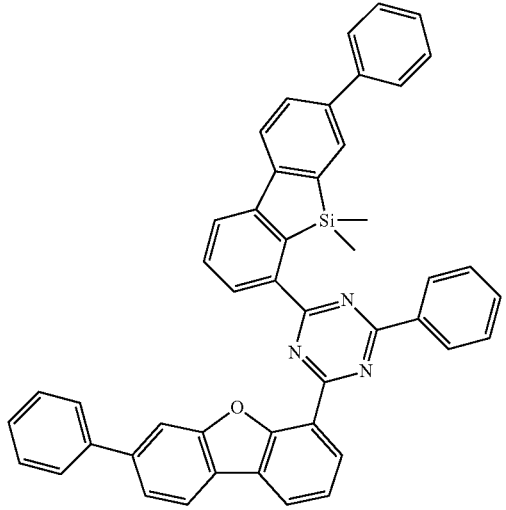

207
-continued
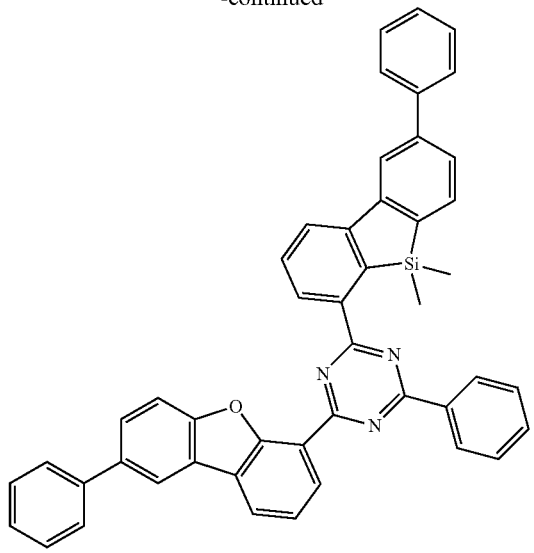
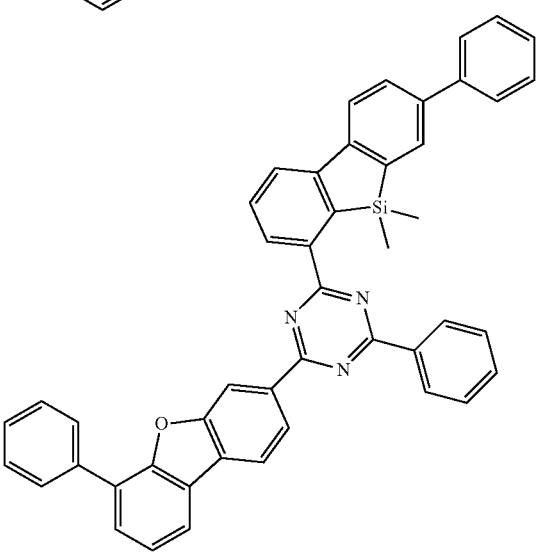
208
-continued
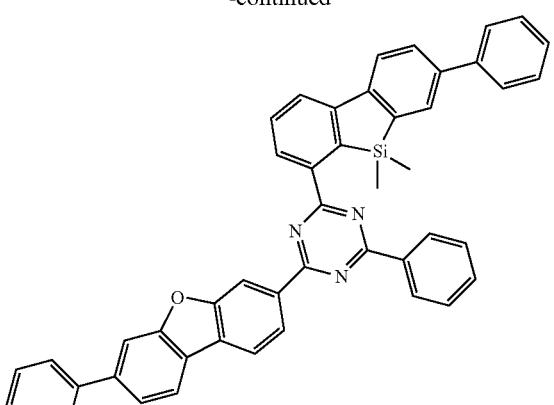
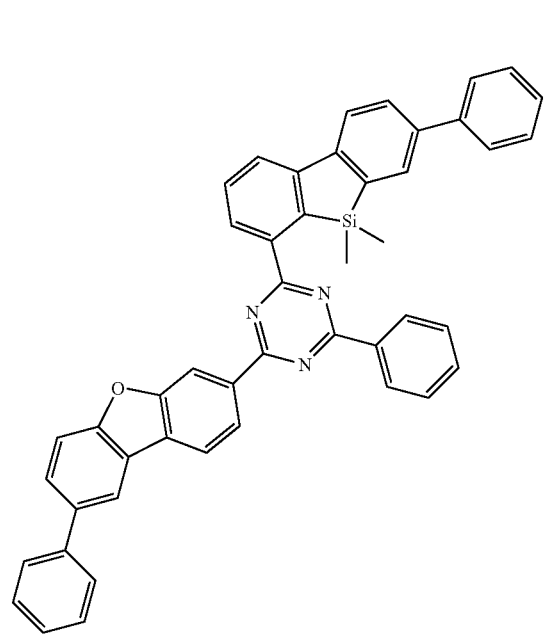
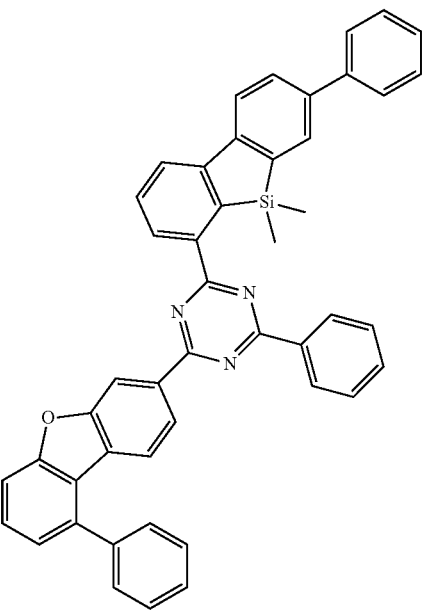

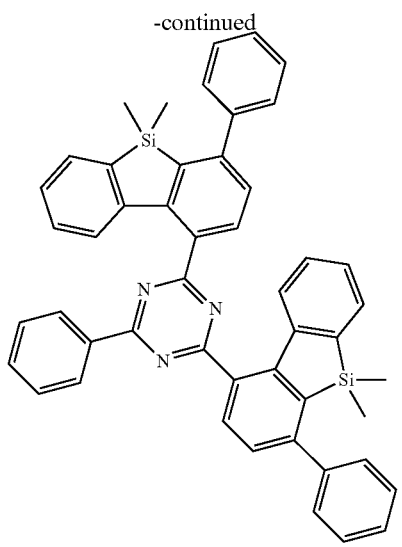
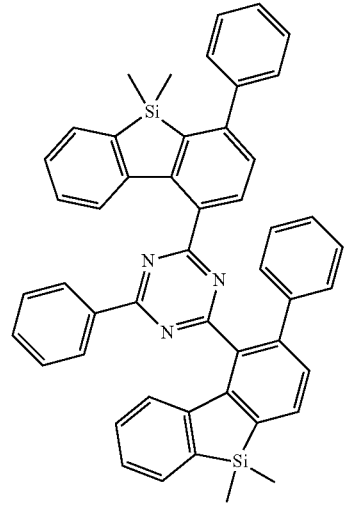
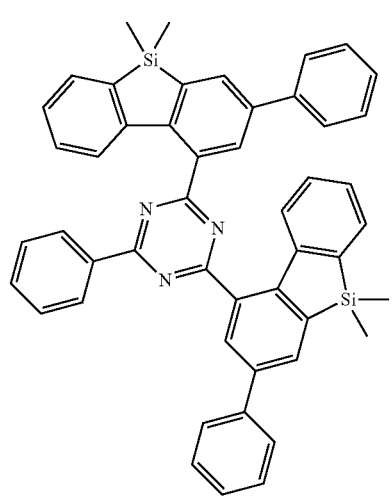
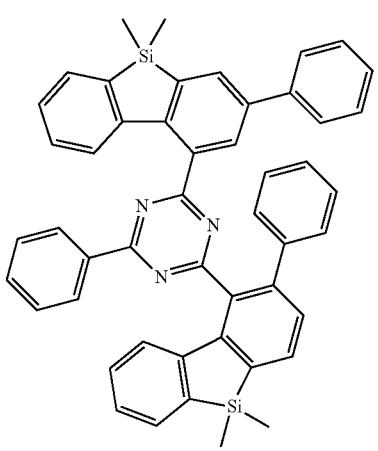
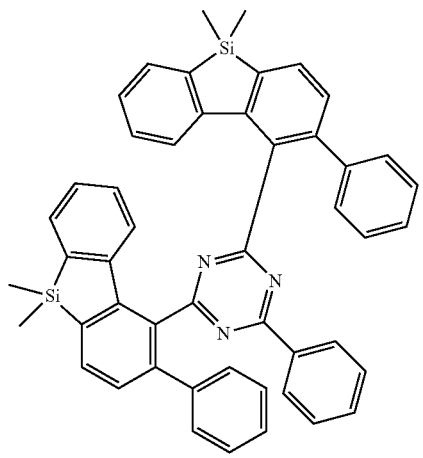
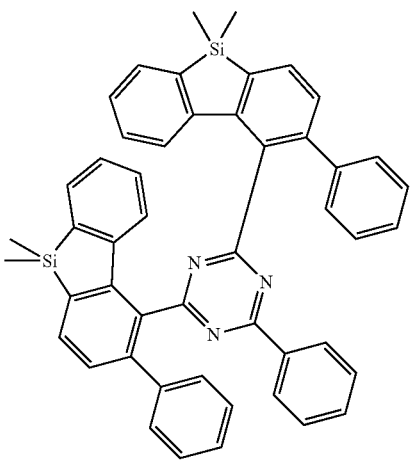

211
-continued
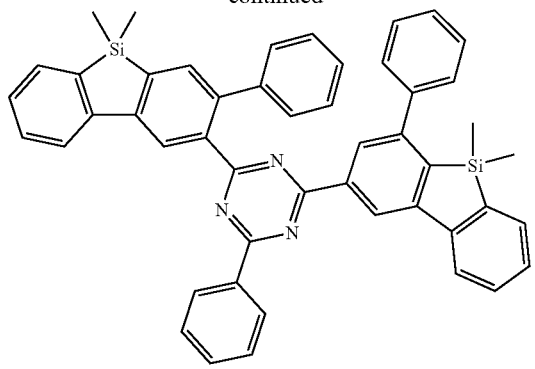
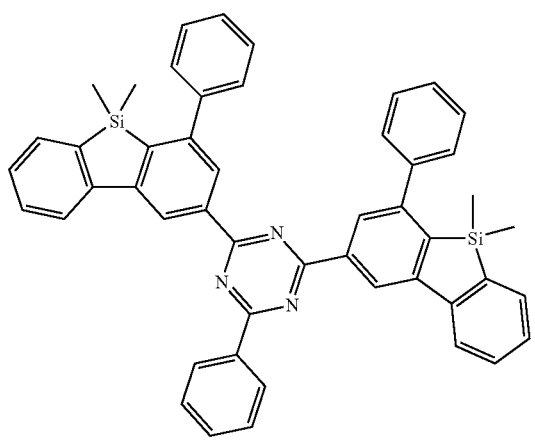
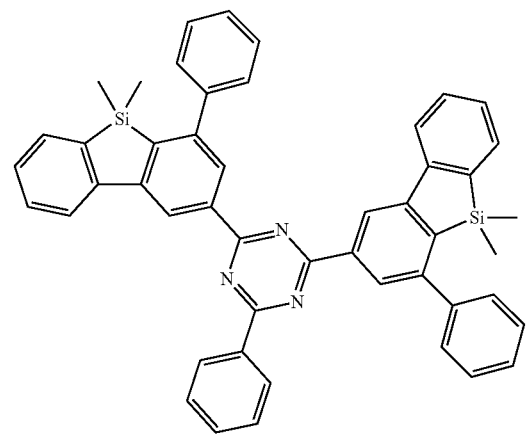
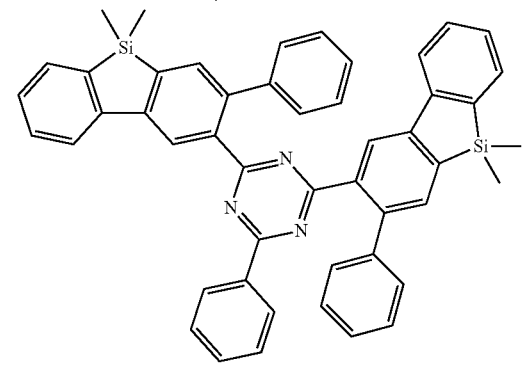
212
-continued
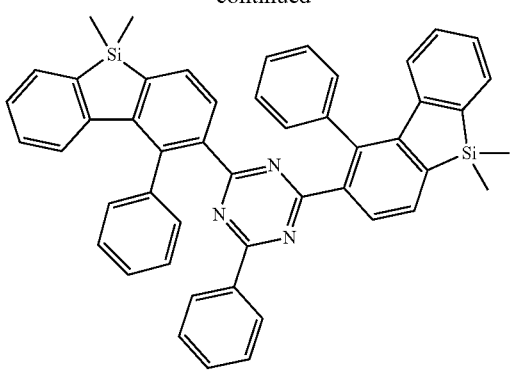
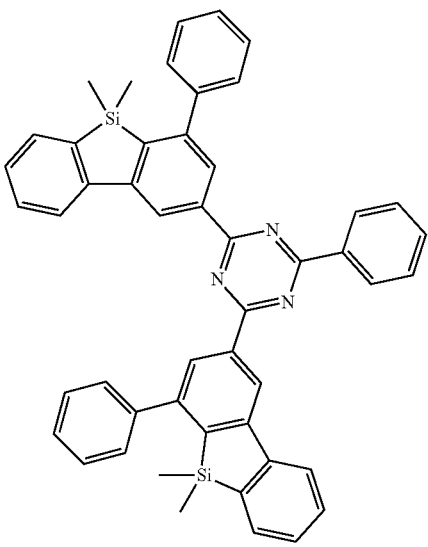
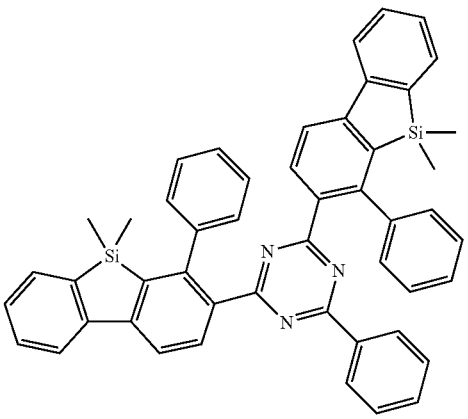

213
-continued
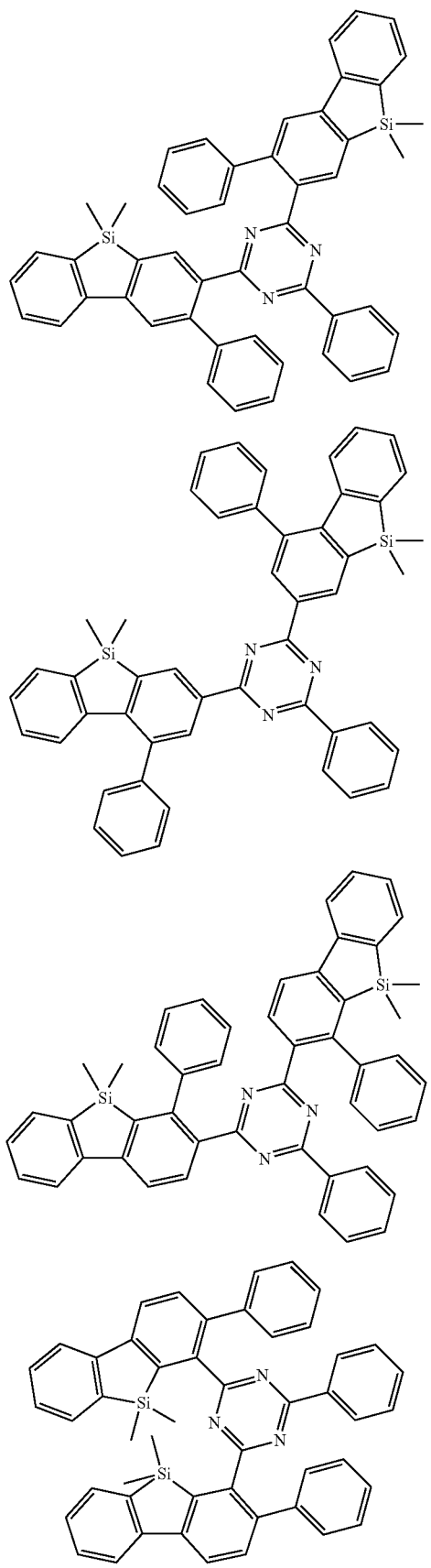
214
-continued
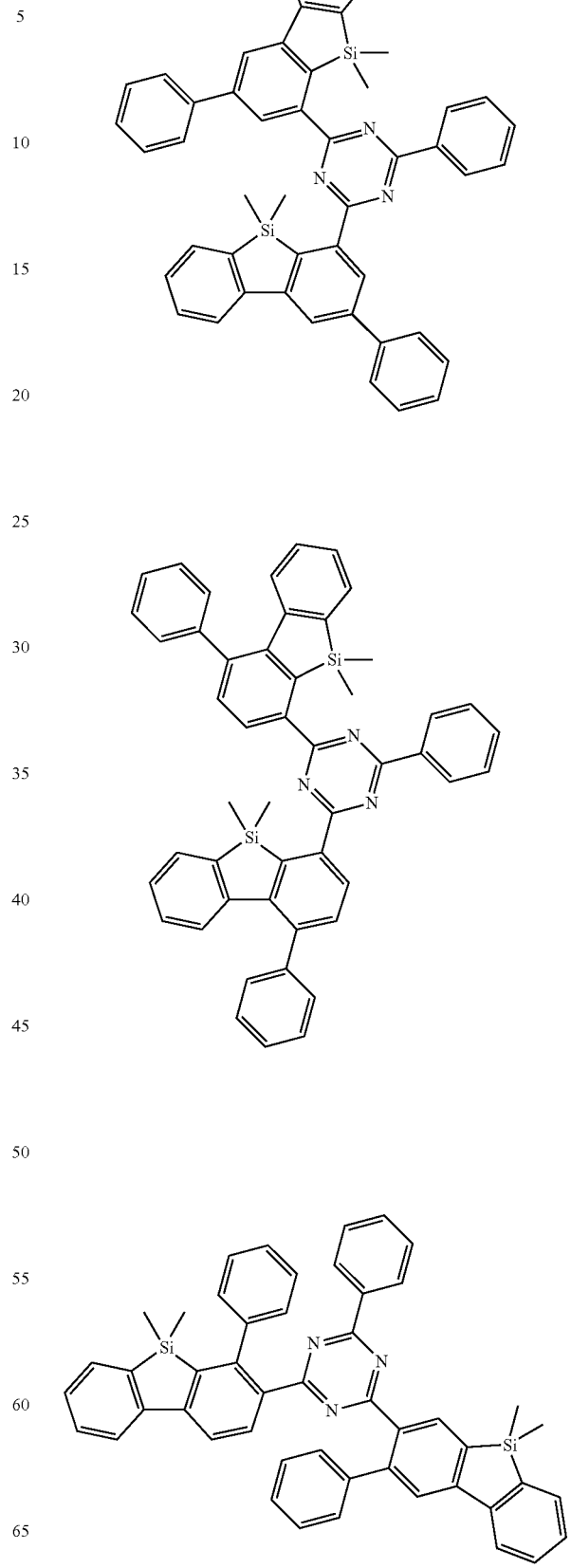

215
-continued
216
-continued
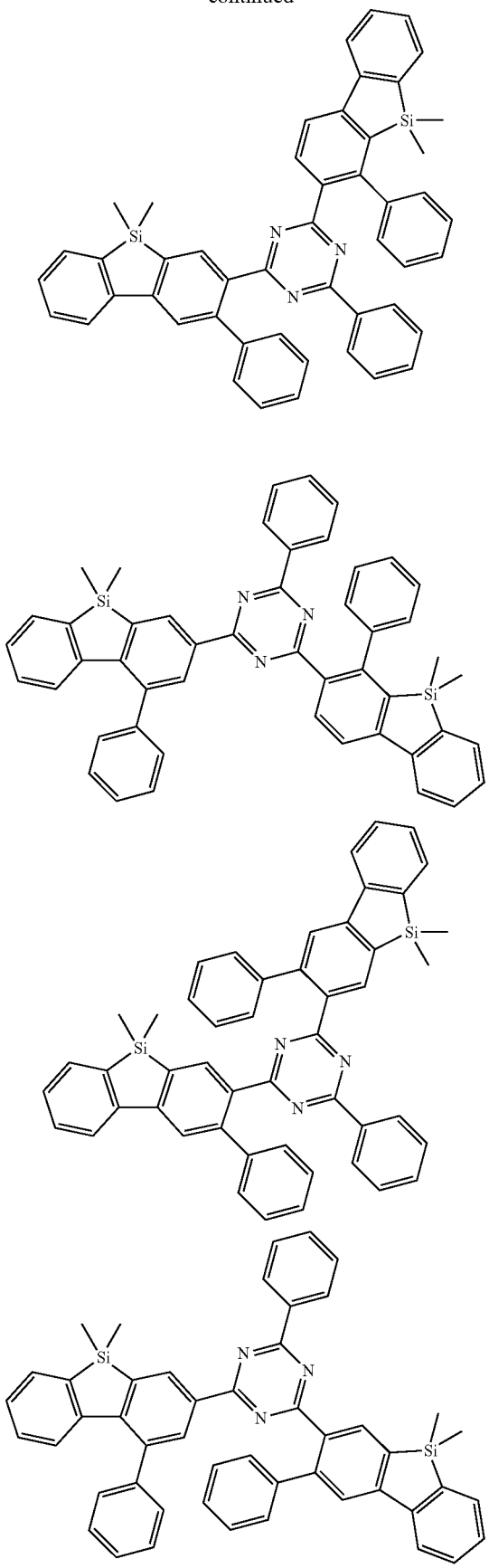
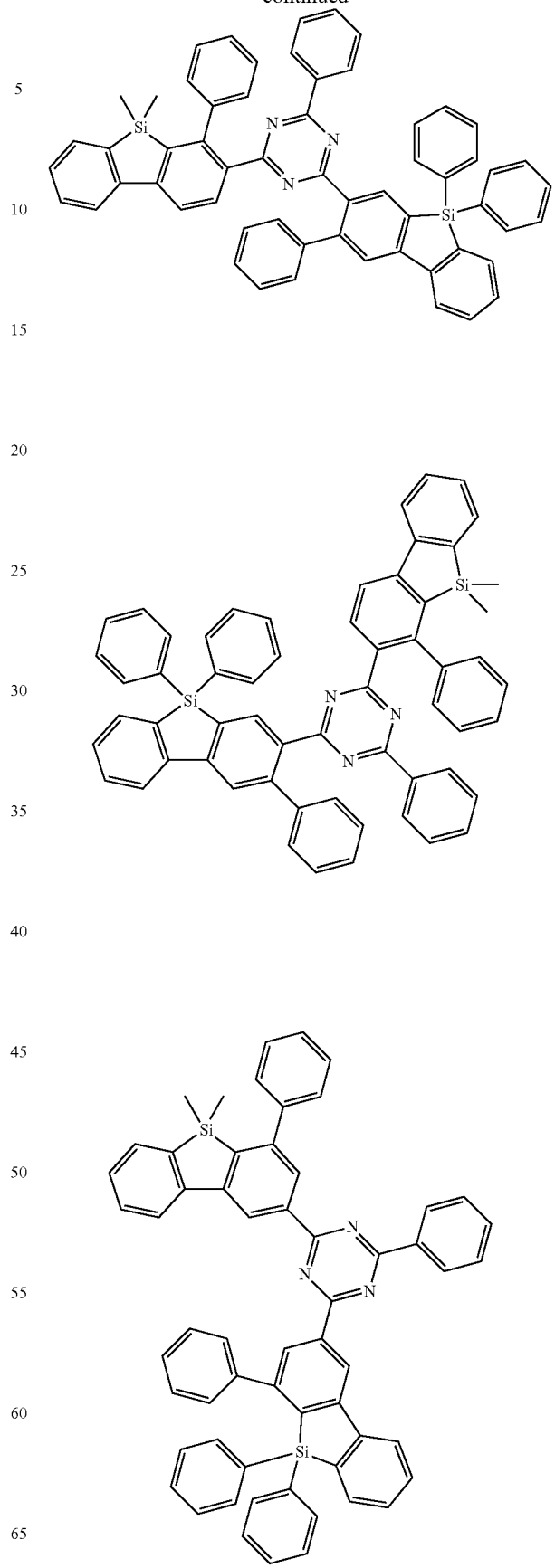

217
-continued
218
-continued
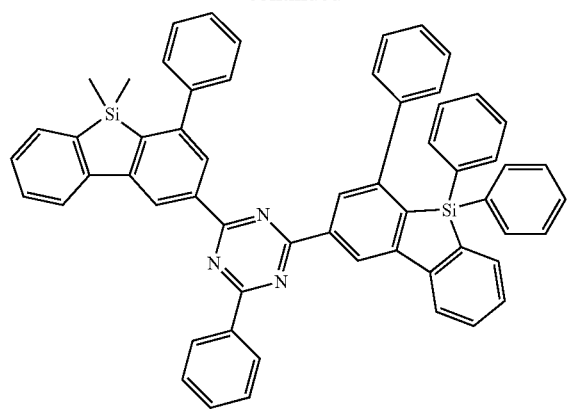
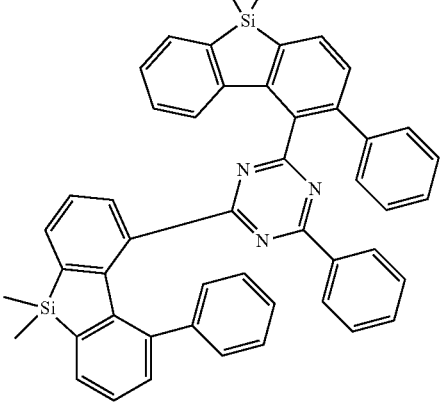

219
-continued
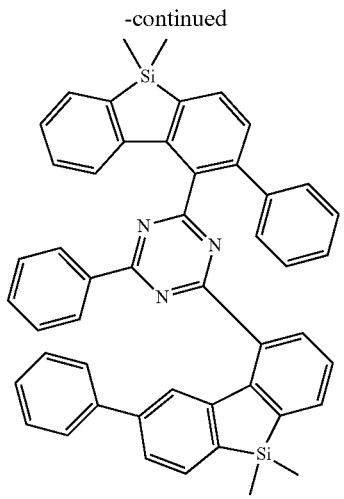
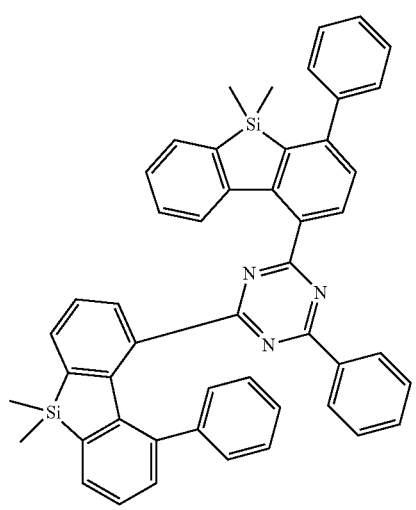
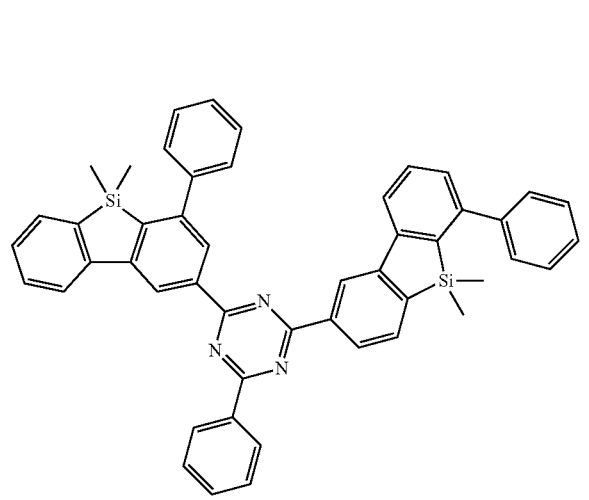
220
-continued
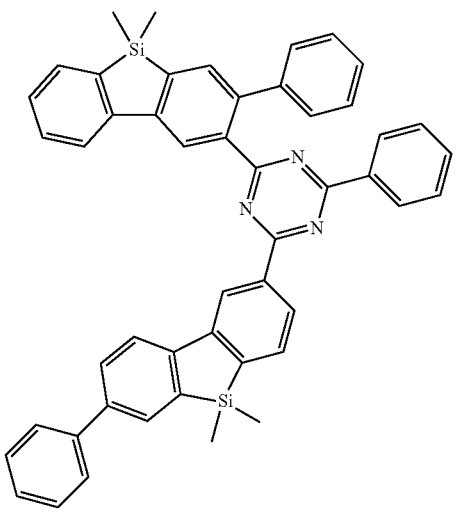
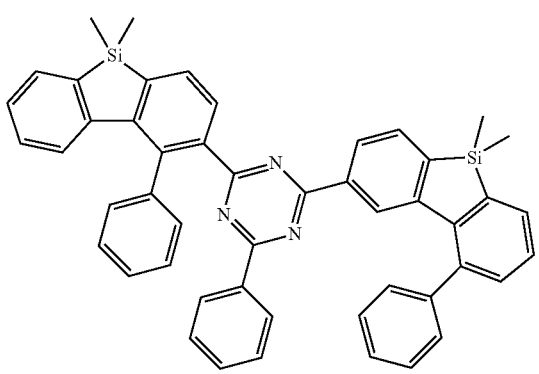
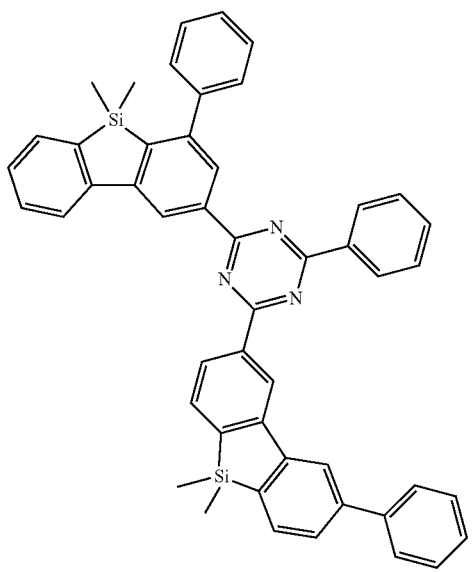

221
-continued
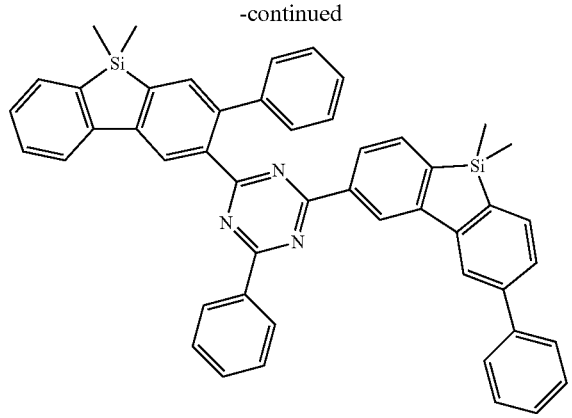
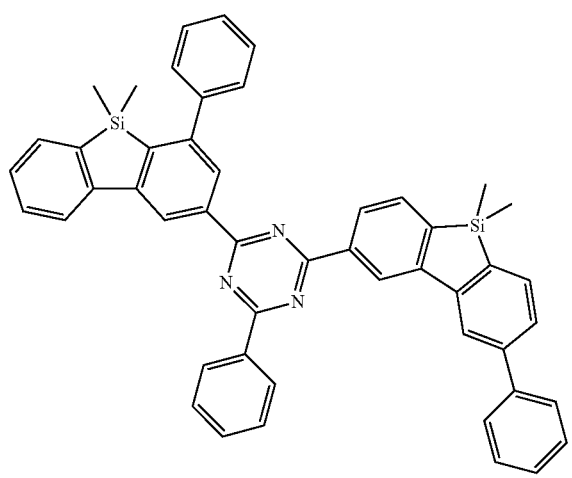
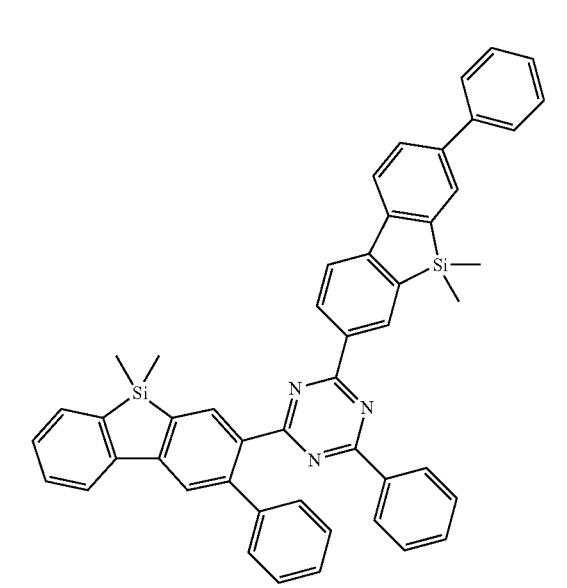
222
-continued
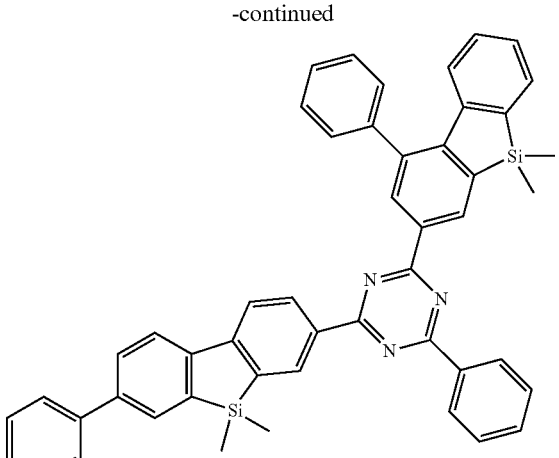
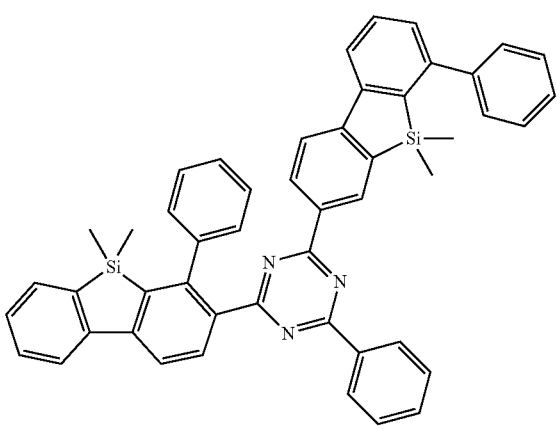
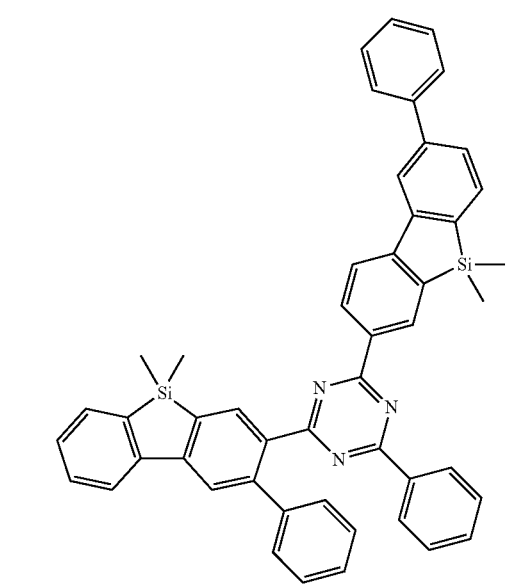

223
-continued
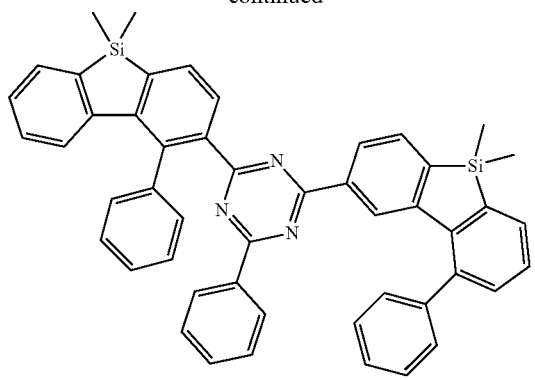
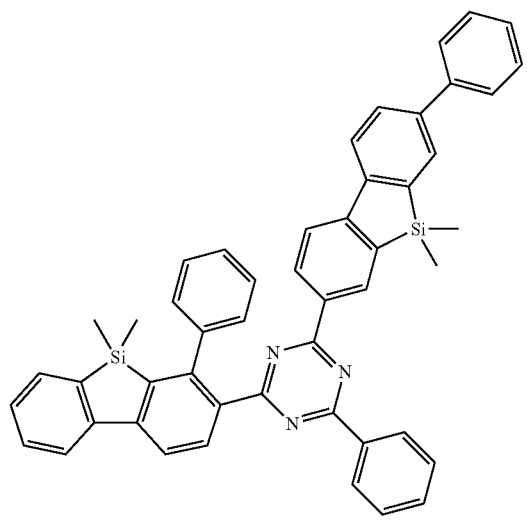
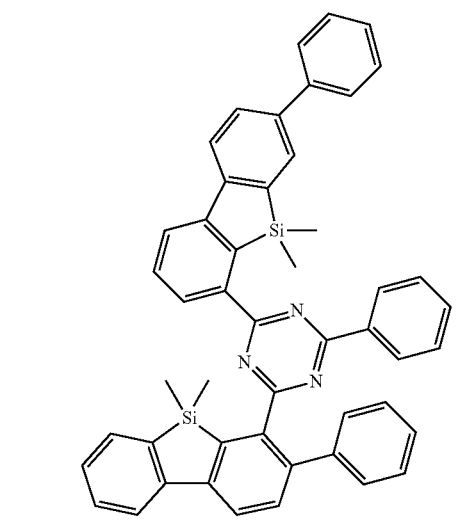
224
-continued
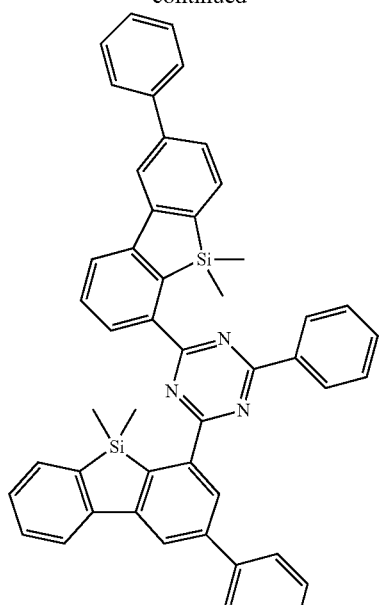
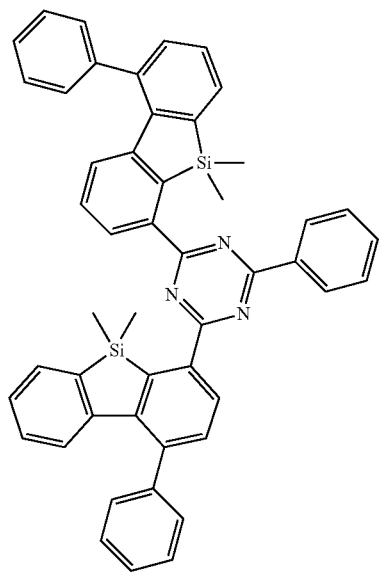
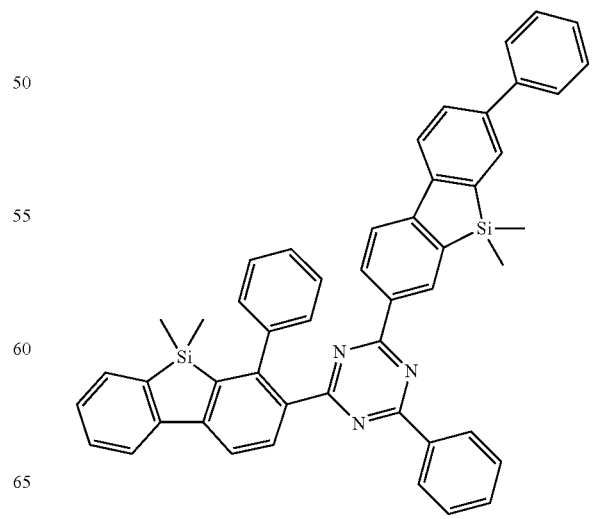

225
-continued
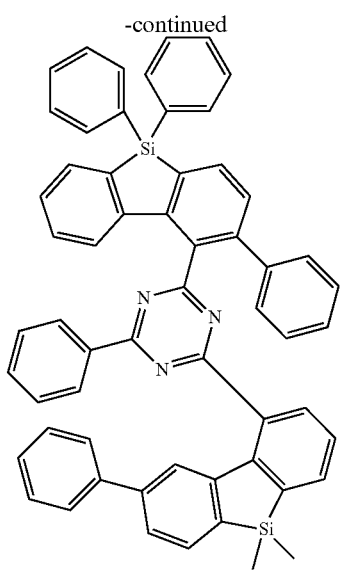
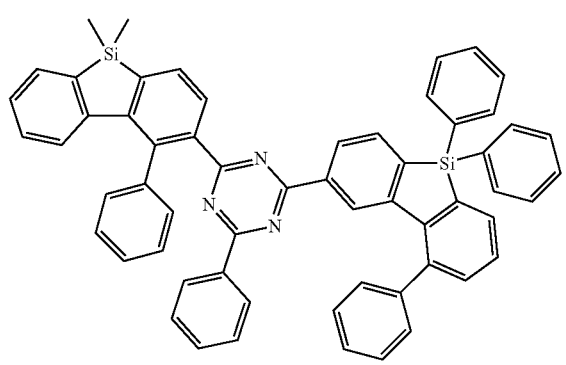
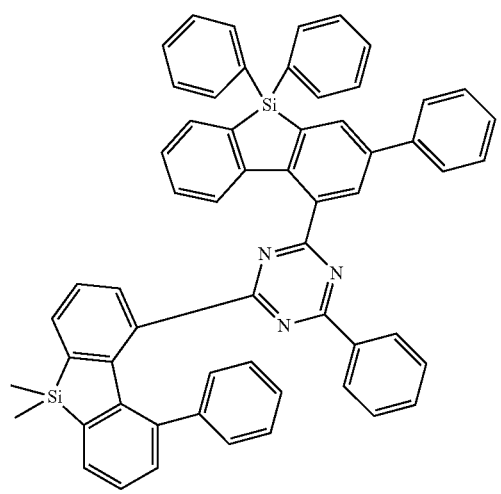
226
-continued
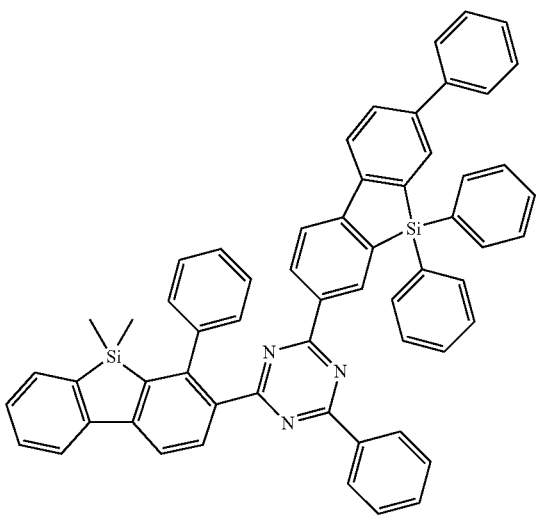
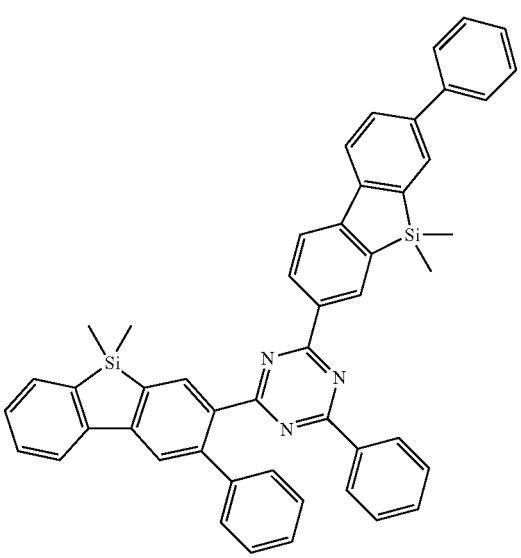
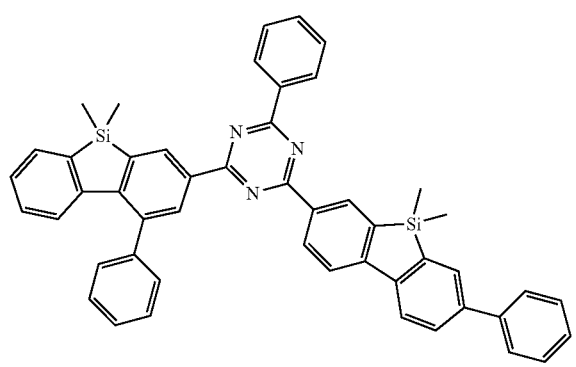

227
-continued
228
-continued
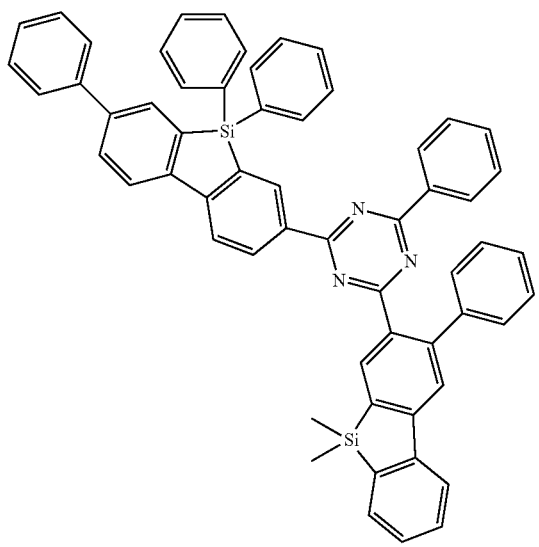
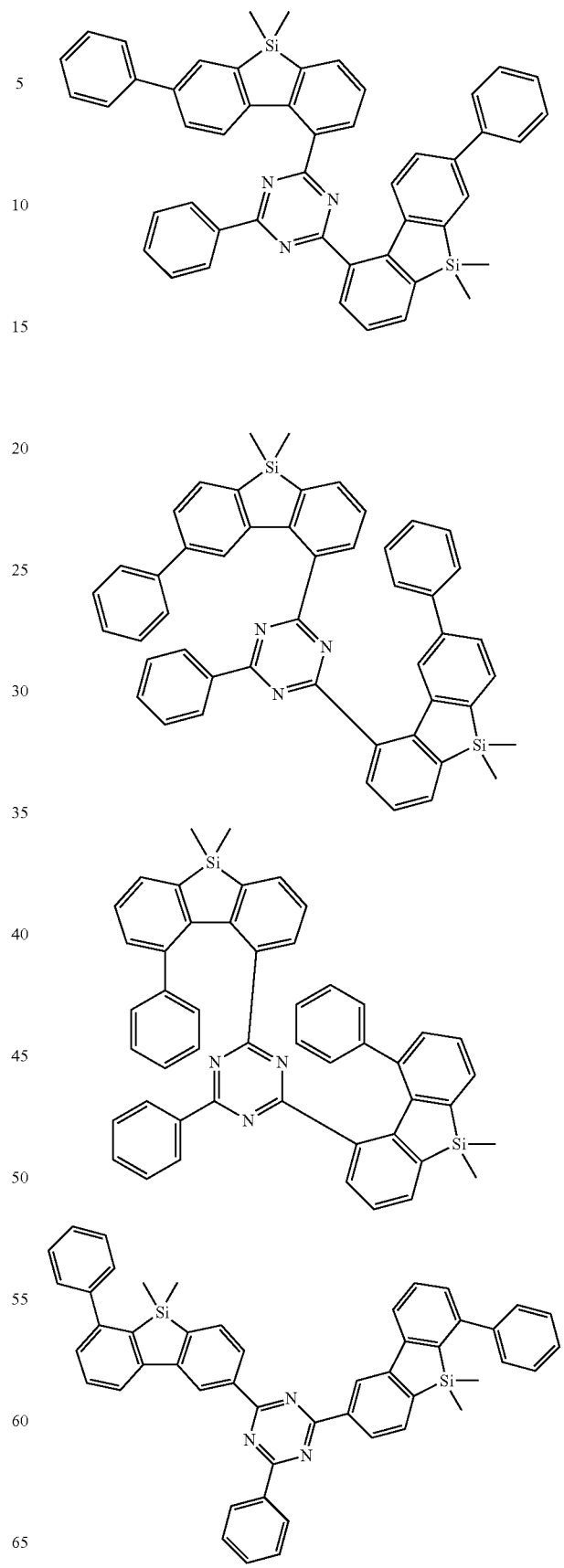

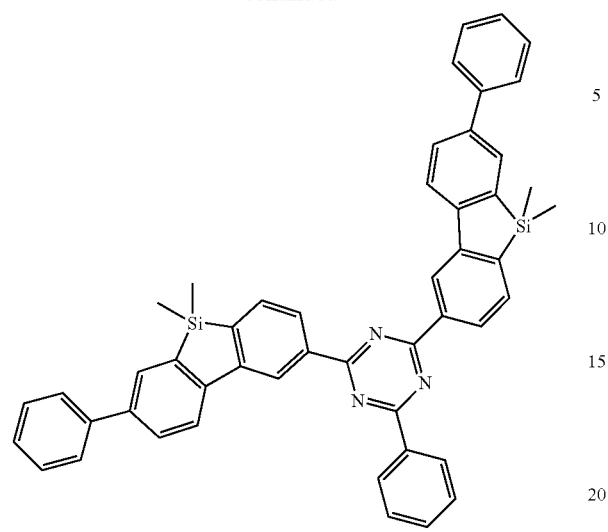
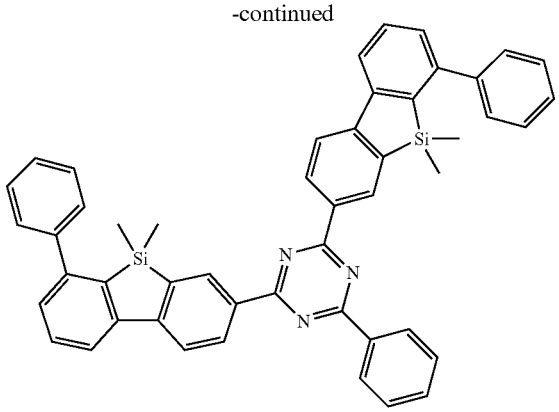
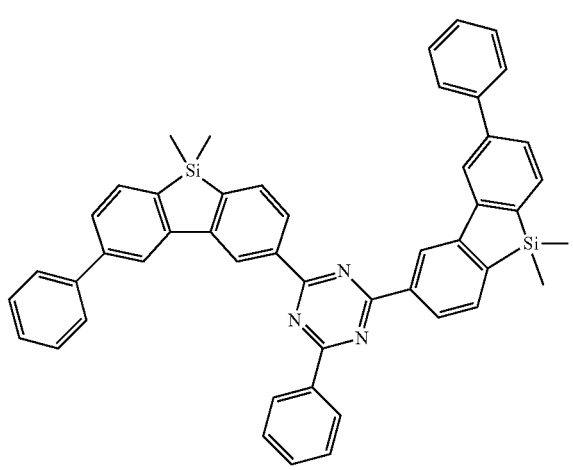
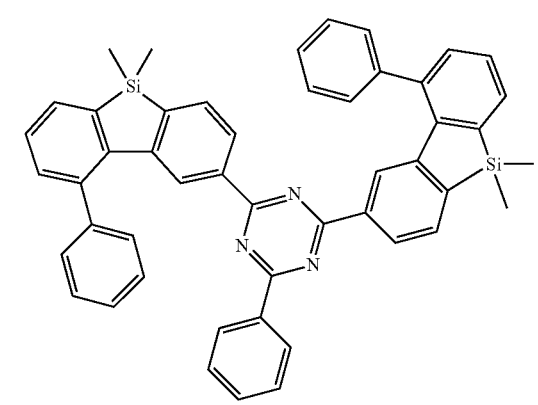
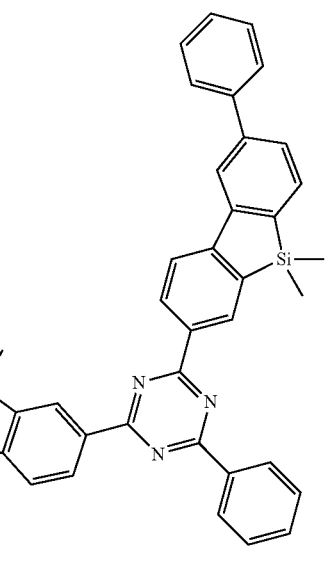

231
-continued
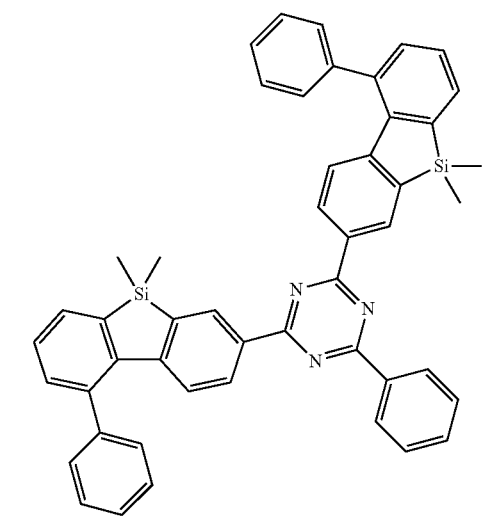
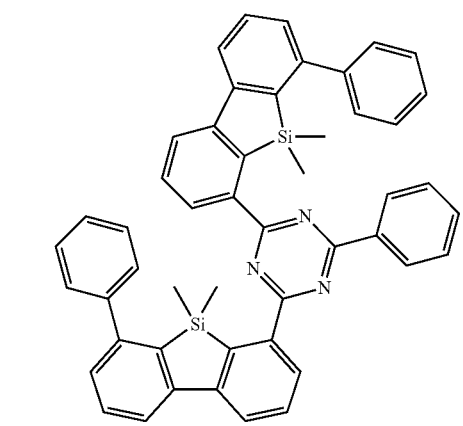
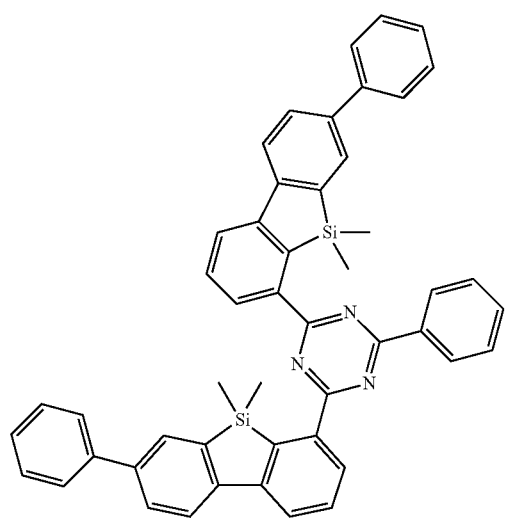
232
-continued
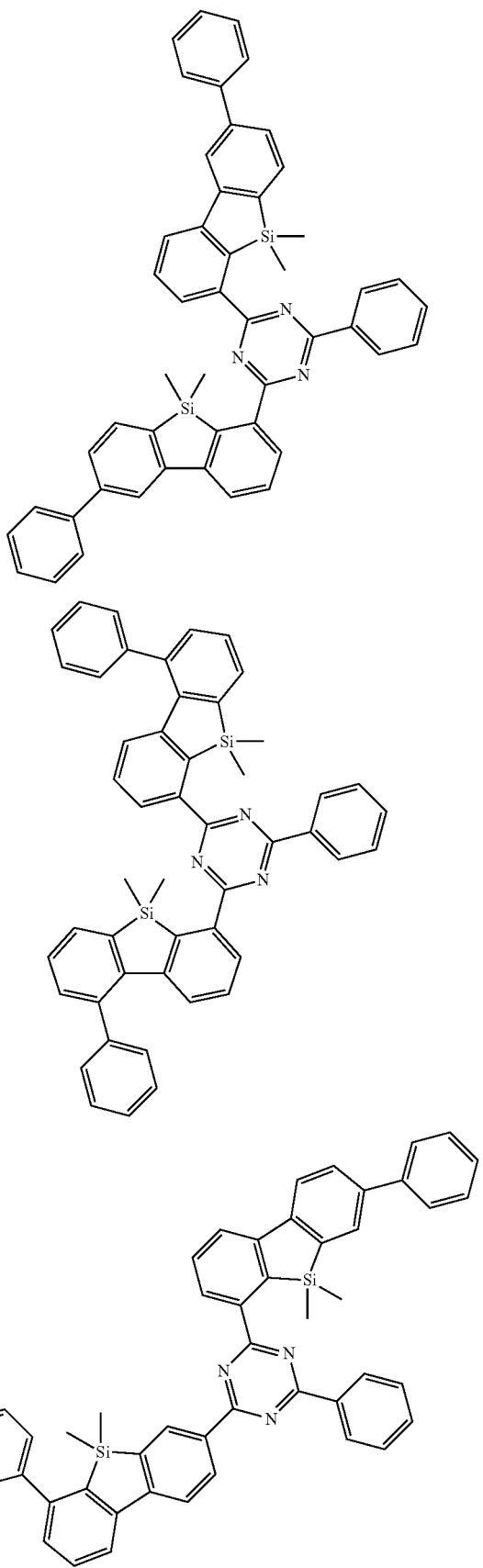

233
-continued
234
-continued
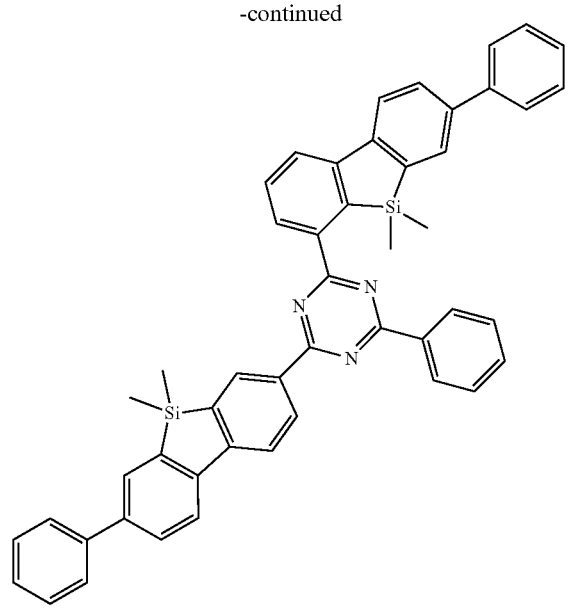
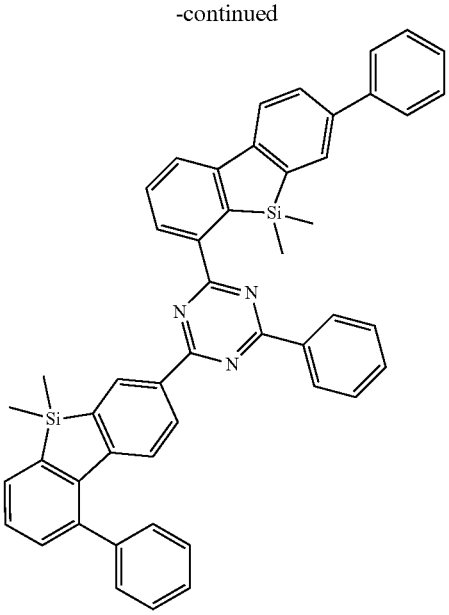
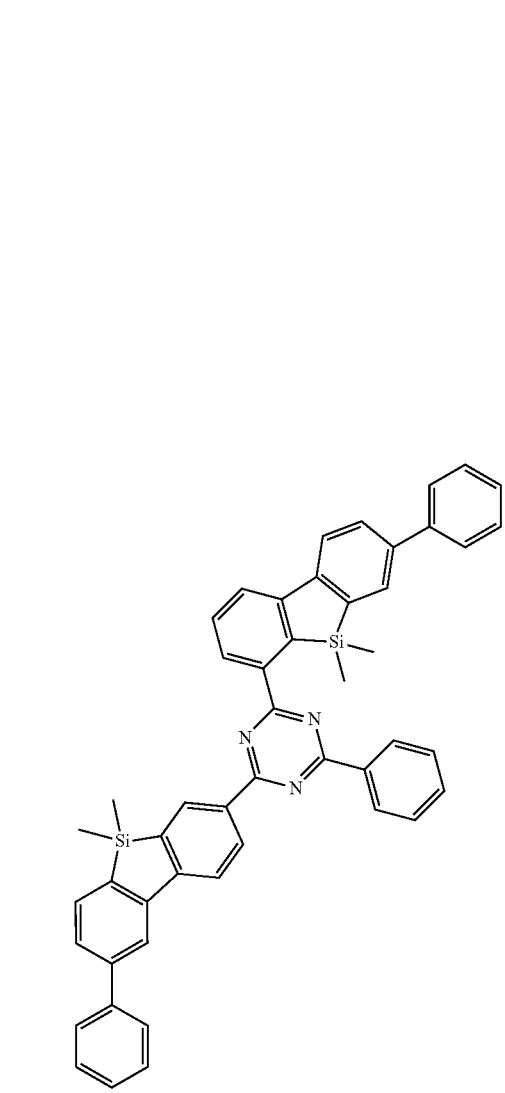
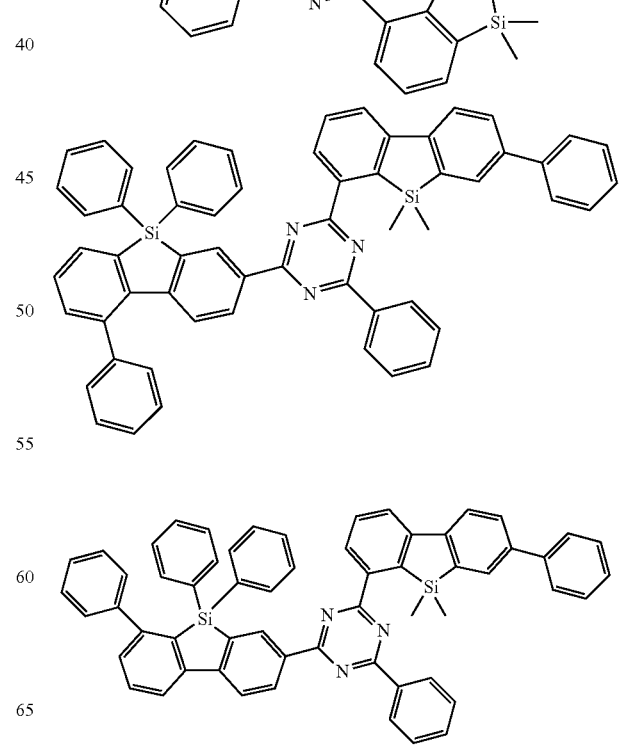

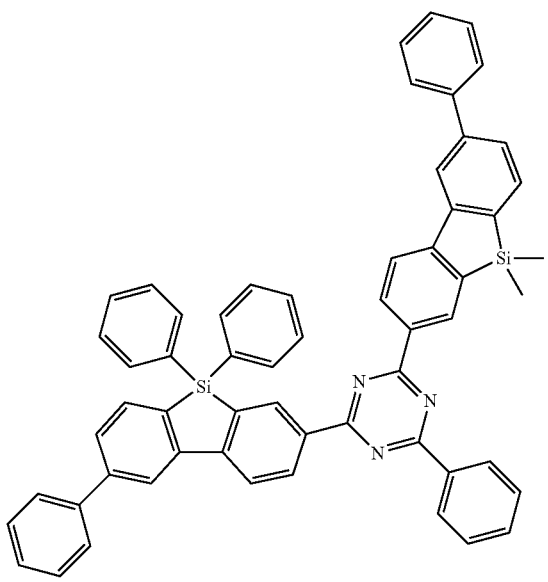

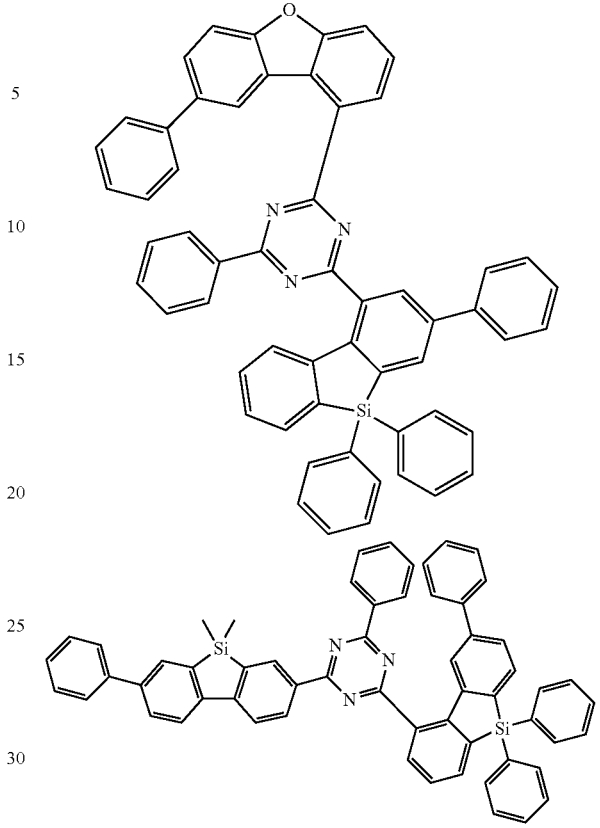

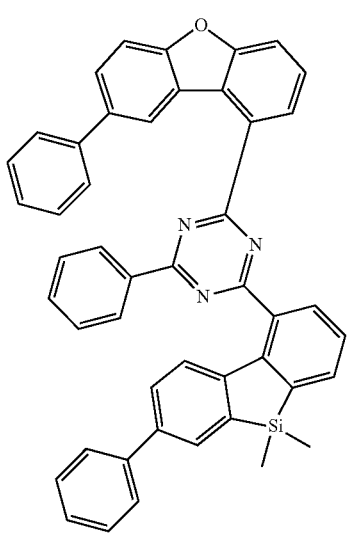

6. An organic light emitting device comprising:
a first electrode;
a second electrode; and
one or more organic material layers provided between the first electrode and the second electrode,
wherein the organic material layer comprises the compound of Chemical Formula 1 of claim 1.

7. The organic light emitting device of claim 6, wherein the organic material layer comprises a light emitting layer, and the light emitting layer comprises the compound of Chemical Formula 1.

8. The organic light emitting device of claim 7, wherein the light emitting layer comprising the compound of Chemical Formula 1 further comprises a dopant.

9. The organic light emitting device of claim 6, wherein the organic material layer comprises a hole injection layer; a hole transfer layer; a layer carrying out hole transfer and injection at the same time; a hole control layer; an electron control layer; an electron injection layer; an electron transfer layer; or a layer carrying out electron transfer and injection at the same time, and the hole injection layer; the hole transfer layer; the layer carrying out hole transfer and injection at the same time; the hole control layer; the electron control layer; the electron injection layer; the electron transfer layer; or the layer carrying out electron transfer and injection at the same time comprises the compound of Chemical Formula 1.

* * * * *